US011788147B2

(12) United States Patent
Pietenpol et al.

(10) Patent No.: US 11,788,147 B2
(45) Date of Patent: Oct. 17, 2023

(54) MARKERS OF TRIPLE-NEGATIVE BREAST CANCER AND USES THEREOF

(71) Applicant: Vanderbilt University, Nashville, TN (US)

(72) Inventors: Jennifer A. Pietenpol, Nashville, TN (US); Brian Lehmann, Nashville, TN (US); Josh Bauer, Nashville, TN (US); Xi Chen, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/746,721

(22) Filed: Jan. 17, 2020

(65) Prior Publication Data

US 2020/0224282 A1    Jul. 16, 2020

Related U.S. Application Data

(63) Continuation of application No. 14/358,330, filed as application No. PCT/US2012/065724 on Nov. 17, 2012, now abandoned.

(60) Provisional application No. 61/561,743, filed on Nov. 18, 2011.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57415* (2013.01); *C12Q 2600/106* (2013.01); *C12Q 2600/112* (2013.01); *C12Q 2600/156* (2013.01); *C12Q 2600/158* (2013.01)

(58) Field of Classification Search
None
See application file for complete search history.

(56) References Cited

PUBLICATIONS

Cobb et al. (Crit Care Med 2002 vol. 30 p. 2711) (Year: 2002).*
Agoff, S.N., et al., "Androgen Receptor Expression in Estrogen Receptor-Negative Breast Cancer", Am J Clin Pathol, 120: 725-731 (2003).
Audeh, M.W., et al., "Phase II Trial of the Oral PARP Inhibitor Olaparib (AZD2281) in BRCA- Deficient Advanced Ovarian Cancer", Journal of Clinnical Oncology, ASCO Annual Meeting Proceedings, 27(15S): 5500 (2009).
Bauer, J.A., et al., "Identification of Markers OfTaxane Sensitivity Using Proteomic and Genomic Analyses of Breast Tumors From Patients Receiving N eoadjuvant Paclitaxel and Radiation", Clin Cancer Res, 16(2): 681-690 (2010).
Bauer, J.A., et al., "RNA Interference (RNAi) Screening Approach Identifies Agents That Enhance Paclitaxel Activity in Breast Cancer Cells", Breast Cancer Research, 12:R41, 16 pages (2010).
Bertucci, F., et al., "Gene Expression Profiling Shows Medullary Breast Cancer is a Subgroup of Basal Breast Cancers", Cancer Res, 66(9): 4636-4644 (2006).
Bertucci, F., et al., "How Baseal Are Triple-Negative Breast Cancers?", Int. J Cancer, 123: 236-240 (2008).
Bhattacharyya, A., et al., "The Breast Cancer-Susceptibility Gene BRCAJ Is Required For Subnuclear Assembly of Rad5 I and Survival Following Treatment With the DNA Crosslinking Agent Cisplatin", J. Biol Chem, 275(31): 23899-23903 (2000).
Birrell, S.N., et al., "Disruption of Androgen Receptor Signaling by Synthetic Progestins May Increase Risk of Developing Breast Cancer", The FASEB Journal, 21: 9 pages (2007).
Boersma, B.J., et al. "A Stromal Gene Signature Associated With Inflammatory Breast Cancer", Int J Cancer, 122: 1324-1332 (2008).
Bos, P.D., et al., "Genes That Mediate Breast Cancer Metastasis to the Brain", Nature, 18:459(7249): 1005-1009 (2009).
Burstein, H.J., et al., "Phase TT Study of Sunitinib Malate, An Oral Multitrageted Tyrosine Kinase Inhibitor, in Patients With Metastatic Breast Cancer Previously Treate With An Anthracycline and a Taxane", J Clin Oneal, 26(11): 1810-1816 (2008).
Carey, L.A., et al., "The Triple Negative Paradox: Primaiy Tumor Chemosensitivity of Breast Cancer Subtypes", Clin Cancer Res, 13(8): 2329-2334 (2007).
Carmeci, C., et al., "Analysis of Estrogen Receptor Messenger RNA in Breast Carcinomas From Archival Specimens is Predictive of Tumor Biology", Am .1 Path, 150(5): 1563-1570 (1997).
Carotenuto, P., et al., "Triple Negative Breast Cancer: From Molecular Portrait to Therapeutic Intervention", Critical Reviews in Eukaryotic Gene Expression, 20: 17-34 (2010).
Carver, B.S., et al., "Reciprocal Feedback Regulation of PI3K and Androgen Receptor Signaling in PTEN-Deficient Prostate Cancer", Cancer Cell, 19: 575-586 (2011).
Chakravarthy, A.B., et al., "Neoadjuvant Concurrent Paclitaxel and Radiation in Stage II/III Breast Cancer", Clin Cancer Res., 12(5): 1570-1576 (2006).
Chen, C.D., et al., "Molecular Determinants of Resistance to Antiandrogen Therapy", Nature Medicine, 10: 33-39 (2004).
Chen, Xi, et al., "TNBCtype: ASubtyping Tool For Triple-Negative Breast Cancer", Cancer Informatics, 11: 147-156 (2012).
Chin, K., et al., "Genomic and Transcriptional Abberations Linked To Breast Cancer Pathophysiologies", Cancer Cell, 10: 529-541 (2006).

(Continued)

*Primary Examiner* — Katherine D Salmon
(74) *Attorney, Agent, or Firm* — Stites & Harbison PLLC; Richard S. Myers, Jr.

(57) ABSTRACT

In one aspect provided herein are methods of determining a triple negative breast cancer (TNBC) subtype in an individual in need thereof comprising determining expression of one or more genes in one or more TNBC cells of the individual; and comparing the expression of the one or more genes in the TNBC cells with the expression of the one or more genes in a control. In another aspect, the methods are directed to determining a treatment protocol for the TNBC patient based on the TNBC subtype. In another aspect, the methods are directed to predicting whether an individual will benefit from a treatment for a particular TNBC subtype. In yet another aspect, the invention is directed to a method of determining whether an agent can be used to treat a TNBC subtype.

17 Claims, 60 Drawing Sheets

Specification includes a Sequence Listing.

(56) References Cited

PUBLICATIONS

D'Andrea, A.D. and Grompe, M., "The Fanconi Anaemia/BRCA Pathway", Nature Reviews Cancer, 3: 23-34 (2003).
Dent, R., et al., "Triple-Negative Breast Cancer: Clinical Features and Patterns of Recurrence", Clin Cancer Res, 13 (15): 4429-4434 (2007).
Desmedt, C., et al., "Strong Time Dependence of the 76-Gene Prognostic Signature For Node- Negative Breast Cancer Patients in the TRANSBIG Multicenter Independent Validation Series", Clin Cancer Res, 13(11 ): 3207-3214 (2007).
Doane, A.S., et al., "An Estrogen Receptor-Negative Breast Cancer Subset Characterized by a Hormonally Regulated Transcriptional Program and Response to Androgen", Oncogene, 25 :3994-4008 (2006).
Ellard, S.L., et al., "Randomized Phase II Study Comparing Two Schedules of Everolimus in Patients With Recurrent/Metastatic Breast Cancer: NCTC Clinical Trials Group TND.163", J Clin Oncol, 27(27): 4536-4541 (2009).
Evers, B., et al., "Selective Inhibition OfBRCA2-Deficient Mammary Tumor Cell Growth By AZD2281 and Cisplatin", Clin Cancer Res, 14(12): 3916-3925 (2008).
Farmer, H., et al., "Targeting the DNA Repair Defect in BRCA Mutant Cells as a Therapeutic Strategy", Nature, 434: 917-920 (2005).
Farmer, P., et al., "Identification of Molecular Apocrine Breast Tumours by Microarray Analysis", Oncogene, 24: 4660-4671 (2005).
Finn, R.S., et al., "Dasatinib, An Orally Active Small Molecule Inhibitor of Both the src and abl Kinases, Selectively Inhibits Growth of Basal-Type/ "Triple-Negative" Breast Cancer Cell Lines Growing In Vitro", Breast Cancer Res Treat, 105: 319-326 (2007).
Fong, P.C., et al., "Inhibition of Poly(ADP-Ribose) Polymerase in Tumors From BRCA Mutation Carriers", The New England Journal of Medicine, 361(2): 123-134 (2009).
Garber, J.E., et al. "Neo-Adjuvant Cisplatin (CDDP) in "Triple -Negative" Breast Cancer (BC)", Breast Cancer Research and Treatment, 29th Annual San Antonio Breast Cancer Symposium, Dec. 14-17, 100: S149, Abstract#3074 (2006).
Gibson, G.R., et al., "Metaplastic Breast Cancer : Clinical Features and Outcomes", The American Surgeon, 71: 725-730 (2005).
Gonzalez-Angulo, A.M., et al., "Androgen Receptor Levels and Association With PIK3CA Mutations and Prognosis in Breast Cancer", Clin Cancer Res, 15(7): 2472-2478 (2009).
Guarino, M., "Src Signaling in Cancer Invasion", Journal of Cellular Physiology, 223: 14-26 (2010).
Haffty, B.G., et al., "Locoregional Relapse and Distant Metastasis in Conservatively Managed Triple Negative Early-Stage Breast Cancer", J Clin Oneal., 24(36): 5652-5657 (2006).
Hayes, M.J., et al., "Genetic Changes OfWnt Pathyway Genes Are Common Events in Metaplastic Carcinomas of the Breast", Clin Cancer Res, 14(13): 4038-4044 (2008).
Hennessy, B.T., et al., Characterization of a Naturally Occurring Breast Cancer Subset Enriched in Epithelial-To-Mesenchymal Transition and Stem Cell Characteristics, Cancer Res, 69(10): 4116-4124 (2009).
Hoeijmakers, J.H., "Genome Maintenance Mechanisms for Preventing Cancer", Nature, 411: 366-374 (2001).
Hu, Z., et al., "The Molecular Portraits of Breast Tumors Are Conserved Across Microarray Platforms", BMC Genomics, 7:96, 12 pages (2006).
Jones, P., et al., "Discovery Of2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors", J. Med. Chem, 52: 7170-7185 (2009).
Juul, N., et al., "Assessment of an RNA Interference Screen-Derived Mitotic and Ceramide Pathyway Metagene as a Predictor of Response to Neoadjuvant Paclitaxel for Primmy Tripl-Negative Breast Cancer: A Retrospective Analysis of Five Clinical Trials", The Lancet, 11: 358-365 (2010).

Kam, T., et al., "Data Driven Derivation of Cutoffs From a Pool of 3,030 Affymetrix Anays to STratify Distinct Clinical Types of Breast Cancer", Breast Cancer Res Treat, 120: 567-579 (2010).
Kenny, P.A., et al., "The Morphologies of Breast Cancer Cell Lines in Three-Dimensional Assays Conelate With Their Profiles of Gene Expression", Molecular Oncology, I: 84-96 (2007).
Kreike, B., et al., "Gene Expression Profiling and Histopathological Characterzation of Triple- Negative/Basal-Like Breast Carcinomas", Breast Cancer Research, 9: R65, 14 pages (2007).
Kwei, K.A., et al., "Genomic Instability in Breast Cancer: Pathogenesis and Clinical Implications", Mal. Oneal, 4(3): 255-266 (2010).
Lehmann, B.D., et al., "Identification of Human Triple-Negative Breast Cancer Subtypes and Preclinical Models for Selection of Targeted Therapies", Journal of Clinical Investigation, 121(7): 2750-2767 (2011).
Li, Y., et al., "Amplification OfLAPTM4B and YWHAZ Contributes to Chemotherapy Resistance and Recunence of Breast Cancer", Nature Medicine, 16(2): 214-218 (2010).
Liu, X., et al., "Simultaneous Targeting of the Androgen Receptor and PI3K/mTOR Pathway in Androgen-Dependent and Androgen-Independent Prostate Cancer Cells", Journal of Clinical Oncology, ASCO Annual Meeting Abstracts, 28 (15_suppl):c15049, 1 page (2010).
MacDonald, B.T., et al., "Wnt/B-Catenin Signaling: Components, Mechanisms, and Disease", Dev. Cell, 17: 9-26 (2009).
Maira, S.M., et al., "Identification and Characterization OF NVP-BEZ235, A New Orally Available Dual Phosphatidylinositol 3-Kinase/ Mammalian Target of Rapamycin Inhibitor With Potentln Vivo Antitumor Activity", Mal Can Ther, 7(7): 1851-1863 (2008).
Mani, S.A., et al., "The Epithclial-Mcscnchymal Transition Generates Cells With Properties of Stem Cells", Cell, 133:705-715 (2008).
Maiiy, B., et al., "Frequent PTEN Genomic Alterations and Activated Phosphatidylinositol 3- Kinase Pathyway in Basal-Like Breast Cancer Cells", Breast Cancer Research, 10: RIOI, 15 pages (2008).
Mayer, I.A., et al., "A Phase II Neoadjuvant Study of Cisplatin/ Paclitaxel With or Without RADOOI in Patients With Triple-Negative (TN) Locally Advanced Breast Cancer (BC)", J. Clin Oneal, 28: 15s (Suppl; abstract TPSI 19) (2010).
Miller, L.D., et al., "An Expression Signature For p53 Status in Human Breast Cancer Predicts Mutation Status, Transcriptional Effects, and Patient Survival", PNAS, 102(38): 13550-13555 (2005).
Minn, A.J., et al., "Genes That Mediate Breast Cancer Metastasis to Lung", Nature, 436: 518-524 (2005).
Morris, G.J., et al., "Differences in Breast Carcinoma Characteristics in Newly Diagnosed African-American and Caucasian Patients", Cancer, 110: 876-884 (2007).
Neve, R.M., et al., "A Collection of Breast Cancer Cell Lines for the Study of Functionally Distinct Cancer Subtypes", Cancer Cell, 10: 515-527 (2006).
Nielsen, T.O., et al., "Immunohistochemical and Clinical Characterization of the Basal-Like Subtype OfInvasive Breast Carcinoma", Clinical Cancer Research, 10: 5367-5374 (2004).
Pal, S.K., et al., "Triple Negative Breast Cancer: Unmet Medical Needs", Breast Cancer Res Treat, 125:627-636 (2011).
Pawitan, Y., et al., "Gene Expression Profiling Spares Early Breast Cancer Patients From Adjuvant Therapy: Derived and Validated in Two Population-Based Cohorts", Breast Cancer Research, 7: R953-R964 (2005).
Pegram., M.D., et al., "Phase II Study of Receptor-Enhanced Chemosensitivity Using Recombinant Humanized Anti-p185HER/ neu Monoclonal Antibody Plus Cisplatin 1n Patients With HER2/ neu-Overexpressing Metastatic Breast Cancer Refractory to Chemotherapy Treatment", Journal of Clinical Oncology, 16(8): 2659-2671 (1998).
Prat, A., et al., "Phenotypic and Molecular Characterization of the Claudin-Low Intrinsic Subtype of Breast Cancer", Breast Cancer Research, 12: R68, 18 pages, (2010).
Press, M.F., et al., "HER-2 GcncAmplification, HER-2 and Epidermal Growth Factor Receptor mRNA and Protein Expression, and Lapatinib Efficacy in Women With Metastatic Breast Cancer", Clincal Cancer Research, 14(23): 7861-7870 (2008).

(56) References Cited

PUBLICATIONS

Rakha, E. and Ellis, I., "Are Triple-Negative and Basal-Like Breast Cancer Synonymous?", Clinical Cancer Research, 14(2): 618 (2008).
Rakha, E.A., et al., "Triple-Negative Breast Cancer: Distinguishing Between Basal and Nonbasal Subtypes", Clinical Cancer Research, 15(7): 2302-2310 (2009).
Richardson, A.L., et al., "X Chromosomal Abnormalities in Basal-Like Human Breast Cancer", Cancer Cell, 9: 121-132 (2006).
Samuels, Y., et al., "High Frequency of Mutations of the PIK3CA Gene in Human Cancers", Science, 304: 554 (2004).
Schmidt, M., et al., "The Humoral Immune System Has a Key Prognostic Impact in Node- Negative Breast Cancer", Cancer Research, 68(13): 5405-5413 (2008).
Shin, S.Y., et al., "Functional Roles of Multiple Feedback Loops in Extracellular Signal-Regulated Kinase and Wnt Signaling Pathways That Regulate Epithelial-Mesenchymal Transition", Cancer Research, 70(17): 6715-6724 (2010).
Shipitsin, M., et al., "Molecular Definition of Breast Tumor Heterogeneity", Cancer Cell, 11: 259-273 (2007).
Silver, D.P., et al., "Efficacy of Neoadjuvant Cisplatin in Triple-Negative Breast Cancer", Journal OfClinical Oncology, 28(7): 1145-1153 (2010).
Solit, D.B., et al., "I 7-Allylamino-17-Demethoxygeldanamycin Induces the Degradation of Androgen Receptor and HER-2/neu and Inhibits the Growth of Prostate Cancer Xenografts", Clinical Cancer Research, 8: 986-993 (2002).
Sotiriou, C., et al., "Gene Expression Profiling in Breast Cancer: Understanding the Molecular Basis OfHistologic Grade to Improve Prognosis", Journal of The National Cancer Institute, 98(4): 262-272 (2006).
Stefansson, O.A., et al., "Genomic Profiling of Breast Tumours 1n Relation To BRCA Abnormalities and Phenotypes", Breast Cancer Research, 11: R4 7, 14 pages (2009).
Stemke-Hale, K., et al., "An Integrative Genomic and Proteomic Analysis of PIK3CA, PTEN, and AKT Mutations in Breast Cancer", Cancer Research, 68(15): 6084-6091 (2008).
Subramanian, A., et al., "Gene Set Enrichment Analysis: A Knowledge-BAsed Approach for Interpreting Genome-Wide Expression Profiles", PNAS, 102(43): 15545-15550 (2005).
Telli, M.L and Ford, J.M., "Novel Treatment Approaches for Triple-Negative Breast Cancer", Clinical Breast Cancer, IO (Supp 1): EI6-E22 (2010).
Feschendorff, A.E., et al., "An Immune Response Gene Expression Module Identifies a Good Prognosis Subtype in Estrogen Receptor Negative Breast Cancer", Genome Biology, 8: RI57, 16 pages (2007).
Wang, Y., et al., "Gene-Expression Profiles to Predict Distant Metastasis of Lymph-Node-Negative Primary Breast Cancer", The Lancet, 365: 671-679 (2005).
Wiggans, R.G., et al., "Phase-II Trial OfTamoxifen in Advanced Breast Cancer", Cancer Chemother Pharmacol, 3: 45-48 (1979).
Yang, X.R., et al., "Associations of Breast Cancer Risk Factors With Tumor Subtypes: A Pooled Anaylsis From the Breast Cancer Association Consortium Studies", J National Cancer Institute, 103(3): 250-263 (2011).
Yu, K, et al., "A Precisely Regulated Gene Expression Cassette Potently Modulates Metastasis and Survival in Multiple Solid Cancers", PLOS Genetics, 4(7): eI 000129, 12 pages (2008).
Zhou, X. and Agazie, Y., "Abstract #3388 SHP2 Promotes Breast Cancer Development", Proc. Am Asso Cancer Res; Apr. 18-22, 2009; Denver, CO: AACR; 2009.
Notification of Transmittal of the International Search Report and the Written Opinion of the International Searching Authority for PCT/US2012/065724, Markers of Triple-Negative Breast Cancer and Uses Thereof, dated Feb. 7, 2013. (4783.1000-001).
Notification Concerning Trnnsmittal of International Preliminary Report on Patentability for PCT/US2012/065724, Markers of Triple-Negative Breast Cancer and Uses Thereof, dated May 30, 2004. (4783.1000-001).
Toyama et al. (BMC Cancer Oct. 25, 2008 vol. 8 p. 309).
Enard et al. (Science 2002 vol. 296 p. 340).
Cheung et al. (Nature Genetics 2003 vol. 33 p. 422).
Wu (Journal of pathology 2001 vol. 195 p. 53).
Newton et al. (Journal of Computational Biology 2001 vol. 8 p. 37).
Uhm et al. (Int J Cancer 2009 vol. 124 p. 1457).

* cited by examiner

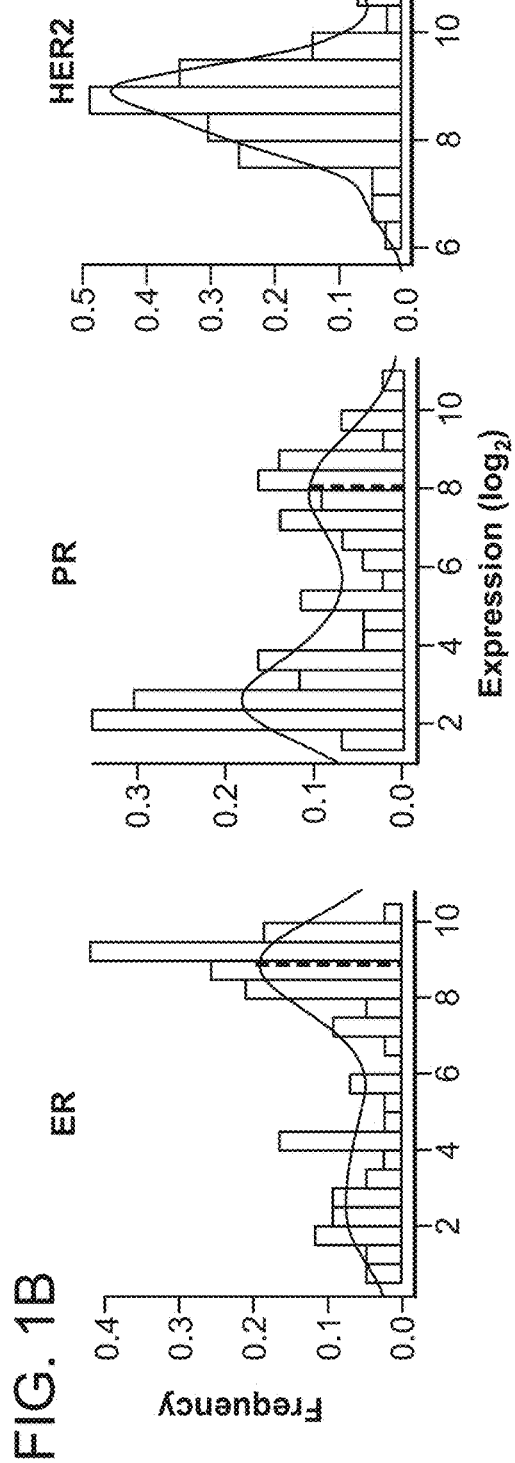
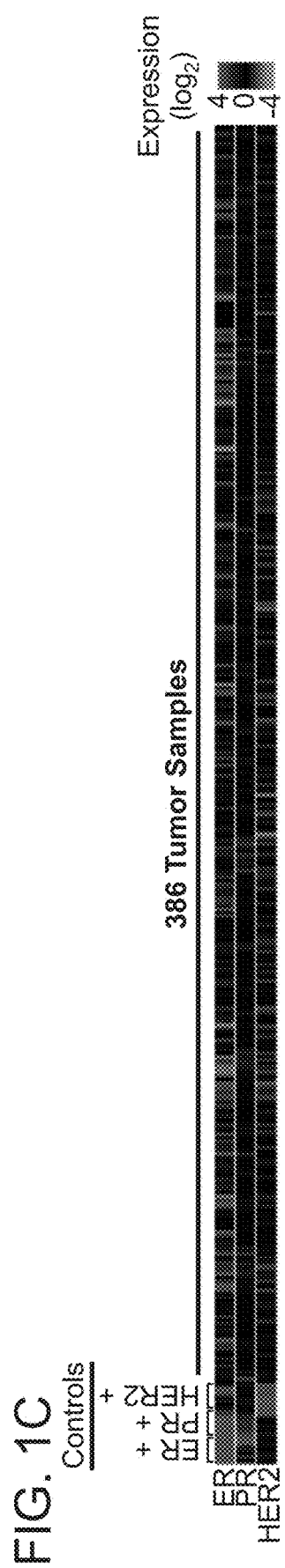
FIG. 1B
FIG. 1C

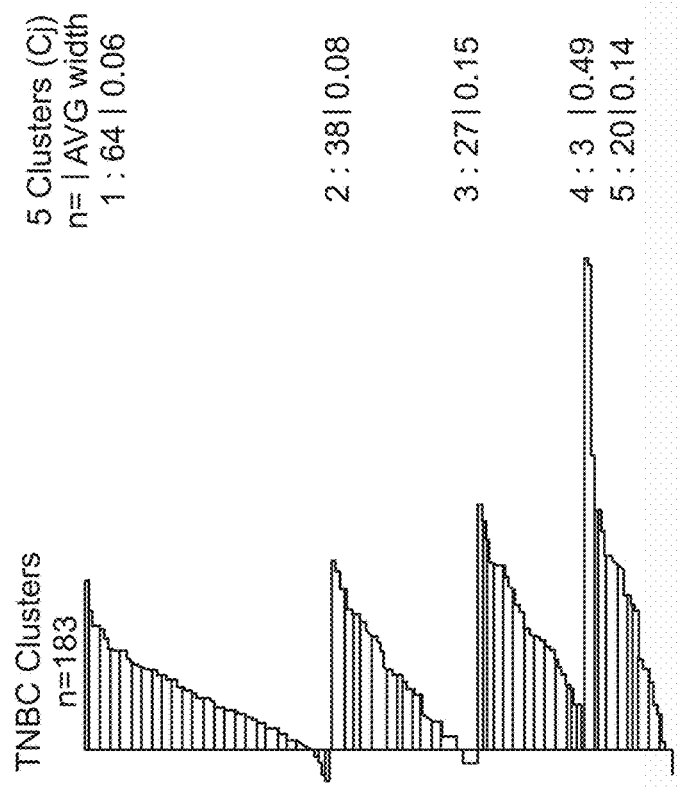
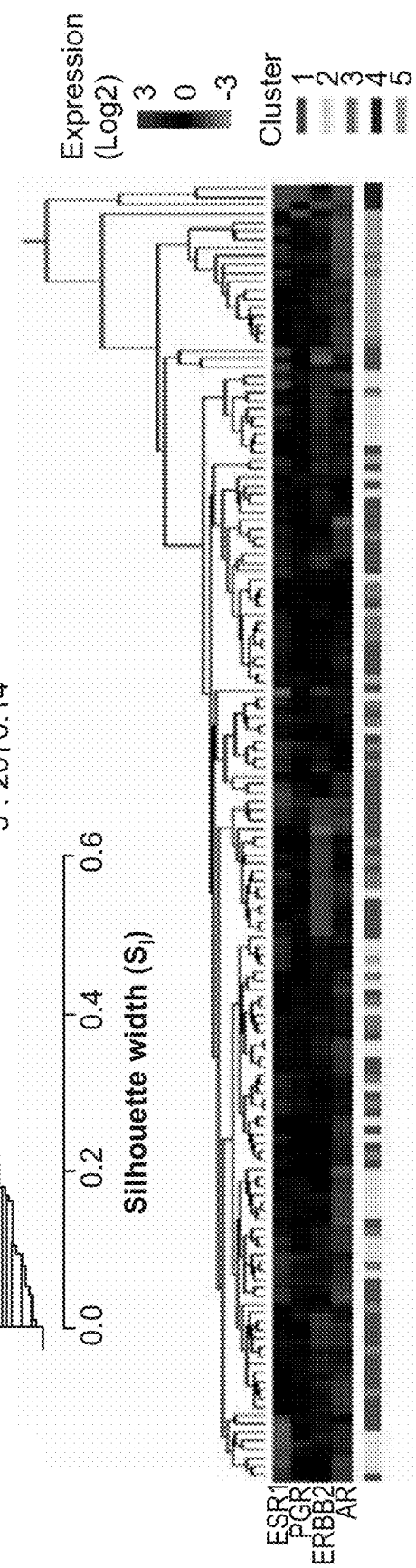

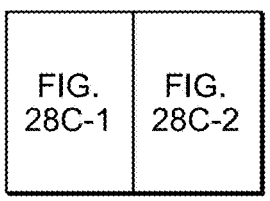
FIG. 28C-1
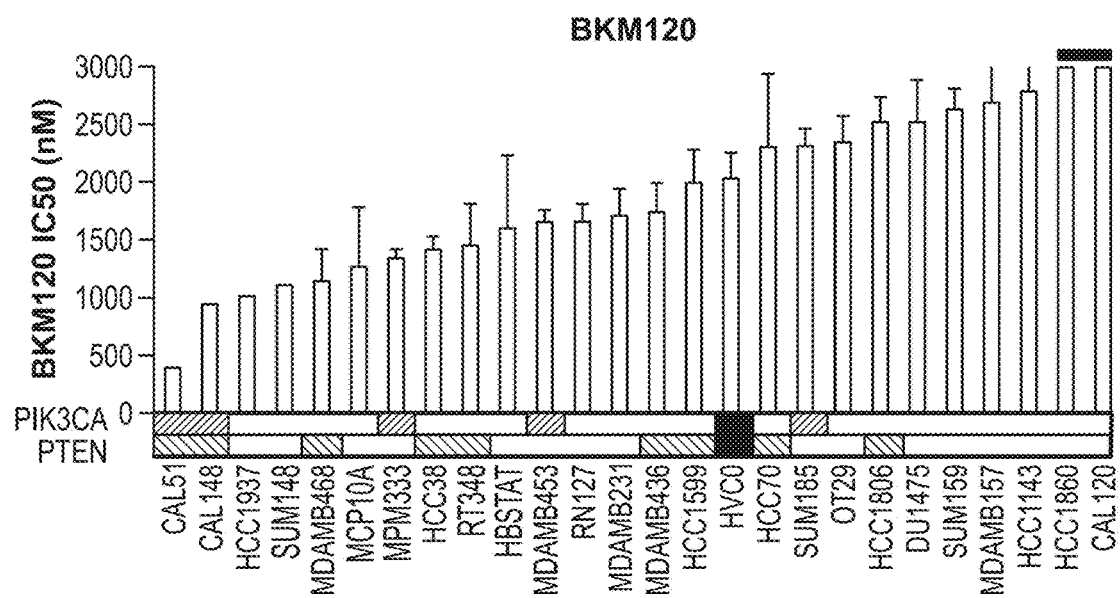
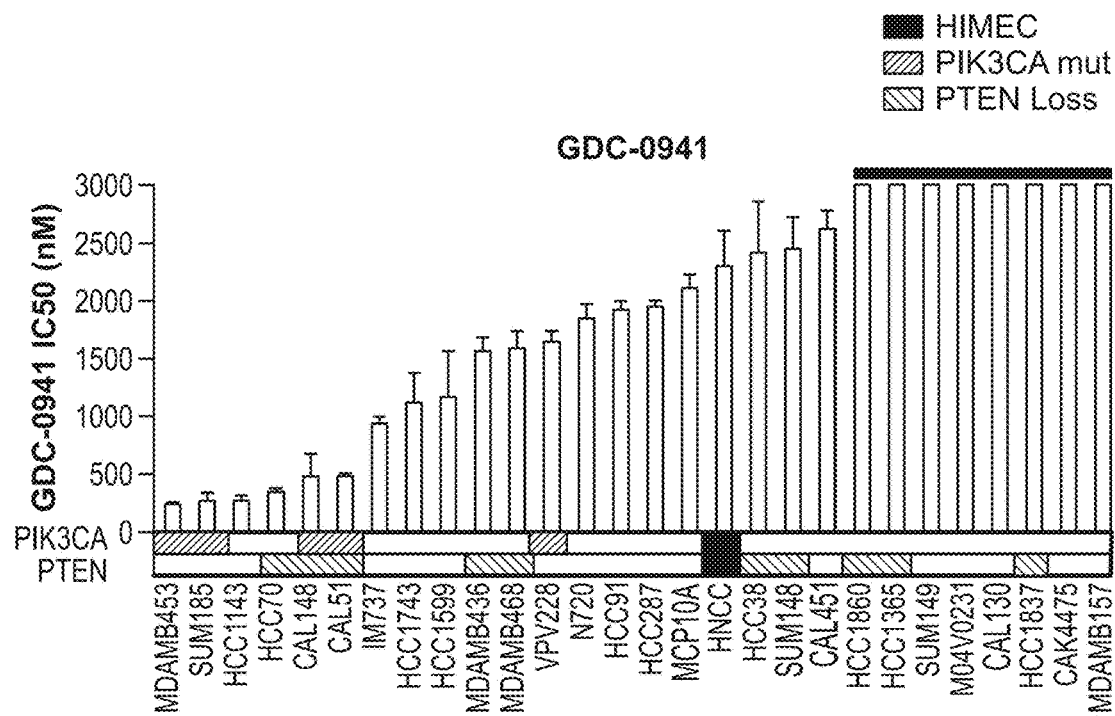
FIG. 28C-1

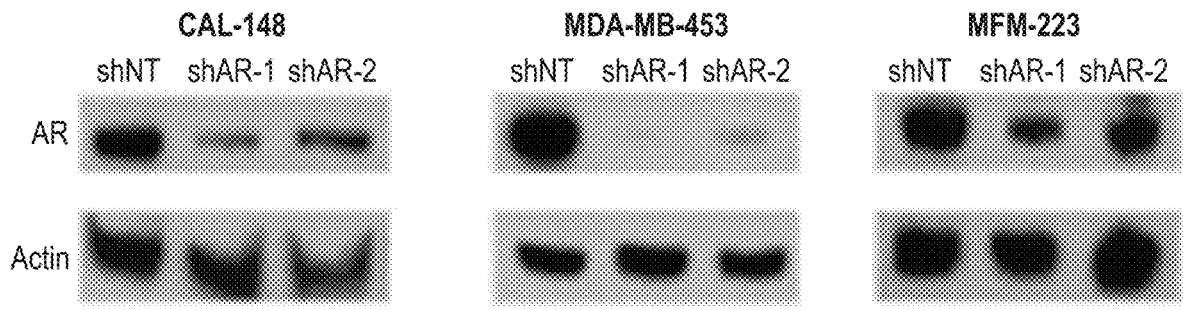
FIG. 29A
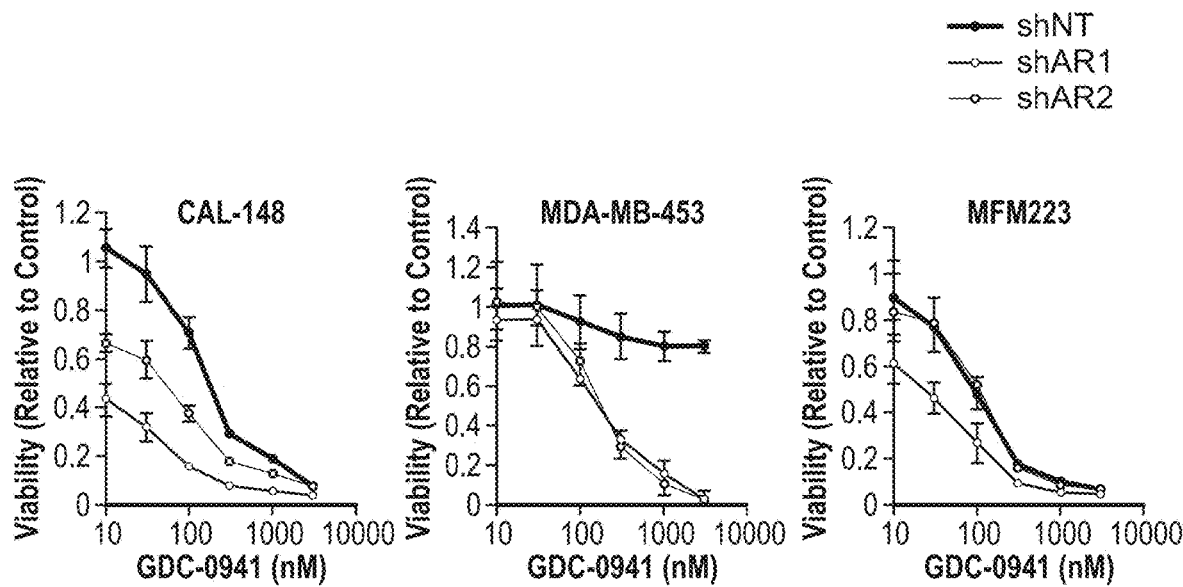
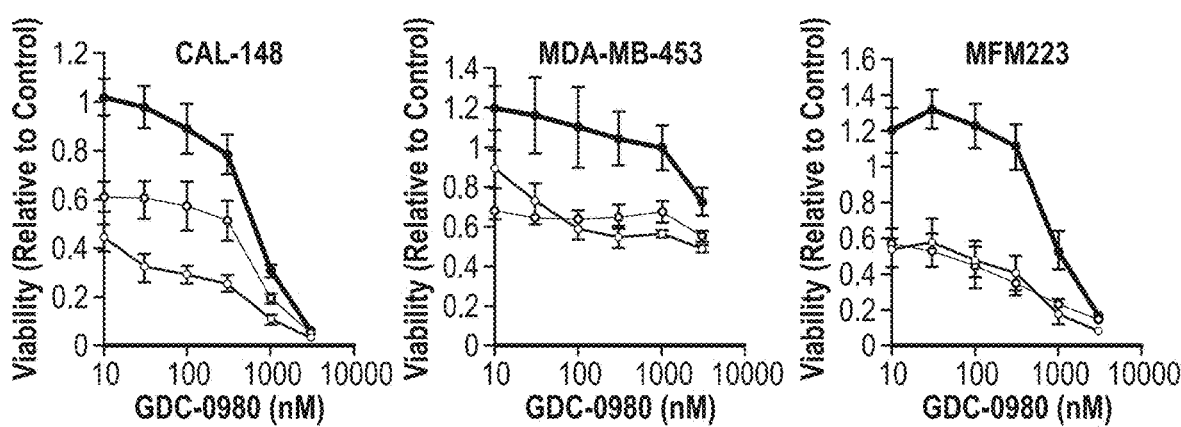
FIG. 29B

SEQUENCE LISTING

```
<160> NUMBER OF SEQ ID NOS: 9

<210> SEQ ID NO 1
<211> LENGTH: 21
<212> TYPE: DNA
<213> ORGANISM: Unknown
<220> FEATURE:
<223> OTHER INFORMATION: Forward primer for amplifying exon 20 of PIK3CA

<400> SEQUENCE: 1
tgacatttga gcaaagacct g                                              21

<210> SEQ ID NO 2
<211> LENGTH: 21
<212> TYPE: DNA
<213> ORGANISM: Unknown
<220> FEATURE:
<223> OTHER INFORMATION: Reverse primer for amplifying exon 20 of PIK3CA

<400> SEQUENCE: 2
cataacatga aattgcgcat t                                              21

<210> SEQ ID NO 3
<211> LENGTH: 21
<212> TYPE: DNA
<213> ORGANISM: Unknown
```

```
<220> FEATURE:
<223> OTHER INFORMATION: Exon forward primer

<400> SEQUENCE: 3
acatcatttg ctccaaactg a                                              21

<210> SEQ ID NO 4
<211> LENGTH: 20
<212> TYPE: DNA
<213> ORGANISM: Unknown
<220> FEATURE:
<223> OTHER INFORMATION: Exon reverse primer

<400> SEQUENCE: 4
cctatgcaat cggtctttgc                                                20

<210> SEQ ID NO 5
<211> LENGTH: 25
<212> TYPE: DNA
<213> ORGANISM: Unknown
<220> FEATURE:
<223> OTHER INFORMATION: Forward primer sequence

<400> SEQUENCE: 5
gataaaactg agcaagaggc tttgg                                          25

<210> SEQ ID NO 6
<211> LENGTH: 26
<212> TYPE: DNA
<213> ORGANISM: Unknown
<220> FEATURE:
<223> OTHER INFORMATION: Reverse primer sequence

<400> SEQUENCE: 6
gctgtttaat tgtgtggaag atccaa                                         26

<210> SEQ ID NO 7
<211> LENGTH: 15
<212> TYPE: DNA
<213> ORGANISM: Unknown
<220> FEATURE:
<223> OTHER INFORMATION: Wild type probe

<400> SEQUENCE: 7
ccaccatgat gtgca                                                     15

<210> SEQ ID NO 8
<211> LENGTH: 15
<212> TYPE: DNA
<213> ORGANISM: Unknown
<220> FEATURE:
<223> OTHER INFORMATION: H1047L probe

<400> SEQUENCE: 8
ccaccatgat gagca                                                     15

<210> SEQ ID NO 9
<211> LENGTH: 15
<212> TYPE: DNA
<213> ORGANISM: Unknown
<220> FEATURE:
<223> OTHER INFORMATION: H1047R probe

<400> SEQUENCE: 9
ccaccatgat gcgca                                                     15
```

MARKERS OF TRIPLE-NEGATIVE BREAST CANCER AND USES THEREOF

RELATED APPLICATION

This application is a continuation of U.S. application Ser. No. 14/358,330, filed May 15, 2014, which is a U.S. National Stage of International Application No. PCT/US2012/065724, filed Nov. 17, 2012, which claims the benefit of U.S. Provisional Application No. 61/561,743, filed on Nov. 18, 2011, the entire disclosures of which are incorporated herein by this reference.

GOVERNMENT SUPPORT

This invention was made with government support under grants CA95131, CA148375; CA105436 and CA070856, CA68485 and CA009385 awarded by the National Institute of Health (NIH). The government has certain rights in the invention.

SEQUENCE LISTING

The instant application contains a Sequence Listing which has been submitted in ASCII format via EFS-Web and is hereby incorporated by reference in its entirety. The ASCII copy of the Sequence Listing, which was created on Jan. 17, 2020, is named 11672N-12047U.txt and is 2 kilobytes in size.

BACKGROUND OF THE INVENTION

Treatment of patients with triple-negative breast cancer (TNBC), lacking estrogen receptor (ER) and progesterone receptor (PR) expression as well as human epidermal growth factor receptor 2 (HER2) amplification, has been challenging due to the heterogeneity of the disease and the absence of well-defined molecular targets (Pegram M D, et al. J Clin Oncol. 1998; 16(8):2659-2671; Wiggans R G, et al. Cancer Chemother Pharmacol. 1979; 3(1):45-48; Carey L A, et al. Clin Cancer Res. 2007; 13(8):2329-2334). TNBCs constitute 10%-20% of all breast cancers, more frequently affect younger patients, and are more prevalent in African-American women (Morris G J, et al. Cancer. 2007; 110(4):876-884). TNBC tumors are generally larger in size, are of higher grade, have lymph node involvement at diagnosis, and are biologically more aggressive (Haffty B G, et al. J Clin Oncol. 2006; 24(36):5652-5657). Despite having higher rates of clinical response to presurgical (neoadjuvant) chemotherapy, TNBC patients have a higher rate of distant recurrence and a poorer prognosis than women with other breast cancer subtypes (Haffty B G, et al. J Clin Oncol. 2006; 24(36):5652-5657; Dent R, et al. Clin Cancer Res. 2007; 13(15 pt 1):4429-4434). Less than 30% of women with metastatic TNBC survive 5 years, and almost all die of their disease despite adjuvant chemotherapy, which is the mainstay of treatment (Dent R, et al. Clin Cancer Res. 2007; 13(15 pt 1):4429-4434).

One of the first molecular insights into TNBCs was the observation that they are likely to arise in BRCA1 mutation carriers and have gene expression (GE) profiles similar to those of BRCA1-deficient tumors (Haffty B G, et al. J Clin Oncol. 2006; 24(36):5652-5657). BRCA1 plays an important role in DNA double-strand break repair, contributing to the maintenance of DNA stability (D'Andrea A D, Grompe M. Nat Rev Cancer. 2003; 3(1):23-34). Poly ADP-ribose polymerase (PARP) enzymes are critical for appropriate processing and repair of DNA breaks (Hoeijmakers J H. Nature. 2001; 411(6835):366-374). Tumor cell lines lacking functional BRCA1 or BRCA2 are sensitive to PARP inhibitors in preclinical studies (Farmer H, et al. Nature. 2005; 434(7035):917-921). Clinical trials using both PARP inhibitors and DNA-damaging agents (e.g., cisplatin) in TNBC are currently underway and show promise in BRCA1/2-mutant tumors (Fong P C, et al. N Engl J Med. 2009; 361(2):123-134). Other studies identifying molecular markers of TNBC, such as VEGF (Burstein H J, et al. J Clin Oncol. 2008; 26(11):1810-1816), EGFR (Nielsen T O, et al. Clin Cancer Res. 2004; 10(16):5367-5374), Src (Finn R S, et al. Breast Cancer Res Treat. 2007; 105(3):319-326), and mTOR (Ellard S L, et al. J Clin Oncol. 2009; 27(27):4536-4541) have been important for the design of clinical trials investigating targeted treatments.

Clearly, there is a major need to better understand the molecular basis of TNBC and to develop effective treatments for this aggressive type of breast cancer.

SUMMARY OF THE INVENTION

In one aspect provided herein are methods of determining a triple negative breast cancer (TNBC) subtype in an individual in need thereof comprising determining expression of one or more genes (e.g., presence of one or more mRNAs and/or protein encoded by gene) in one or more TNBC cells of the individual; and comparing the expression of the one or more genes in the TNBC cells with the expression of the one or more genes in a control. Increased expression of one or more genes comprising one or more cell cycle genes, cell division genes, proliferation genes, DNA damage response genes or a combination thereof in the TNBC cells compared to the control indicates that the TNBC is a TNBC BL1 subtype. Increased expression of one or more growth factor signaling genes, glycolysis genes, gluconeogenesis genes or a combination thereof in the TNBC cells compared to the control indicates that the TNBC is a TNBC BL2 subtype. Increased expression of one or more immune cell signaling genes, cytokine signaling genes, antigen processing and presentation genes, core immune signal transduction genes or a combination thereof in the TNBC cells compared to the control indicates that the TNBC is a TNBC IM subtype. Increased expression of one or more cell motility genes, extracellular matrix (ECM) receptor interaction genes, cell differentiation genes or a combination thereof in the TNBC cells compared to the control indicates that the TNBC is a TNBC M subtype. Increased expression of one or more cell motility genes, cellular differentiation genes, growth pathway genes, growth factor signaling genes, angiogenesis genes, immune signaling genes, stem cell genes, HOX genes, mesenchymal stem cell-specific marker genes or a combination thereof in the TNBC cells compared to the control indicates that the TNBC is a TNBC MSL subtype. Increased expression of one or more hormone regulated genes in the TNBC cells compared to the control indicates that the TNBC is a TNBC LAR type.

In another aspect, the methods are directed to methods of determining a treatment protocol for the triple negative breast cancer (TNBC) patient based on the TNBC subtype.

In another aspect, the methods are directed to predicting whether an individual (e.g., patient) will benefit from a (one or more) treatment for a particular TNBC subtype.

In yet another aspect, the invention is directed to a method of determining whether an agent can be used to treat a triple negative breast cancer (TNBC) subtype comprising contacting a cell line that is a model for the TNBC subtype of interest with an agent to be assessed; and determining viability of the cell line in the presence of the agent, wherein if the viability of the cell line decreases in the presence of the agent, then the agent can be used to treat the TNBC subtype of interest. The TNBC subtype of interest can be a TNBC BL-1 subtype, a TNBC BL-2 subtype, a TNBC IM subtype, a TNBC M subtype, a TNBC MSL subtype or a TNBC LAR subtype.

BRIEF DESCRIPTION OF THE DRAWINGS

FIGS. 1A-1C: Filtering GE data sets to identify TNBCs. (1A) Flow chart of analysis. Human breast cancer GE profiles (training=2353, validation=894) were normalized within individual data sets and a bimodal filter was applied to select ER, PR, and HER2 negative samples by GE, resulting in 386 samples in the training set and 201 samples in the validation set with a triple-negative phenotype. k-means clustering was performed on the training set, and a GE signature representing the TNBC subtypes from the training set was used to predict the best-fit subtype for each TNBC profile in an independent validation set. GSE-A was performed on the training and validation sets to identify enriched canonical pathways for each TNBC subtype. (1B) Histograms show the distribution and frequency of tumors using relative ER, PR, and HER2 GE levels (log 2) and bimodal fit to identify TN tumor samples. Dashed line indicates the expression value at the center of the positive expression peak used to select controls for C. (1C) Heat map representation of GE for 386 TNBCs relative to 5 IHC-validated controls for each ER, PR, and HER2.

FIGS. 11A-11B: TNBC subtypes identified by IHC. (11A) Silhouette plot showing the composition (n=number of tumors) and stability (AVG width) of k-means clustering on the TNBC training sel. Clusters with a silhouette width, s(i)>O were considered stable. (11B) Heatmap displays hierarchical clustering of ERBB2, PGR, ESR1 and AR expression in the tumors identified by IHC. Color bar identifies the cluster associated with each tumor.

FIGS. 29A-29B: Genetic targeting of AR increases the efficacy of the PI3K inhibitor GDC-0941 and PI3K/mTOR inhibitor GDC-0980. (29A) Immunoblot displays decreased AR expression at 72 h following infection with two shRNAs targeting AR (shAR1 and shAR2) compared to infection with nontargeting shRNA (shNT) in three AR-positive TNBC cell lines. Actin levels below serve as loading controls. (29B) Line graphs display relative viability of LAR cell lines infected with nontargeting (shNT) or shRNAs targeting AR (shAR1 and shAR2) following a 72 h treatment with the pan-PI3K inhibitor GDC-0941 (top) or the dual PI3K/mTOR inhibitor GDC-0980.

Colorbar below designates the TNBC subtype (basal-like=black, mesenchymal-like=grey) or normal cells (white).

Figure 40:
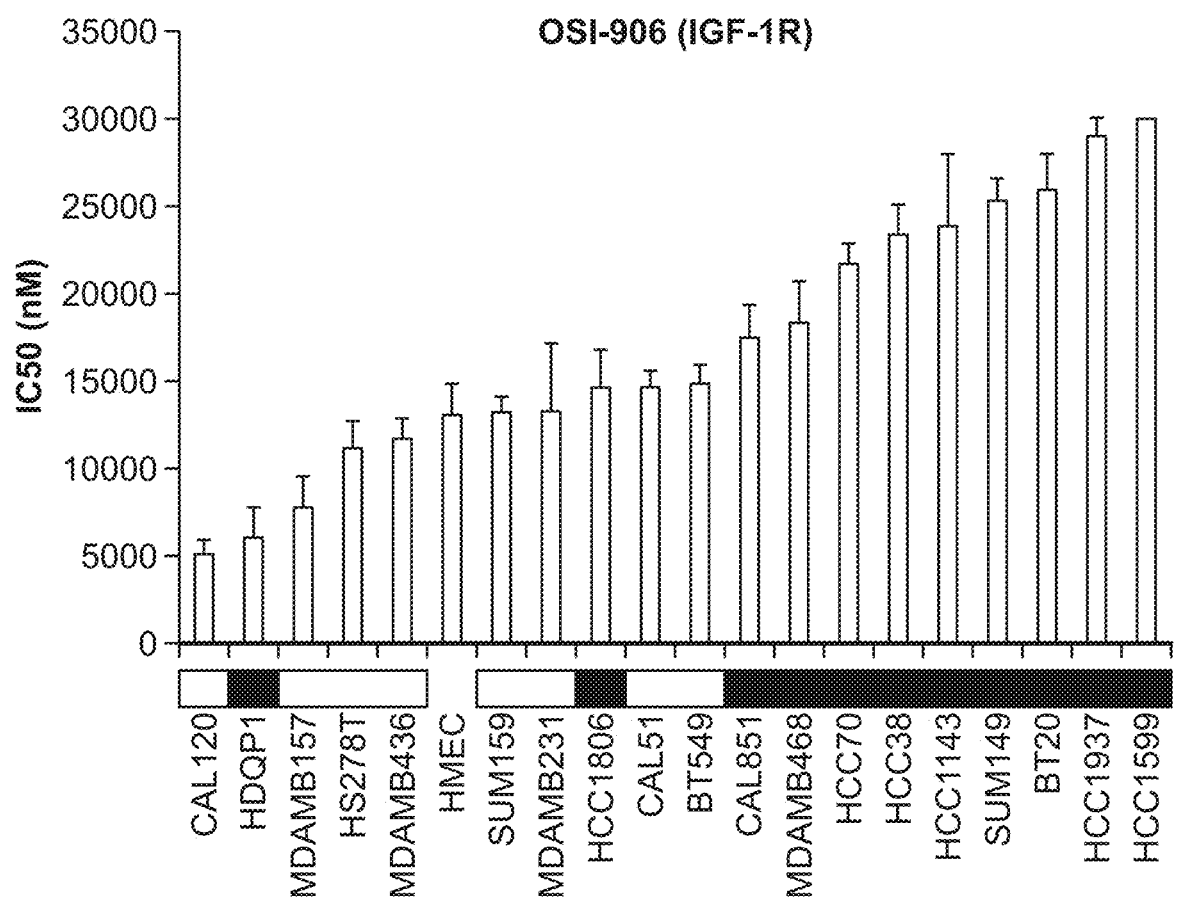

FIG. 40: IGF1R inhibition selectively inhibits viability of mesenchymal-like TNBC cell lines. Bar graph displays the half-maximal inhibitory concentration (nM) of the IGF1R inhibitor OSI-906 for a panel of TNBC cell lines. Colorbar below designates the TNBC subtype (basal-like=black, mesenchymal-like=grey) or normal cells (white).

Figure 41:
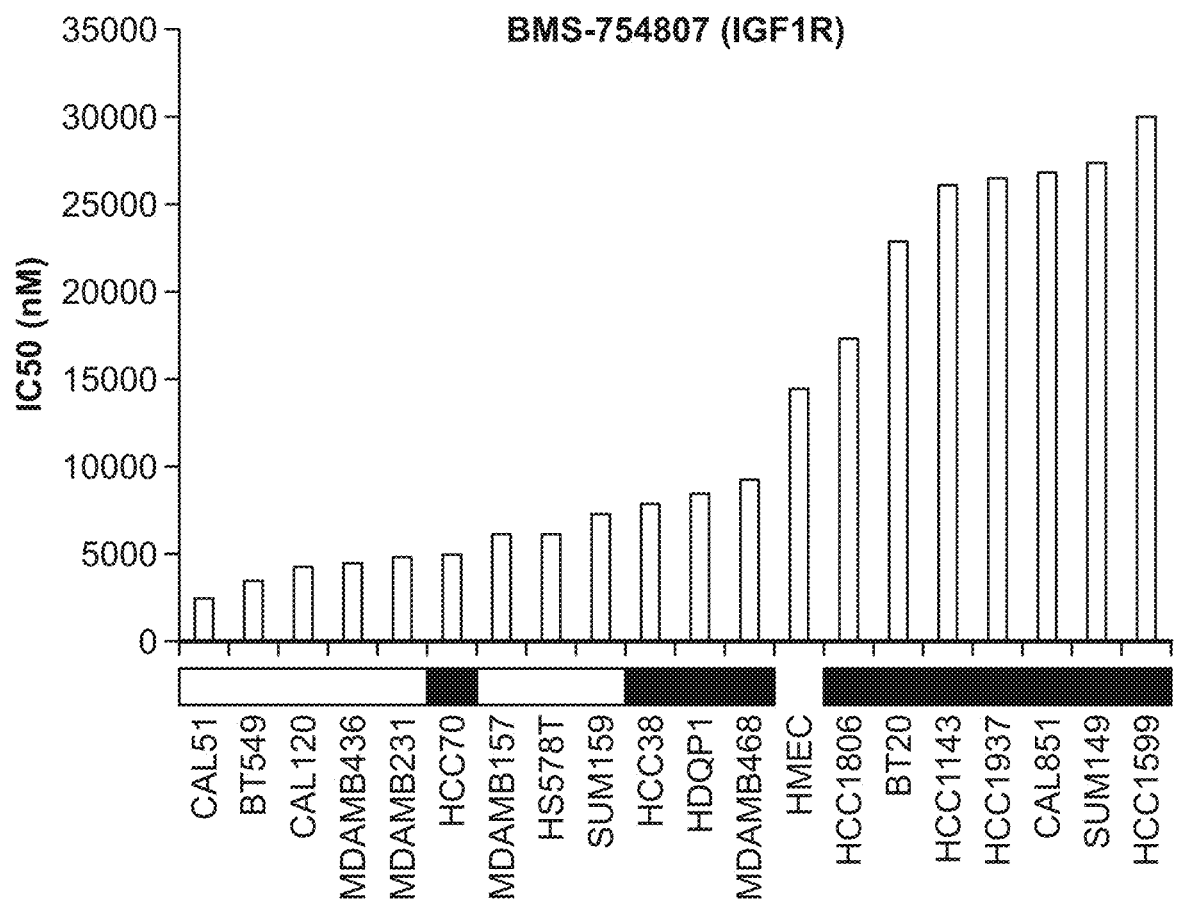

FIG. 41: IGF1R inhibition selectively inhibits viability of mesenchymal-like TNBC cell lines. Bar graph displays the half-maximal inhibitory concentration (nM) of the IGF1R inhibitor BMS-754807 for a panel of TNBC cell lines. Colorbar below designates the TNBC subtype (basal-like=black, mesenchymal-like=grey) or normal cells (white).

Figure 42:
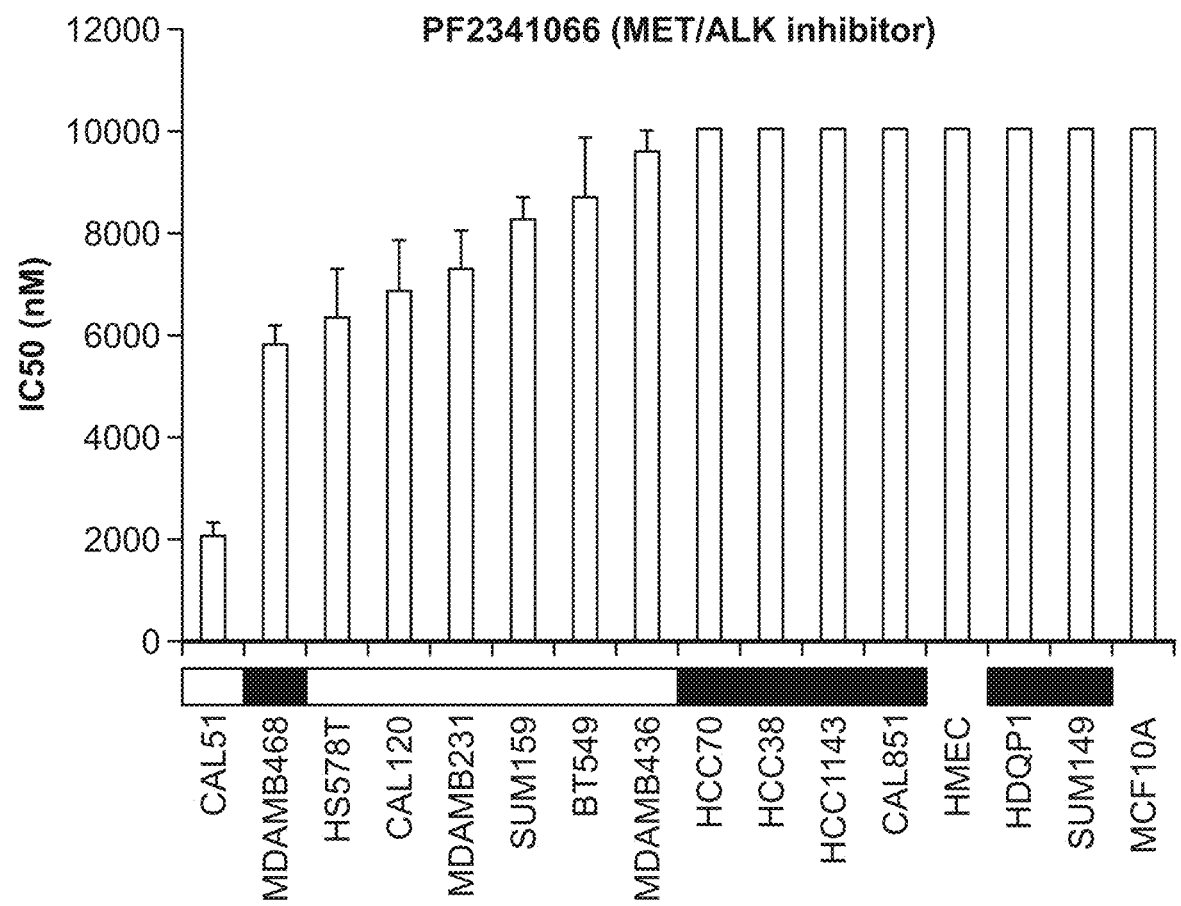

FIG. 42: MET inhibition selectively inhibits viability of mesenchymal-like TNBC cell lines. Bar graph displays the half-maximal inhibitory concentration (nM) of the MET inhibitor PF2341066 for a panel of TNBC cell lines. Colorbar below designates the TNBC subtype (basal-like=black, mesenchymal-like=grey) or normal cells (white).

DETAILED DESCRIPTION OF THE INVENTION

Triple-negative breast cancer (TNBC) is a highly diverse group of cancers, and subtyping is necessary to better identify molecular-based therapies. In this study, gene expression (GE) profiles from 21 breast cancer data sets were analyzed and 587 TNBC cases were identified. Cluster analysis identified 6 TNBC subtypes displaying unique GE and ontologies, including 2 basal-like (BL1 and BL2), an immunomodulatory (IM), a mesenchymal (M), a mesenchymal stem-like (MSL), and a luminal androgen receptor (LAR) subtype. Further, GE analysis allowed identification of TNBC cell line models representative of these subtypes. Predicted "driver" signaling pathways were pharmacologically targeted in these cell line models as proof of concept that analysis of distinct GE signatures can inform therapy selection. BL1 and BL2 subtypes had higher expression of cell cycle and DNA damage response genes, and representative cell lines preferentially responded to cisplatin. M and MSL subtypes were enriched in GE for epithelial-mesenchymal transition, and growth factor pathways and cell models responded to NVP-BEZ235 (a PI3K/mTOR inhibitor) and dasatinib (an abl/src inhibitor). The LAR subtype includes patients with decreased relapse-free survival and was characterized by androgen receptor (AR) signaling. LAR cell lines were uniquely sensitive to bicalutamide (an AR antagonist). These data provide biomarker selection, drug discovery, and clinical trial design that align TNBC patients to appropriate targeted therapies.

An extensive number of TNBC GE profiles was compiled with the intent of molecularly subtyping the disease. Six (6) TNBC subtypes were identified. Further, using GE signatures derived from each TNBC subtype, representative TNBC cell lines that serve as models for the different subtypes of the disease were aligned. Using the panel of cell lines, prominent signaling pathways revealed by GE signatures were pharmacologically targeted and it was found that the cell lines representing the various subtypes had different sensitivities to targeted therapies currently under laboratory and clinical investigation. The identification of diverse TNBC subtypes and the molecular drivers in corresponding cell line models provides great insight to the heterogeneity of this disease and provides preclinical platforms for the development of effective treatment (see Lehmann, B. D., et al., *J Clin Invest*, 121(7): 2750-2767 (July 2011), the entire teachings of which are incorporated herein by reference).

Also described herein is further investigation of a panel of AR-positive TNBC tumors which showed that PIK3CA kinase mutations are a frequent event in the LAR subtype (65.3% vs. 38.4%) and were not just selected for in vitro during establishment of the tumor-derived cell lines. Also shown herein is that PI3K pathway activation plays a role in resistance to AR antagonists, as there are elevated levels of activated AKT in residual tumors after bicalutamide treatment of xenograft tumors. Further, it was found that genetic or pharmacological targeting of AR synergizes with PI3K/mTOR inhibition in both two- and three-dimensional cell culture models. Based on the cell culture-based results, the combination of these inhibitors in in vivo xenograft studies was examined using bicalutamide +/−GDC0980 or NVP-BEZ235. The preclinical data herein provide the rationale for pre-selecting AR-positive TNBC patients for treatment with the combination of AR antagonists and/or PI3K/mTOR inhibitors.

As discussed herein, triple negative breast cancer (TNBC) refers to breast cancers that are estrogen receptor (ER) negative, progesterone receptor (PR) negative and human epidermal growth factor receptor 2 (HER-2) negative. The invention is based, in part, of the discovery of six TNBC subtypes.

Accordingly, in one aspect provided herein are methods of determining a triple negative breast cancer (TNBC) subtype in an individual in need thereof comprising determining expression of one or more genes (e.g., presence of one or more mRNAs and/or protein encoded by gene) in one or more TNBC cells of the individual; and comparing the expression of the one or more genes in the TNBC cells with the expression of the one or more genes in a control. Increased expression of one or more genes comprising one or more cell cycle genes, cell division genes, proliferation genes, DNA damage response genes or a combination thereof in the TNBC cells compared to the control indicates that the TNBC is a TNBC BL1 subtype. Increased expression of one or more growth factor signaling genes, glycolysis genes, gluconeogenesis genes or a combination thereof in the TNBC cells compared to the control indicates that the TNBC is a TNBC BL2 subtype. Increased expression of one or more immune cell signaling genes, cytokine signaling genes, antigen processing and presentation genes, core immune signal transduction genes or a combination thereof in the TNBC cells compared to the control indicates that the TNBC is a TNBC IM subtype. Increased expression of one or more cell motility genes, extracellular matrix (ECM) receptor interaction genes, cell differentiation genes or a combination thereof in the TNBC cells compared to the control indicates that the TNBC is a TNBC M subtype. Increased expression of one or more cell motility genes, cellular differentiation genes, growth pathway genes, growth factor signaling genes, angiogenesis genes, immune signaling genes, stem cell genes, HOX genes, mesenchymal stem cell-specific marker genes or a combination thereof in the TNBC cells compared to the control indicates that the TNBC is a TNBC MSL subtype. Increased expression of one or more hormone regulated genes in the TNBC cells compared to the control indicates that the TNBC is a TNBC LAR type.

In a particular aspect, the invention is directed to a method of determining a TNBC BL1 subtype in an individual in need thereof comprising determining increased expression of one or more cell cycle genes, cell division genes, proliferation genes, DNA damage response genes or a combination thereof in the TNBC cells of the individual compared to the control. Increased expression of the one or more genes indicates that the TNBC is a BL1 subtype TNBC. In one aspect, the method of determining a TNBC BL1 subtype in an individual in need thereof comprises selectively detecting increased expression of a gene combination comprising AURKA, AURKB, CENPA, CENPF, BUB1, BUB1B, TTK, CCNA2, PLK1, PRC1, MYC, NRAS, PLK1, BIRC5, CHEK1, FANCA, FANCG, FOXM1, HNGA1, RAD54BP, RAD51, NEKS, NBN, EXO1, MSH2, MCM10, RAD21, SIX3, Z1C1, SOX4, SOX1 and MDC1 wherein detection of increased expression of the gene combination indicates that the TNBC is TNBC BL1 subtype. Determination that the TNBC is a TNBC BL1 subtype can further comprise detecting increased expression of Ki-67 mRNA in the TNBC cells compared to the control. In addition, determination that the TNBC is a TNBC BL1 subtype can further comprise detecting one or more mutated genes. Examples of such mutated genes include mutated BRCA1, STAT4, UTX, BRCA2, TP53, CTNND1, TOP2B, CAMK1G, MAPK13, MDC1, PTEN, RB1, SMAD4, CDKN2A, ATM, ATR, CLSPN, HDAC4, NOTCH1, SMARCAL1, and TIMELESS.

In another aspect, the invention is directed to a method of determining a TNBC BL2 subtype in an individual in need thereof comprising determining increased expression of one or more growth factor signaling genes, glycolysis genes, gluconeogenesis genes or a combination thereof in the TNBC cells compared to the control. Increased expression of the one or more genes indicates that the TNBC is a TNBC BL2 subtype. In one aspect, the method of determining a TNBC BL subtype in an individual in need thereof comprises selectively detecting increased expression of a gene combination comprising EGFR, MET, ELF4, MAF, NUAK1, JAG1, FOSL2, 1D1, ZIC1, SOX11, 1D3, FHL2, EPHA2, TP63 and MME wherein detection of increased expression of the gene combination indicates that the TNBC is TNBC BL2 subtype. Determination that the TNBC is a TNBC BL2 subtype can further comprise detecting one or more mutated genes. Examples of such genes comprise mutated BRCA1, RB1, TP53, PTEN, CDKN2A, UTX, BRAC2, PTCH1, PTCH2, and RET.

In another aspect, the invention is directed to a method of determining a TNBC M subtype in an individual in need thereof comprising determining increased expression of one or more cell motility genes, extracellular matrix (ECM) receptor interaction genes, cell differentiation genes or a combination thereof in the TNBC cells compared to the control. Increased expression of the one or more genes indicates that the TNBC is a TNBC M subtype. In one aspect, the method of determining a TNBC M subtype in an individual in need thereof comprises selectively detecting increased expression of a gene combination comprising TGFB1L1, BGN, SMAD6, SMAD7, NOTCH1, TGFB1, TGFB2, TGFB3, TGFBR1, TGFBR2, TGFBR3, MMP2, ACTA2, SNAI2, SPARC, SMAD7, PDGFRA, TAGLN, TCF4, TWIST1, ZEB1, COL3A1, JAG1, EN1, MYLK, STK38L, CDH11, ETV5, IGF1R, FGFR1, FGFR2, FGFR3, TBX3, COL5A2, GNG11, ZEB2, CTNNB1, DKK2, DKK3, SFPR4, TCF4, TCF7L2, FZD4, CAV1, CAV2, CCND1 and CCND2 wherein detection of increased expression of the gene combination indicates that the TNBC is TNBC M subtype. Determination that the TNBC is a TNBC M subtype can further comprise detecting decreased E-cadherin (CDH1) expression compared to the control. Determination that the TNBC is a TNBC M subtype can further comprise detecting one or more mutated genes. Examples of such mutated genes include mutated PTEN, RB1, TP53, PIK3CA, APC, BRAF, CTNNB1, FGFR1, GLI1, HRAS, KRAS, NOTCH1, and NOTCH4. Determination that the TNBC is a TNBC M subtype can further comprise detecting chromosomal amplifications in KRAS, IGF1R or MET.

In another aspect, the invention is directed to a method of determining a TNBC MSL subtype in an individual in need thereof comprising determining increased expression of one or more cell motility genes, cellular differentiation genes, growth pathway genes, growth factor signaling genes, angiogenesis genes, immune signaling genes, stem cell genes, HOX genes, mesenchymal stem cell-specific marker genes or a combination thereof in the TNBC cells compared to the control. Increased expression of the one or more genes indicates that the TNBC is a TNBC MSL subtype. In one aspect, the method of determining a TNBC MSL subtype in an individual in need thereof comprises selectively detecting increased expression of a gene combination comprising VEGFR2 (KDR), TEK, TIE1, EPAS1, ABCA8, PROCR, ENG, ALDHA1, PER1, ABCB1, TERF2IP, BCL2, BMP2, EPAS1, STAT4, PPARG, JAK1, ID1, SMAD3, TWIST1, THY1, HOXA5, HOXA10, GL13, HHEX, ZFHX4, HMBOX1, FOS, PIK3R1, MAF, MAFB, RPS6KA2, TCF4, TGFB1L1, MEIS1, MEIS2, MEOX1, MEOX2, MSX1, ITGAV, KDR, NGFR, NTSE, PDGFRA, PDGFRB, POU2F1, and VCAM1 wherein detection of increased expression of the gene combination indicates that the TNBC is TNBC MSL subtype. Determination that the TNBC is a TNBC MSL subtype can further comprise detecting low expression of claudins 3, 4, 7 or a combination thereof compared to the control. Determination that the TNBC is a MSL subtype TNBC can further comprise detecting one or more mutated genes. Examples of such mutated genes include mutated CDKN2A, HRAS, TP53, NF1, PIK3CA, BRCA1, BRAF, KRAS, NF2, PDGFRA, APC, CTNNB1, FGFR1, PDGFRB.

In another aspect, the invention is directed to a method of determining a TNBC IM subtype in an individual in need thereof comprising determining increased expression of one or more immune cell signaling genes, cytokine signaling genes, antigen processing and presentation genes, core immune signal transduction genes or a combination thereof in the TNBC cells compared to the control. Increased expression of the one or more genes indicates that the TNBC is a TNBC IM subtype. In one aspect, the method of determining a TNBC IM subtype in an individual in need thereof comprises selectively detecting increased expression of a gene combination comprising CCL19, CCL3, CCL4, CCL5, CCL8, CCR1, CCR2, CCR5, CCR7, CD2, CD37, CD38, CD3D, CD48, CD52, CD69, CD74, and CD8A wherein detection of increased expression of the gene combination indicates that the TNBC is TNBC IM subtype. Determination that the TNBC is a TNBC IM subtype can further comprise detecting one or more mutated genes. Examples of such mutated genes include TP53, CTNNA1, DDX18, HUWE1, NFKBIA, APC, BRAF, MAP2K4, RB1, STAT4, STAT1, and RET.

In another aspect, the invention is directed to a method of determining a TNBC LAR subtype in an individual in need thereof comprising determining increased expression of one or more hormone regulated genes in the TNBC cells compared to the control. Increased expression of the one or more genes indicates that the TNBC is a TNBC LAR type. In one aspect, the method of determining a TNBC LAR subtype in an individual in need thereof comprises selectively detecting increased expression of a gene combination comprising AR, DHCR24, ALCAM, GATA2, GATA3, IDIH1, IDIH2, CDH11, ERBB3, CUX2, FGFR4, HOPX, FASN, FKBP5, APOD, PIP, SPDEF, CLDN8, FOXA1, KRT18, and XBP1 wherein detection of increased expression of the gene combination indicates that the TNBC is TNBC LAR subtype. Determination that the TNBC is a LAR subtype TNBC can further comprise detecting one or more mutated genes. Examples of such mutated genes include PIK3CA, CDH1, PTEN, RB1, TP53, and MAP3K1.

A variety of methods (e.g. spectroscopy, colorometry, electrophoresis, chromatography) can be used to detect increased expression of a (one or more) gene. As is apparent to those of skill in the art, increased expression of one or more genes can be detected by measuring all or a portion of nucleic acid (e.g., DNA, mRNA) of the gene and/or protein (polypeptide) expressed by the gene. The level, expression and/or activity of a gene and or its encoded polypeptide can be measured. For example, nucleic acid such as genes, mRNA or a combination thereof, can be determined using PCR (e.g., RT-PCR, RT-qPCR), gene chips or microarray analysis (DNA arrays, gene expression arrays, nanostrings), next generation sequencing (e.g., next generation RNA sequencing), in situ hybridization, blotting techniques, and the like. Protein can be detected using immunoassays (e.g., immunohistochemistry, immunofluorescence, immunoprecipitation), arrays (e.g., reverse phase protein microarrays), blotting techniques (e.g., Western blots), SDS-PAGE, and the like As described herein, the methods can further comprise detecting one or more mutated genes. A variety of methods can be used to detect one or more mutated genes. Examples of such methods include a SNaPshot assay, exome sequencing, Sanger gene sequencing, resequencing array analysis, mRNA analysis/cDNA sequencing polymerase chain reaction (PCR), single-strand conformation polymorphism (sscp), heteroduplex analysis (het), allele-specific oligonucleotide (aso), restriction fragment analysis, allele-specific amplification (asa), single nucleotide primer extension, oligonucleotide ligation assay (ola), denaturing gradient gel electrophoresis (DGGE), temperature gradient gel electrophoresis (TGGE) and single strand conformation polymorphism (SSCP).

The methods can further comprise comparing the expression of the one or more genes in the individual to the expression of the one or more genes in a control. As will be apparent to those of skill in the art, a variety of suitable controls can be used. Examples of such controls include one or more non-cancer cells (e.g., breast cells from one or more individuals that do not have cancer) and/or non-TNBC cells (e.g., from the individual being tested). The control can also be a (one or more) standard or reference control established by assaying one or more (e.g., a large sample of) individuals which do not have cancer (e.g., TNBC) and using a statistical model to obtain a control value (standard value; known standard). See, for example, models described in Knapp, R. G. and Miller M. C. (1992) *Clinical Epidemiology and Biostatistics*, William and Wilkins, Harual Publishing Co. Malvern, PA, which is incorporated herein by reference.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one aspect, an individual in need thereof is a mammal, such as a human. In other aspects, the individual has been diagnosed with breast cancer, the individual has not been diagnosed with breast cancer, or the individual is at risk of developing breast cancer.

The methods of the invention can further comprise detecting expression (increased expression) of one or more genes in a sample (biological sample) of the individual. Thus, the method can further comprise obtaining a (one or more) sample from the individual. The sample can be, for example, a biological fluid, a biological tissue (e.g., a biopsy) and combinations thereof from the individual. In particular aspects, the sample is one or more TNBC cells (e.g., epithelial cells, mesenchymal cells, immune cells). Methods for obtaining such biological samples from an individual are known to those of skill in the art.

As also shown herein, the methods can further comprise determining a treatment protocol for the triple negative breast cancer (TNBC) patient based on the TNBC subtype. As described herein, a "cancer therapy", "treatment for cancer" or "cancer treatment" comprises administering one or more agents to the individual. In one embodiment, the agent is a chemotherapeutic agent which targets the TNBC cells. Examples of such agents include an alkylating agent (e.g., busulfan, cisplatin, carboplatin, chlorambucil, cyclophosphamide, ifosfamide, dacarbazine (DTIC), mechlorethamine (nitrogen mustard), melphalan, temozolomide); a nitrosoureas (e.g., carmustine (BCNU), lomustine (CCNU)); an antimetabolite (e.g., 5-fluorouracil, capecitabine, 6-mercaptopurine, methotrexate, gemcitabine, cytarabine (ara-C), fludarabine, pemetrexed); an anthracycline or related drug (e.g., daunorubicin, doxorubicin (adriamycin), epirubicin, idarubicin, mitoxatrone); a topoisomerase (topoisomerase I inhibitor; topoisomerase inhibitor II) inhibitor (e.g., topotecan, irinotecan, etoposide (VP-16), teniposide); and a mitotic inhibitor (e.g., taxanes (paclitaxel, docetaxel, taxol) vinca alkaloids (vinblastine, vincristine, vinorelbine).

In another embodiment, the agent is a targeted therapy agent which attacks cancer cells more specifically than chemotherapeutic agents. Examples of such agents include imatinib (Gleevec), gefitinib (Iressa), erlotinib (Tarceva), rituximab (Rittman), and bevacizumab (Avastin). In yet another embodiment, the agent is a sex hormone, or hormone-like drug that alters the action or production of female or male hormones and can be used to slow the growth of breast, prostate, and endometrial (uterine) cancers. Examples of such agents include anti-estrogens (e.g., tamoxifen, fulvestrant), aromatase inhibitors (e.g., anastrozole, exemestane, letrozole), progestins (e.g., megestrol acetate), anti-androgens (e.g., bicalutamide, flutamide) and LHRH agonists (leuprolide, goserelin). In addition, the agent can be a drug which is used to stimulate the immune system to more effectively recognize and attack cancer cells of an individual with cancer. Other examples of agents include a hormone such as a selective estrogen receptor modulator (SERM); an antibody or antigen binding fragment thereof (e.g., herceptin); a protein tyrosine kinase inhibitor; a combination of chemotherapeutic agents such as cytoxan (C), methotrexate (M), fluorouracil (F), an anthracylcin such as adriamycin (A), epirubicin (E), doxorubicin, and/or daunorubicin; a targeted kinase inhibitor; a metalloproteinase inhibitor; and a proteosome inhibitor.

The one or more agents can be administered to the individual before (e.g., neoadjuvant therapy), during or after (e.g., adjuvant therapy) primary treatment of the cancer. As used herein "primary treatment of a cancer" generally refers to a treatment involving surgery (e.g., surgical removal of a tumor) and/or radiation (e.g., local radiation). In the methods of the present invention, the "treatment for cancer" can be a neoadjuvant treatment wherein an agent (e.g., a hormone, a chemotherapeutic) is administered prior to surgical removal of a (residual) tumor, or prior to localized radiation (e.g., radiation used to shrink the tumor in order to simplify subsequent surgical removal of the tumor). In another embodiment, the "treatment for cancer" can be an adjuvant treatment wherein an agent (e.g., a hormone, a chemotherapeutic agent) is administered after surgical removal of a (residual) tumor, or after localized radiation. In yet another embodiment, the treatment can be a palliative treatment in which one or more chemotherapeutic agents are administered to an individual to treat metastatic cancer (e.g., to make the individual more comfortable and/or to prolong survival of the individual after the cancer has metastasized).

In particular aspects, the TNBC BL1 or BL2 subtype is detected in the individual and the individual is treated with one or more drugs that damages DNA. Examples of such drugs include an alkylating-like agent (e.g., cisplatin) and a PARP inhibitor (e.g., veliparib, olaparib).

In another aspect, the TNBC ML subtype is detected in the individual and the individual is treated with one or more drugs that inhibits Src (e.g., disatinib), IGF1R (e.g., OSI-906, BMS-754807), MET (e.g., PF2341066), PDGFR (e.g., sorafinib), P13K (e.g., BKM-120, GDC0941), P13K/mTOR (e.g., NVP-BEZ235, GDC0980) or a combination thereof.

In another aspect, the TNBC LAR subtype is detected in the individual and the individual is treated with one or more drugs that inhibit androgen receptor (AR). Examples of such drugs include bicalutamide, MVD3100, and abiraterone. The method can further comprise treating the individual with P13K/mTOR (e.g., NVP-BEZ235, GDC0980) or a combination thereof. The method can further comprise treating the individual with an inhibitor of HSP90 (e.g., DMAG).

In other aspects, the invention can further comprise predicting whether an individual (e.g., patient) will benefit from a (one or more) treatment for a particular TNBC subtype.

Also described herein are TNBC cell lines that serve as models for each of the six TNBC subtypes. Thus, in another aspect, the invention is directed to a method of determining whether an agent can be used to treat a triple negative breast cancer (TNBC) subtype comprising contacting a cell line that is a model for the TNBC subtype of interest with an agent to be assessed; and determining viability of the cell line in the presence of the agent, wherein if the viability of the cell line decreases in the presence of the agent, then the agent can be used to treat the TNBC subtype of interest. The TNBC subtype of interest can be a TNBC BL-1 subtype, a TNBC BL-2 subtype, a TNBC IM subtype, a TNBC M subtype, a TNBC MSL subtype or a TNBC LAR subtype. In addition, as will be apparent to those of skill in the art, the viability of a cell decreases when e.g., the cell undergoes apoptosis, proliferation of the cell is inhibited or slowed and/or metastasis of the cell is inhibited to slowed.

Examples of agents (test agent; agent of interest) include nucleic acids, polypeptides, fusion proteins, peptidomimetics, prodrugs, drugs, receptors, binding agents (e.g., antibodies), small molecules, etc and libraries (e.g., combinatorial libraries) of such agents. Test agents can be obtained made or obtained from libraries of natural, synthetic, and/or semi-synthetic products (e.g., extracts). Those skilled in the field of drug discovery and development will understand the precise source of such agents.

In one aspect, the invention is directed to a method of determining whether an agent can be used to treat a triple negative breast cancer (TNBC) BL-1 subtype comprising contacting one or more TNBC BL-1 subtype cell lines with an agent to be assessed. The viability of the one or more cell lines in the presence of the agent is detected, wherein if the viability of the one or more cell lines decreases in the presence of the agent, then the agent can be used to treat the TNBC BL-1 subtype. Examples of TNBC BL-1 subtype cell lines include HCC2157, HCC1599, HCC1937, HCC1143, HCC3153, MDA-MB-468, and HCC38.

In another aspect, the invention is directed to a method of determining whether an agent can be used to treat a triple negative breast cancer (TNBC) BL-2 subtype comprising contacting one or more TNBC BL-2 subtype cell lines with an agent to be assessed. The viability of the one or more cell lines in the presence of the agent is determined, wherein if the viability of the one or more cell lines decreases in the presence of the agent, then the agent can be used to treat the TNBC BL-2 subtype. Examples of TNBC BL-2 subtype cell lines include SUM149PT, CAL-851, HCC70, HCC1806 and HDQ-P1.

In another aspect, the invention is directed to a method of determining whether an agent can be used to treat a triple negative breast cancer (TNBC) IM subtype comprising contacting one or more TNBC IM subtype cell lines with an agent to be assessed. The viability of the one or more cell lines in the presence of the agent is determined, wherein if the viability of the one or more cell lines decreases in the presence of the agent, then the agent can be used to treat the TNBC IM subtype. Examples of TNBC IM subtype cell lines include HCC1187 and DU4475.

In another aspect, the invention is directed to a method of determining whether an agent can be used to treat a triple negative breast cancer (TNBC) M subtype comprising contacting one or more TNBC M subtype cell lines with an agent to be assessed. The viability of the one or more cell lines in the presence of the agent is determined, wherein if the viability of the one or more cell lines decreases in the presence of the agent, then the agent can be used to treat the TNBC M subtype. Examples of TNBC M subtype cell lines include BT-549, CAL-51 and CAL-120.

In another aspect, the invention is directed to a method of determining whether an agent can be used to treat a triple negative breast cancer (TNBC) MSL subtype comprising contacting one or more TNBC MSL subtype cell lines with an agent to be assessed. The viability of the one or more cell lines in the presence of the agent is determined, wherein if the viability of the one or more cell lines decreases in the presence of the agent, then the agent can be used to treat the TNBC MSL subtype. Examples of TNBC MSL subtype cell lines include HS578T, MDA-MB-157, SUM159PT, MDA-MB-436, and MDA-MB-231.

In another aspect, the invention is directed to a method of determining whether an agent can be used to treat a triple negative breast cancer (TNBC) LAR subtype comprising contacting one or more TNBC LAR subtype cell lines with an agent to be assessed. The viability of the one or more cell lines in the presence of the agent is determined, wherein if the viability of the one or more cell lines decreases in the presence of the agent, then the agent can be used to treat the TNBC LAR subtype. Examples of TNBC LAR subtype cell lines include MDA-MB, SUM185PE, HCC2185, CAL-148, and MFM-223.

In the methods of the invention, viability of one of more of the cells can be determined using a variety of methods. Examples of such methods include a membrane leakage assay, a mitochondrial activity assay, a functional assay, a proteomic assay, a genomic assay or a combination thereof.

The methods can further comprise comparing the viability of the one or more cell lines in the presence of the agent to the viability of a control such as a non-cancerous cell line (e.g., a culture of normal human and immortalized MCF210A).

EXEMPLIFICATION

Example 1 Identification of Human Triple Negative Breast Cancer Subtypes and Models for Selection of Targeted Therapies Methods Laser capture microdissection, RNA extraction, and GE profiling. Invasive tumor cells from serial sections of primary breast cancers (n=112) were captured onto polymeric caps using the PixCell II lasercapture microdissection system (Arcturus) as previously described (Bauer J A, et al. Clin Cancer Res. 2010; 16(2):681-690). Areas of ductal carcinoma in situ and normal breast tissue were excluded and areas of inflammation and areas with tumor-associated fibroblasts were avoided. Total RNA was isolated from captured cells, quantified, and integrity analyzed, and microarray analyses were done using Affymetrix GeneChip Human Genome U133 Plus 2.0 arrays as previously described (Bauer J A, et al. Clin Cancer Res. 2010; 16(2):681-690).

Data set collection and TNBC identification by bimodal filtering. 2353 human breast cancer GE profiles were compiled from 14 publicly available breast cancer microarray data sets (GEO, www.ncbi.nlm.nih.gov/gds; Array Express, www.ebi.ac.uk/microarray-as/ae/) including 112 primary breast cancer GE profiles from our institution (Vanderbilt University Medical Center). All Vanderbilt tissue samples were taken from individuals treated at Vanderbilt University with institutional review board approval, and all patients signed a protocol-specific consent. All GE profiles were generated on Affymetrix microarrays and collected for identification of TNBCs for the training data set (Table 1). An additional 894 breast cancer GE profiles from 7 data sets were collected for the identification of TNBCs for the validation data set (Table 2). Raw GE values for each data set (n=21) were normalized independently using RMA procedure. The Affymetrix probes 205225_at, 208305_at and 216836_s_at were chosen to represent ER, PR, and HER2 expression, respectively (Karn T, et al. Breast Cancer Res Treat. 2010; 120(3):567-579). For each data set, empirical expression distributions of ER, PR, and HER2 were analyzed using a 2-component Gaussian mixture distribution model and parameters were estimated by maximum likelihood optimization, using optim function (R statistical software, www.r-project.org). The posterior probability of negative expression status for ER, PR, and HER2 was then estimated. A sample was classified as having negative expression if its posterior probability was less than 0.5. Upon initial hierarchical clustering, it was evident that some samples were from the same tumors, but in different data sets. These and additional outliers were removed after PCA. To ensure all ER/PR/HER2-positive tumors were removed, a secondary filter was performed on the combined samples identified by bimodal filtering. TNBC tumors were renormalized along with 5 positive controls for each parameter (ER, PR, and HER2) from 4 data sets that were positive by IHC and expressed mRNA near the center of the positive bimodal peak (FIG. 1B). Only tumors that displayed a greater than 10-fold reduction in expression than the positive controls were considered negative in expression and used for further analysis, resulting in 386 TNBC tumors (training set) and 201 TNBC tumors (validation set).

Normalization, data reduction, and cross-platform batch effect removal. Training (n=386) and validation (n=201) TNBC data sets identified by the 2-component Gaussian distribution model were collectively RMA normalized, summarized and log-transformed using the combined raw GE from each data set. For genes containing multiple probes, the probe with the largest interquartile range across the samples was chosen to represent the gene. Batch effects were removed by fitting each gene to a linear model with 14 and 7 fixed effects for each data set, respectively. The residual genes from this model (n=13,060) were used for subsequent clustering analysis.

GE-based identification of TNBC subtypes. k-means clustering and consensus clustering were used to determine the optimal number of stable TNBC subtypes. Cluster robustness was assessed by consensus clustering using agglomerative k-means clustering (1,000 iterations), with average linkage on the 386 TNBC profiles using the most differentially expressed genes (SD >0.8; n=1510 genes) (Gene Pattern version 3.2.1, GSE-A, www.broadinstitute.org/gsea/) (19). The optimal number of clusters was determined from the CDF, which plots the corresponding empirical cumulative distribution, defined over the range [0, 1], and from calculation of the proportion increase in the area under the CDF curve. The number of clusters is decided when any further increase in cluster number (k) does not lead to a corresponding marked increase in the CDF area. PCA and heat maps were generated using Genespring GX ver.10 software (Agilent).

Functional annotation. Each TNBC subtype was tested for gene enrichment compared with all other samples using GSE-A software (Subramanian A, et al. Proc Natl Acad Sci USA. 2005; 102(43):15545-15550). Genes were tested for enrichment in the C2 curated gene sets of canonical pathways. Using the GSE-A algorithm (1,000 permutations), the top significantly enriched canonical pathways were selected based on a normalized enrichment score (NES) greater than 0.4 and false discovery rate (FDR) q value of less than 0.60. The FDR cutoff of 0.60 was chosen because of the lack of coherence in the data set collection spanning 21 studies, and more stringent FDR cutoffs resulted in fewer results, potentially overlooking significant pathways.

TNBC subtype gene signature derivation. The 20% of genes with the highest and lowest expression levels in at least 50% of the samples for each subtype were chosen for further analysis. Within each cluster, for each selected gene, the nonparametric Kruskal-Wallis test was applied to identify genes significantly different from the median GE among all 6 groups. Significant genes with a Bonferroni's adjusted P value of less than 0.05 were included in the combined gene signature (n=2188) for the TNBC subtypes and used to predict an independent validation set as well as to classify TNBC cell lines. Each sample from the validation set was assigned to a TNBC subtype based on highest Pearson correlation and lowest P value to one of the subtypes derived from the training data set. Samples with correlations differing by a P value of less than 0.05 were considered unclassifiable.

TNBC cell-line classification. GE data for TNBC cell lines (GSE-10890 and E-TABM-157) were correlated (Spearman) to the centroids of the GE signatures for each TNBC subtype. GE data from both the TNBC tumors and cell lines were combined so that each gene was standardized to have mean=0 and SD=1. GE profiles from the cell lines were correlated to the centroids for each of the 6 TNBC subtypes. To remove size effects of the 6 gene signatures, the empirical P values were estimated for the correlations using a resampling (bootstrap, n=1000) approach and estimating correlation coefficients for each resample. Cell lines were assigned to the TNBC subtype with the highest correlation (Table 3), and those that had low correlations (<0.1) or were similar between multiple subtypes (P>0.05) were considered unclassified.

Cell proliferation/viability assays and IC50 determinations. All cell lines and culture conditions used can be found in Supplemental Methods (Table 5). Short tandem repeat (STR) DNA fingerprinting analysis was performed on all TNBC cell lines used in this study (Cell Line Genetics). All cell lines matched STR databases (ATCC, DSMZ, and Asterand), and their identity was confirmed by a certified process at Cell Line Genetics. Breast cancer cell lines and HMECs were seeded (3,000-10,000 cells) in quadruplicate wells in 96-well plates. Cells were incubated in the presence of alamar-Blue (Invitrogen), and baseline (predrug) fluorescence (Ex/Em: 560/590 nm) measurements were obtained following overnight attachment. Medium was then replaced with either fresh medium (control) or medium containing half-log serial dilutions of the following drugs: 0.3-30 µM olaparib (ChemieTek), 0.3-30 µM veliparib (ChemieTek), 1-100 µM bicalutamide (IPR Pharmaceutical), 0.3-30 µM cisplatin (APP Pharmaceutical), 3-300 nM NVP-BEZ235 (Chemdea), 10-1000 nM 17-DMAG (ChemieTek), and 0.1-10 µM dasatinib (LC Laboratories). Viability was determined from measuring fluorescent intensity after metabolic reduction of alamarBlue in the presence/absence of the drug after 72 hours. Viability assays were performed in triplicate, and replicates were normalized to untreated wells. Inhibitory concentration (ICH) values were determined after double-log transformation of dose response curves as previously described (Bauer J A, et al. Breast Cancer Res. 2010; 12(3):R41). For analysis of cell-line drug assays, data generated from the different cell lines representative of TNBC subtypes were compared using the nonparametric Mann-Whitney U test. All analyses and graphic representations were performed using Prism software (version 4.0c; GraphPad Software), and values are represented as the mean±SEM.

Kaplan-Meier survival analysis and Hr. Log-rank test was used to determine survival significance in TNBC subtypes from Kaplan-Meier survival curves, RFS, and DMFS. Cox proportional hazards model was used to calculate Hr, demonstrating differences in survival by pairwise comparison between TNBC subtypes (P<0.05).

Xenograft tumor studies. Five-week-old female athymic nude-Foxnlnu mice (Harlan Sprague-Dawley) were injected (s.c.) with either approximately $5 \times 10^6$ (CAL-51, HCC1806, MDA-MB-468, and SUM185PE) or approximately $10 \times 10^6$ (CAL-148 and SUM159PT) cells suspended in medium (200 µl) into each flank using a 22-gauge needle. The protocols describing the process of xenograft tumor formation in athymic mice were reviewed and approved by the Vanderbilt Institutional Review Board. Once tumors reached a volume of 25-50 mm³, mice were randomly allocated to treatment or vehicle arms. Treatments included bicalutamide per oral (100 mg/kg/d), cisplatin i.p. (8 mg/kg/wk), or NVP-BEZ235 per oral (50 mg/kg/d) in 1:9 N-methylpyrolidone: PEG300. Tumor diameters were serially measured at the indicated times with digital calipers, and tumor volumes were calculated as width²×length/2. Data points reflect the means and SEM for 16 tumors per treatment.

Statistics. Description of the relevant statistical methods used and analyses performed are described in the relevant Methods sections above. Comparisons between cell lines representative of TNBC subtypes were performed using the nonparametric Mann-Whitney U test. Statistical significance of drug effects on tumor growth in athymic mice was determined by 2-tailed unpaired t test.

Supplemental Methods

Immunostaining. Both formalin fixed paraffin embedded (FFPE) and frozen tissue were used for immunohistochemical studies. When frozen tissue was used for immunohistochemistry, staining was performed on sections taken from the same tissue block from which RNA was isolated for microarray. AR, Ki67, EGFR and CK 5/6 expression were evaluated in frozen tissue using the DAKO (Carpinteria, CA) antibodies: AR (clone AR411) at a 1:50 dilution, EGFR at 1:200, CK5/6 at 1:50 and Ki67 antibody (MIB1 clone) at a 1:200 dilution for 1 h at room temperature. FFPE tissue was subject to antigen retrieval with high pH buffer (pH 8.0) followed by overnight incubation with an AR (1:30) or Ki67 (1:75) antibody dilution overnight. AR expression was scored as both the percentage of tumor cells with nuclear staining as well as the intensity of staining (scored as 0-3+). An AR intensity score was calculated as follows: (AR intensity×100)+% AR positive cells. For Ki67 the percentage of cells demonstrating nuclear staining at any intensity was recorded.

Immunoblotting. Cells were trypsinized, lysed and relative protein expression was determined by Western blot as previously described with the following antibodies; HSP90 monoclonal antibody, clone F-18 (Santa Cruz Biotechnology, Santa Cruz, CA) and the AR polyclonal antibody, SC-N20 (Santa Cruz Biotechnology).

Colony Formation. MFM-223, MDA-MB-453 and CAL-148 cells (3000 cells/well) were reverse-transfected with 1.25 pmole of siRNAs to AR [ONTARGET plus SMARTpool, cat #L-003400-00 (Dharmacon, Lafayette, CO)] or non-targeting control (ON-TARGETplus Non-targeting Pool cat #D-001810-10-05) with 0.25 µL Dharmafect #3 (MFM-223), or 0.25 µL Dharmafect #1 (MDAMB-453 and CAL-148). Colonies were stained and quantified 14 d following transfection using Cell Profiler 2.0 (Broad Institute, Cambridge, MA). Experiments were preformed in triplicate and error bars reflect standard deviation.

Results

Figure 1A:
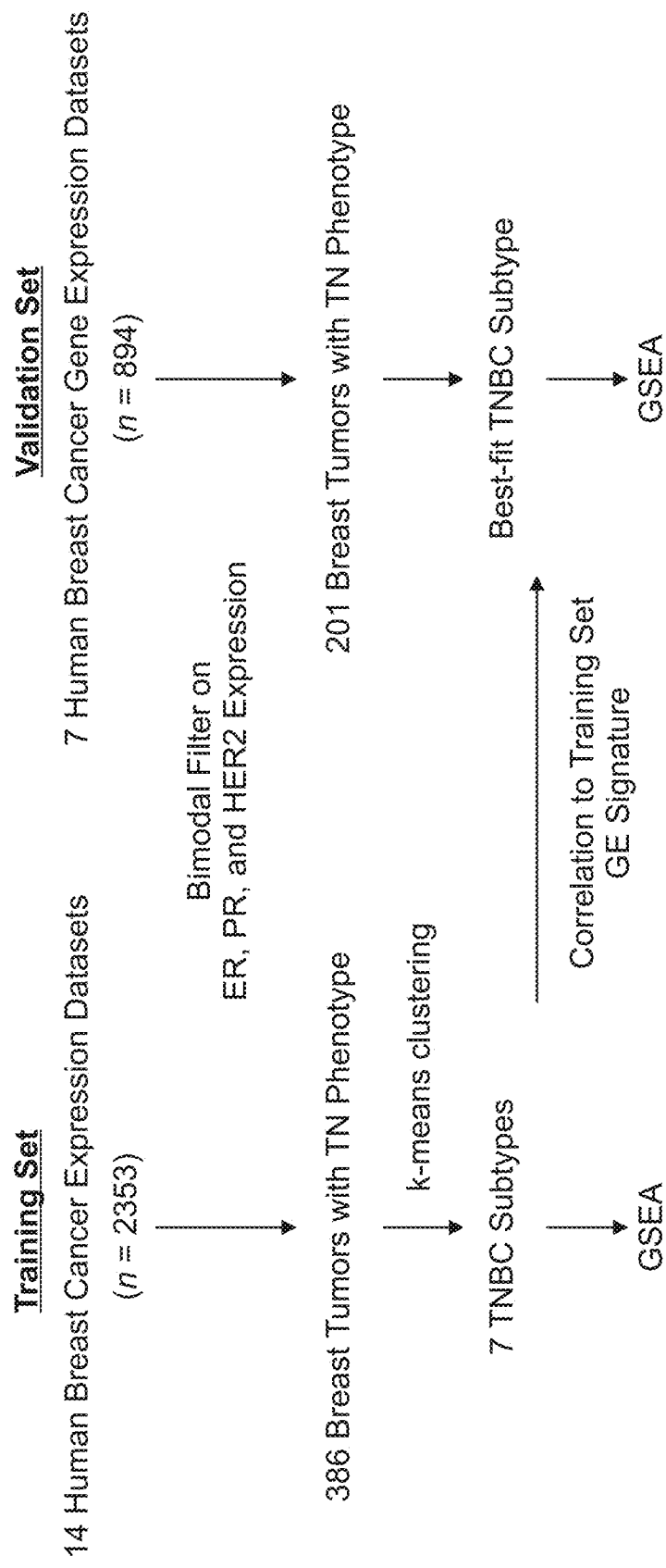
Figure 2A:
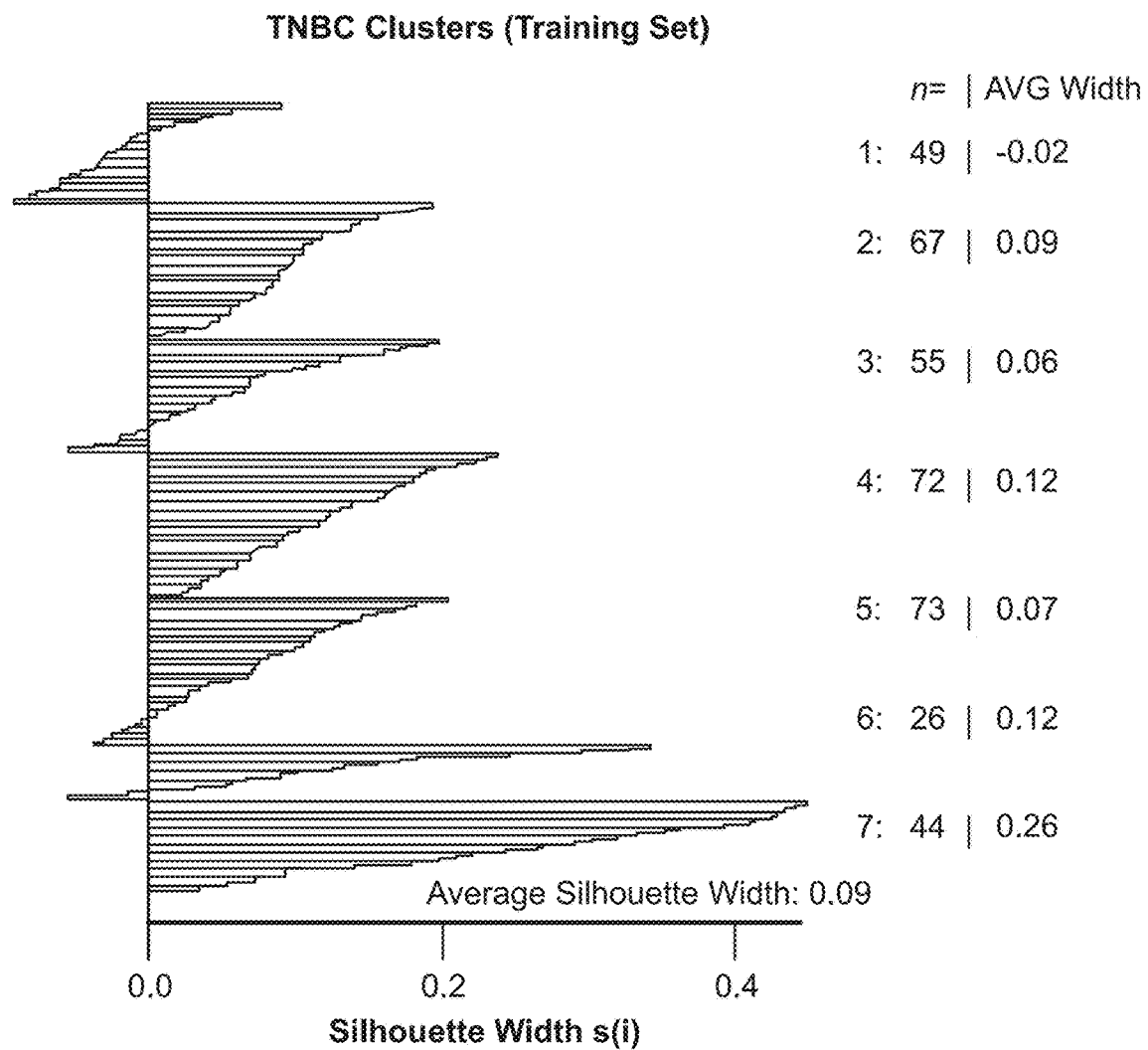
FIGS. 2A-2E: Identification of TNBC subtypes. (2A) Silhouette plot showing the composition (n=number of tumors) and stability (AVG width) of k-means clustering on the TNBC training set. Clusters with s(I)>0 were considered stable. (2B) Consensus clustering displaying the robustness of sample classification using multiple iterations (×1000) of k-means clustering. (2C) The CDF depicting the cumulative distribution from consensus matrices at a given cluster number (k). (2D) The optimal cluster number is 7 at the point in which the relative change in area ($\Delta$) under the CDF plot does not change with increasing k. (2E) Principal component analysis graphically depicting fundamental differences in GE between the TNBC clusters. The cluster (subtypes) are named as shown.
Figure 2B:
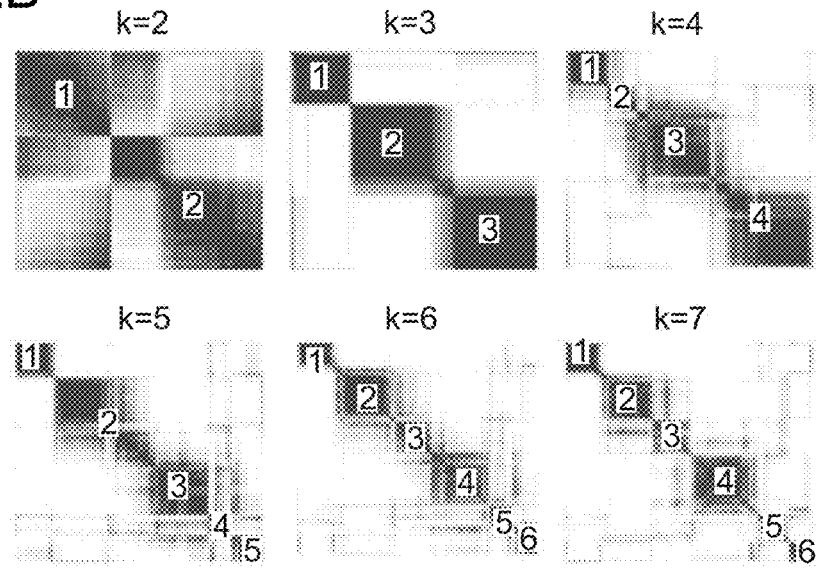
Figure 2C:
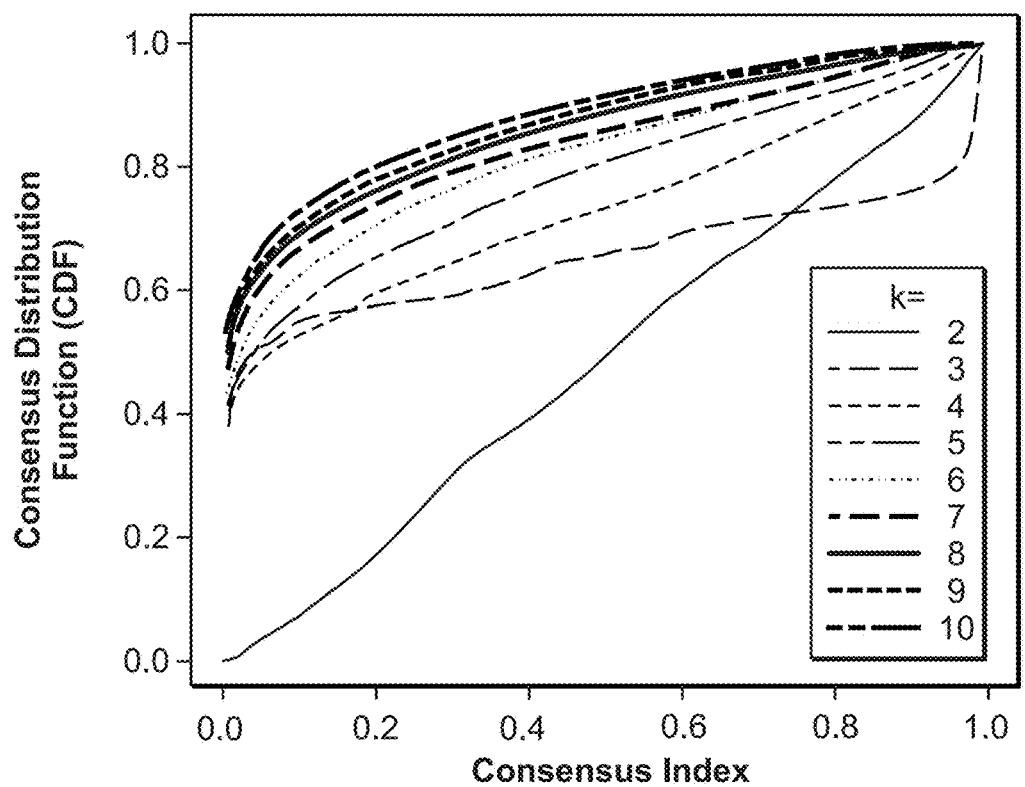
Figure 2D:
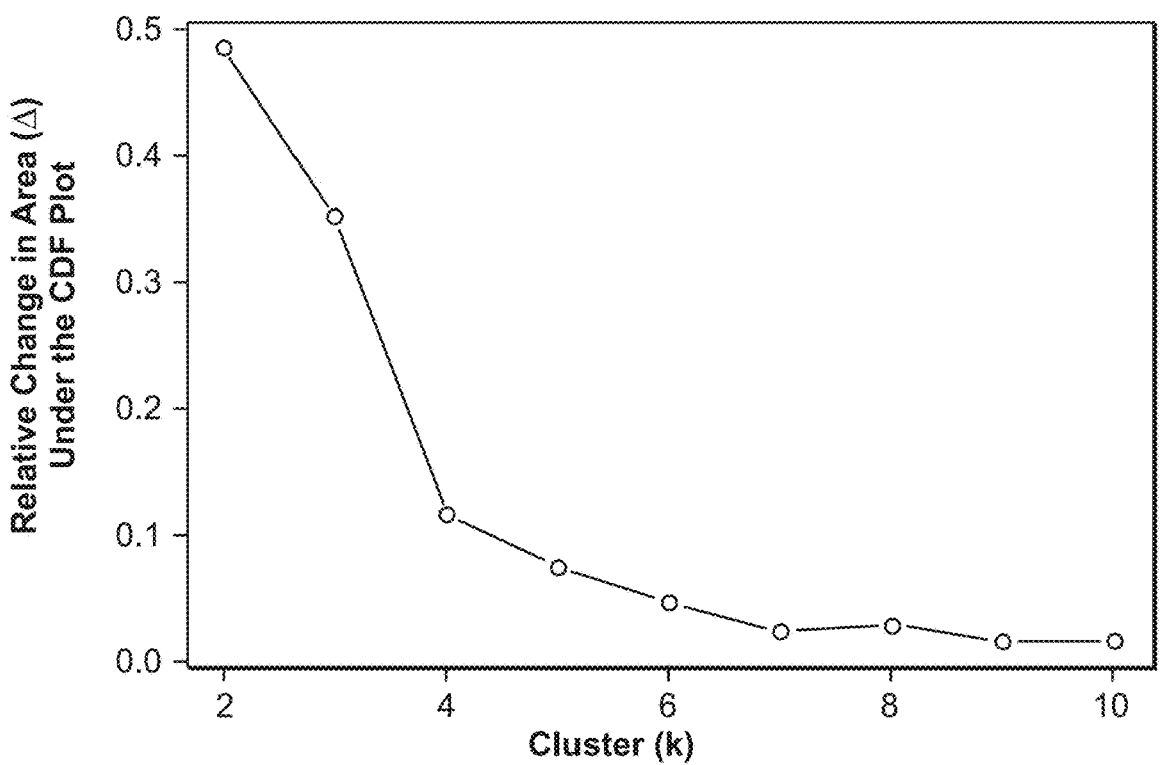
Figure 2E:
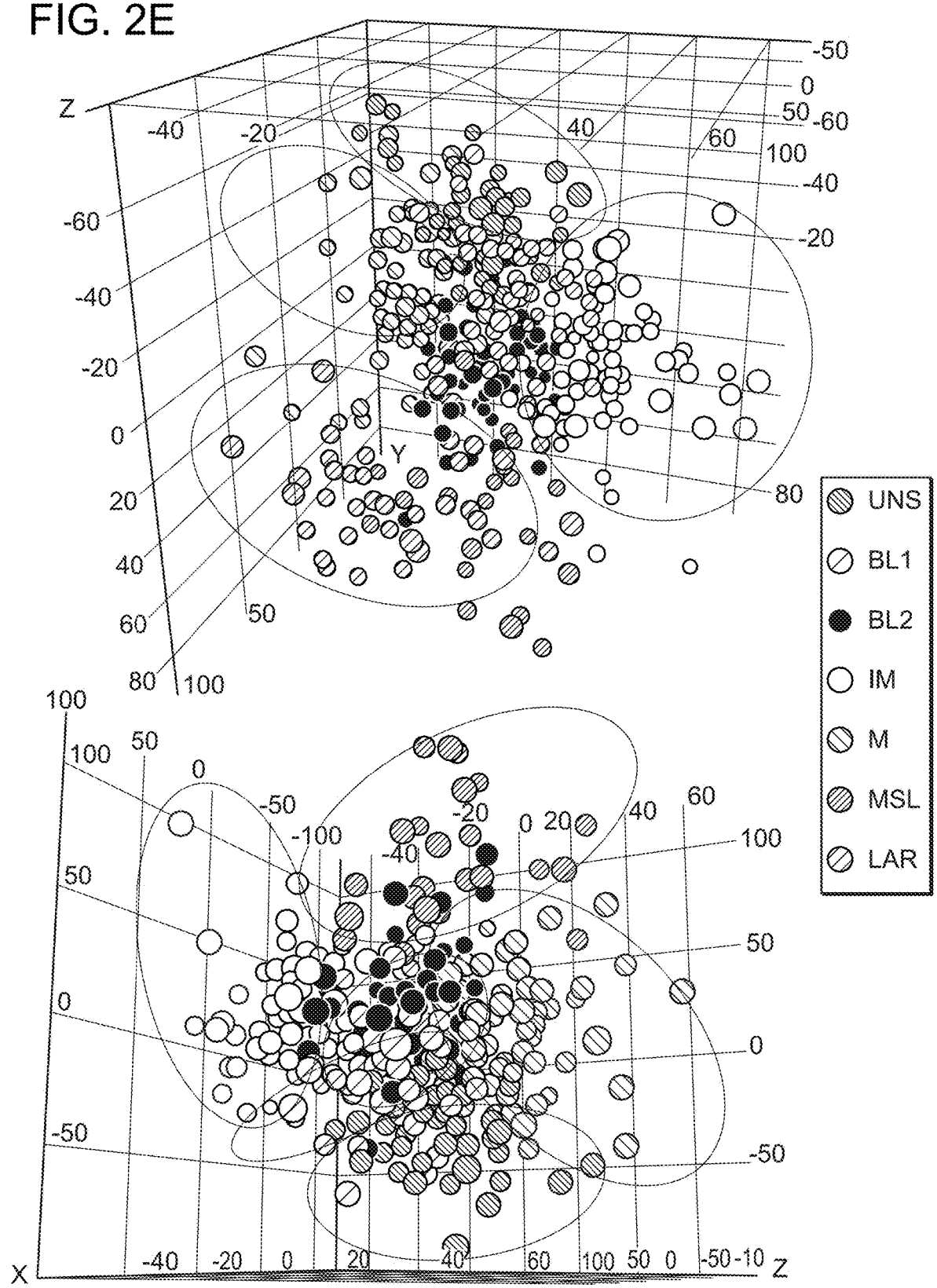
Figure 8:
FIG. 8: Random distribution of TNBC subtypes found within datasels. The percent of tumors in each cluster is displayed across 14 studies that comprise the training dataset.

Analysis of human tumor GE profiles identifies TNBC subtypes. GE profiles were obtained from 21 publicly available data sets that contained 3,247 primary human breast cancers and processed according to the flow chart in FIG. 1A. To allow for robust analysis, these data sets were further divided into training (Table 1; 14 data sets, cases n=2353) and validation data sets (Table 2; 7 data sets, cases n=894). Since the majority of these tumors lacked sufficient molecular analysis of ER, PR, and HER2, we filtered each data set for ER, PR, and HER2 mRNA expression to identify triple-negative status (see Methods for bimodal filter description; supplemental material available in Lehmann, B. D., et al., *J Clin Invest*, 121 (7): 2750-2767 (July 2011), the entire teachings of which are incorporated herein by reference). Previous studies have shown that ER and HER2 mRNA expression correlates with immunohistochemistry (IHC) and FISH analyses, respectively (Carmeci C. et al. Am J Pathol. 1997; 150(5):1563-1570; Press M F, et al. Clin Cancer Res. 2008; 14(23):7861-7870). Using a bimodal filter on the GE data (FIG. 1B), 386 and 201 TNBC tumor samples were identified in the training and validation sets, respectively. The 386 TNBC GE profiles of the training set were robust multiarray average (RMA) normalized, summarized, transformed, and corrected for "batch effect," resulting in 13,060 identical probes representing unique genes across all platforms. The triple-negative GE pattern is shown compared with 5 positive controls for each parameter (ER, PR, and HER2) from data sets that were confirmed IHC positive and expressed mRNA near the center of the positive bimodal peak (FIG. 1C). Of the 14 data sets in the training set, 4 (GSE-7904, E-TABM-158, MDA133, GSE-22513, GSE-28821, and GSE-28796) included IHC data for all 3 markers, while others lacked information on ER, PR, or HER2 status (Table 1). The IHC data provided were used to calculate false-positive rates for each study, defined as tumors that were predicted negative for ER, PR, or HER2 by bimodal filtering of mRNA expression, but were positive by IHC. The overall false-positive rates were 1.7%, 1.7%, and 0.9% for ER, PR, and HER2, respectively, demonstrating that bimodal filtering of data sets by mRNA expression is a reliable method for identifying TNBC tumors from data sets lacking IHC information (Table 1). The overall frequency of TNBC across the training data set was 16% and is consistent with the prevalence of TNBC previously reported in 2 other large studies performed on 3,744 cases (17%) (17) and 1,726 cases (16%) (18).

k-means and consensus clustering reveal 6 TNBC subtypes. To identify global differences in GE between TNBC subtypes, k-means clustering was performed on the most differentially expressed genes (SD >0.8). Using the silhouette width (s[i]) as a measure of relative closeness of individual samples to their clusters, k-means clustering classified 337 of the 386 TNBC tumors into 6 stable clusters (s[i]>0) and 49 tumors into 1 unstable cluster (s[i]>0) (FIG. 2A). Clustering resulted in a distribution of samples in all 7 clusters independent of each data set, n=14, indicating that confounding factors such as batch effect, RNA amplification, and sample quality did not influence cluster distribution (FIG. 8). Sample classification robustness was analyzed by consensus clustering, which involves k-means clustering by resampling (1,000 iterations) randomly selected tumor profiles. The consensus matrix is a visual representation of the proportion of times in which 2 samples are clustered together across the resampling iterations (FIG. 2B). Groups of samples that frequently cluster with one another are pictorially represented by darker shades of red. To determine the number of clusters present in the data, the area under the curve of the consensus distribution function (CDF) plot was examined (FIG. 2C). The point at which the area under the curve ceases to show marked increases with additional cluster number (k) indicates the ideal number of clusters (FIG. 2D; Monti S. Machine Learning. 2003; 52(1-2):91-118). Therefore, the optimal number of clusters is 7, as defined by the consensus plots consistent with the k-means clustering (6 stable, 1 unstable). Unsupervised dimension reduction by principal component analysis demonstrated fundamental differences in GE between tumor subtypes identified by k-means and consensus clustering (FIG. 2E).

Figure 9:
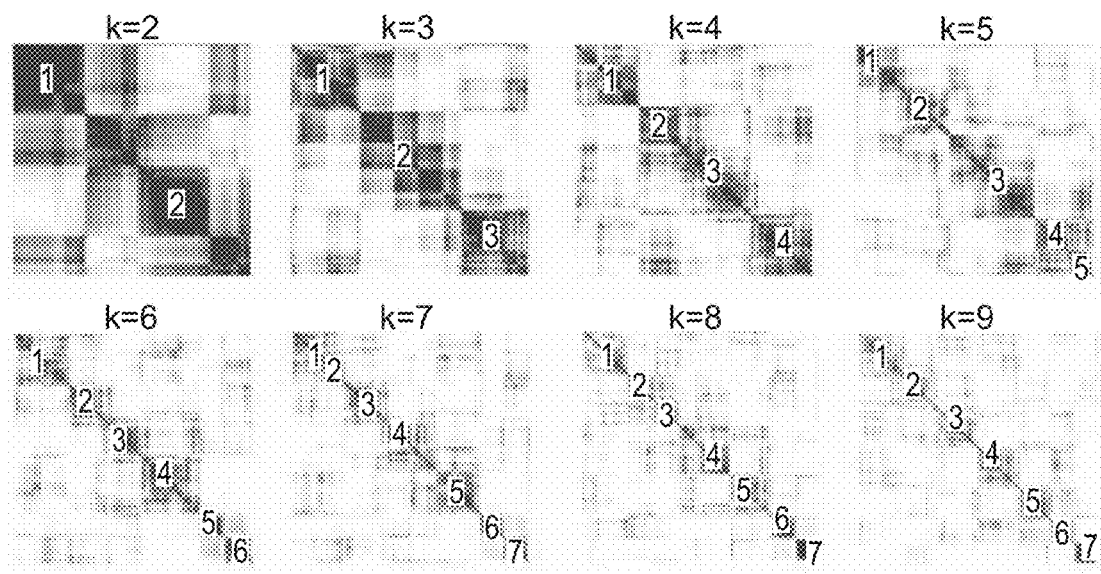
FIG. 9: Consensus clustering of training and validation TNBC datasets (n=587). Heat map displays consensus clustering results depicting the robustness of sample classification. Red areas indicate samples that frequently cluster with each other over multiple iterations (1000) of k-means clustering (k::c 2 to k=9).
Figure 10:
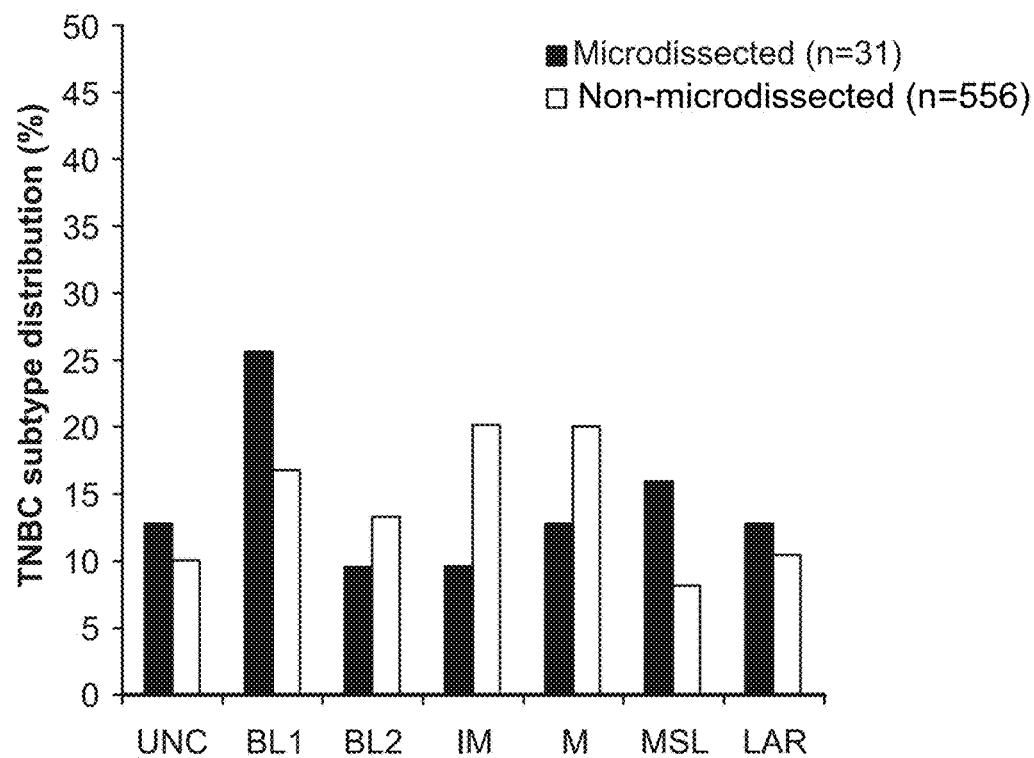
FIG. 10: Gene expression profiles derived from tumors that were laser-capture microdissected represent all TNBC subtypes. Bar graph depicts the percentage of tumors that were microdissected (blue bars) present in the GSE584 (n=17) and Vanderbilt (n=14) datasets relative to non-microdissected tumors in the combined dataset (red bars).

To assess whether similar TNBC subtypes could be generated from an independent TNBC cohort, 201 TNBC samples were compiled from bimodal filtering of 7 additional publicly available data sets (Table 2). A GE signature was derived from the most differentially expressed genes found in the TNBC training set (see Methods) and used to predict which TNBC subtype was best-fit for each of the tumors in the validation set. Each sample from the validation set was assigned to 1 of the TNBC subtypes derived from the training data set based on the highest Pearson correlation and lowest P value. Samples with correlations differing by P<0.05 were considered unclassifiable. The validation set resulted in proportioned subtypes similar to those of the initial k-means clustering of the training set. After the analysis was completed, an ad hoc analysis was performed by combining the training and validation data sets (587 tumors), which resulted in 7 subtypes identified by consensus clustering (FIG. 9), with similar enrichment in gene ontologies. This further validates the stability of the subtypes and shows that increasing sample size does not change optimal cluster number. Evaluation of GE profiles of RNA obtained from laser-capture microdissection of tumor cells from 2 data sets (GSE-22513; GSE-28821; GES-28796, Table 1; GSE-5847, Table 2) showed a similar pattern of distribution across all 7 subtypes, suggesting that these subtypes are indeed representative primarily of GE resulting from epithelial tumor cells rather than stromal components surrounding the tumor (i.e., inflammatory cells, myofibroblasts, etc.) (FIG. 10).

Figure 3:
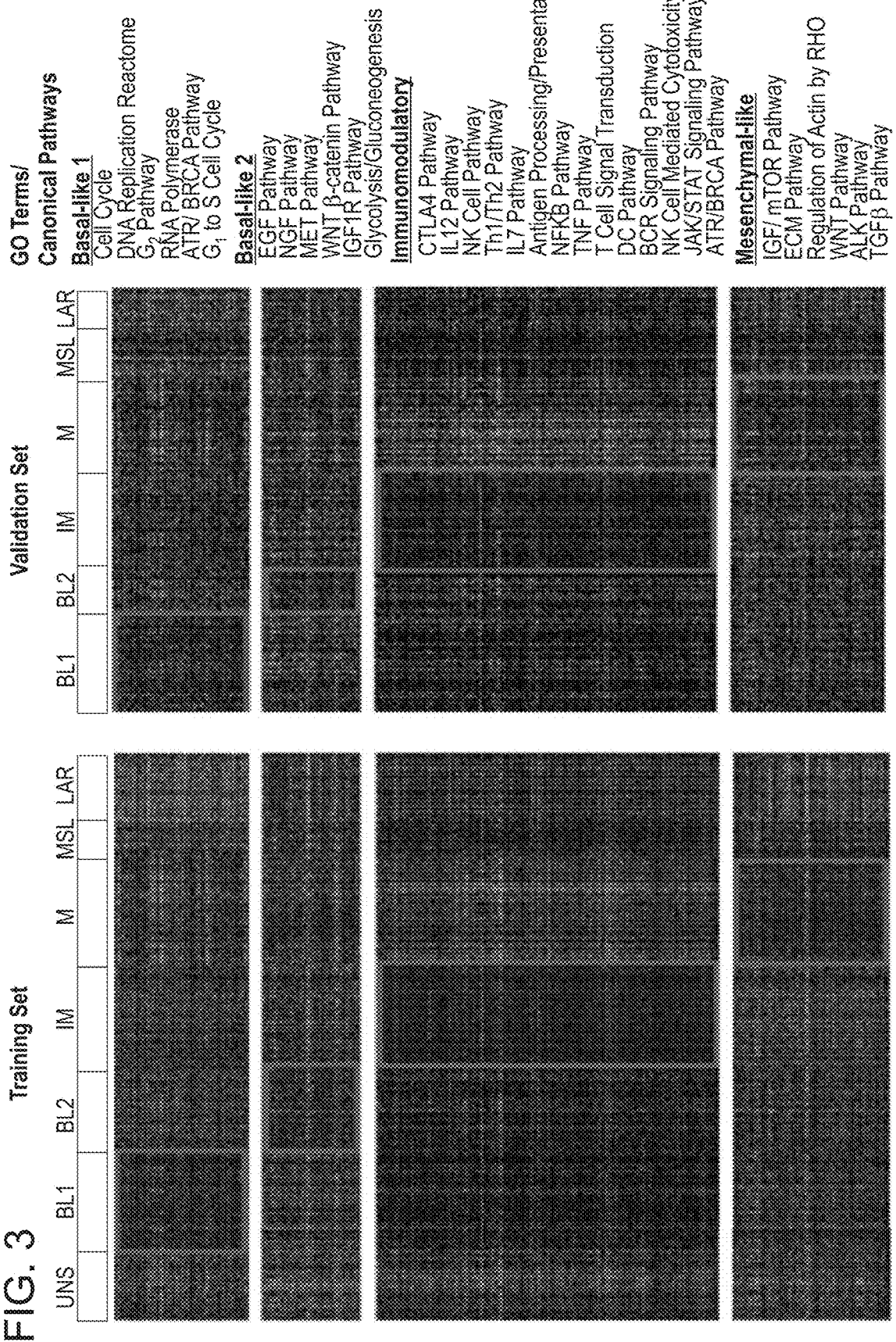
FIG. 3: GE patterns within TNBC subtypes are reproducible. Heat maps showing the relative GE (log 2, −3 to 3) of the top differentially expressed genes (P<0.05) in each subtype in the training set (left) and the same differentially expressed genes used to predict the best-fit TNBC subtype of the validation set (right). Overlapping gene ontology (GO) terms for top canonical pathways in both the training and validation sets as determined by GSE-A are shown to the right of the heat maps.
Figure 3:
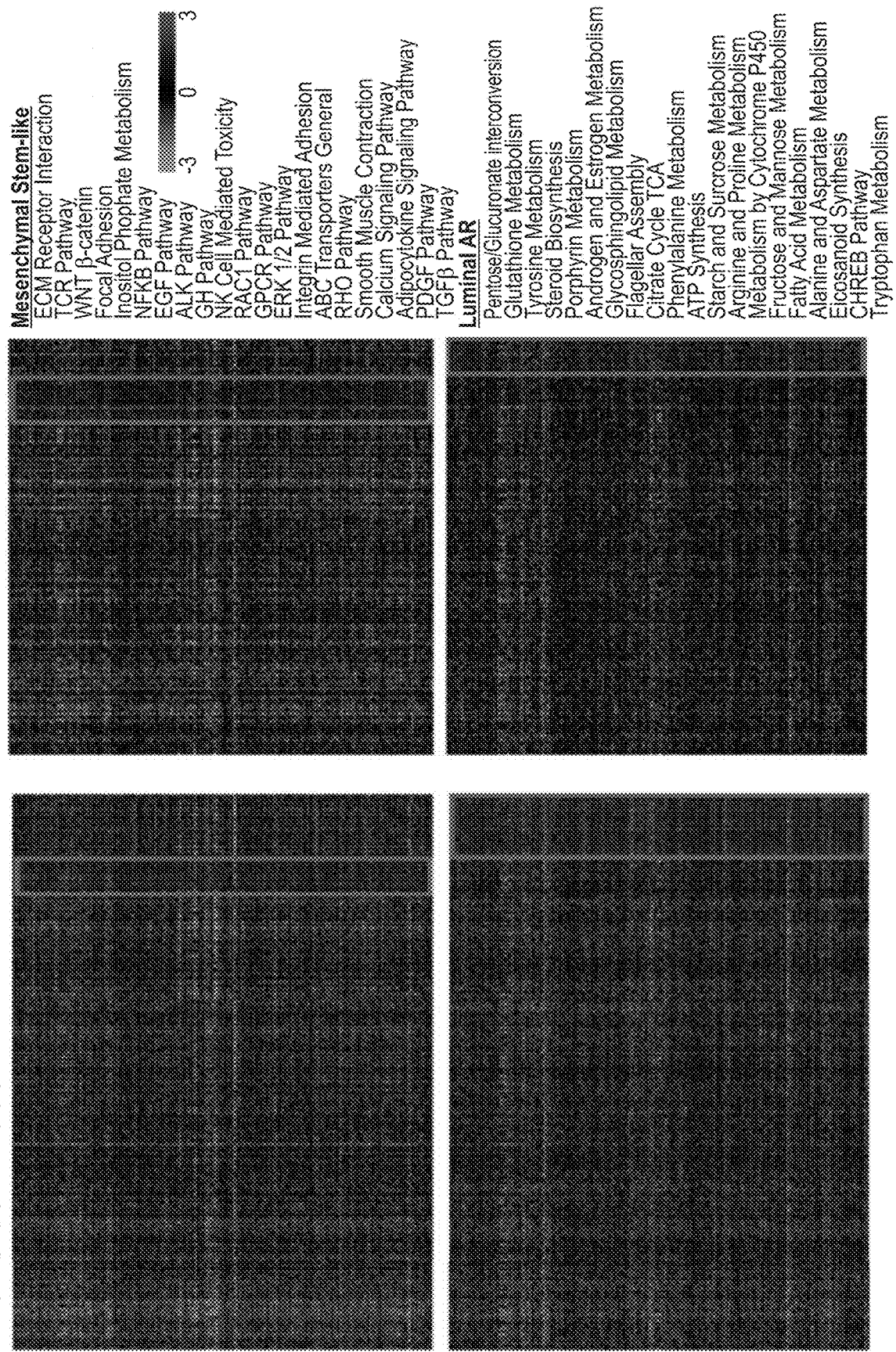
Figure 12:
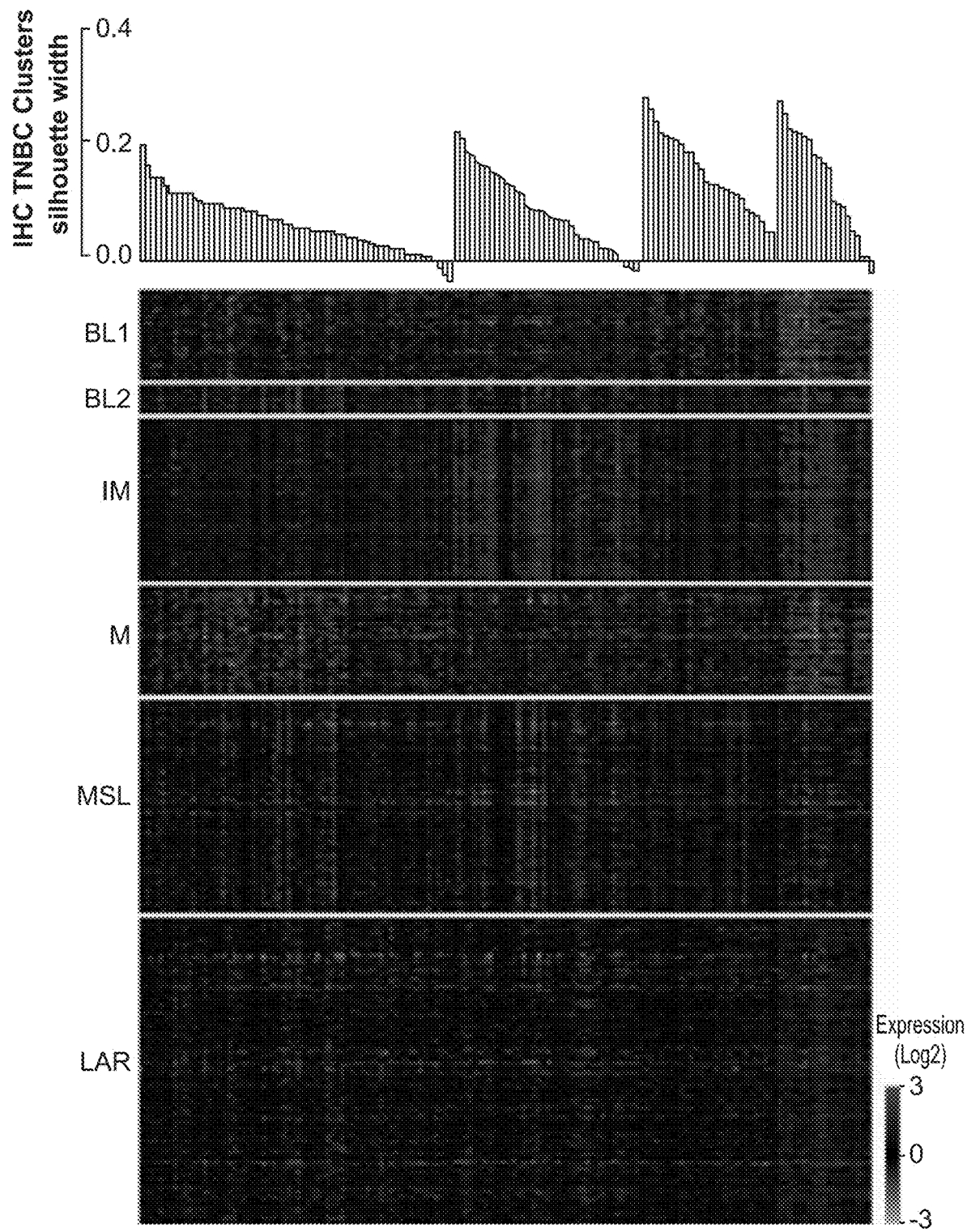
FIG. 12: TNBC subtypes Identified by IHC display similar GE patterns to the six TNBC subtypes. IHC TNBC clusters are shown in silhouette plot with relative GE for genes unique to the six TNBC subtypes shown below.

Distinct gene ontologies are associated with each TNBC subtype. As an independent method to analyze TNBC subtypes, Gene Set Enrichment Analysis (GSE-A) (Subramanian A, et al. Proc Natl Acad Sci USA. 2005; 102(43): 15545-15550) was performed on all genes from both the training and validation sets to determine the top canonical pathways associated with each TNBC subtype. The top enriched genes (P<0.05), identified from the training set used to predict the validation set, are displayed in a heat map in FIG. 3. The top canonical pathways substantially overlapped between the training and validation sets for each subtype, indicating that the subtypes were reproducibly enriched in unique pathways (Table 4). Our 7 TNBC subtypes were characterized on the basis of gene ontologies and differential GE and subsequently labeled as follows: basal-like 1 (BL1); basal-like 2 (BL2); immunomodulatory (IM); mesenchymal (M); mesenchymal stem-like (MSL); luminal androgen receptor (LAR); and unstable (UNS) (FIG. 3). Independent analysis of 5 data sets based on TNBCs identified by IHC staining (n=183) resulted in 4 clusters with GE similar to that of basal-like, IM, mesenchymal-like, and LAR subtypes (FIGS. 11A, 11B and 12).

Figure 13:
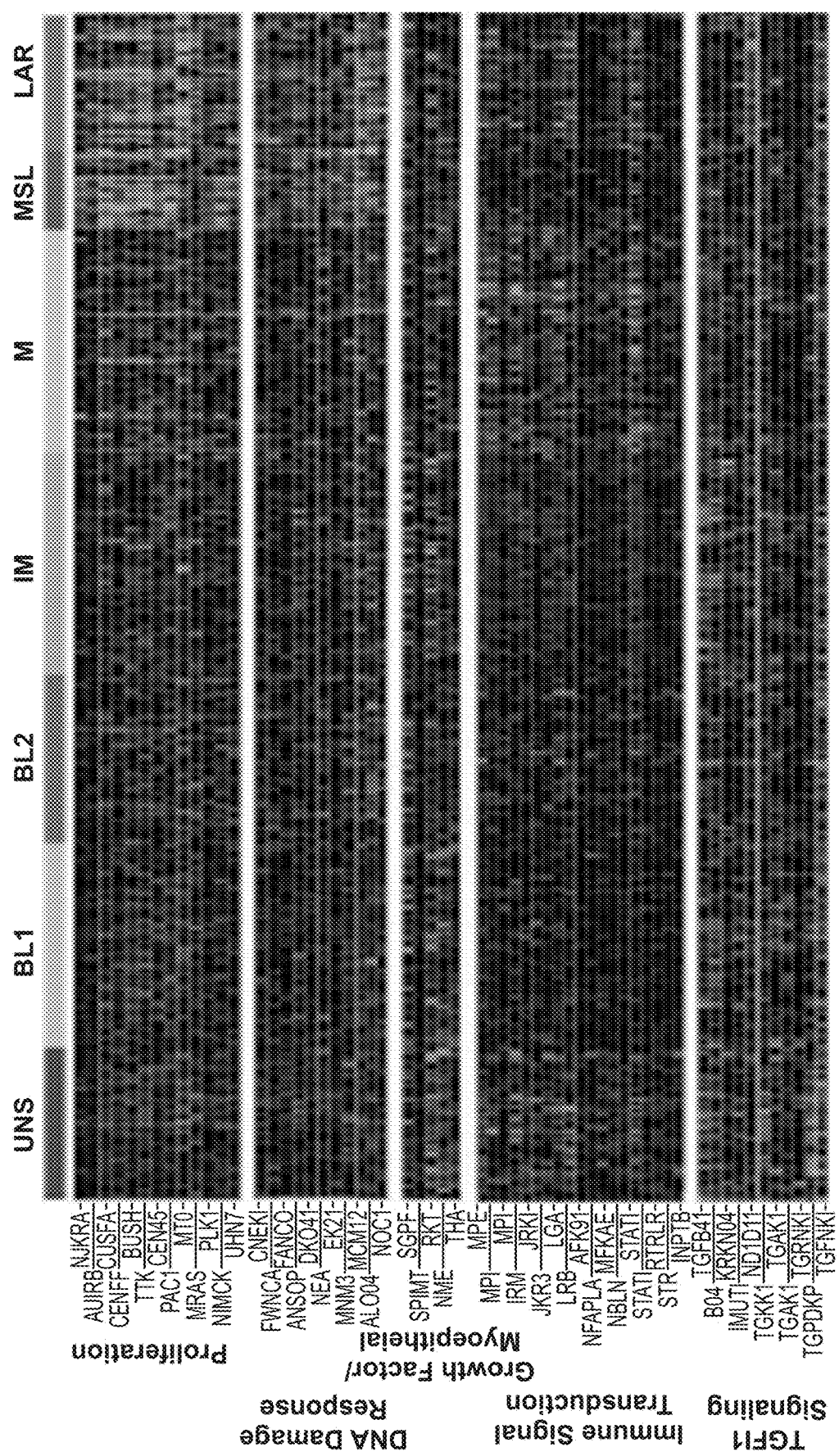
FIG. 13: Differential GE across TNBC subtypes. Heatmaps show relative GE (log 2, −2 to 2) associated with proliferation, DNA damage response, myoepithelial genes, immune signal transduction, TGFβ signaling, growth factor receptors, EMT, WNT signaling, stem-like, claudin (CL), angiogenesis, AR and of AR target genes across TNBC subtypes (as in FIG. 3).
Figure 13:
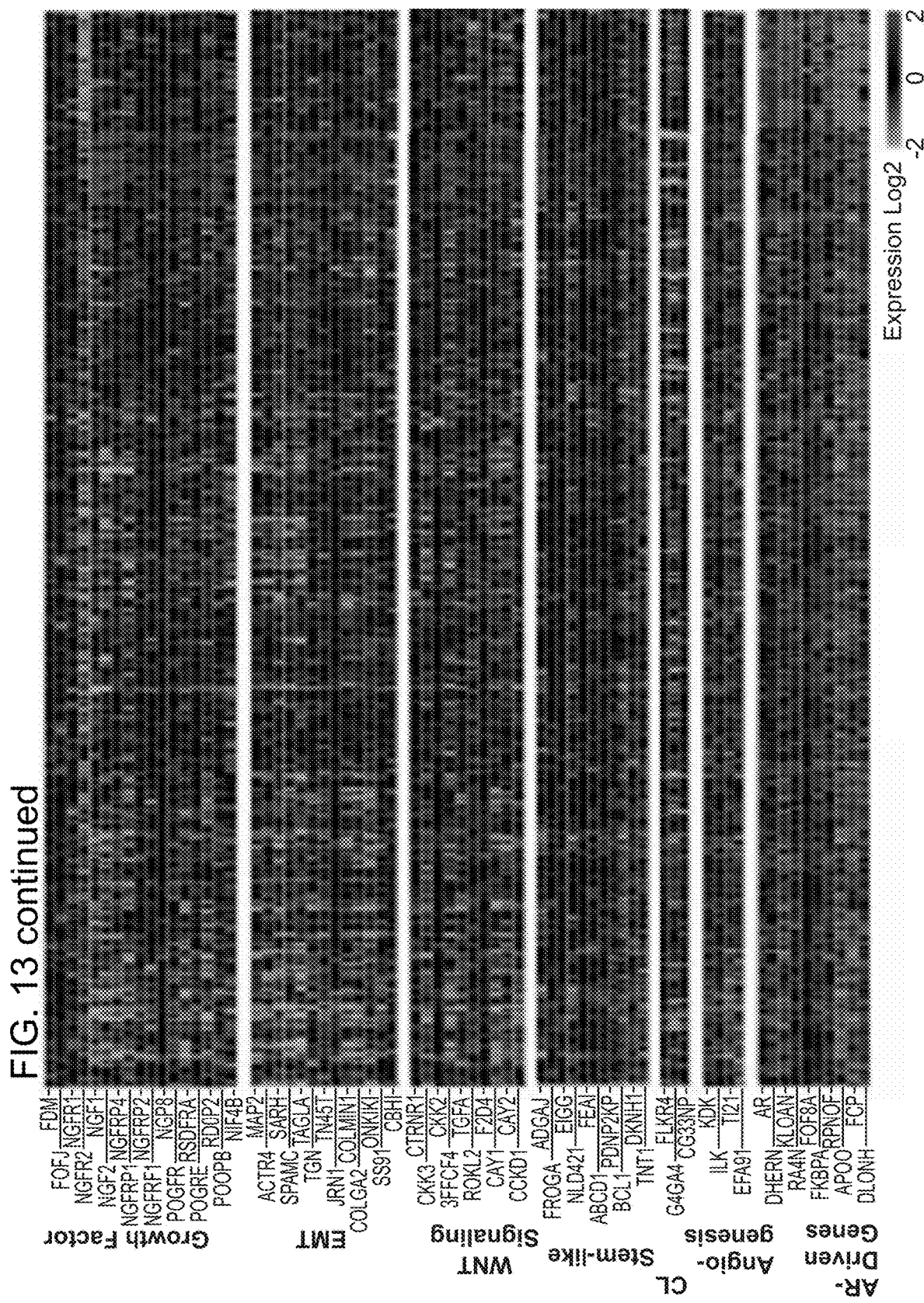

BL1 and BL2 subtypes. The top gene ontologies for the BL1 subtype are heavily enriched in cell cycle and cell division components and pathways (cell cycle, DNA replication reactome, $G_2$ cell-cycle pathway, RNA polymerase, and $G_1$ to S cell cycle) (FIG. 3). The annotations are supported by the expression of genes associated with proliferation, such as AURKA, AURKB, CENPA, CENPF, BUB1, TTK, CCNA2, PRC1, MYC, NRAS, PLK1, and BIRC5 (FIG. 13). Elevated DNA damage response (ATR/BRCA) pathways accompany the proliferation pathways in the BL1 subtype (FIG. 3). Increased proliferation and cell-cycle checkpoint loss are consistent with the elevated expression of the DNA damage response genes observed (CHEK1, FANCA, FANCG, RAD54BP, RAD51, NBN, EXO1, MSH2, MCM10, RAD21, and MDC1) (FIG. 13).

Figure 14A:
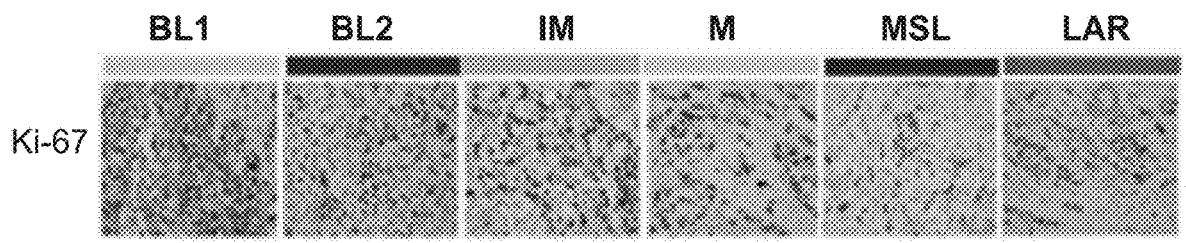
FIGS. 14A-14B: TNBC tumor subtypes differentially stain for the proliferation marker Ki-67. (14A) Representative micrographs from 20 tumors showing IHC staining of the proliferation marker, Ki-67, in tumors from different TNBC subtypes. (14B) Dol plot showing the mean and distribution of Ki-67 staining within TNBC subtypes as scored by study pathologist. Subtypes: BL1=basal-like 1, BL2=basal-like 2, IM=immunomodulatory, M=mesenchymal-like, MSL=mesenchymal stem-like and LAR=luminal AR.
Figure 14B:
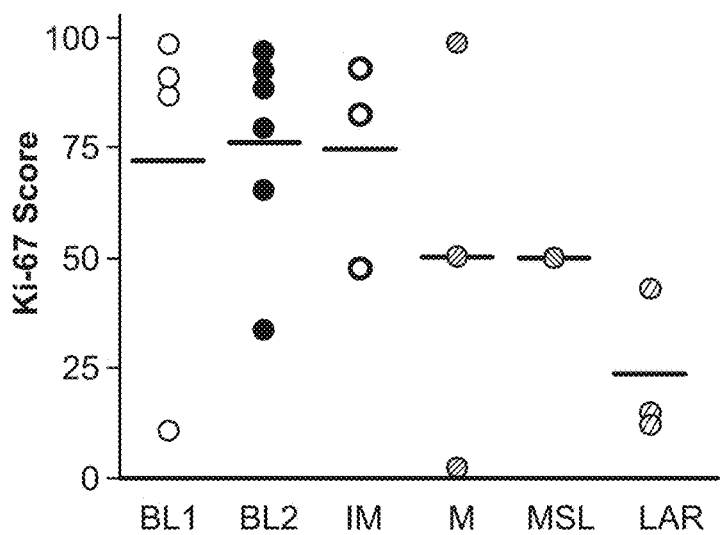
Figure 15:
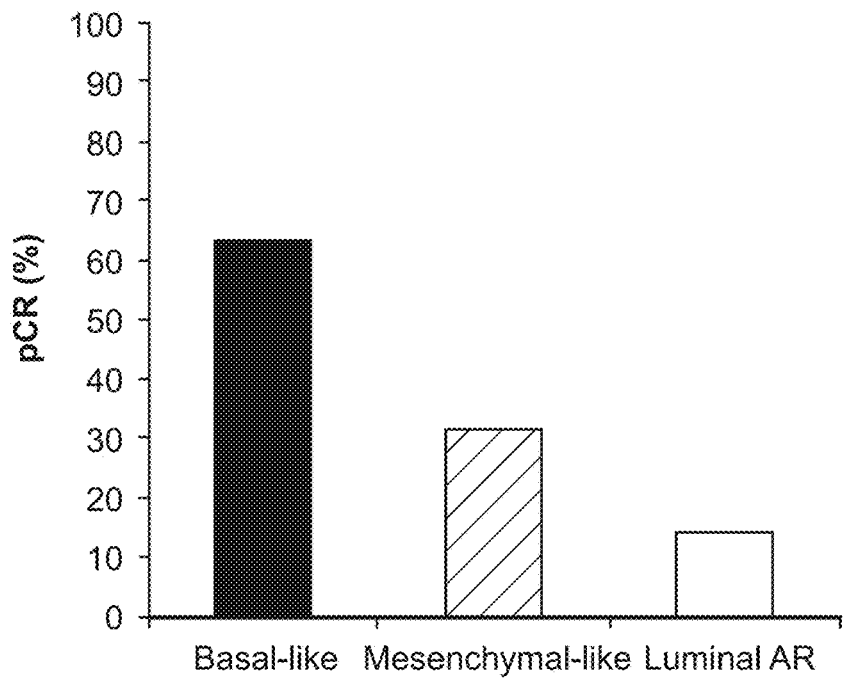
FIG. 15: Response rates differ across TNBC subtypes in taxane-treated patients. Percent of patients achieving pathologic complete response (pCR) after taxane-based treatment was significantly (P=0.042, chi-squared analysis) different for patients whose tumors correlated to basal-like (n=19), mesenchymal-like (n=16) and luminal AR (n=7) subtypes, from studies in which response data were available.

The highly proliferative nature of this subtype is further supported by the finding of high Ki-67 mRNA expression (MKI67) (FIG. 13) and nuclear Ki-67 staining as assessed by IHC analysis (BL1+BL2=70% vs. other subtypes=42%; P<0.05) (FIGS. 14A-14B). Enrichment of proliferation genes and increased Ki-67 expression in basal-like TNBC tumors suggest that this subtype would preferentially respond to antimitotic agents such as taxanes (paclitaxel or docetaxel) (Chakravarthy A B, et al. Clin Cancer Res. 2006; 12(5):1570-1576; Bauer J A, et al. Clin Cancer Res. 2010; 16(2):681-690). This is indeed the case when comparing the percentage of patients achieving a pathologic complete response (pCR) in 42 TNBC patients treated with neoadjuvant taxane in 2 studies (Bauer J A, et al. Clin Cancer Res. 2010; 16(2):681-690; Juul N, et al. Lancet Oncol. 2010; 11(4):358-365). In these combined studies, TNBC patients whose tumors correlated to the basal-like (BL1 and BL2) subtype had a significantly higher pCR (63%; P=0.042) when treated with taxane-based therapies as compared with mesenchymal-like (31%) or LAR (14%) subtypes (FIG. 15).

The BL2 subtype displays unique gene ontologies involving growth factor signaling (EGF pathway, NGF pathway, MET pathway, Wnt/β-catenin, and IGF1R pathway) as well as glycolysis and gluconeogenesis (FIG. 3). Likewise, the BL2 subtype is uniquely enriched in growth factor receptor GE such as EGFR, MET, and EPHA2 (FIG. 13). This subtype has features suggestive of basal/myoepithelial origin as demonstrated by higher expression levels of TP63 and MME (CD10) (FIG. 13).

Figure 16:
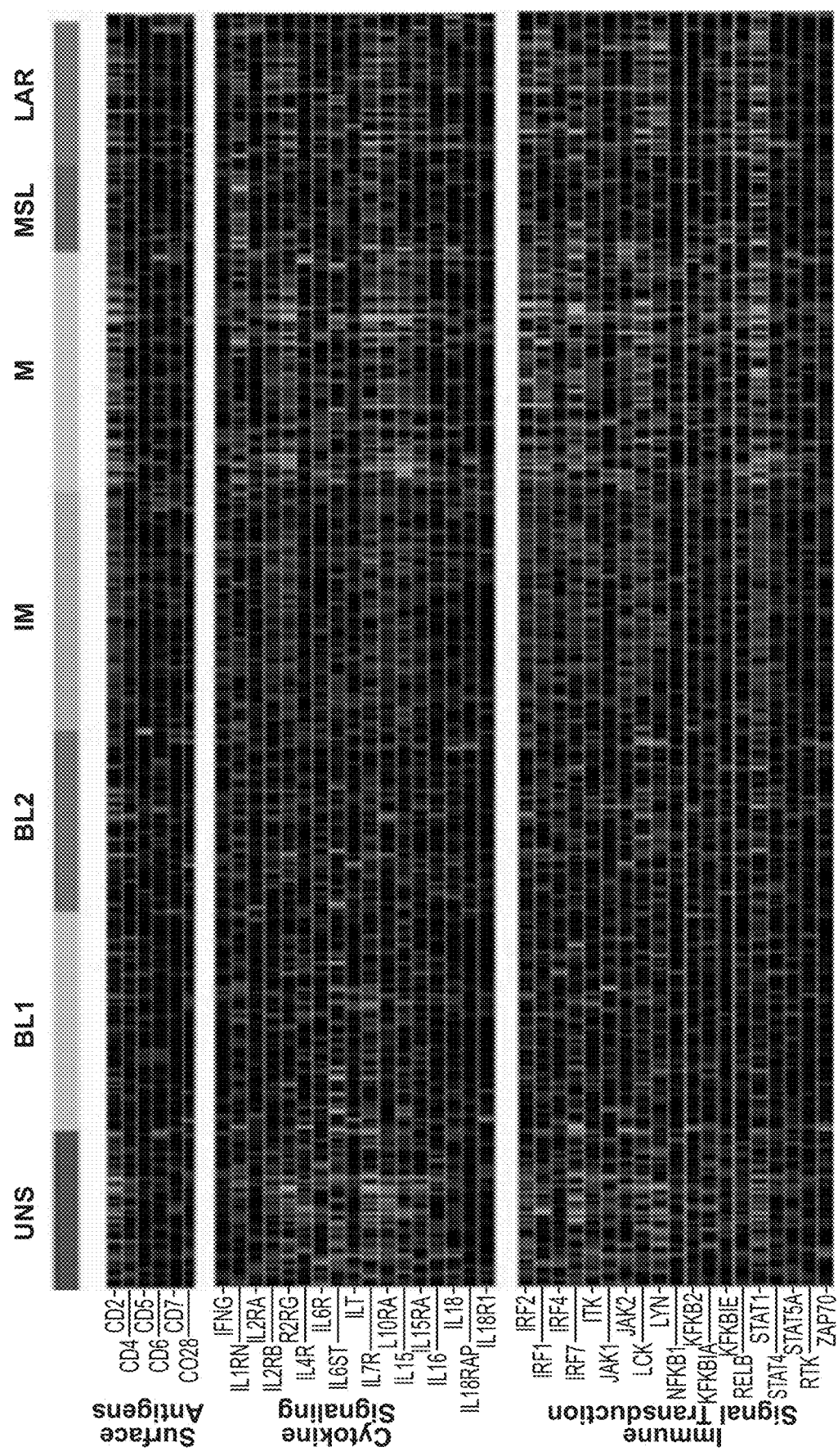
FIG. 16: 1M subtype Is enriched in Immune cell signaling. Heatmaps showing the relative GE (log 2, −2 to 2) for genes involved in immune cell surface antigens, cytokines, immune cell signal transduction, complement, chemokine, and antigen presentation across TNBC subtypes (as in FIG. 3).
Figure 16:
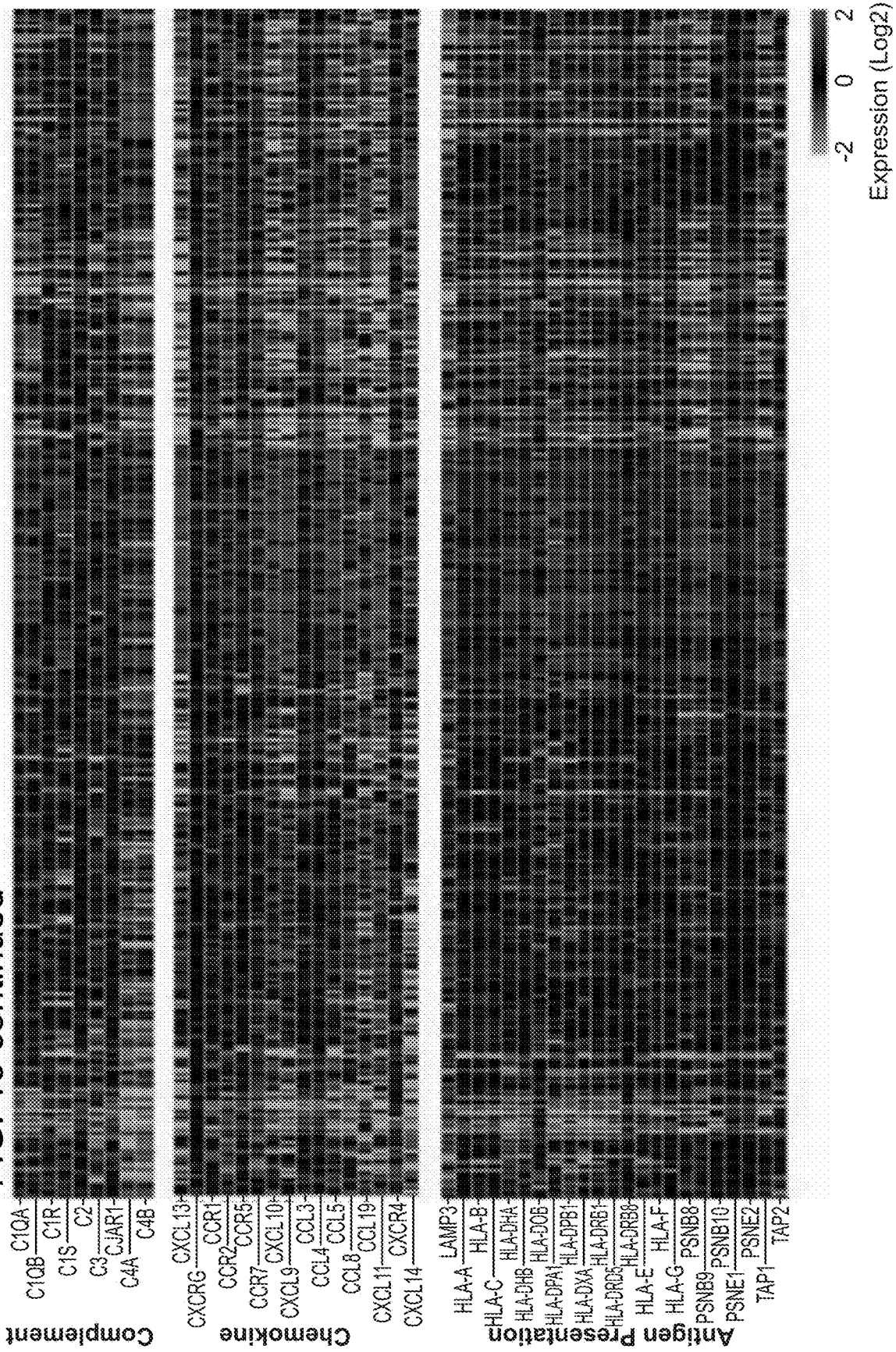

IM subtype. The IM subtype is enriched for gene ontologies in immune cell processes. These processes include immune cell signaling (TH1/TH2 pathway, NK cell pathway, B cell receptor [BCR] signaling pathway, DC pathway, and T cell receptor signaling), cytokine signaling (cytokine pathway, IL-12 pathway, and IL-7 pathway), antigen processing and presentation, and signaling through core immune signal transduction pathways (NFKB, TNF, and JAK/STAT signaling) (FIG. 3). The IM signaling is evidenced by immune signal transduction GE (FIG. 13), in addition to immune cell-surface antigens, cytokine signaling, complement cascade, chemokine receptors and ligands, and antigen presentation (FIG. 16). Since a similar proportion of samples that were microdissected fell into the IM subtype, it is likely that the IM characteristics are unique to the tumor cells themselves and not a reflection of immune cell infiltrate (FIG. 10). Immune signaling genes within the IM subtype substantially overlap with a gene signature for medullary breast cancer, a rare, histologically distinct form of TNBC that despite its high-grade histology is associated with a favorable prognosis (Bertucci F, et al. Cancer Res. 2006; 66(9):4636-4644).

M and MSL subtypes. The M subtype displays a variety of unique gene ontologies that are heavily enriched in components and pathways involved in cell motility (regulation of actin by Rho), ECM receptor interaction, and cell differentiation pathways (Wnt pathway, anaplastic lymphoma kinase [ALK] pathway, and TGF-β signaling) (FIG. 3). The MSL subtype shares enrichment of genes for similar biological processes with the M subtype, including cell motility (Rho pathway), cellular differentiation, and growth pathways (ALK pathway, TGF-β signaling and Wnt/β-catenin pathway). However, unique to the MSL are genes representing components and processes linked to growth factor signaling pathways that include inositol phosphate metabolism, EGFR, PDGF, calcium signaling, G-protein coupled receptor, and ERK1/2 signaling as well as ABC transporter and adipocytokine signaling (FIG. 3).

The prevalence of cell differentiation and growth factor signaling pathways is illustrated by expression of TGF-β signaling pathway components (TGFB1L1, BGN SMAD6, SMAD7, NOTCH1, TGFB1, TGFB2, TGFB3, TGFBR1, TGFBR2, and TGFBR3), epithelial-mesenchymal transition-associated (EMT-associated) genes (MMP2, ACTA2, SNAI2, SPARC, TAGLN, TCF4, TWIST1, ZEB1, COL3A1, COL5A2, GNG11, ZEB2, and decreased E-cadherin [CDH1] expression), growth factors (FGF, IGF, and PDGF pathways), and Wnt/β-catenin signaling (CTNNB1, DKK2, DKK3, SFRP4, TCF4, TCF7L2, FZD4, CAV1, CAV2, and CCND2) (FIG. 13). The MSL subtype is also uniquely enriched in genes involved in angiogenesis, including VEGFR2 (KDR), TEK, TIE1, and EPAS1 as well as immune signaling evidenced by an overlap in GE unique to the IM subtype (FIG. 16).

One interesting difference between the M and MSL subtypes is that the MSL subtype expresses low levels of proliferation genes (FIG. 13). This decreased proliferation is accompanied by enrichment in the expression of genes associated with stem cells (ABCA8, PROCR, ENG, ALDHA1, PER1, ABCB1, TERF2IP BCL2, BMP2, and THY1), numerous HOX genes (HOXA5, HOXA10, MEIS1, MEIS2, MEOX1, MEOX2, and MSX1), and mesenchymal stem cell-specific markers (BMP2, ENG, ITGAV, KDR, NGFR, NT5E, PDGFRB, THY1, and VCAM1) (FIG. 13). The signaling pathway components differentially expressed in the M and MSL groups share similar features with a highly dedifferentiated type of breast cancer called metaplastic breast cancer, which is characterized by mesenchymal/sarcomatoid or squamous features and is chemoresistant (Gibson G R, et al. Am Surg. 2005; 71(9):725-730).

Figure 17:
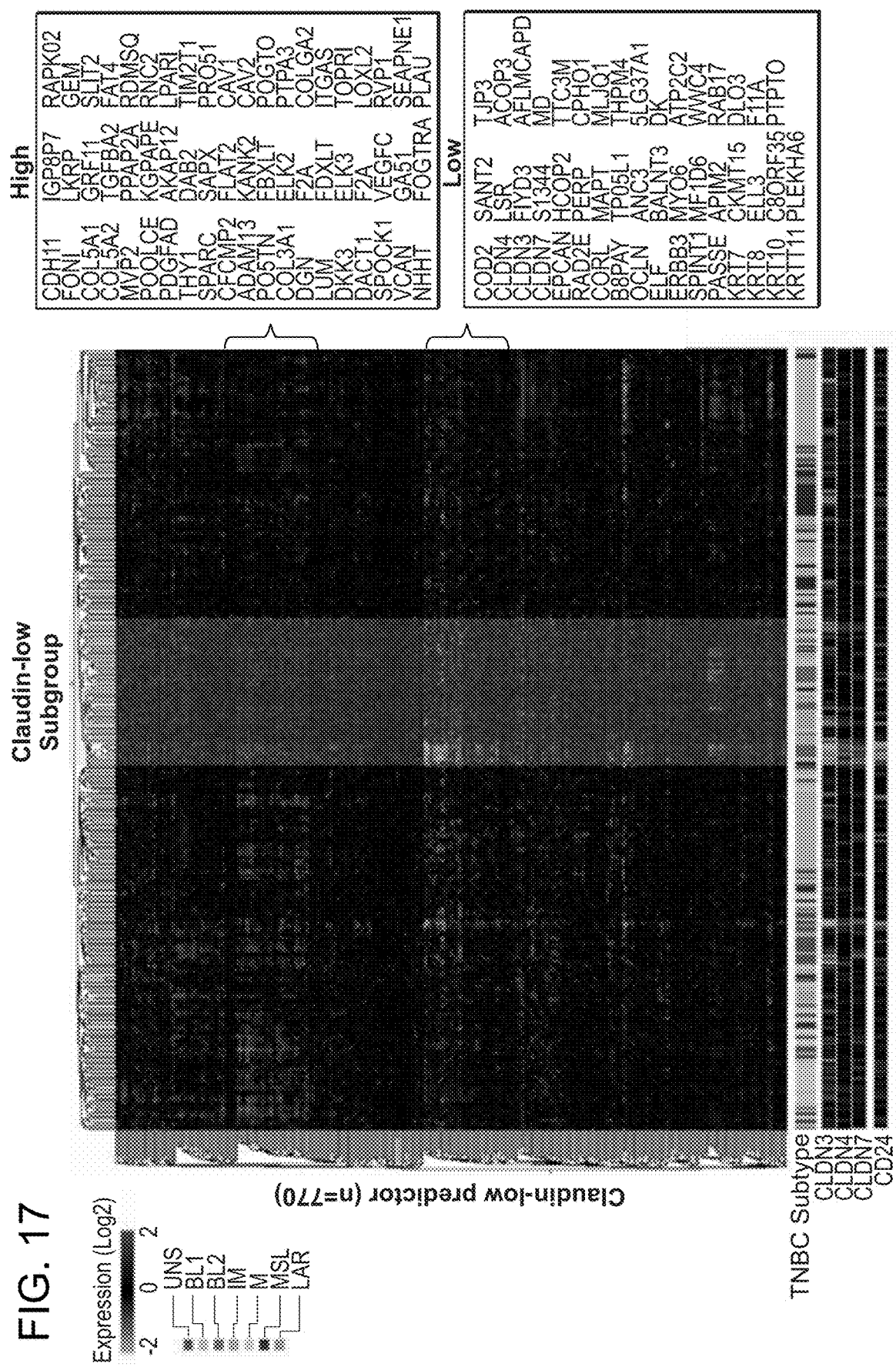
FIG. 17: The claudin-Iow predictor gene set identifies a sub-population of MSL tumors. Unsupervised hierarchical clustering was performed on the training TNBC tumors using genes (n=770) unique to the claud in•low subgroup [26]. Displayed to the right of the heatmap are the genes that are most differentially expressed (either high or low) in the claudin-Iow tumor set. Colorbar displays the TNBC subtype and heatmaps show relative levels (Log 2) 01 claudins (3, 4 and 7) and CD24, markers of this subgroup.

The MSL subtype also displays low expression of claudins 3, 4, and 7, consistent with a recently identified claudin-low subtype of breast cancer (FIGS. 13 and 17; Prat et al., Breast Cancer Res, 2010; 12(5):R68). Hierarchical clustering of TNBC GE profiles using the claudin-low gene predictor set (n=770) segregated a portion of the M and MSL subtypes with low claudin (3, 4, and 7), cytokeratin (KRT7, KRT8, KRT18, and KRT19), and CD24 expression (FIG. 17; Prat A, et al. Breast Cancer Res. 2010; 12(5):R68). This population of claudin-low-expressing tumors also had high expression of genes associated with EMT (FBN1, MMP2, PDGFRB, THY1, SPARC, TGFBR2, PDGFRA, TWIST, CAV1, CAV2, and SERPINE1).

Figure 18A:
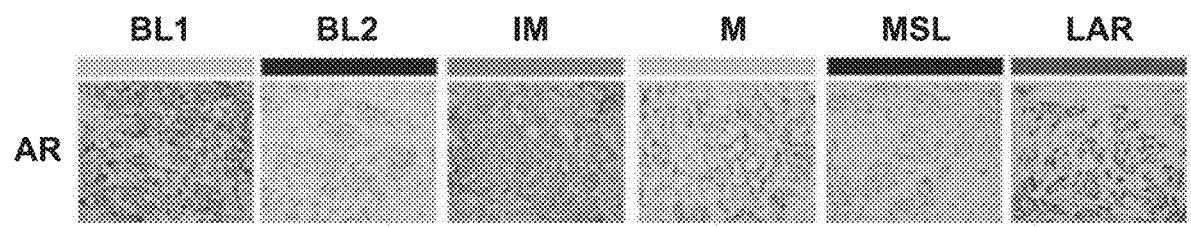
FIGS. 18A-18B: TNBC tumor subtypes differentially stain for AR by IHC. (18A) IHC staining for AR from 20 tumors with representative samples from each TNBC subtype shown. (18B) Dot plot showing the quantification of nuclear AR staining based on intensity and the percent of nuclei staining positive for AA in 20 tumors; Note, in some cases one dot represents overlapping dots from multiple tumors.
Figure 18B:
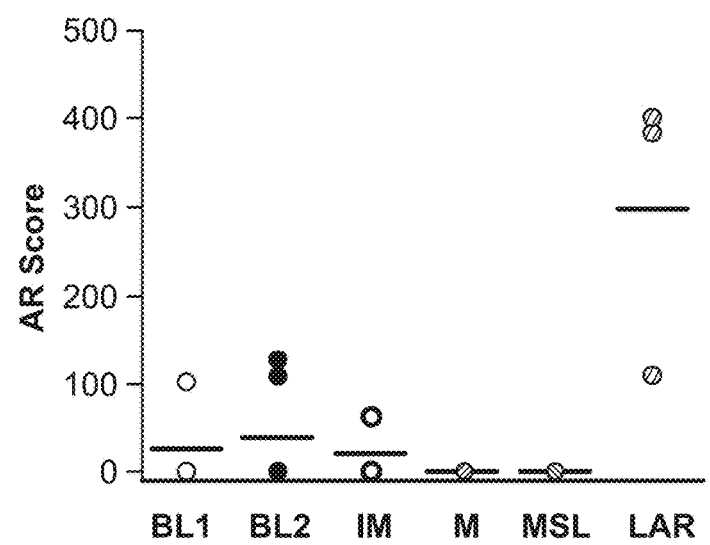
Figure 19A:
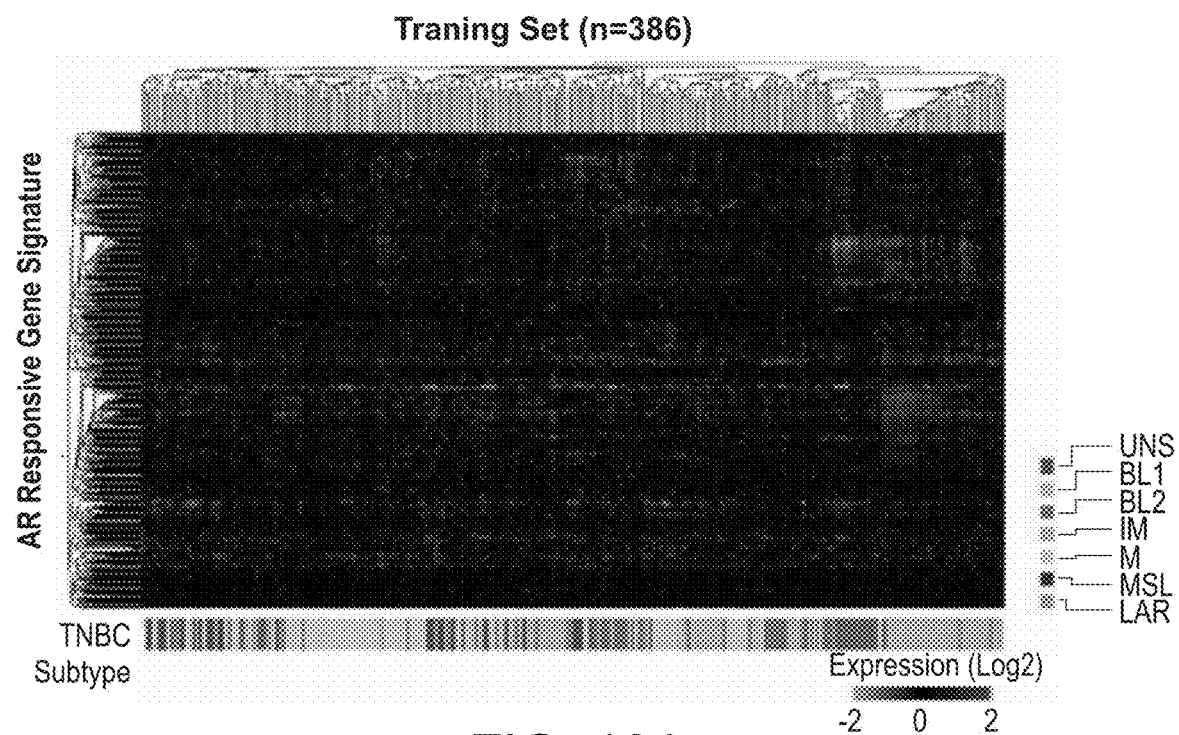
FIGS. 19A-19B: An androgen-inducible gene signature segregates LAR tumors. Hierarchical clustering was performed on both the (19A) training and (19) validation TNBC tumor sel using a 559 androgen-inducible gene signature (Hayes M J et al. Clin Cancer Res. 2008; 14(13):4038-4044).
Figure 19B:
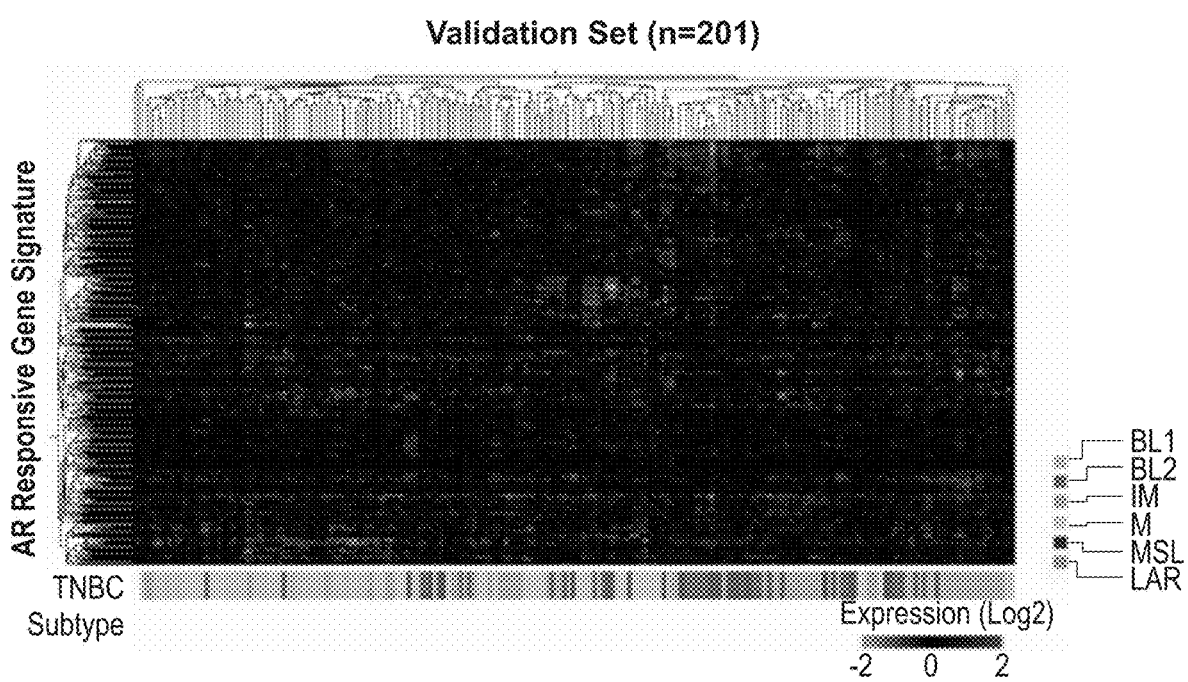
Figure 20A:
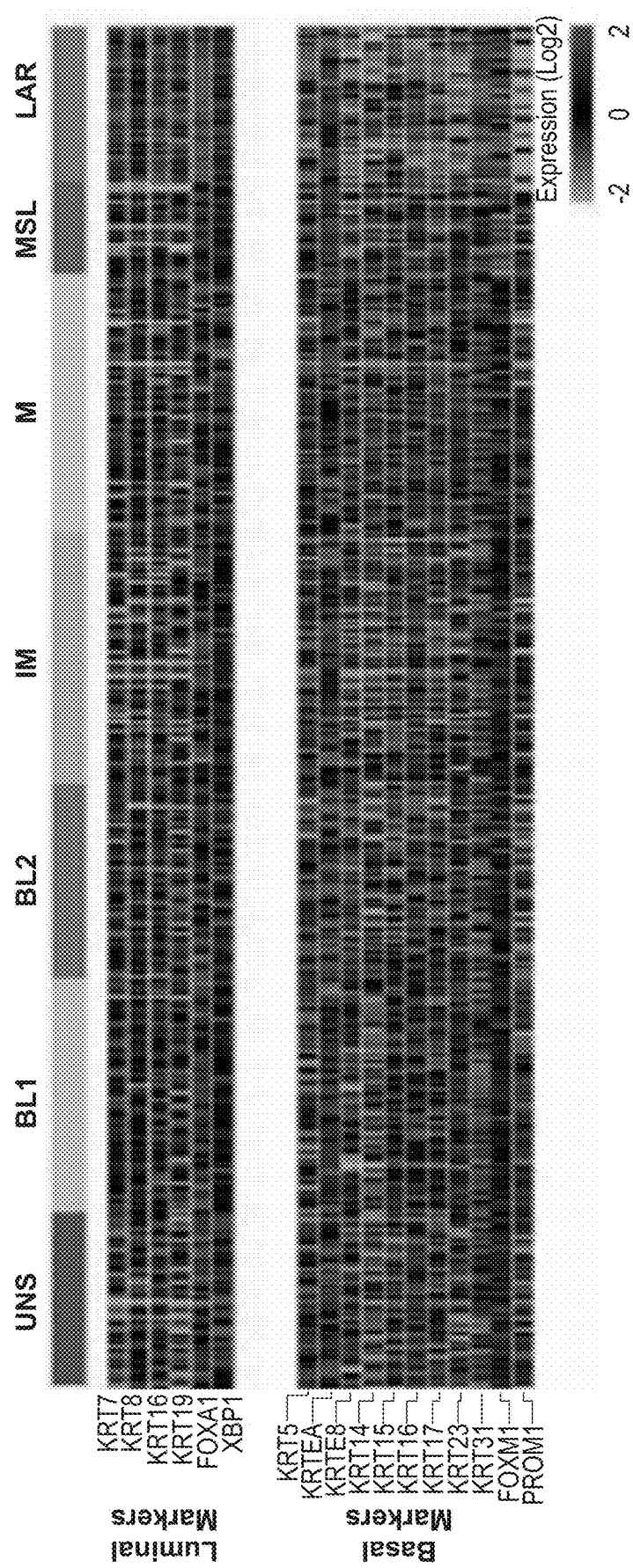
FIGS. 20A-20B: TNBC subtypes differentially correlate with the intrinsic molecular subtypes. (20A) Heatmaps show relative GE (log 2, −2 to 2) of luminal and basal markers of breast cancer across all TNBC subtypes. (20B) Bar graph shows the distribution of intrinsic molecular subtypes of breast cancer (luminal A and B, normal breast-like, HER2, basal-like or unclassified) within each TNBC subtype (UNS=unstable, BL1=basal-like 1, B12=basal-like 2, 1M=immunomodulatory, M=mesenchymal-like, MSL=mesenchymal stem-like and LAR=luminal AR) as determined by best-fit Spearman correlation to the intrinsic centroids.

LAR subtype. GE in the LAR group was the most differential among TNBC subtypes. This subtype is ER negative, but gene ontologies are heavily enriched in hormonally regulated pathways including steroid synthesis, porphyrin metabolism, and androgen/estrogen metabolism (FIG. 3). Whether other hormone-regulated pathways such as androgen receptor (AR) signaling, previously reported in ER-negative breast cancer (Hayes M J et al. Clin Cancer Res. 2008; 14(13):4038-4044), could be responsible for the GE patterns in this LAR subtype was investigated. Indeed, it was found that AR mRNA was highly expressed, on average at 9-fold greater than all other subtypes (FIG. 13). Tumors within the LAR group also expressed numerous downstream AR targets and coactivators (DHCR24, ALCAM, FASN, FKBP5, APOD, PIP, SPDEF, and CLDN8) (FIG. 13). In addition to AR mRNA expression, AR protein expression was investigated by IHC across all TNBC tumors from the Vanderbilt cohort (n=20). The percentage of tumor cells scored with nuclear AR staining and the intensity of staining were significantly higher in the LAR subtype (>10-fold; P<0.004) compared with all other TNBC subtypes (FIGS. 18A-18B). Hierarchical clustering was performed using an AR-activated gene signature (Chen C D, et al. Nat Med. 2004; 10(1):33-39) on the training and validation TNBC tumor data sets. Hierarchical clustering with this signature segregated the majority of LAR tumor profiles from other subtypes (FIGS. 19A-19B). Tumors in the LAR subtype display luminal GE patterns, with FOXA1, KRT18, and XBP1 among the most highly expressed genes (FIG. 20A). Others have previously described a breast cancer subgroup expressing AR termed molecular apocrine (Chen C D, et al. Nat Med. 2004; 10(1):33-39). While we do not have detailed pathology reports for all of the LAR tumors in this study, the TNBC subgroup GE centroids were used to correlate the apocrine samples from GSE-1561 (Farmer P, et al. Oncogene. 2005; 24(29):4660-4671; Table 1). The GE profiles of all 6 apocrine tumors (GSM26883, GSM26878, GSM26886, GSM26887, GSM26903, and GSM26910)

described in the study strongly correlate with LAR, suggesting that the LAR TNBC subtype is composed of AR-driven tumors that include the molecular apocrine subtype.

Figure 20B:
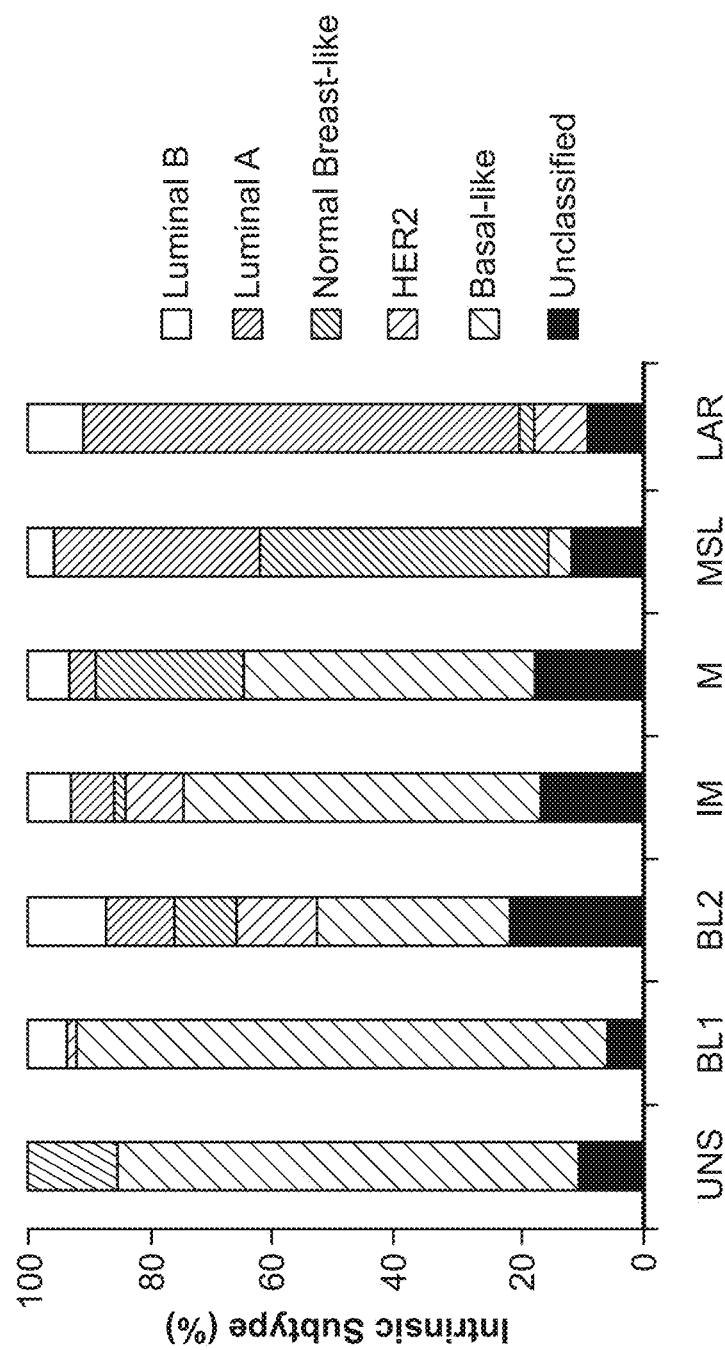

Intrinsic molecular breast cancer subtype classification of TNBC. Breast cancers can be classified as luminal or basal-like, dependent on their expression of different cytokeratins. TNBC tumor subtypes display differential expression of both basal-like cytokeratins (KRT5, KRT6A, KRT6B, KRT14, KRT16, KRT17, KRT23, and KRT81) and luminal cytokeratins (KRT7, KRT8, KRT18, and KRT19) across the subtypes (FIGS. 20A-20B). The UNS, BL1, BL2, and M subtypes expressed higher levels of basal cytokeratin expression, while tumors within the LAR subtype lacked basal cytokeratin expression and expressed high levels of luminal cytokeratins and other luminal markers (FOXA1 and XBP1) (FIG. 20A). In addition to cytokeratin expression, breast cancers can be classified by an "intrinsic/UNC" 306-gene set into 5 major subtypes (basal-like, HER2-like, normal breast-like, luminal A, and luminal B) (Hu Z, et al. BMC Genomics. 2006; 7:96). Since TNBCs are largely considered basal-like, each of the 386 TNBC tumor profiles were correlated to the intrinsic gene set centroids of the 5 molecular subtypes, as previously described (Hu Z, et al. BMC Genomics. 2006; 7:96). Tumors were assigned to 1 of the molecular subtypes based on the highest correlation coefficient between each TNBC expression profile and the 5 molecular subtype centroids. This analysis resulted in 49% (n=188) of the TNBC training set classified as basal-like, 14% (n=54) as luminal A, 11% (n=42) as normal breast-like, 8% (n=31) as luminal B, 5% (n=19) as HER2, and 13% (n=52) as unclassifiable (FIG. 20B). This confirms that most TNBCs classify to the basal-like molecular subtype. Both the unstable tumors and BL1 tumors correlated strongly to the basal-like intrinsic molecular classification (76% and 85%, respectively). However, the BL2, IM, and M subtypes only moderately correlated to the basal-like molecular class (31%, 58%, and 47%, respectively), with a portion of tumors unclassified (22%, 17%, and 18%, respectively) (FIG. 20B). The M and MSL subtypes displayed the largest portion of tumors classified as normal breast-like (25%, and 46%, respectively). The BL2, M, and MSL subtypes were a mixture of classifications, suggesting the intrinsic classification system may not be suitable for characterizing these TNBC subtypes. The majority of TNBC tumors within the LAR subtype were classified as either luminal A or luminal B (82%), and none were classified as basal-like, further supporting the luminal origin of the LAR subtype (FIGS. 20A-20B). While only 49% of the tumors were classified as basal-like according to the intrinsic gene set, IHC staining performed on the Vanderbilt subset of tumors (n=25) showed that the majority (88%) of TNBCs stained positive for the basal cytokeratins CK5/6. Additionally, 56% of the Vanderbilt tumors stained positive for EGFR, similar to a previous study that found 56% of n=929 pooled from 34 studies that were positive for EGFR or CK5/6 (Yang X R, et al. J Natl Cancer Inst. 2011; 103(3):250-263). There were no statistical differences between CK5/6 and EGFR staining across TNBC subtypes. Thus, the majority of TNBCs display a basal-like phenotype by IHC, while only approximately half correlate to the basal-like intrinsic gene set.

Figure 21A:
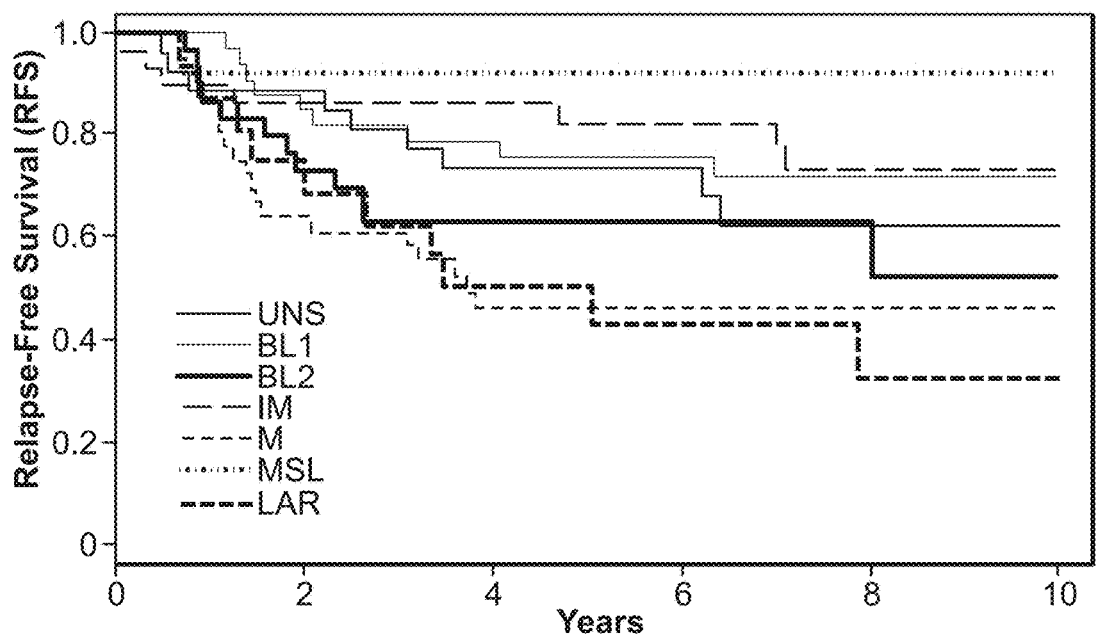
FIGS. 21A-21D TNBC subtypes differ in relapse-free survival and distant metastasis-free survival. Kaplan-Meier plot showing (21A) to-year RFS or (21C) DMFS in TNBC subtypes. RFS (21B) and DMFS (21D) hazard ratios (bold) and 95% CI (parentheses) for patients from TNBC subtypes. Shaded boxes indicate significant (P<0.05) comparisons.
Figure 21B:
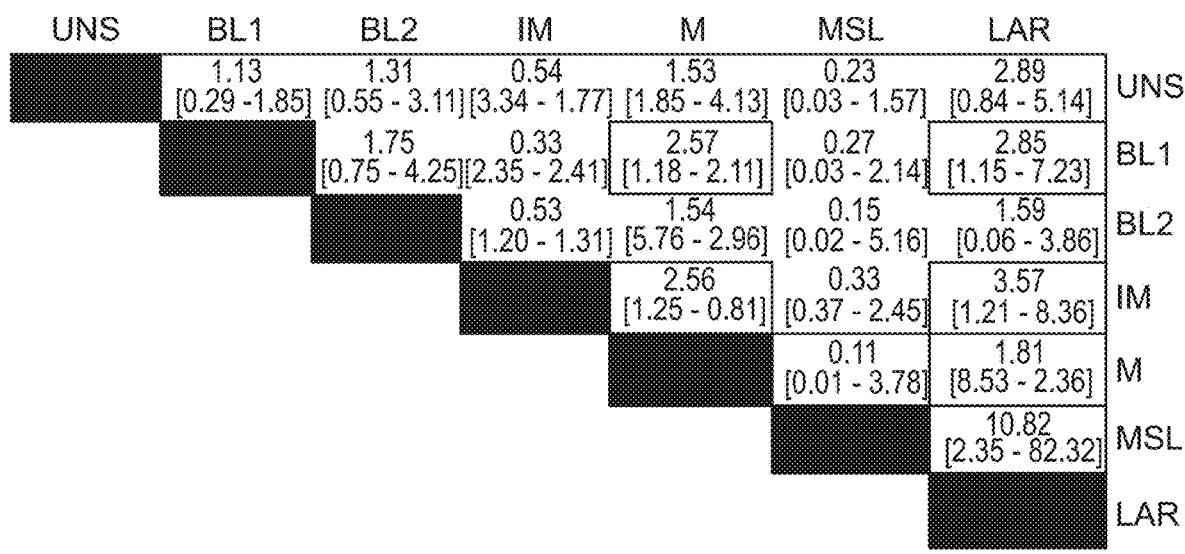
Figure 21C:
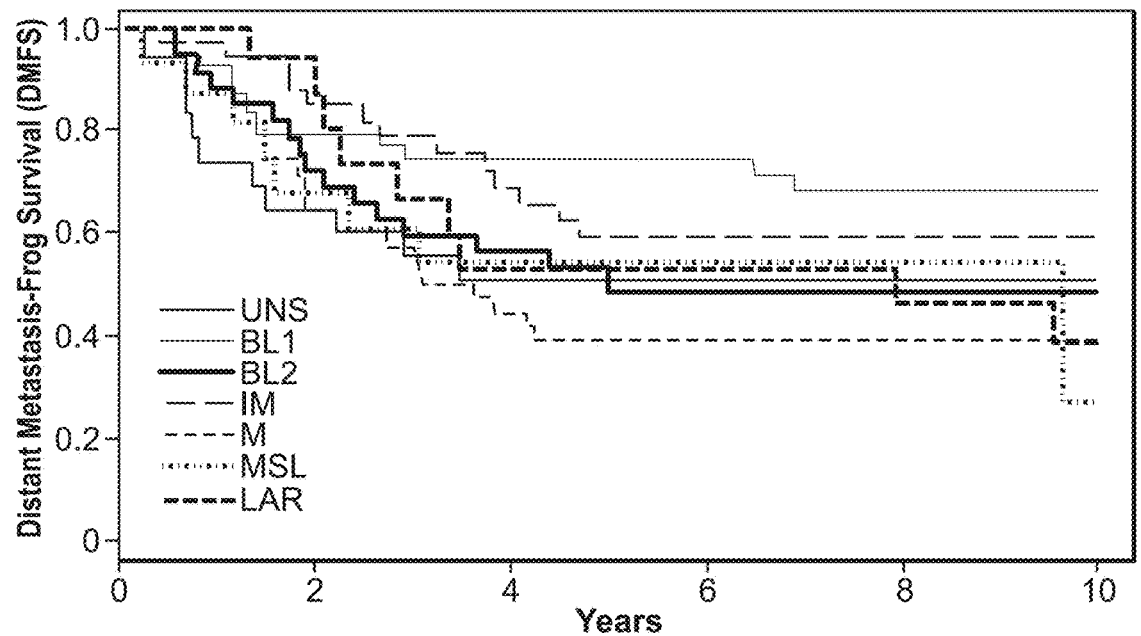
Figure 21D:
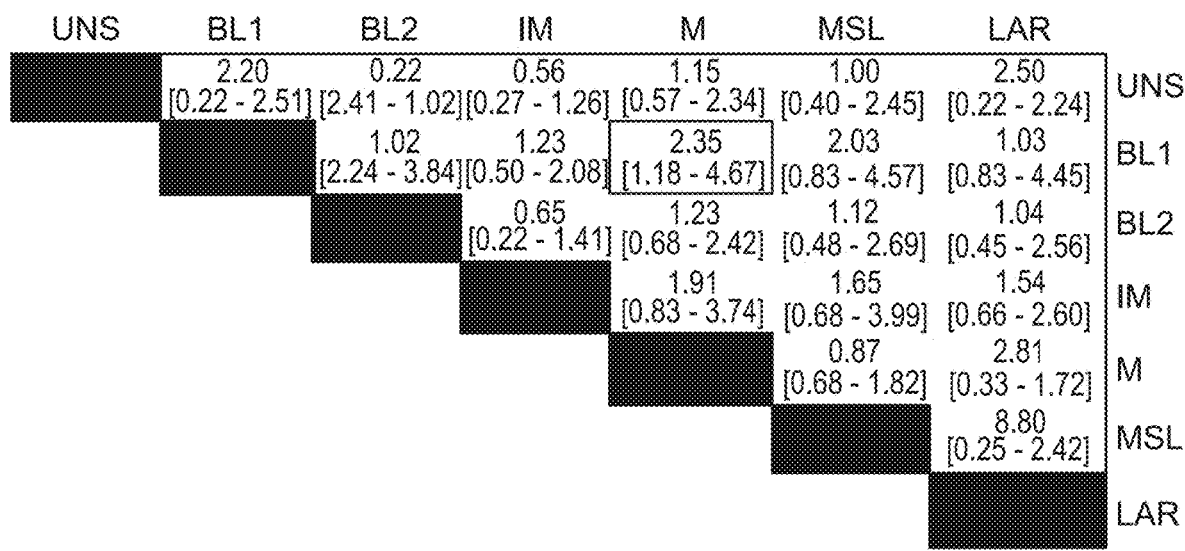
Figure 22A:
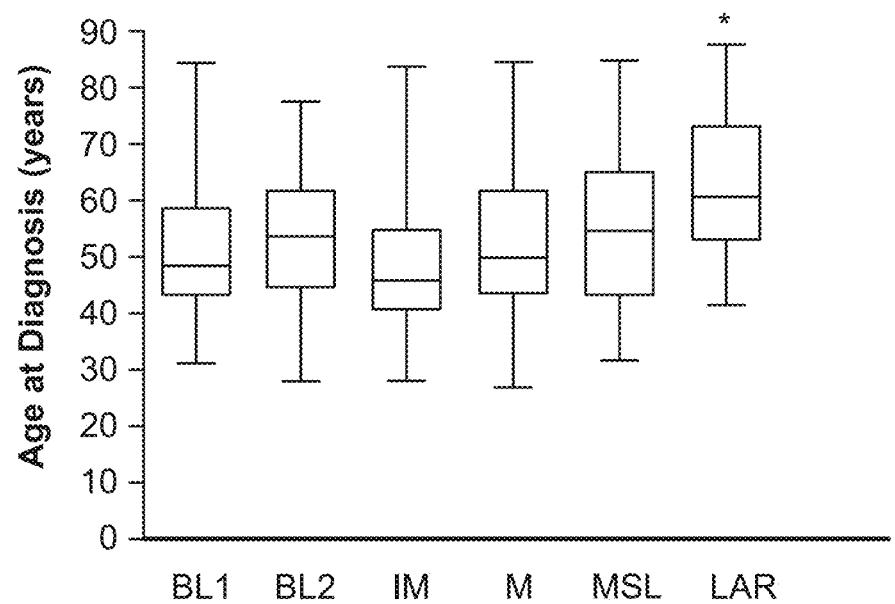
FIGS. 22A-22B: TNBC subtypes differ in age, but are similar size upon diagnosis. Box plots show the median (horizontal line), range (rectangle) and SD (error bars) of (22A) age at diagnosis and (22B) tumor size (mm) between TNBC subtypes (as in FIG. 3); •P=9.0e-6
Figure 22B:
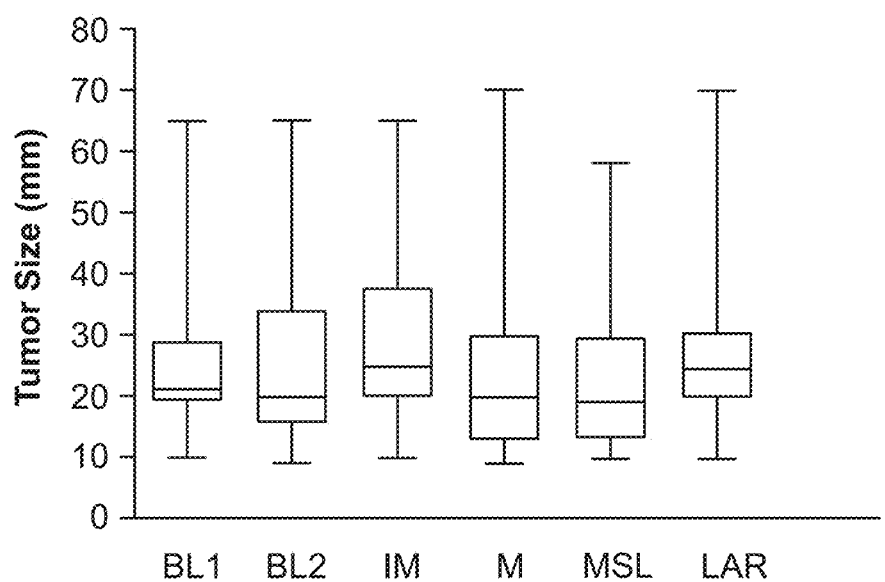

Patient relapse-free survival and distant-metastasis-free survival differs among TNBC subtypes. Relapse-free survival (RFS) between TNBC subtypes was significantly different (log-rank test; P=0.0083) (FIG. 21A), despite variability of therapy and duration of treatment. RFS was significantly decreased in the LAR subtype compared with the BL1 (hazard ratio [Hr]=2.9), IM (Hr=3.2), and MSL (Hr=10.5) subtypes (P<0.05) (FIG. 21B). RFS was significantly decreased in the M subtype compared with BL1 (Hr=2.6) and IM (Hr=2.9), while the MSL subtype had higher RFS than the M subtype (FIG. 21B). Distant-metastasis-free survival (DMFS) did not vary between TNBC subtypes (log-rank test; P=0.2176), but the M subtype had a significantly higher Hr compared with the BL1 (Hr=2.4, P <0.05) and IM (Hr=1.9, P<0.06) subtypes (FIGS. 21C and 21D). The increased RFS in the absence of increased DMFS for patients in the LAR subtype suggests that recurrence is due to local relapse. Tumor size and grade were not significantly different among TNBC subtypes, but age at diagnosis was greater in the LAR subtype (P<0.0001), potentially contributing to decreased RFS of this subtype compared with other subtypes (FIGS. 22A-22B).

TNBC cell line models for TNBC subtypes. Cell line models would facilitate preclinical experiments to define differential drug sensitivity of the distinct subtypes within this heterogeneous disease. Using the bimodal filtering approach on ER, PR, and HER2 GE levels from 2 independent breast cancer cell line data sets (GSE-10890 and ETABM-157), 24 and 25 triple-negative cell lines were identified in the GSE-10890 and ETABM-157 GE data sets, respectively. Of the cell lines present in both data sets, nearly all had similar predictions of triple-negative status by bimodal filtering. Discrepancies in some cell lines (e.g., HCC1500 and HCC1937) may be the result of differences in culturing methods and/or loss of hormone receptor expression over time in culture. Analysis of these 2 data sets identified 30 nonoverlapping TNBC cell lines.

Figure 23A:
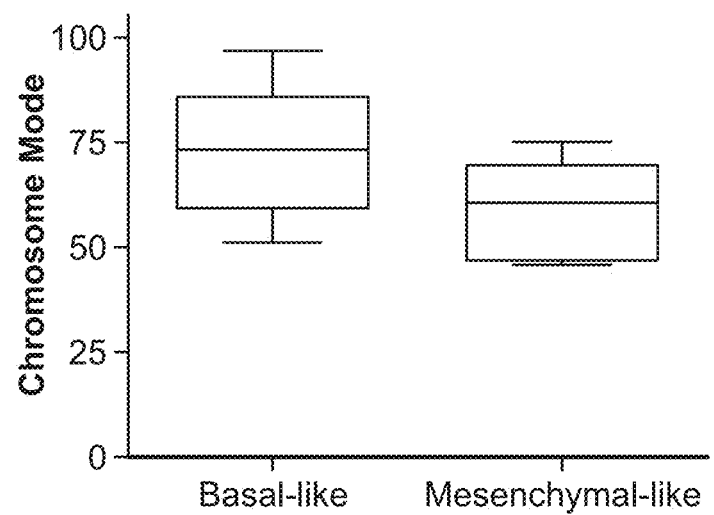
FIGS. 23A-23B: Chromosomal Aberrations in TNBC cell lines. (23A) Box plots depicting the average number of chromosomes (mode) in breast cancer cell lines correlating to basal-like (n=8) vs. mesenchymal-like (n=6) subtypes. (23B) Box plots depicting the average number of chromosomal rearrangements (translocations, inversions, and deletions) in basal-like vs. mesenchymal-like subtypes. Chromosome mode and rearrangements were obtained from Departments of Pathology and Oncology, Univ of Cambridge (www.path.cam.ac.uk/~pawefish/cell%20line%20catalogues/breast-cell-lines.htm). *P<0.01 by unpaired t-test.
Figure 23B:
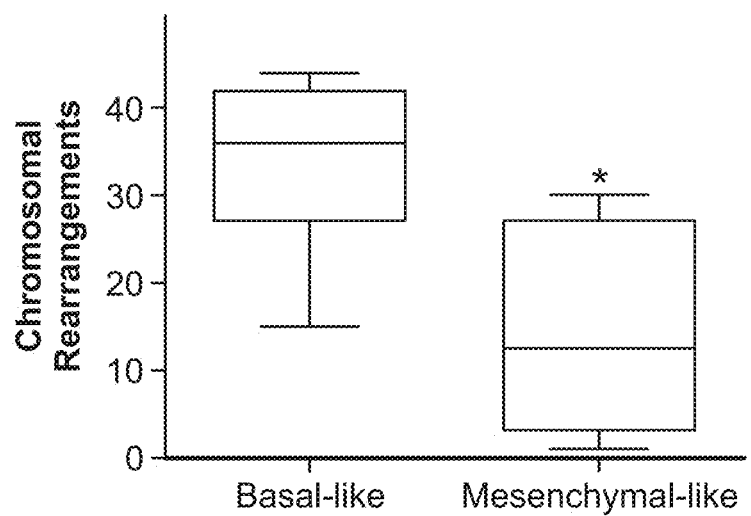

GE profiles from the cell lines were correlated to the centroids for each of the 6 TNBC subtypes. The majority of cell lines (27 of 30) were assigned to TNBC subtypes (Table 3), except for BT20, HCC1395, and SW527, which had low correlations (<0.1) or were similar between multiple subtypes (P >0.05). Of the 7 cell lines that contained known BRCA1 and BRCA2 mutations, 5 correlated with the BL1 or BL2 subtypes (HCC1937, HCC1599, HCC2157, HCC3153, and SUM149PT), consistent with this subtype containing tumors with defects in DNA repair pathways (Table 3) and gene ontologies enriched for GE involved in cell cycle and DNA repair functions (FIG. 13). Additionally, cell lines in the BL1 and BL2 subtypes were more genomically unstable, displaying significantly more chromosomal rearrangements than those in the mesenchymal subtypes (M and MSL) (average translocations, inversions, deletions=34 versus 14, respectively; P<0.01), as determined by SKY-FISH (www.path.cam.ac.uk/~pawefish/index.html) (FIGS. 23A-23B). All cell lines that correlated to the basal-like intrinsic molecular subtype were in the BL1, BL2, or IM subtypes (Table 3). Only 2 cell lines (HCC1187 and DU4475) were placed into the IM subtype, suggesting that the IM subtype is underrepresented in cell culture.

Cell lines in the M and MSL subtypes were generated from highly dedifferentiated tumors derived from unique pathologies (e.g., HS578T, carcinosarcoma; and SUM159PT, anaplastic carcinoma) and expressed both epithelial and mesenchymal components. All cell lines assigned to the M and MSL subtype have spindle-like morphology in 2D culture (CAL-120, CAL-51, MDA-MB-157, MDA-MB-231, MDA-MB-436, SUM159PT, HS578T, and BT549) or stellate-like morphology in 3D (Kenny P A et al., Mol Oncol, 2007; 1:84-96). Five cell lines matched to the LAR subtype (MDA-MB-453, SUM185PE, HCC2185, CAL-148, and MFM-223).

Two distinct basal groups (A and B) have been identified by GE profiling of breast cancer cell lines (Neve R M, et al.

Figure 24:
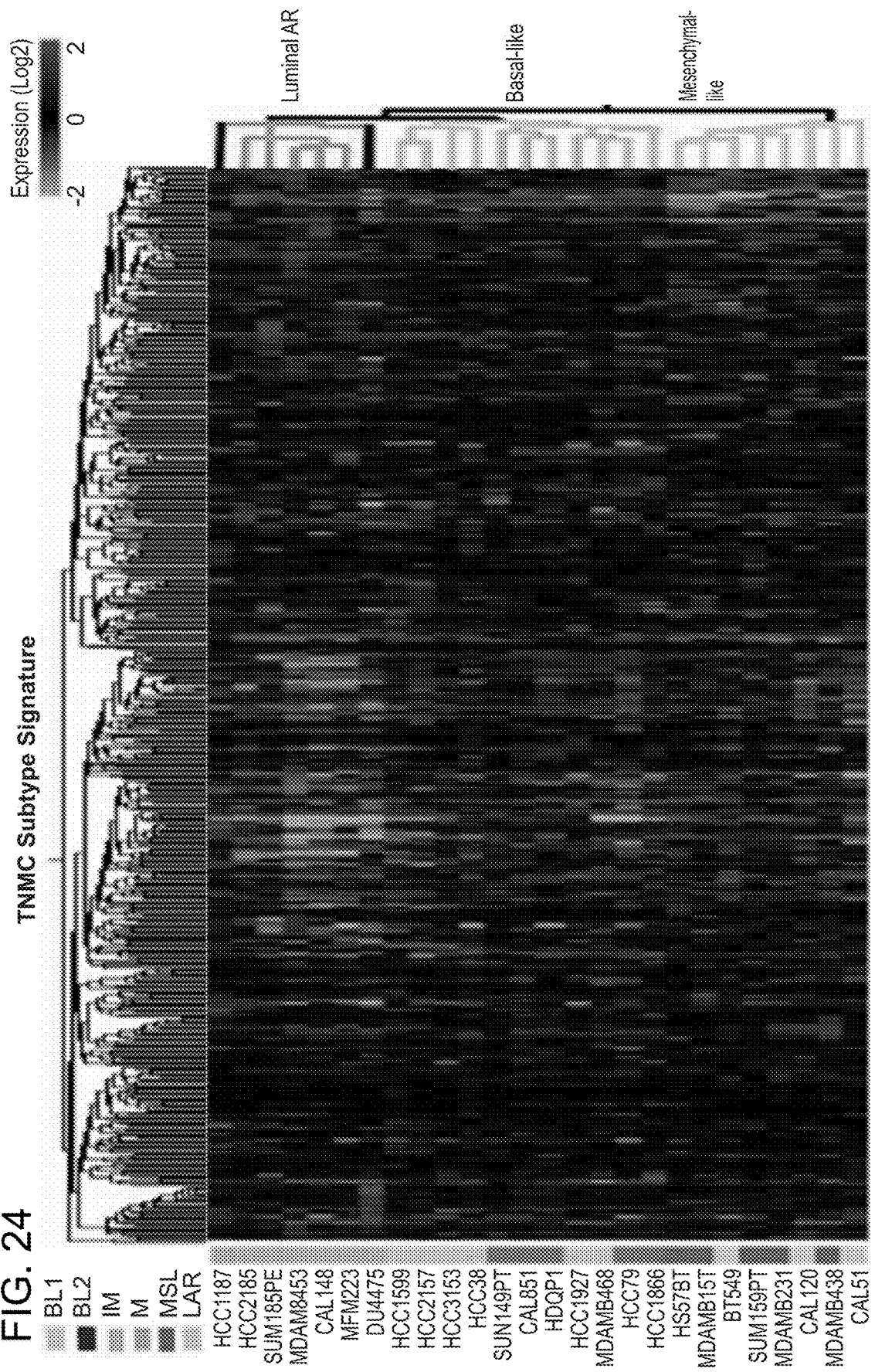
FIG. 24: TNBC cell lines cluster in three major groups: luminal AR, basal-like and mesenchymal-like. Unsupervised hierarchical clustering of TNBC cell lines performed on genes unique to TNBC subtypes (n=2188). Colorbar shows the best correlation of cell lines to the TNBC subtypes.

Cancer Cell. 2006; 10(6):515-527). Basal A cell lines display epithelial characteristics and are associated with BRCA1 gene signatures, while basal B cell lines are more invasive and display mesenchymal and stem/progenitor-like characteristics. The GE analyses revealed that the majority of basal A cell lines belong to the BL1 and BL2 subtypes, while the majority of basal B cell lines fall into the M and MSL subtypes (Table 3). Hierarchical clustering analysis was tested on all TNBC cell lines using the most differentially expressed genes from the tumors to determine whether GE patterns of the cell lines are similar within TNBC subtypes (FIG. 24). Three clusters were identified: LAR, containing all 4 LAR lines; basal-like, containing lines in the BL1 and BL2 subtypes; and mesenchymal-like, containing lines in the M and MSL subtypes. This clustering analysis indicates that TNBC cell lines can be classified into 3 main groups: basal-like (BL1 and BL2); mesenchymal-like (M and MSL); and LAR. This classification will be used in subsequent sections.

TNBC cell lines have differential sensitivity to therapeutic agents. There are a variety of targeted therapies undergoing clinical investigation in patients with TNBC including those targeting PARP (Farmer H, et al. Nature. 2005; 434(7035): 917-921), AR (Agoff N S et al. Am J Clin Pathol. 2003; 120(5):725-731), Src (Finn R S, et al. Breast Cancer Res Treat. 2007; 105(3):319-326), and PI3K/mTOR (Marty B, et al. Breast Cancer Res. 2008; 10(6):R101) signaling. The panel of TNBC cell lines was used to assess differential response to several agents targeting these pathways. For comparison primary human mammary epithelial cells (HMECs) were analyzed in cell viability assays. The half-maximal inhibitory concentration ($IC_{50}$) values were determined for the following drugs [targets]: veliparib (ABT-888) [PARP1/2]; olaparib (AZD2281) [PARP1/2]; cisplatin [DNA]; bicalutamide [AR]; 17-DMAG [Hsp90]; dasatinib [Src/Abl]; and NVP-BEZ235 [PI3K and mTOR].

Figure 4A:
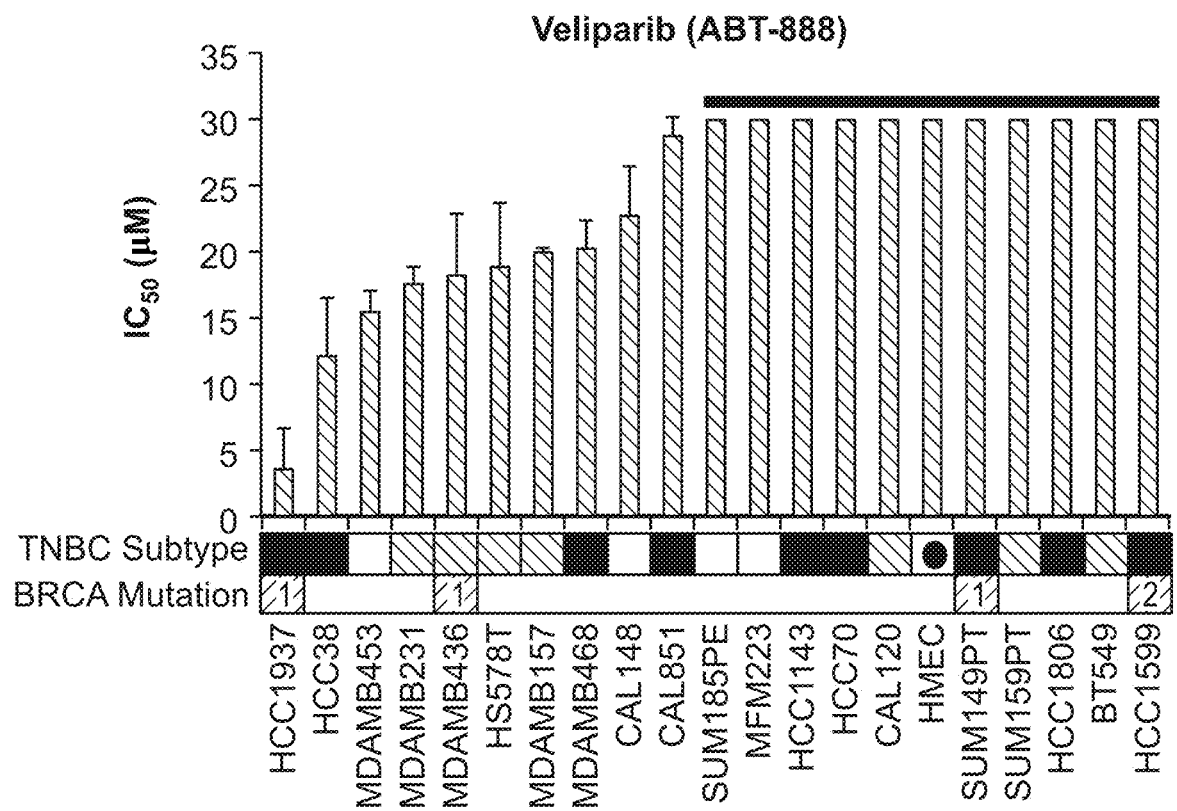
FIGS. 4A-4F: Basal-like TNBC subtypes have differential sensitivity to DNA-damaging agents. IC50 values for TNBC cell lines treated with PARP inhibitors (4A) veliparib, (4C) olaparib, or (4E) cisplatin for 72 hours. Error bars reflect SEM for 3 independent experiments. Black horizontal lines above various bars in the plots indicate cell lines that failed to achieve an IC50 at the highest dose of veliparib (30 μM), olaparib (100 μM), or cisplatin (30 μM). Cell lines that carry BRCA1 or BRCA2 mutations (pink) are displayed below the graph. Dot plot shows the log distribution of drug sensitivity to PARP inhibitors (B) veliparib, (4D) olaparib, or (4F) cisplatin in the basal-like subtypes (BL=BL1+BL2), the mesenchymal-like subtypes (ML=M+MSL), and the LAR subtype. Black horizontal bars in the dot plot indicate the mean IC50 for each of the subtypes. *Statistically significant differences in IC50 values of BL compared with ML (P=0.017) and LAR (P=0.032), as determined by Mann-Whitney U test.
Figure 4B:
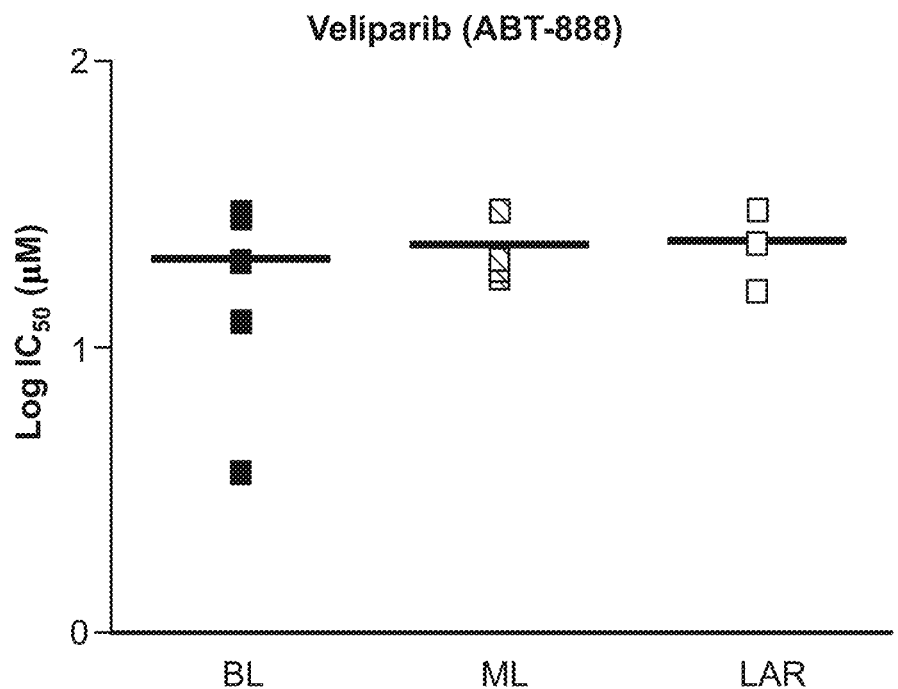
Figure 4C:
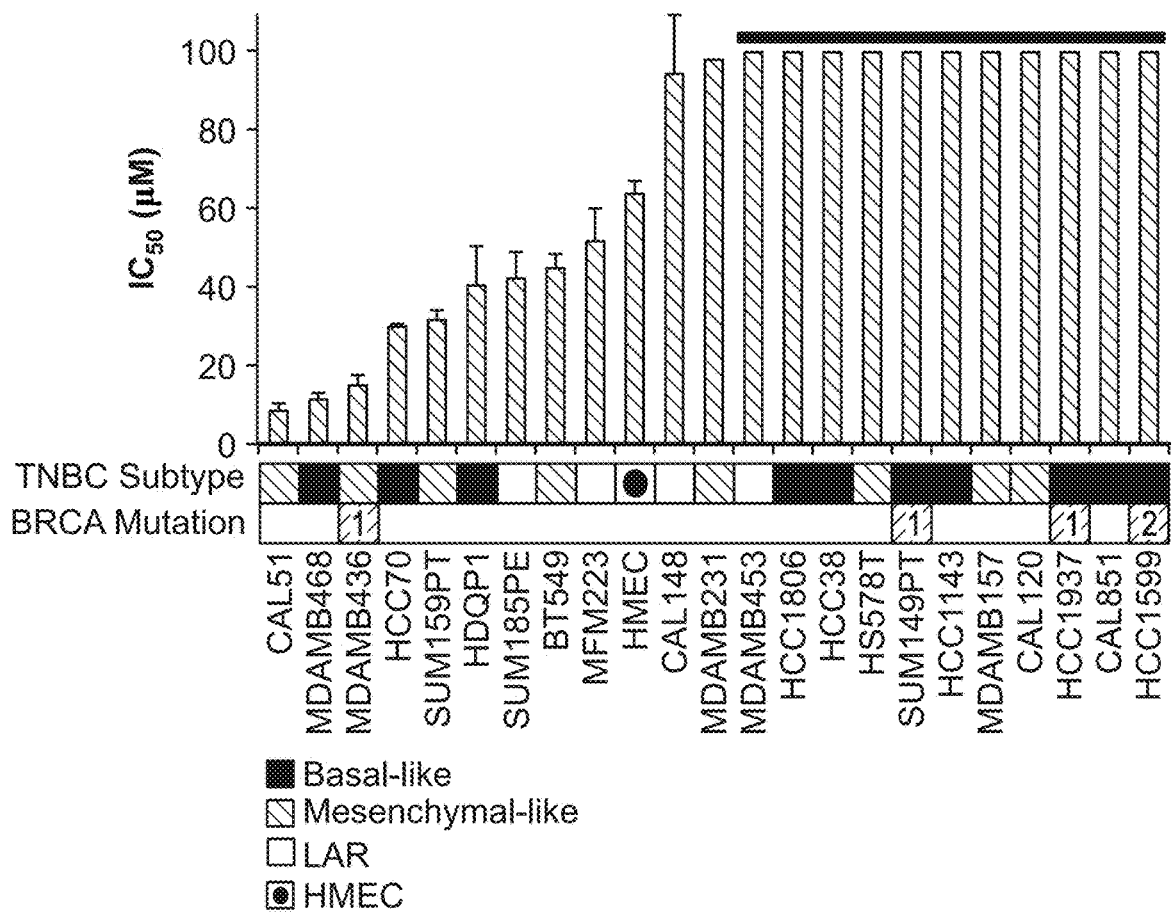
Figure 4D:
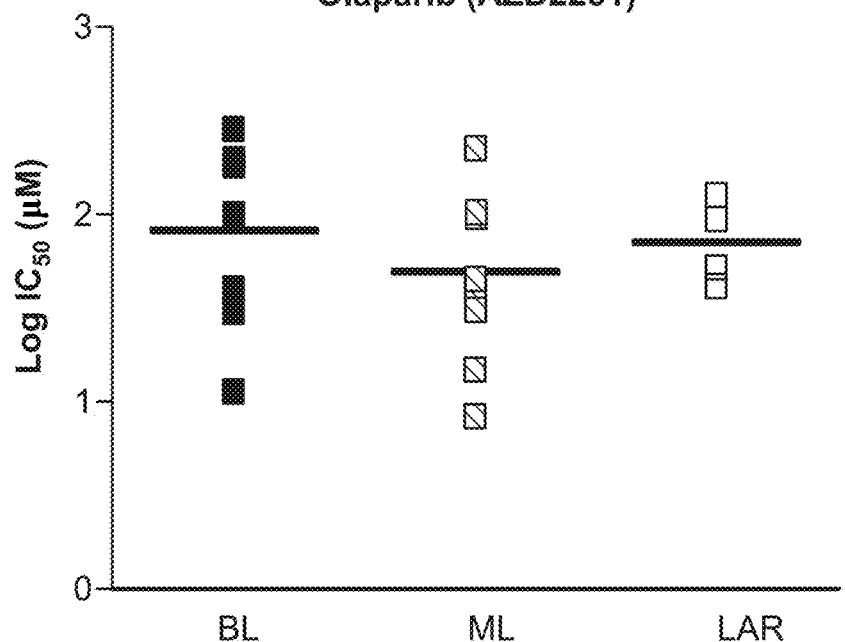
Figure 4E:
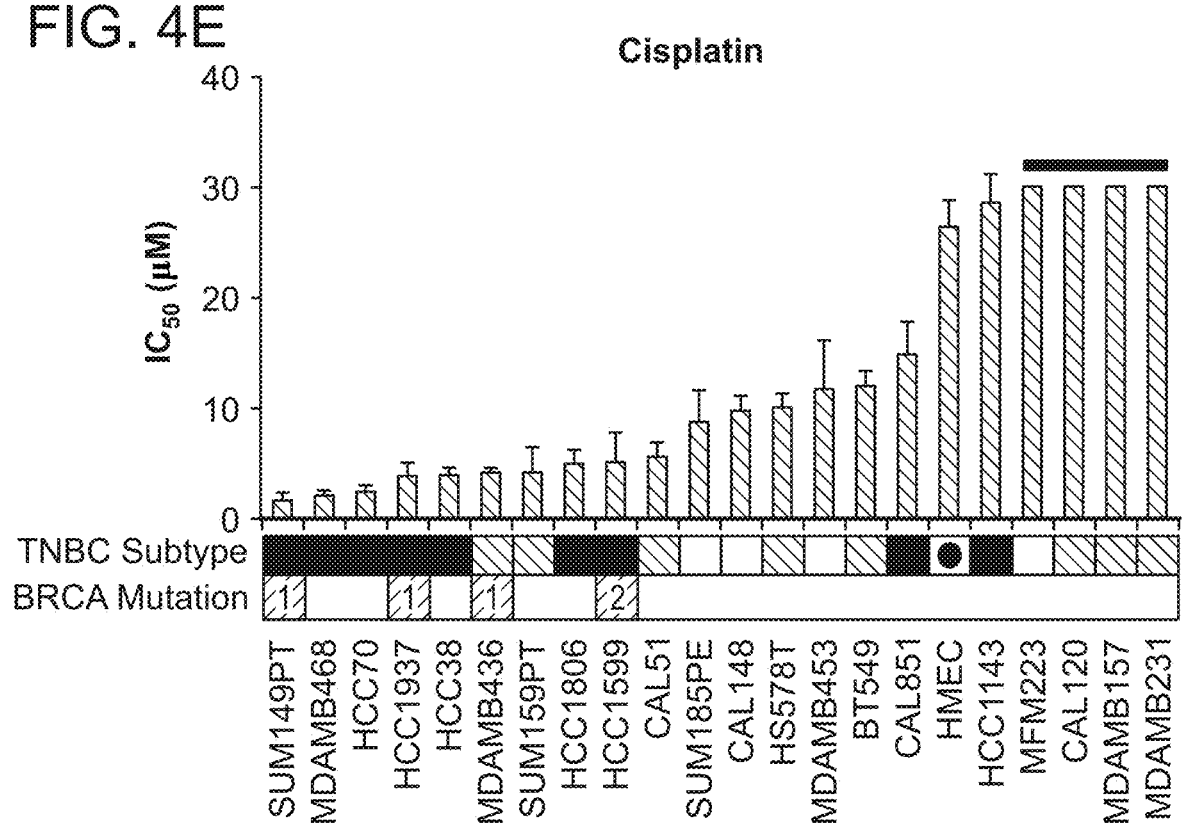
Figure 4F:
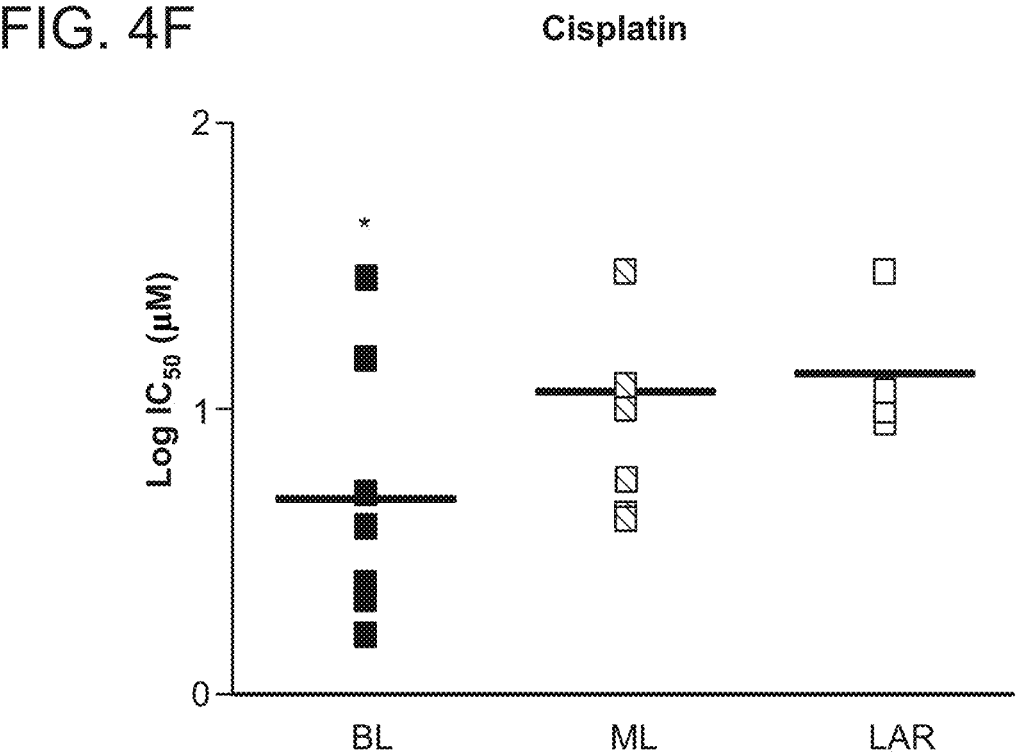

Cell-cycle and DNA damage response genes are elevated in the BL1 and BL2 subtypes (FIG. 13), and 5 of the 7 lines in the cell line panel that carry BRCA1/2-mutations reside in these subtypes (Table 3). Given the previous clinical trial observations with PARP inhibitors and cisplatin (Bhattacharyya A et al. J Biol Chem. 2000; 275(31):23899-23903; Jones P, et al. J Med Chem. 2009; 52(22):7170-7185; Evers B, et al. Clin Cancer Res. 2008; 14(12):3916-3925), it was predicted that these agents would preferentially decrease viability in cell lines with DNA repair defects that are representative of the BL1 and BL2 subtypes. The TNBC cell line panel was treated with the PARP inhibitors veliparib and olaparib, but not all cell lines representative of the basal-like TNBC subtypes were sensitive to PARP inhibition (FIGS. 4A-4D). The BRCA1-null cell line HCC1937 was sensitive to veliparib ($IC_{50}$=4 µM) but not olaparib ($IC_{50}$>100 µM), while the BRCA1-mutant MDA-MB-436 was sensitive to both PARP inhibitors (veliparib $IC_{50}$=18 µM and olaparib $IC_{50}$=14 µM). The BRCA2-mutant cell line HCC1599 lacked sensitivity to either PARP inhibitor (veliparib $IC_{50}$>30 µM and olaparib $IC_{50}$>100 µM). Thus, in addition to BRCA1/2 status, other properties of the tumor may dictate sensitivity to a given PARP inhibitor. Unlike PARP inhibitor sensitivity, basal-like lines were significantly more sensitive to cisplatin than mesenchymal-like lines (average $IC_{50}$=81.1M vs. $IC_{50}$=161.1M, P=0.032) or LAR lines (average $IC_{50}$=81.1M vs. $IC_{50}$=15 µM, P=0.017) (FIGS. 4, E and F). The BRCA1-mutant cells (SUM149PT, HCC1937, and MDA-MB-436) and BRCA2-mutant cells (HCC1599) were among the most sensitive to cisplatin treatment (FIG. 4E).

Figure 5A:
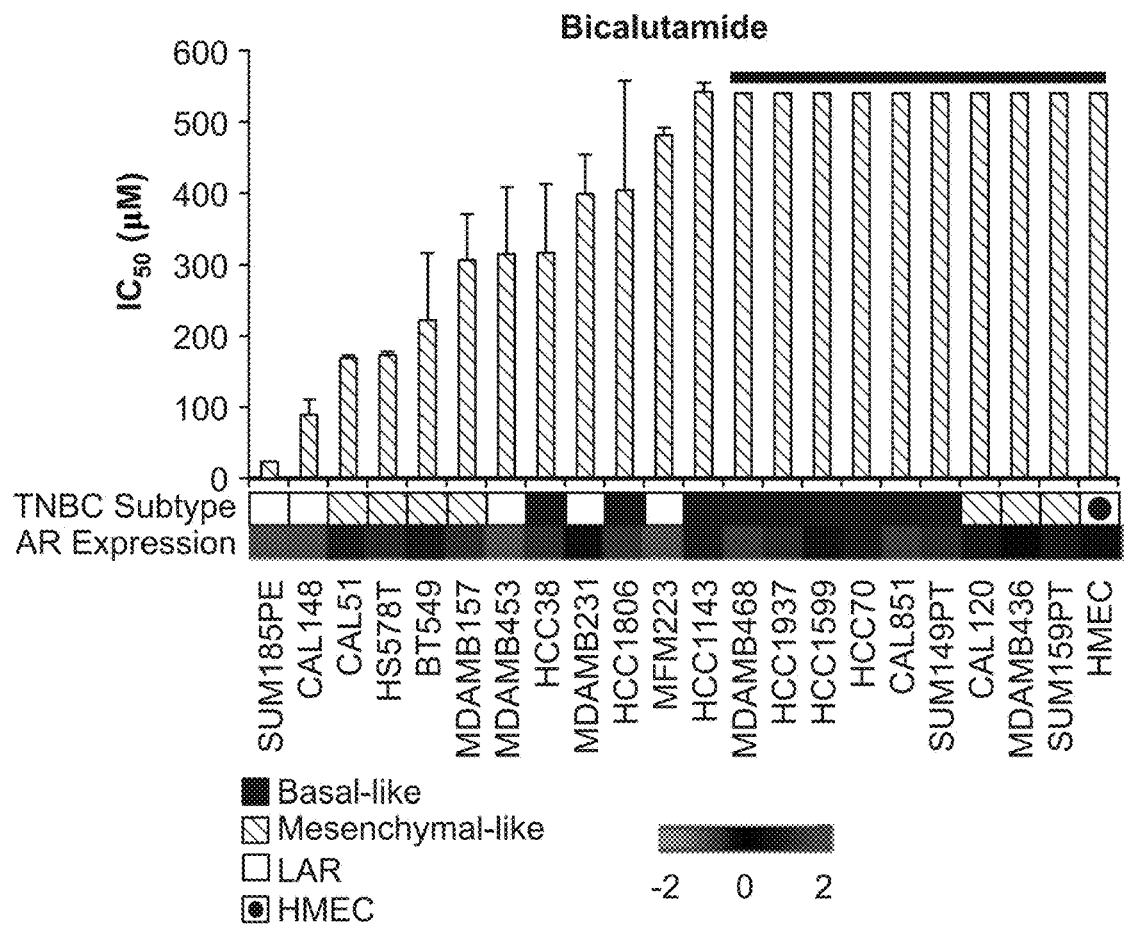
FIGS. 5A-5D: Differential sensitivity of the LAR TNBC subtype to AR and Hsp90 inhibitors. IC50 values for each TNBC cell line after treatment with (5A) bicalutamide or (5C) the Hsp90 inhibitor 17-DMAG for 72 hours. Black bar above bicalutamide indicates cell lines that failed to achieve an IC50. Heat map displays relative AR expression (log 2) across TNBC cell lines. Dot plot shows log distribution of drug sensitivity to (5B) bicalutamide or (5D) 17-DMAG in the basal-like (BL=BL1+BL2), mesenchymal-like (ML=M+MSL), and LAR subtypes. Black horizontal bars in the dot plot indicate the mean IC50 for each of the subtypes. *Statistically significant differences in IC50 values of LAR versus BL (P=0.007) or ML (P=0.038) after bicalutamide and LAR versus BL and ML (P=0.05) after 17-DMAG treatments, as determined by Mann-Whitney U test.
Figure 5B:
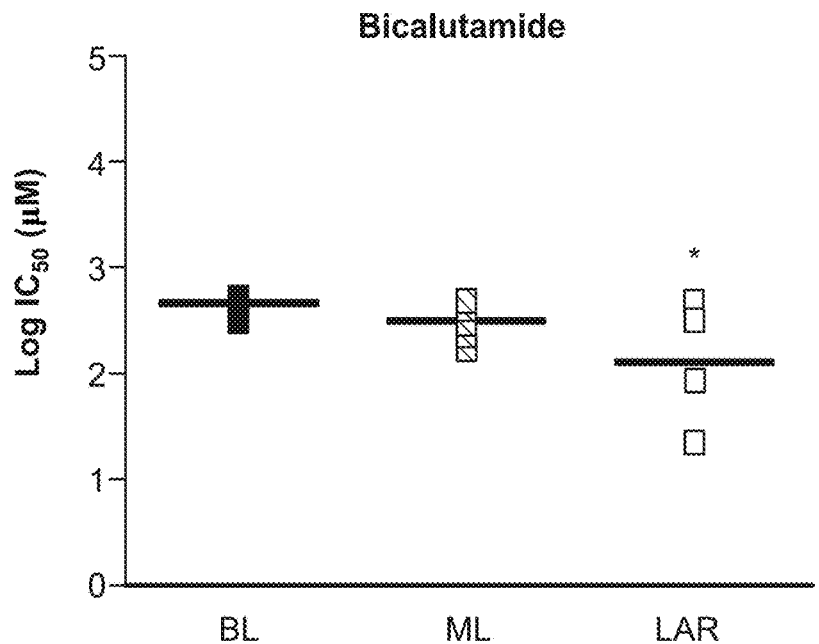
Figure 25A:
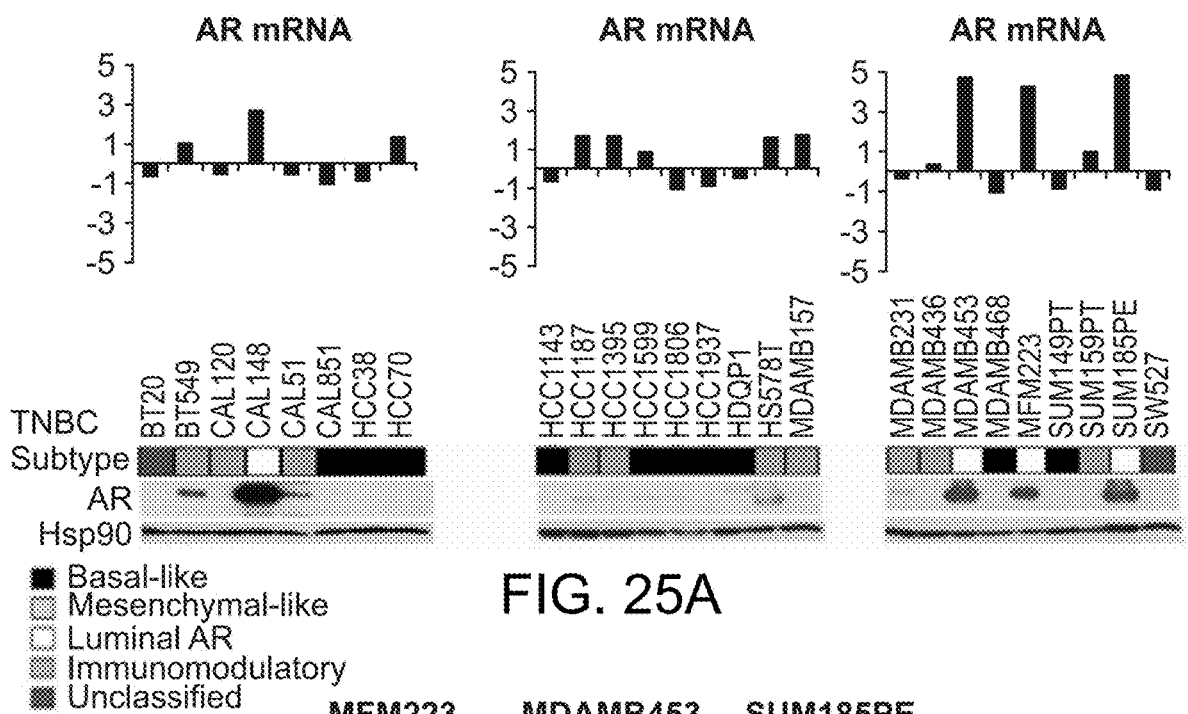
FIGS. 25A-25C: LAR cell lines depend on AR expression for colony formation. (25A) Top panel depicts relative AR mRNA levels obtained from GE microarrays performed on TNBC cell lines (log 2, centered on 0). Color bar identifies TNBC subtype classification for each cell line (immunomodulatory shown in orange and unclassified shown in red). Immunoblots showing relative expression AR protein in TNBC cell lines, Hsp90 serves as a loading control. (25B) AR expression 72 h following transfection with siRNA pools of non-targeting (NT) or targeting AR in MFM-223, MDA-MB-453 and SUM185PE cells. GAPDH expression serves as a loading control. (25C) Colony formation of MFM-223, MDA-MB-453 and SUM185PE cells 14d following siRNA transfection of AR or non-targeting control (NT).

Since cell lines representative of the LAR subtype (MDA-MB-453, SUM185PE, CAL-148, and MFM-223) express high levels of AR mRNA and protein (FIG. 25A), we compared the sensitivity of TNBC cell lines to the AR antagonist bicalutamide (FIGS. 5A and 5B). $IC_{50}$ values for the majority of TNBC cell lines were not achieved using the highest dose of 500 µM. However, all LAR cell lines tested (SUM185PE, CAL-148, MDA-MB-453, and MFM-223) and a subset of mesenchymal-like cell lines that express low levels of AR (HS578T, BT549, CAL-51, and MDA-MB-231) were more sensitive to bicalutamide than basal-like cell lines (average $IC_{50}$=227 µM vs. $IC_{50}$>600 µM, P=0.007; and average $IC_{50}$=361 µM vs. $IC_{50}$>600 µM, P=0.038, respectively) (FIG. 5A).

Figure 5C:
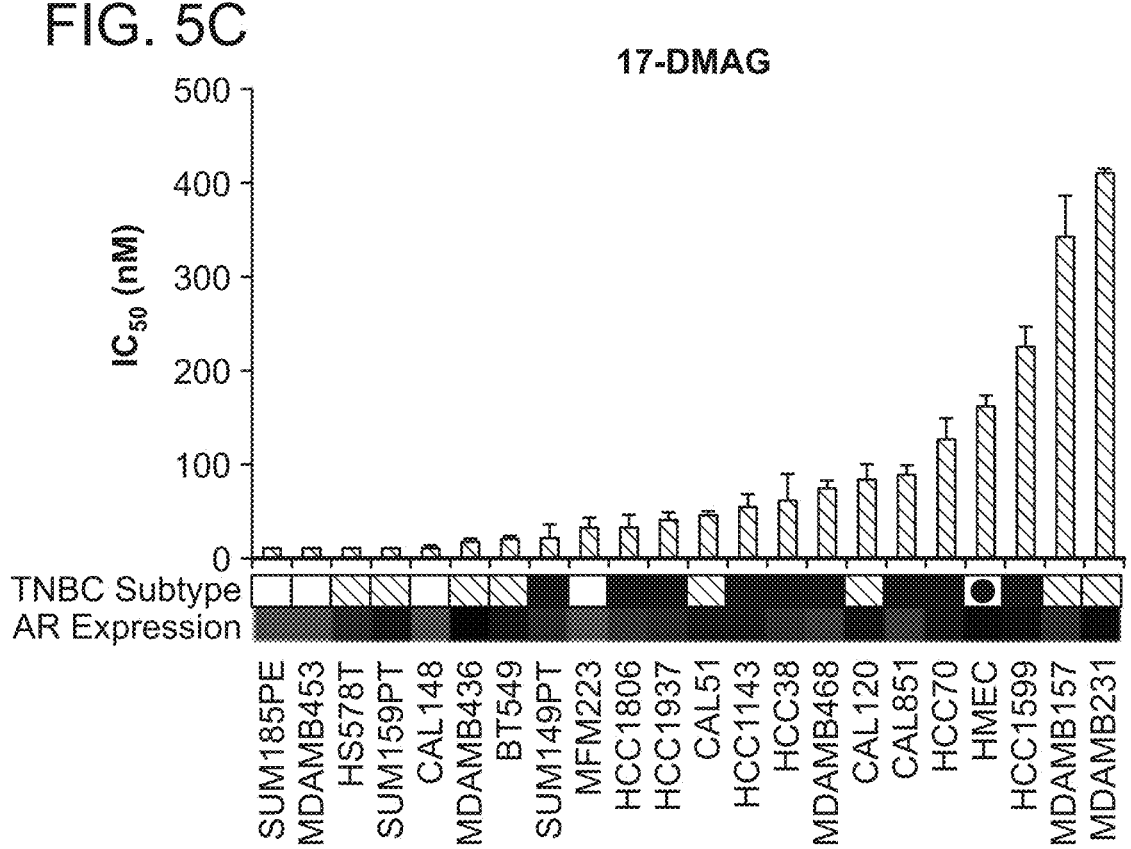
Figure 5D:
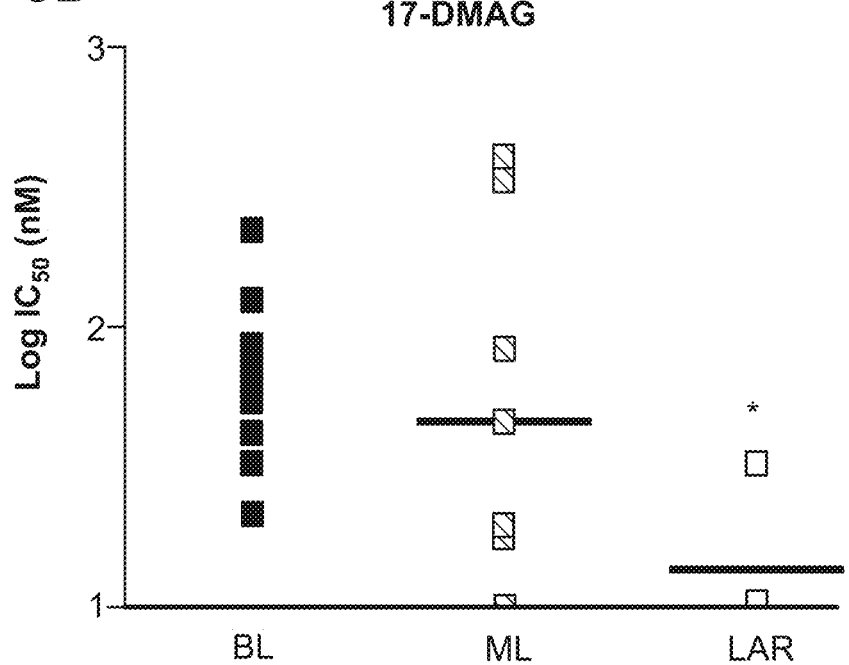

Since AR requires the Hsp90 chaperone for proper protein folding and stability (Solit D B, et al. Clin Cancer Res. 2002; 8(5):986-993), the sensitivity of the cell line panel to an Hsp90 inhibitor, 17-dimethylaminoethylamino-17-demethoxy-geldanamycin (17-DMAG), was determined. Again, the LAR cell lines were more sensitive to 17-DMAG compared with the majority of basal-like (average $IC_{50}$=16 nM vs. $IC_{50}$=81 nM; P=0.004) and mesenchymal-like (average $IC_{50}$=16 nM vs. $IC_{50}$=117 nM; P=0.05) cell lines (FIGS. 5C and 5D), albeit 17-DMAG has many other targets. These data strongly suggest that LAR tumors are driven by AR signaling and AR represents a therapeutic target for this subtype. Importantly, AR status in TNBC patients represents a molecular marker for preselection of patients for antiandrogen therapy.

Figure 25B:
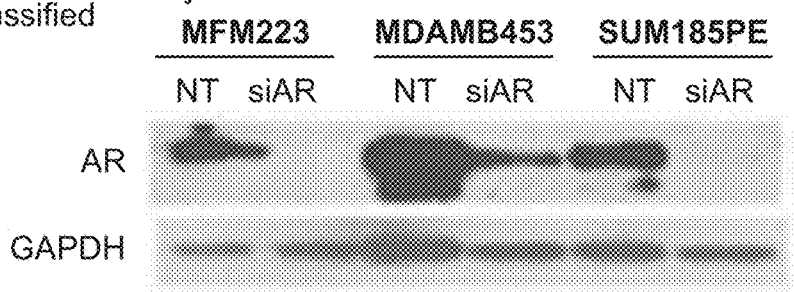
Figure 25C:
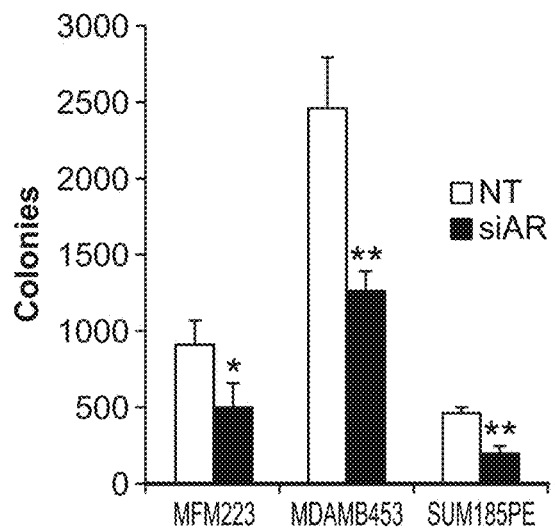

To determine whether the growth of the LAR cell lines was AR dependent, MFM-223, MDA-MB-453, and SUM185PE cell lines were treated with control and AR-targeting siRNA. Knockdown of AR in the experimental samples at the protein level was verified (FIG. 25B), colony growth assays were performed, and the number of colonies formed after 14 days of siRNA transfection were analyzed. The ability of all the LAR cell lines to form colonies was significantly reduced after knockdown of AR expression as compared with control samples (MFM-223=55%, P=0.031; MDA-MB-453=51%, P=0.004; and SUM185PE=42.3%, P=0.002) (FIG. 25C), indicating that AR expression is in part responsible for tumor cell viability/survival.

Figure 6A:
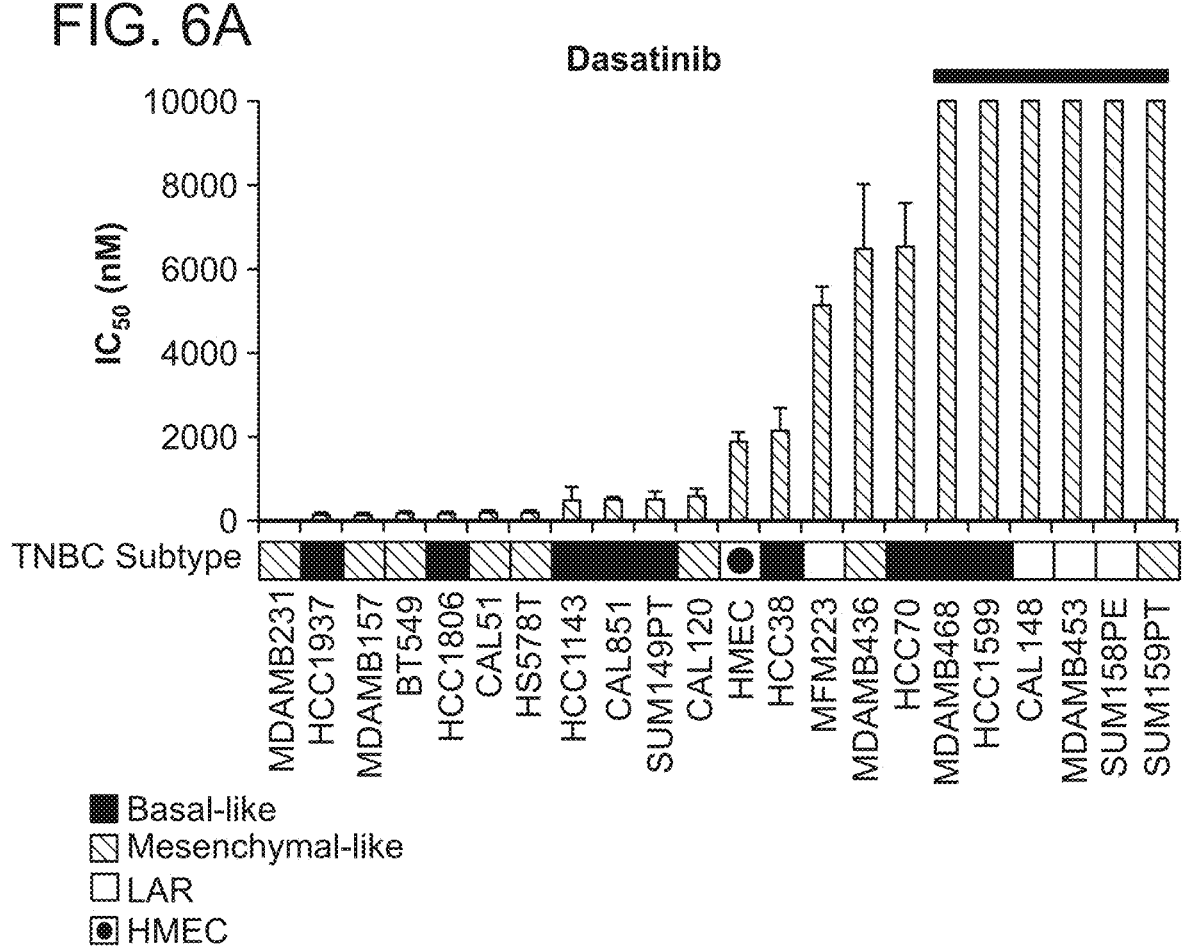
FIGS. 6A-6D: Mesenchymal-like TNBC subtypes are sensitive to dasatinib and NVP-BEZ235. IC50 values for each TNBC cell lined treated with (6A) dasatinib or (6C) NVP-BEZ235 for 72 hours. Cell lines that have PIK3CA mutations (red) or are deficient in PTEN (blue, circle indicates mutated) are displayed below the NVP-BEZ235 graph. Dot plots show the log distribution of drug sensitivity to (6B) dasatinib or (6D) NVP-BEZ235 in the basal-like subtypes (BL=BL1+BL2), mesenchymal-like subtypes (ML=M+MSL), and LAR. Black horizontal bars in the dot plots indicate the mean IC50 for each of the subtypes. *Statistically significant differences in IC50 values of BL versus ML (P=0.020) when treated with dasatinib and ML versus BL (P=0.001) and LAR versus BL (P=0.01) when treated with NVP-BEZ235, as determined by Mann-Whitney U test.
Figure 6B:
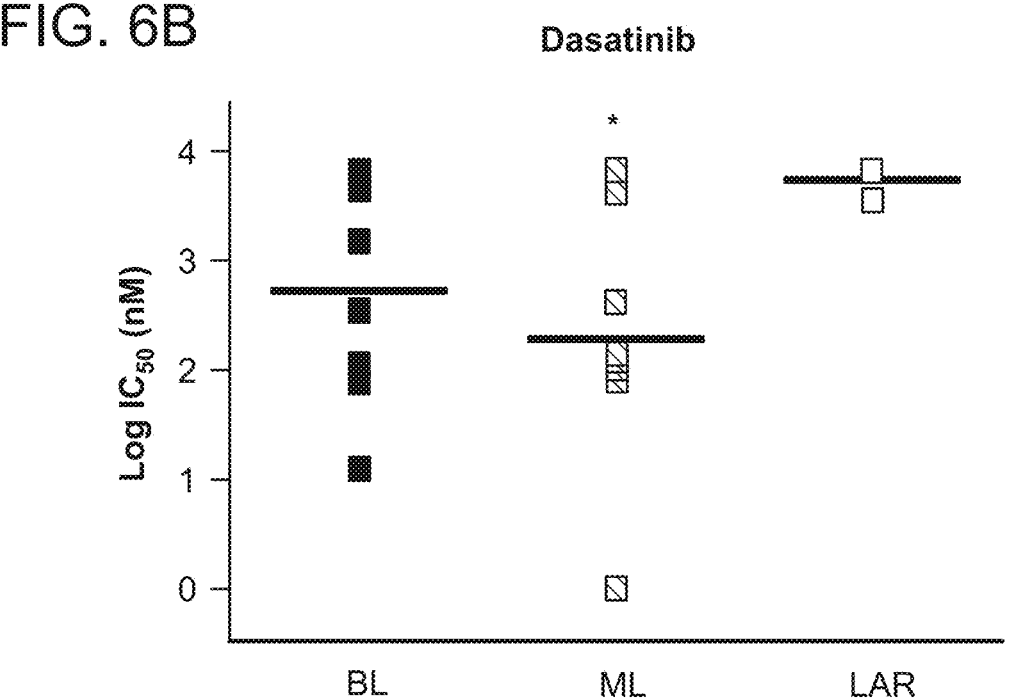

GE analysis of the mesenchymal-like subtypes demonstrated enrichment in the expression of genes that make up components and pathways associated with EMT (TGFβ, ECM-receptor interaction, ALK, Wnt/β-catenin, and Rac1) and those associated with cell motility (focal adhesion, integrin signaling, Rac1, striated muscle contraction, and regulation of actin by Rho GTPase) FIG. 3). Since the nonreceptor tyrosine kinase Src plays critical roles in cell migration and the mesenchymal-like subtypes are enriched in cell motility pathways, the effect of the Src inhibitor dasatinib on the panel of TNBC lines was analyzed. Cell lines belonging to the mesenchymal-like subtypes (M and MSL) were more sensitive to dasatinib than the LAR cell lines (average $IC_{50}$=22 µM vs. $IC_{50}$=88 µM, P=0.024) (FIGS. 6A and 6B).

Figure 6C:
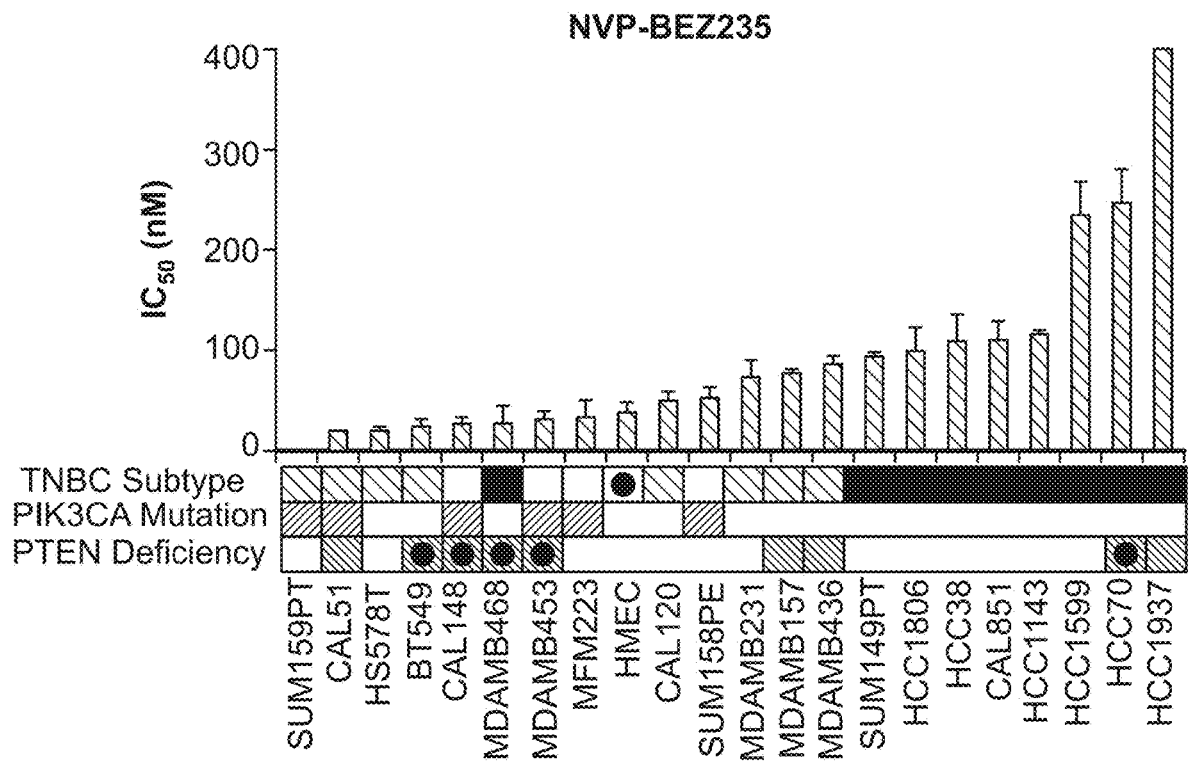
Figure 6D:
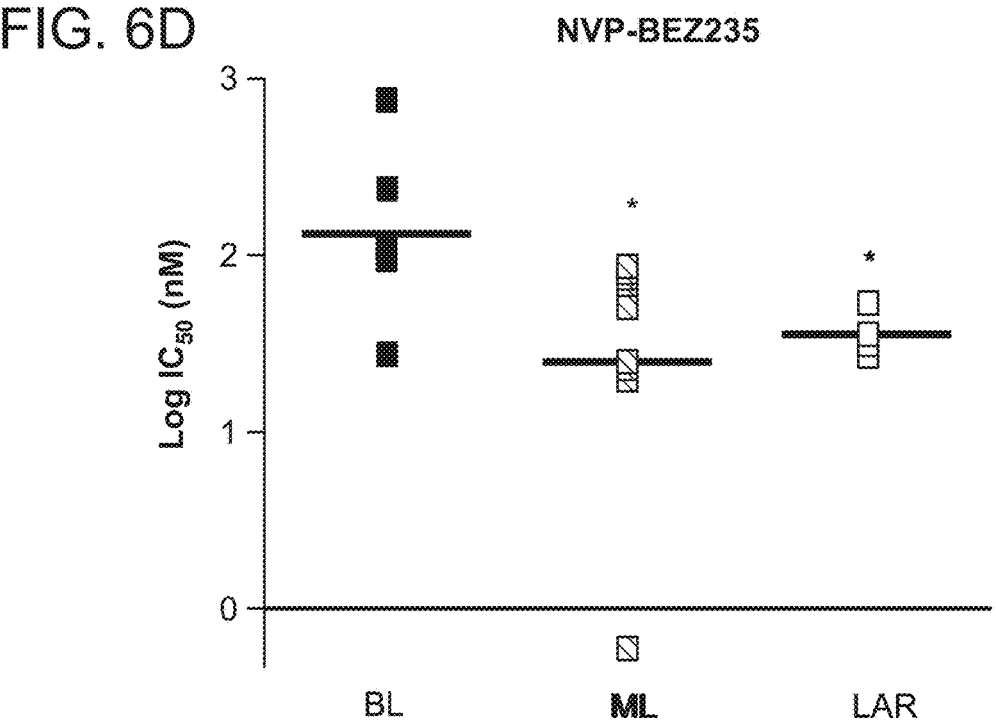

Since activating mutations in PIK3CA are the most frequent genetic event in breast cancer (Samuels Y, et al. Science. 2004; 304(5670):554), the TNBC cell lines were treated with the dual PI3K/mTOR inhibitor NVP-BEZ235 (Maira S M, et al. Mol Cancer Ther. 2008; 7(7):1851-1863). TNBC cell lines that have activated PI3K/AKT signaling due to PIK3CA mutations or PTEN deficiency (Table 3) were highly sensitive to NVPBEZ235 (FIG. 6C). In addition, mesenchymal-like TNBC cell lines were more sensitive to NVP-BEZ235 compared with basal like cell lines (average IC$_{50}$=44 nM vs. IC$_{50}$=201 nM; P=0.001) (FIGS. 6C and 6D), which may suggest that deregulation of the PI3K pathway is important for this subtype. LAR cell lines were also more sensitive to NVP-BEZ235 compared with basal-like cell lines (average IC$_{50}$=37 nM vs. 116 nM; P=0.01) (FIGS. 6C and 6D). This sensitivity can be explained by PIK3CA mutations, frequent in the LAR subtype, with all LAR cell lines containing PIK3CA-activating mutations (HCC2185, MDA-MB-453 CAL-148, MFM-223, and SUM185PE) (Table 3). While PIK3CA mutations predicted NVP-BEZ235 sensitivity, PTEN deficiencies (mutation or loss of protein expression) did not correlate with sensitivity.

Figure 7:
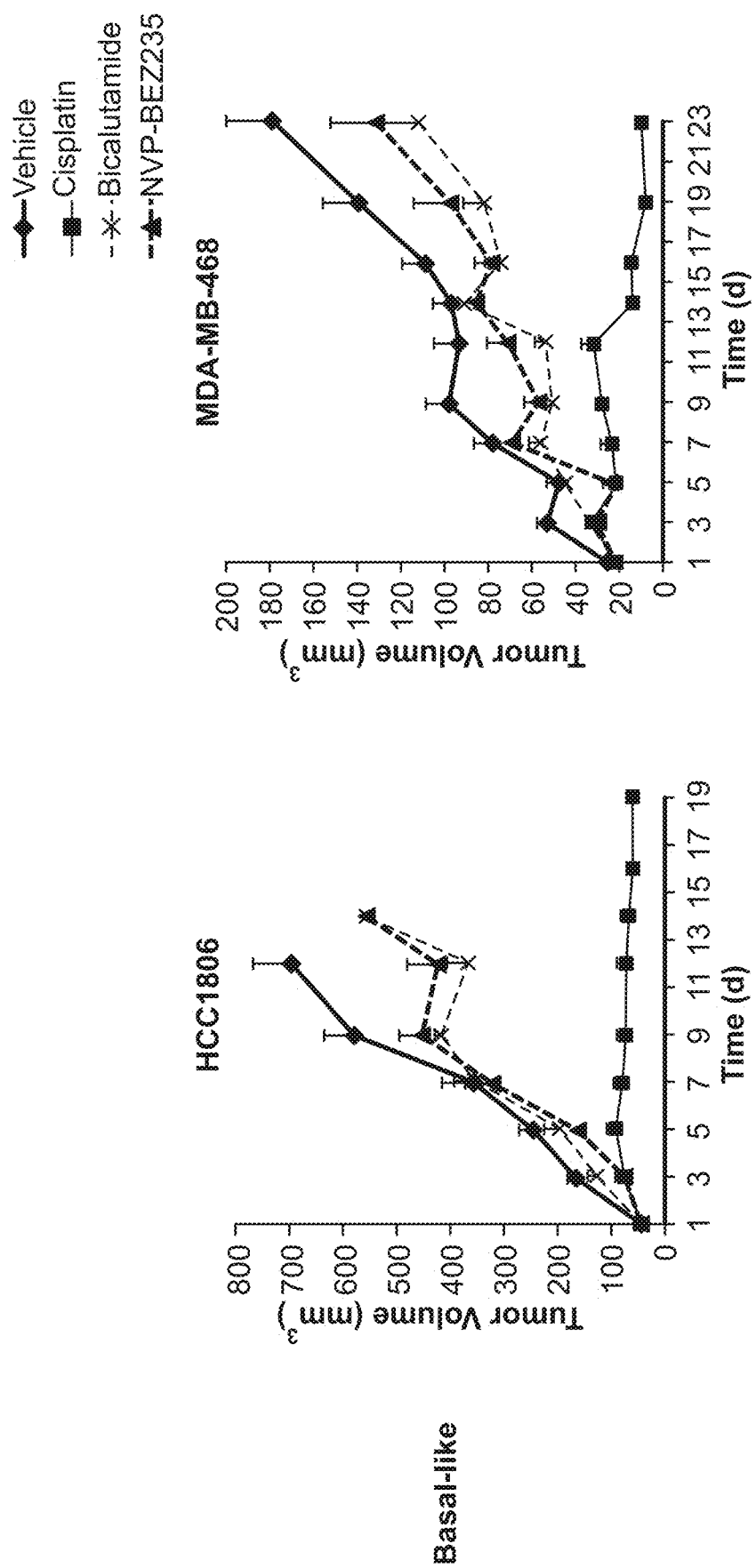
FIG. 7: Xenograft tumors established from TNBC subtypes display differential sensitivity to cisplatin, bicalutamide, and NVP-BEZ235. Nude mice bearing established tumors (25-50 mm3) from basal-like (HCC1806 and MDA-MB-468), LAR (SUM185PE and CAL-148), or mesenchymallike (CAL-51 and SUM159PT) were treated with cisplatin (red), bicalutamide (purple), NVP-BEZ235 (green), or vehicle (blue) for approximately 3 weeks. Serial tumor volumes (mm3) were measured at the indicated days. Each data point represents the mean tumor volume of 16 tumors; error bars represent SEM.
Figure 7:
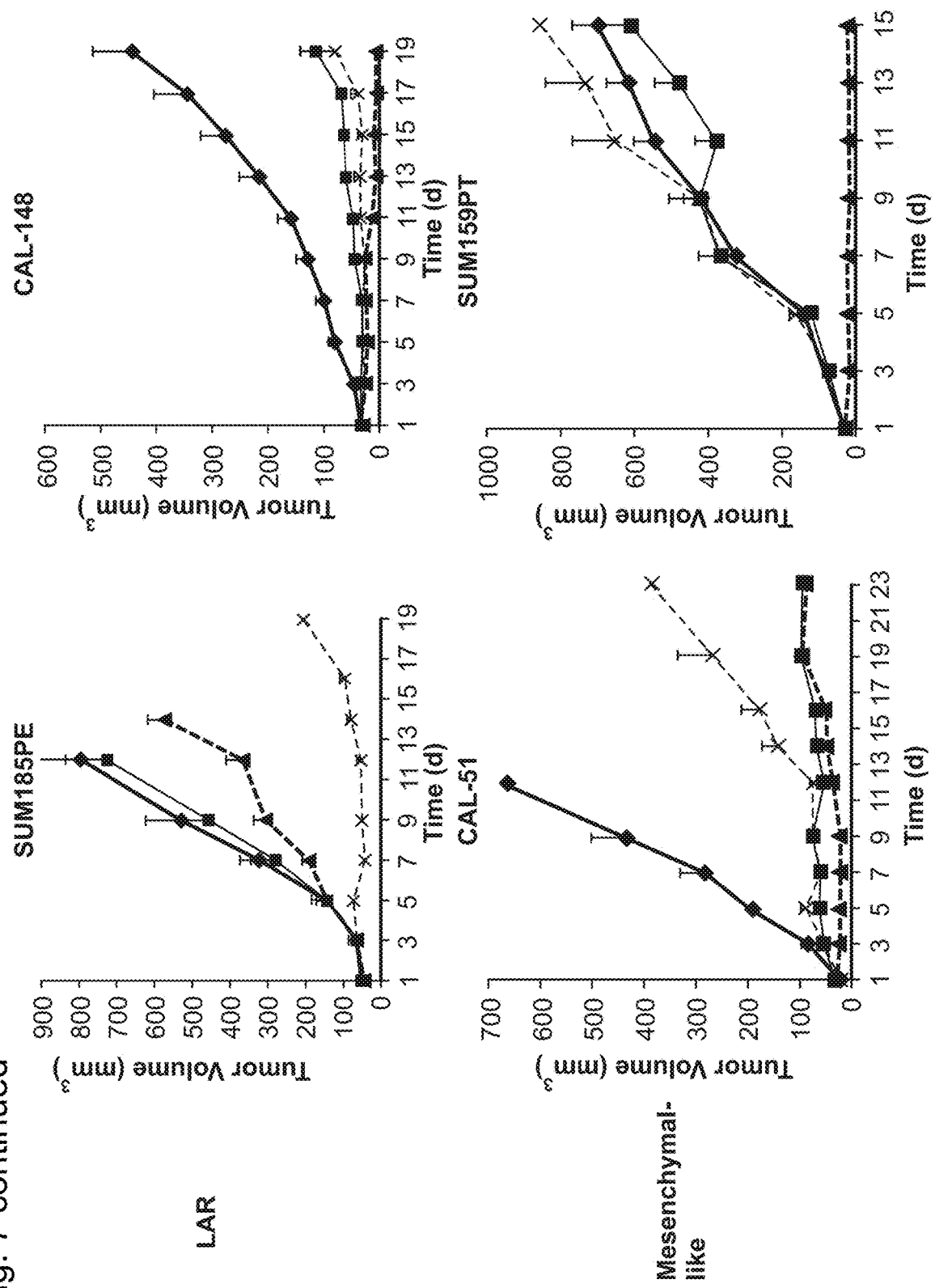

Xenograft tumors derived from TNBC cell lines display differential sensitivity to therapeutic agents in vivo. In order to further analyze the susceptibility or resistance of TNBC subtypes to therapeutic agents in a more physiological setting than 2D culture, xenograft tumors were established in nude mice from cell lines representative of the basal like (HCC1806 and MDA-MB-468), mesenchymal-like (CAL-51 and SUM159PT), or LAR (SUM185PE and CAL-148) subtypes. After tumors reached an approximate volume of 25-50 mm$^3$, the mice were treated with cisplatin, NVP-BEZ235 or bicalutamide. The sensitivity of the TNBC cell lines to the therapeutic agents when grown as 3D xenograft tumors in vivo was very similar to that seen with the cell lines grown in 2D monolayer culture. The xenograft tumors derived from the 2 cell lines representative of basal-like tumors (HCC1806 and MDA-MB-468) were highly and differentially sensitive to cisplatin and were significantly growth inhibited (P<0.0001) relative to treatment with vehicle control or the other experimental treatments (bicalutamide and NVP-BEZ235) (FIG. 7). The tumors derived from the LAR cell lines (SUM185PE and CAL-148) and the mesenchymal-like cell line that expresses low level AR protein (CAL-51) (FIGS. 25A-25C) displayed significant sensitivity to bicalutamide (FIG. 7). The xenograft tumors derived from all the cell lines carrying activating PIK3CA mutations (SUM185PE, CAL-148, CAL-51, and SUM159PT) had partial response or complete compared with NVP-BEZ235 (FIG. 7).

In summary, cell lines representative of the 6 TNBC subtypes display different sensitivities to a variety of agents, and importantly, these differences can be attributed to distinct expression of cellular components and presence of mutations in key oncogenes and tumor suppressors. The results have immediate clinical translation, as they provide a valuable platform and insights for ongoing and future clinical investigation. The data indicate that patients with basal-like TNBC should be treated with agents that engage DNA damage signaling response pathways; those with tumors expressing AR should receive bicalutamide alone or in combination with PI3K inhibitors; and those with mesenchymallike TNBC should be considered for trials exploring the activities of an Src antagonist in combination with a PI3K inhibitor.

Supplemental Results

K-means Clustering of a subset of five datasets that were identified as TNBC by IHC. Since TNBCs are not identified by GE in the clinical setting, a similar GE analysis was performed on a dataset from TNBCs identified using IHC (n=183) complied from five datasets: GSE7904 (n=22), GSE19615 (n=34), GSE20194 (n=67), E-TABM-158 (n=30) and GSE22513, GSE-XXX (n=30). This compilation included 136 tumors (74.3%) that were identified by our bimodal filtering analysis. K-means clustering performed on the most differentially expressed genes (SD>0.8) resulted in the identification of 5 TNBC subtypes (FIGS. 11A-11B). One subtype contained only three tumors and analysis of GE showed these tumors to have high levels of ER and PR FIG. 11B). These tumors were considered to be false negatives by IHC and were removed from further analysis. Comparison of these IHC-identified TNBC samples using genes differentially expressed from the six TNBC subtypes revealed similar patterns of gene enrichment (FIG. 12).

Discussion

Through GE analysis of 3247 breast cancers, demonstrate herein is that TNBCs can be reliably identified by filtering GE profiles for ER, PR, and HER2 mRNA levels. 587 TNBC GE profiles from 21 studies (training set=386 and validation set=201) were compiled. An 18% incidence rate of TNBC across the 21 independent studies (training and validation combined) was observed, similar to previously reported TNBC prevalence (Bertucci F, et al. Int J Cancer. 2008; 123(1):236-240; Rakha E A, et al. Clin Cancer Res. 2009; 15(7):2302-2310). k-means and consensus clustering of tumor profiles revealed that TNBC is composed of 6 stable subtypes enriched in distinct gene ontologies and GE patterns. Furthermore, using a GE signature derived from TNBC patient tumors, cell-line models for each of the TNBC subtypes were identified.

Previously, the majority (50%-90%) of TNBCs have been classified as basal-like either by IHC or by correlation to the intrinsic molecular breast cancer subtypes (Bertucci F, et al. Int J Cancer. 2008; 123(1):236-240; Rakha E A, et al. Clin Cancer Res. 2009; 15(7):2302-2310; Kreike B, et al. Breast Cancer Res. 2007; 9(5):R65). A previous TNBC study identified 5 distinct hierarchical clusters in which 91% (88 of 97) of TNBCs identified by IHC correlated to the basal-like subtype (Kreike B, et al. Breast Cancer Res. 2007; 9(5):R65). However, the study lacked molecular analysis of the tumors and conclusions were limited to clinical outcomes based on pathological markers. The relationship between TNBC and basal-like breast cancer remains controversial (Rakha E et al. Clin Cancer Res. 2008; 14(2):618). The proportion of TNBCs with basal-like GE in our study was 47%, resulting in a higher proportion of TNBCs that correlate with other molecular subtypes: luminal A (17%), normal breast-like (12%), luminal B (6%), HER2 (6%), or unclassified (12%). The study herein indicates that TNBC is not limited to tumors with a basal-like phenotype; rather it is a heterogeneous collection of tumors with distinct phenotypes, as evidenced by the diverse GE patterns and varying sensitivity of representative cell lines to the targeted therapies assessed in this study.

The BL1 and BL2 subtypes express high levels of genes involved in cell proliferation and DNA damage response, suggesting patients with basal-like tumors would benefit from agents that preferentially target highly proliferative tumors (e.g., anti-mitotic and DNA-damaging agents). Consistent with this notion, patients with basal-like tumors had up to a 4-fold higher pCR after taxane-based and radiation-based treatment as compared with patients with tumors that displayed characteristics of the ML or LAR subtypes (Bauer J A, et al. Clin Cancer Res. 2010; 16(2):681-690; Juul N, et al. Lancet Oncol. 2010; 11(4):358-365).

Nearly all of the cell lines with known mutations in BRCA1 and BRCA2 had GE patterns that correlated with the basal-like subtype, which is in agreement with the current view that BRCA-mutant tumors display a basal-like phenotype (Stefansson O A, et al. Breast Cancer Res. 2009; 11(4):R47). A number of non-BRCAmutant cell lines that correlated with the basal-like TNBC subtypes contained nearly 2-fold the number of chromosome rearrangements as all other subtypes. These findings suggest that a predominant characteristic of basal-like TNBC is genomic instability (Kwei K A et al. Mol Oncol. 2010; 4(3):255-266). Because of GE similarities between basal-like TNBC and BRCA1-mutation carriers, PARP inhibitors are currently being tested in clinical trials for TNBC (Silver D P, et al. J Clin Oncol. 2010; 28(7):1145-1153). Despite success in BRCA-null cells, there is not sufficient evidence for PARP inhibitor efficacy in BRCA1/2-mutant breast cancer cells (Farmer H, et al. Nature. 2005; 434(7035):917-921). PARP sensitivity across a panel of TNBC cell lines did not correlate with TNBC subtype alignment or BRCA1/2-status in this study using short-term cell viability assays (72 hours). However, the synthetic lethal effects of PARP inhibition in homologous recombination-deficient cells may require multiple cell divisions and may be more appropriately tested in long-term survival assays. Other studies show that a subset of BRCA1-mutant tumors lack large-scale genomic alterations and these tumors represent a distinct disease entity and may not be susceptible to PARP inhibition (Stefansson O A, et al. Breast Cancer Res. 2009; 11(4):R47). Previous analyses of PARP inhibitors in isogenic BRCA2+/+ and BRCA2−/− cell lines suggest that sensitivity to this targeted therapy is dependent on the molecular context of the DNA repair machinery and that DNA repair requiring homologous recombination involves multiple redundant pathways (Farmer H, et al. Nature. 2005; 434(7035):917-921; Fong P C, et al. N Engl J Med. 2009; 361(2):123-134). BRCA1 is a relatively large protein (1863 aa) that forms numerous complexes that may not be entirely disrupted when BRCA1 and BRCA2 are mutated, as opposed to BRCA-null cells. Despite an incomplete understanding of the molecular mechanism of the PARP inhibitors in vivo, these drugs have been proven to be highly effective in the clinical trial setting (41% objective response rate; 6.2 month progression-free survival) (Audeh M W, et al. J Clin Oncol. 2009; 27:5500).

It was also found that BRCA1-mutant and non-BRCA-mutant basal like cell lines had relatively higher sensitivity to cisplatin treatment compared with all other TNBC subtypes. The results are consistent with the observed 21% pCR in a clinical trial investigating neoadjuvant cisplatin as a single agent in a heterogeneous TNBC patient population (Garber J E, et al. Breast Cancer Res Treat. 2006; 105:S149; Telli M L, Ford J M. Clin Breast Cancer. 2010; 10 suppl 1:E16-E22). These data collectively suggest that the use of proliferation biomarkers such as Ki-67 and development of markers identifying defects in DNA damage response signaling could provide patient selection and tailored treatments for basal-like TNBC. Use of cisplatin as a "targeted" agent alone or in combination with antimitotics (taxanes) and/or radiation may benefit patients with this subtype and a current trial is underway with these agents (Mayer I A, et al. J Clin Oncol. 2010; 28(1):15).

The IM subtype is highly enriched in immune cell signaling. Other studies have described the presence of immune response gene signatures in ER-negative and medullary breast cancers (Bertucci F, et al. Cancer Res. 2006; 66(9):4636-4644; Teschendorff A E et al. Genome Biol. 2007; 8(8):R157). Similar to these studies, it was found elevated expression of T cell—associated genes, immune transcription factors, IFN regulatory factors, TNF, complement pathway, and antigen processing. It cannot be ruled out that the GE profile of the IM subtype comprises, at least in part, stromal components including immune cell infiltrate. However, the finding that the same proportion of microdissected tumors belongs to this group argues against stromal contamination.

The M and MSL subtypes share similar gene ontologies and GE profiles involving TGF-β, mTOR, Rac1/Rho, Wnt/β-catenin, FGFR, PDGFR, and VEGF signaling pathways. These signaling pathways are prominent in processes of EMT and stem cell-like properties of a CD44+CD24-population of normal mammary cells (Mani S A, et al. Cell. 2008; 133(4):704-715; Shipitsin M, et al. Cancer Cell. 2007; 11(3):259-273). Similarly, the MSL subtype is made up at least in part by the recently described claudin-low tumors, which lack luminal differentiation markers, high enrichment for EMT markers, immune response genes, and cancer stem cell-like features (Prat A, et al. Breast Cancer Res. 2010; 12(5):R68). Interestingly, the M and MSL subtypes differed clinically, with patients in the M subtype presenting with shorter RFS. This may be a reflection of differences in proliferation, as the M subtype displayed higher expression of proliferation-associated genes, including Ki-67. Additionally, patients with the M and MSL subtypes had decreased 5-year DMFS, consistent with enrichment in pathways associated with metastasis and motility.

Tumors within the mesenchymal-like subtypes have GE profiles that are similar to those from mesenchymal cells and metaplastic breast cancers (Hennessy B T, et al. Cancer Res. 2009; 69(10):4116-4124). Metaplastic breast cancers have lineage plasticity, including foci of spindle cell, as well as osseous or cartilaginous differentiation (Gibson G R, et al. Am Surg. 2005; 71(9):725-730). A recent study found that 47% of metaplastic breast cancers sequenced have PIK3CA mutations and have higher phosho-AKT expression (Hennessy B T, et al. Cancer Res. 2009; 69(10):4116-4124). It was found herein that TNBC mesenchymallike cell lines preferentially responded to the dual PI3K/mTOR inhibitor NVP-BEZ235. This response to NVP-BEZ235 was demonstrated in cell lines that carry PIK3CA mutations in xenografts in addition to an MSL cell line (SUM159PT) that lacks PIK3CA mutation or PTEN deficiencies, suggesting that the PI3K/mTOR pathway is important in the mesenchymal-like subtype.

The mesenchymal-like subtypes were enriched in pathways associated with EMT and cell motility. There is evidence of a prominent role for Src in tumor cells that are highly invasive, such as those that have undergone EMT (Guarino M. J Cell Physiol. 2010; 223(1):14-26). Accordingly, we found that mesenchymal-like TNBC cell lines had differential sensitivity to dasatinib. Markers of EMT may have clinical value for patient preselection for trials using dasatinib. In addition, Wnt-signaling pathways regulate EMT and may contribute to tumor cell invasion (Shin S Y, et al. Cancer Res. 2010; 70(17):6715-6724). Mutations in the Wnt/β-catenin pathway (CTNNB1, APC, and WISP3) occur frequently (52%) in metaplastic breast cancer, suggesting that deregulated Wnt/β-catenin pathway in these tumors may be a viable therapeutic target (Hayes M J et al. Clin Cancer Res. 2008; 14(13):4038-4044). Inhibitors of Wnt/β-catenin are of great interest and currently are in preclinical development (MacDonald B T, et al. Dev Cell. 2009; 17(1):9-26). Drugs targeting this pathway could be of value for treating mesenchymal-like TNBC.

The LAR subtype was readily subclassified by an AR gene signature and high levels of luminal cytokeratin expression. GE analysis of the LAR subtype is consistent with a prior report of a subset of ER-negative tumors expressing AR-regulated genes (Doane A S, et al. Oncogene. 2006; 25(28):3994-4008). In addition, Farmer et al. described an apocrine tumor subtype based on GE profiling that was characterized by AR expression distinguishing this tumor subtype from other basal-like tumors (Farmer P, et al.

Oncogene. 2005; 24(29):4660-4671). In the GE analysis of tumors from 21 studies described herein, the prevalence of the LAR tumors was 11% (62 of 587) of TNBCs or 2% (62 of 3247) of all breast cancers. Analysis of clinical data demonstrated that patients in the LAR subtype had higher RFS but no difference in DMFS compared with all other TNBC subtypes, suggesting these patients have local relapse. The higher RFS could imply that this group of patients received ineffective therapies (standard chemotherapy); however, patients in the LAR group were significantly older at diagnosis and the extent of disease or age-associated comorbidities that affect the ability to deliver treatment as planned may have contributed to relapse. Older age at diagnosis has previously been reported in patients with AR-positive TNBC and is associated with postmenopausal status (Agoff N S et al. Am J Clin Pathol. 2003; 120(5):725-731). Whether this AR-driven subtype is arising from hormone-replacement therapy (HRT) merits further investigation; however, it is becoming clear that the risk of breast cancer increases with HRT, and synthetic progestins such as medroxyprogesterone acetate have been shown to bind and disrupt AR (Birrell S N et al. FASEB J. 2007; 21(10):2285-2293). As described herein, five (5) cell lines were identified that represent the LAR subtype and it was shown that they are sensitive to bicalutamide and 17-DMAG, suggesting that therapies targeting AR may be effective against tumors that express this hormone receptor. In fact, there is a clinical trial (NCT00468715) underway testing the effect of bicalutamide in preselected patients with ER/PR-negative AR-positive tumors. This further supports using in silico-based approaches to provide leads for trials with other targeted therapies in TNBC subtypes.

In addition to agents that target AR function, LAR cell lines were also sensitive to PI3K inhibition. This sensitivity correlated with PIK3CA mutations. All 5 LAR cells lines have activating PIK3CA mutations and are sensitive to the PI3K inhibitor NVP-BEZ235, similar to ER-positive breast cancer in which PIK3CA mutations are common (Gonzalez-Angulo A M, et al. Clin Cancer Res. 2009; 15(7):2472-2478; Stemke-Hale K, et al. Cancer Res. 2008; 68(15):6084-6091). These findings suggest simultaneous targeting of AR and the PI3K/mTOR pathway may be of clinical benefit for LAR TNBC patients, as this combination has been shown to be synergistic in AR-dependent prostate cancer cells (Liu X et al. J Clin Oncol. 2010; 28:(suppl; abstr e15049)).

The GE analysis of TNBC described herein demonstrates that with sufficient sample size, distinct subtypes of TNBC can be identified with putative molecular targets. The analyses provides biomarkers that can be used for patient selection in the design of clinical trials for TNBC as well as identification of potential markers of response to treatment. The identification of cell lines representing TNBC tumor subtypes provides key models for preclinical studies with newly developed targeted agents.

Example 2 Frequent PIKCA Mutations in AR-Positive TNBC Confer Sensitivity to PI3K and AR Inhibitors Described herein is the further investigation of the molecular features of the LAR subtype to identify rationale combinations of drugs that would show robust efficacy against AR-positive TNBC cells with the added goal of generating preclinical data for rationale clinical trial design. It was discovered that PIK3CA kinase mutations were a frequent event in AR-positive TNBC tumors. It was found that genetic or pharmacological targeting of AR in LAR cells increased the therapeutic benefit of PI3K/mTOR inhibition. Further, it was discovered that after bicalutamide treatment of mice bearing LAR xenograft tumors, the PI3K pathway signaling increased. Thus, the combination of AR antagonism and PI3K/mTOR inhibition was examined and an additive or synergistic effect, depending on the TNBC cell line, was found. Given that AR expression is a robust biomarker for selection of LAR TNBC patients, the preclinical findings provide the rationale for preselecting AR-positive TNBC patients for treatment with AR inhibitors and/or PI3K/mTOR inhibitors, and future clinical trials exploring the efficacy of combinations of drugs that target AR and PI3K signaling.

Results and Discussion

AR-positive TNBC tumors are enriched for PIK3CA kinase domain mutations. High frequency PIK3CA mutations in AR-positive TNBC cell lines are described in Example 1. To determine if PIK3CA mutation was the result of in vitro selection during establishment of the tumor-derived cell lines or if PIK3CA mutations were frequent in AR-positive TNBC tumors, performed Sanger sequencing was performed on 26 AR-positive TNBC cases. PCR-amplified regions from exons 9 and 20 that harbor the most frequently occurring activating mutations in PIK3CA were sequenced. Consistent with the observations in cell lines, nearly all of the detected mutations occurred at amino acid H1047 (20 of 21) with only one occurring at E545K. Mutation status was confirmed with digital droplet PCR on DNA amplified from exon 20. Using both Sanger sequencing of exons 9 and 20 and digital droplet PCR, PIK3CA mutations were significantly ($P<0.0056$) enriched in AR-positive TNBC tumors (17 of 26, 65.3%) versus AR-negative TNBC tumors (10 of 26, 38.4%).

Validation of PIK3CA Mutations in AR-Expressing TNBC

Figure 26A:
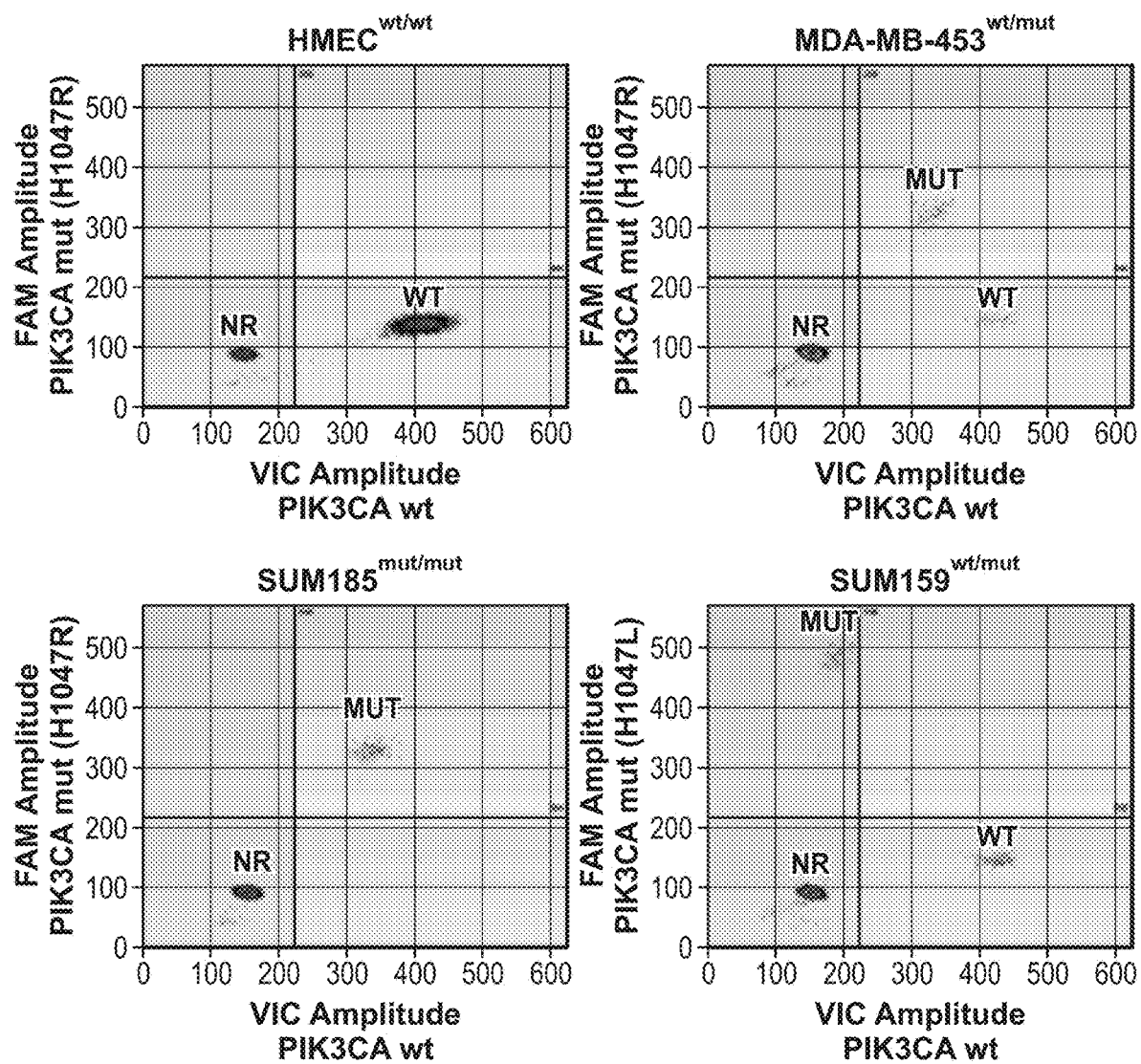
FIGS. 26A-26B: Identification of PIK3CA mutations in AR-positive TNBC cell lines and tumors. (26A) Detection of PIK3CA 1047 mutation using digital droplet PCR. DNA from cell lines with varying PIK3CA status (HMEC=H1047R wt/wt, MDAMB453=H1047R wt/mut, SUM185=H1047R mut/mut and SUM159=H1047L wt/mut) were simultaneously amplified with fluorescent-conjugated primers to wild-type (VIC) or mutant (FAM) and the percentage of wt vs. mut DNA was measured by digital droplet PCR. DNA that did not undergo PCR amplification is indicated by no reaction (NR). (26B) Heatmap displays the TNBC molecular subtype based of TCGA samples with corresponding levels of AR RNA (RNA-seq) and protein (RPPA) for AR and phosphorylated AKT (T308 and S473). Color bar indicates PIK3CA mutations (red) within TNBC from the TCGA.
Figure 26B:
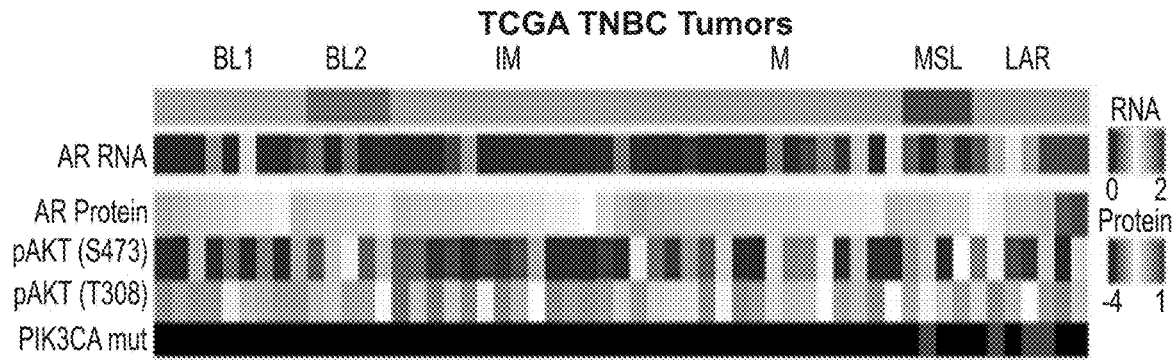

To verify that PIK3CA mutations were enriched in AR-expressing TNBC, RNA-seq, DNA-seq and reverse-phase protein array (RPPA) data available from The Cancer Genome Atlas (TCGA) breast cohort (Cancer Genome Atlas Network, Nature, 490:61-70 (2012)) was analyzed. Following removal of false negatives for ER, 66 TNBC samples were identified and classified according to molecular subtypes (Chen et al., Cancer informatics, 11:147-156 (2012)). The distribution of samples across the TNBC molecular subtypes was similar to that previously published (Lehmann et al., J Clin Invest, 121:2750-2767 (2011)). (BL1=14 (21.1%), BL2=6 (9.0%), IM=15 (22.7%), M=17 (25.7%), MSL=7 (10.6%) and LAR=7 (10.6%) (FIG. 26B). As expected, RNA-seq data confirmed significant levels of AR RNA (6.8 vs. 0.3, $p<0.0001$) and protein (1.7 vs. 0.35, $p<0.0001$) in the LAR subtype. Overall, PIK3CA mutations were relatively rare in TNBC cases in the TCGA dataset (4 of 66, 6.0%). However, when sorted by subtype, PIK3CA mutations were significantly enriched in LAR TNBC (3 of 7, 42.8%) compared to all other subtypes (1 of 59, 1.7%, $p<0.0001$), supporting our analysis of 26 TNBC cases above (FIG. 26B).

LAR TNBC Cell Lines have Increased PI3K Pathway Activation and are Sensitive to PI3K and PI3K/mTOR Inhibition.

Figure 27:
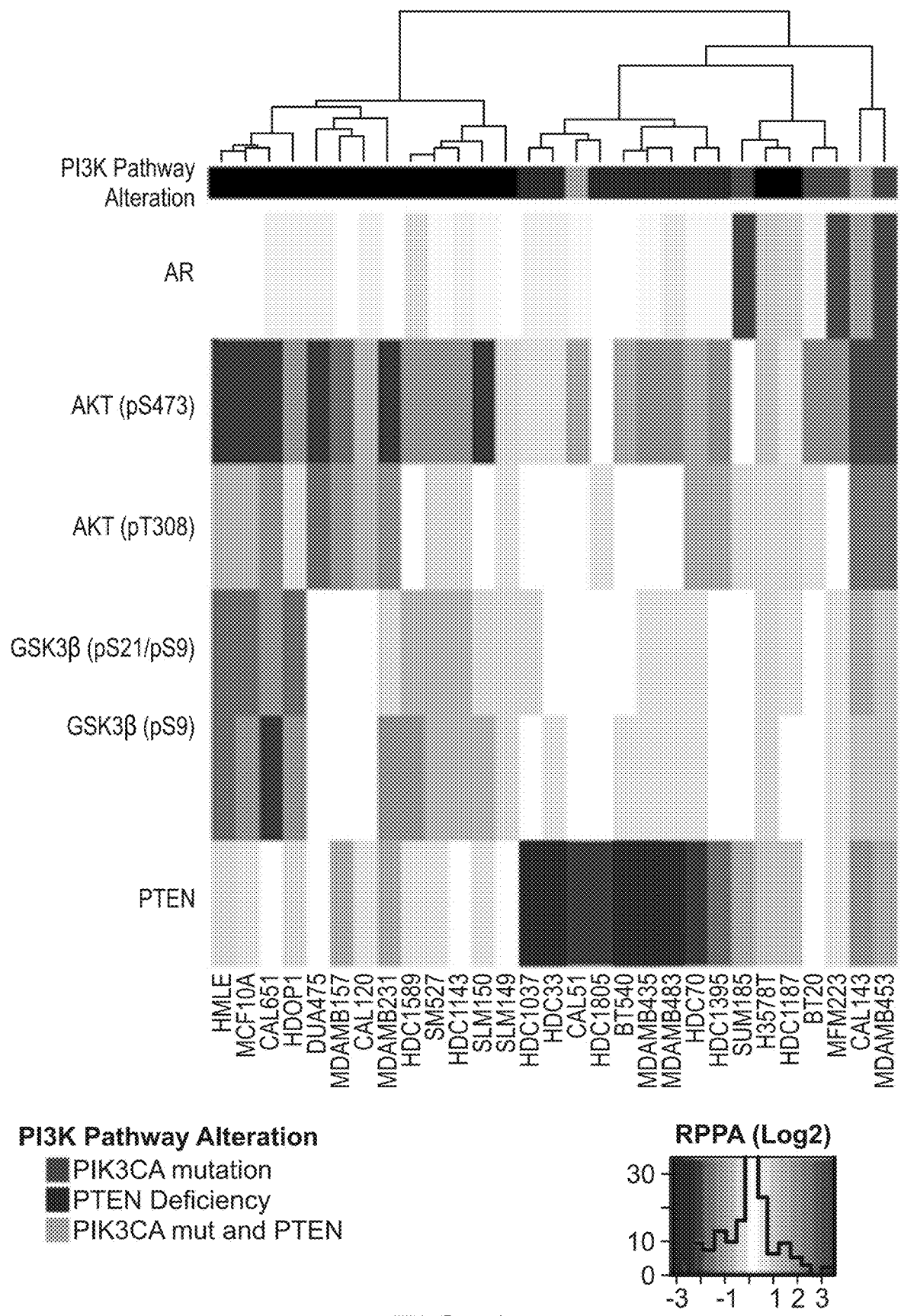
FIG. 27: AR-expressing TNBC cells display active PI3K pathway. Heatmap displays relative protein levels (RPPA) of AR, AKT (S473 and T308), GSK3β (S9 and S21) and PTEN across a large panel of TNBC cell lines. Hierarchical clustering was performed on cell lines and revel clusters of cell lines with active PI3K through PTEN loss or PIK3CA mutations.
Figure 28A:
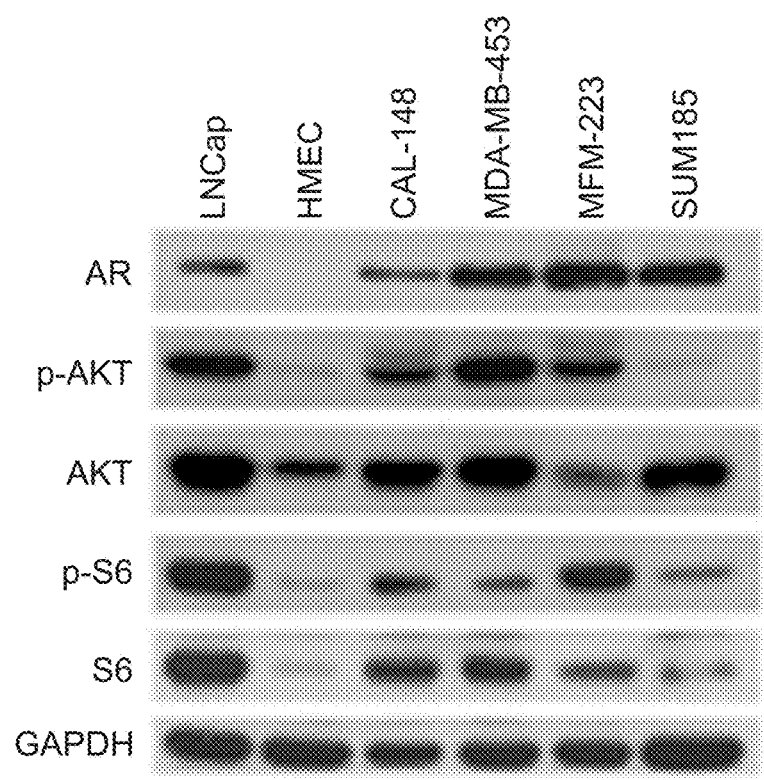
FIGS. 28A-28C-2: AR-positive TNBC cell lines display active PI3K pathway and are sensitive to PI3K inhibitors. (28A) Immunoblot displays relative levels of AR, p-AKT, p-S6 in AR-dependent prostate cancer (LNCaP), human mammary epithelial cells (HMEC) and LAR TNBC, with GAPDH serving as a loading control. (28B) IHC-stained sections display cellular levels of AR, and p-AKT in cell lines from the same tissue microarray (TMA). (28C-1 and 28C-2) Bar graphs display the 50% inhibitory concentration ($IC_{50}$) for TNBC cell lines treated with single-agent pan PI3K inhibitors (BKM-120 and GDC-0941) (28C-1) or PI3K/mTOR inhibitors (NVP-BEZ235 or GDC-0980) (28C-2) for 72 h. Black bars above graphs indicate cell lines in which the $IC_{50}$ was not reached at maximal dose. Bar below indicates normal HMEC cells and cell lines carrying PIK3CA mutations.
Figure 28B:
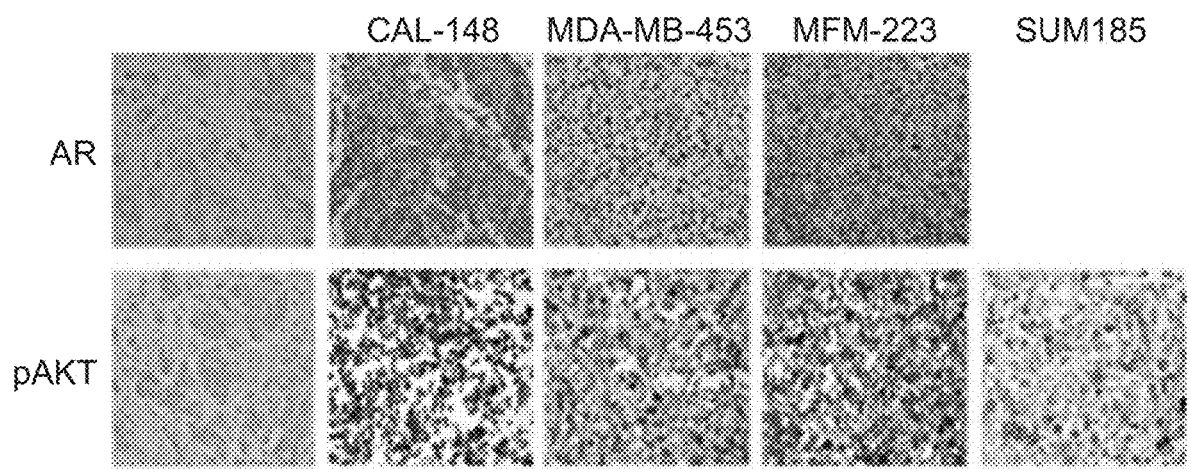
Figures 2, 28C:
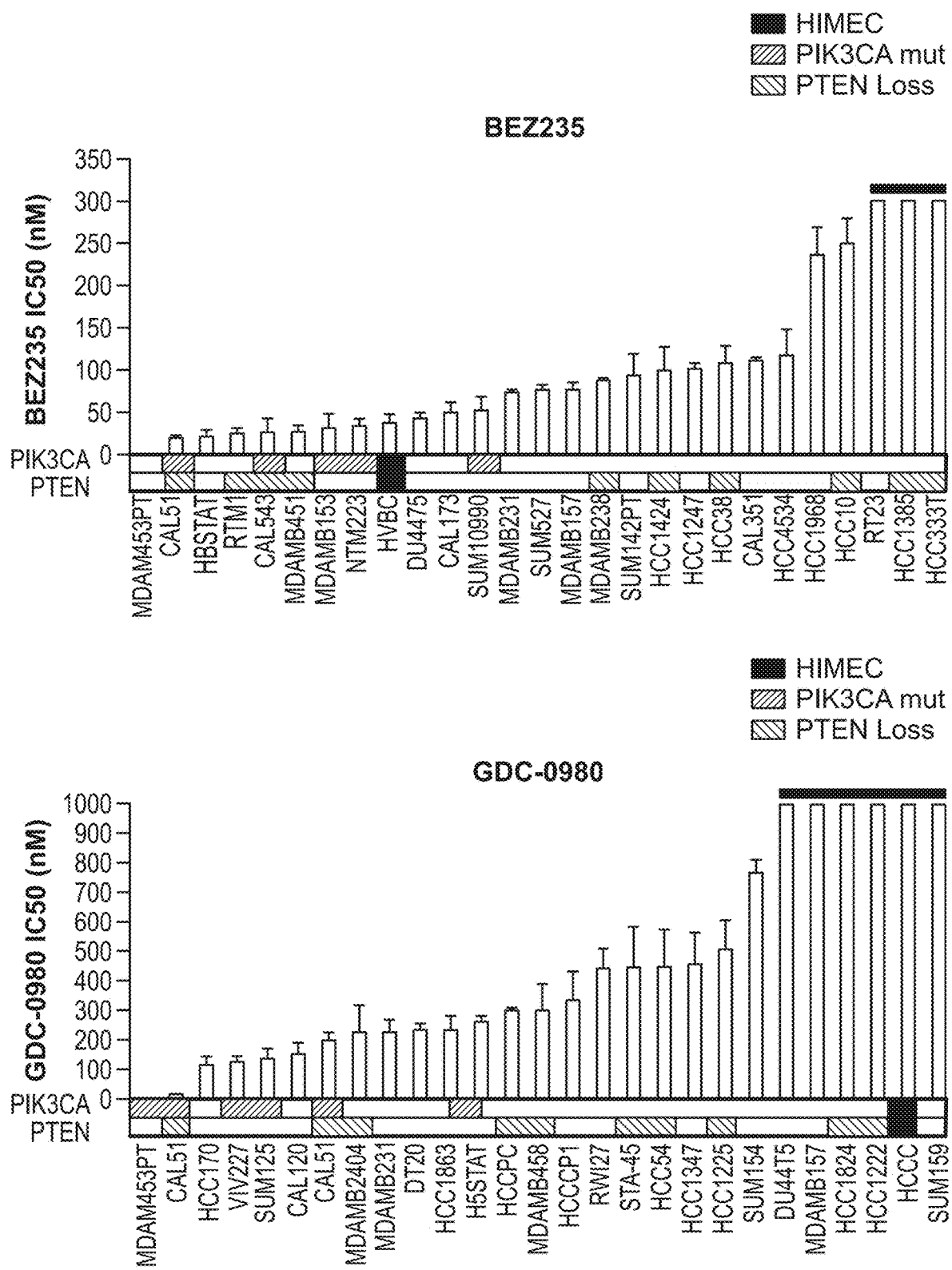

RPPA was used to investigate AR, PTEN, active AKT (pS473 and PT308) and active GSK3β (pS21/pS9) protein levels in LAR cell lines to determine if the PI3K pathway was active in AR expressing, PI3K mutant TNBC. Activated PI3K signaling correlated with PIK3CA mutation and PTEN loss. AR-expressing TNBC cell lines expressed higher levels of active AKT as evidenced by increased pS473 (2.18 vs. −0.23, p=0.007) and pS308 (1.45 vs. −0.10, p=0.0032) and increased downstream phosphorylation of GSK3β at pS9 (1.00 vs. −0.26, p=0.0094) and pS21/pS9 (1.12 vs. −0.19, p=0.0026) (FIG. 27). Similarly, those cell lines that were null for PTEN (BT549, CAL51, HCC1395, HCC1937, HCC38, HCC70, MDA-MB-436 and MDA-MB-468) displayed higher levels of active PI3K signaling (p-AKT S473 1.28 vs. −1.28, p=0.0001, p-AKT T308 0.41 vs. −0.53, p=0.0018, p-GSK S9 0.37 vs. −0.76, p=0.0002 and pGSKαβ S9/S21 0.26 vs. −0.59, p=0.0009).

To validate the RPPA data, immunoblot analysis of the PI3K/mTOR pathway in four of the LAR cell lines, as well as primary cultures of normal mammary epithelial cells (HMEC) and the AR-dependent prostate cancer cell line LNCaP (FIG. 27), was also performed. AR receptor protein in the LAR TNBC cell lines was expressed at levels equal to or greater than LNCaP cells. AR-expressing cell lines displayed higher levels of phosphorylated AKT (S473) and phosphorylated ribosomal S6, confirming an activated PI3K pathway and downstream mTOR activation, respectively (FIG. 27).

To evaluate the clonality of AR expression, immunohistochemistry (IHC) for AR and p-AKT was performed on a cell line-based array (FIG. 27). The AR-expressing cell lines displayed differing percentage of cells positive for AR protein expression (CAL148: 20%, MDA-MB-453: 50%, MFM-223: 50% and SUM185: 90%). However, p-AKT expression was much more homogenous, indicating that activation of PI3K/AKT signaling was an earlier clonal event.

To determine the sensitivity of PIK3CA mutation-bearing LAR cell lines to PI3K inhibitors relative to other TNBC cell lines, a large panel of TNBC cell lines was treated with pan-PI3K inhibitors BKM120 (Novartis) and GDC-0941 (Genentech) or with the dual PI3K/mTOR inhibitors NVP-BEZ235 (Novartis) and GDC-0980 (Genentech). AR-expressing and other TNBC cell lines containing PIK3CA mutations were among the most sensitive to PI3K inhibition, as indicated by low half maximal inhibitory concentration (IC50) values (FIGS. 28A-28C-2). In contrast, PTEN deficiencies, while conferring PI3K pathway activation, did not predict for sensitivity to PI3K inhibitors (FIGS. 28A-28C-2). Nearly all of the PIK3CA mutant cell lines were more sensitive to PI3K/mTOR inhibitors than primary cultures of human mammary epithelial cells (HMEC).

Genetic and Pharmacologic Inhibition of AR Increases the Efficacy of PI3K Inhibition.

Figure 34:
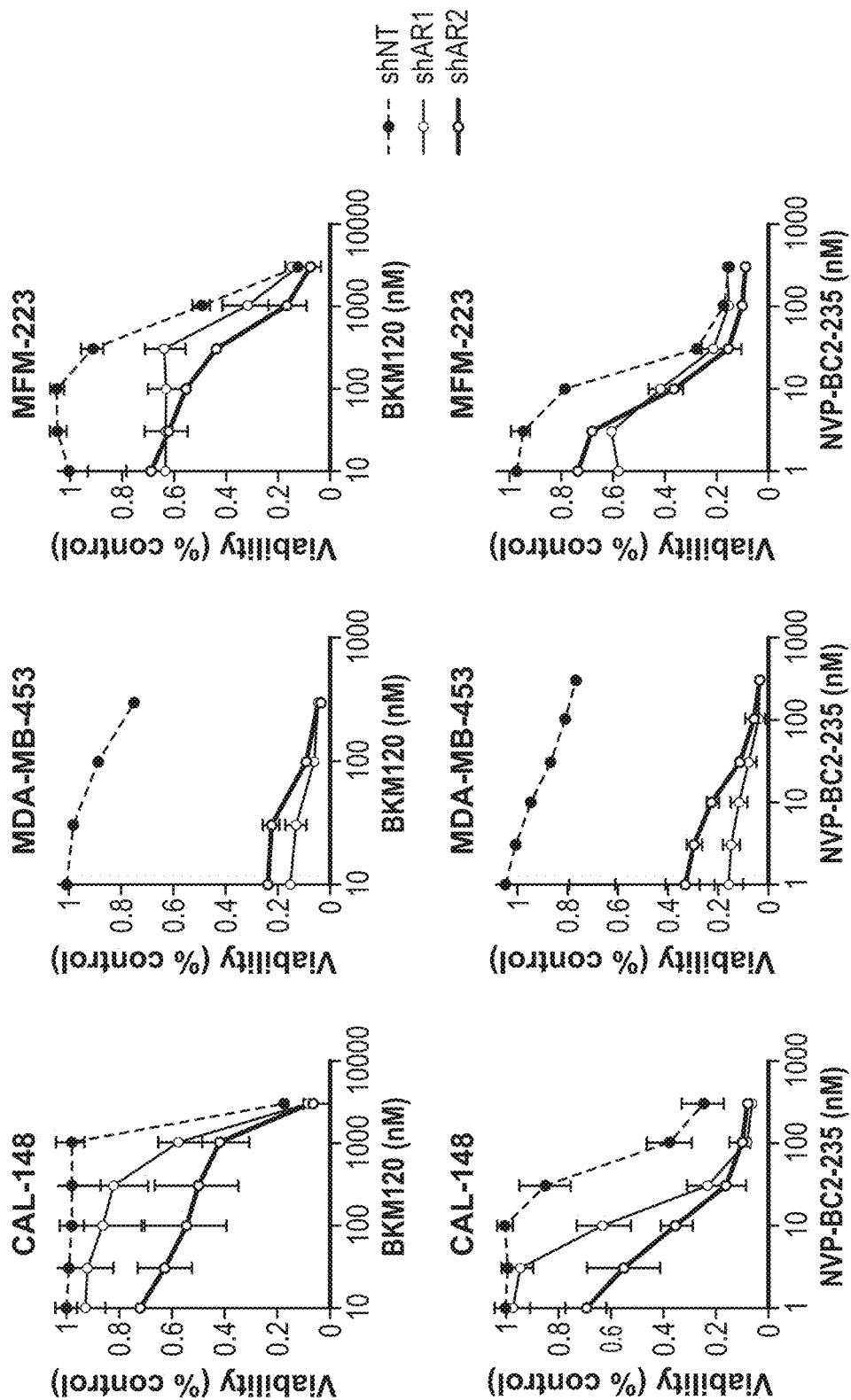
FIG. 34: Genetic targeting of AR increases the efficacy of the PI3K inhibitor BKM-120 and PI3K/mTOR inhibitor NVP-BEZ235. Line graphs display relative viability of LAR cell lines infected with nontargeting (shNT) or shRNAs targeting AR (shAR1 and shAR2) following a 72 h treatment with the pan-PI3K inhibitor BKM-120 (top) or the dual PI3K/mTOR inhibitor NVP-BEZ235.

Whether the combined targeting of AR and PI3K would be more effective than either agent alone was investigated. To determine the effectiveness of combinatorial treatment both genetic knockdown and pharmacological inhibition of AR with shRNA and bicalutamide, respectively, in the presence and absence of PI3K inhibitors were performed (FIGS. 29A-29B). Immunoblot analysis confirmed decreased AR protein levels in three AR-expressing TNBC cell lines infected with lentiviral particles containing non-targeting shRNA or two AR-targeting hairpins (FIG. 29A). Both shRNA expression vectors targeting AR decreased cell viability across multiple doses of PI3K or PI3K/mTOR inhibitors (FIG. 29B). Efficacy of AR-targeting in combination with PI3K or PI3K/mTOR inhibitors was independent of compound, as similar results were obtained with BKM-120 and NVP-BEZ235 (FIG. 34).

Figure 30A:
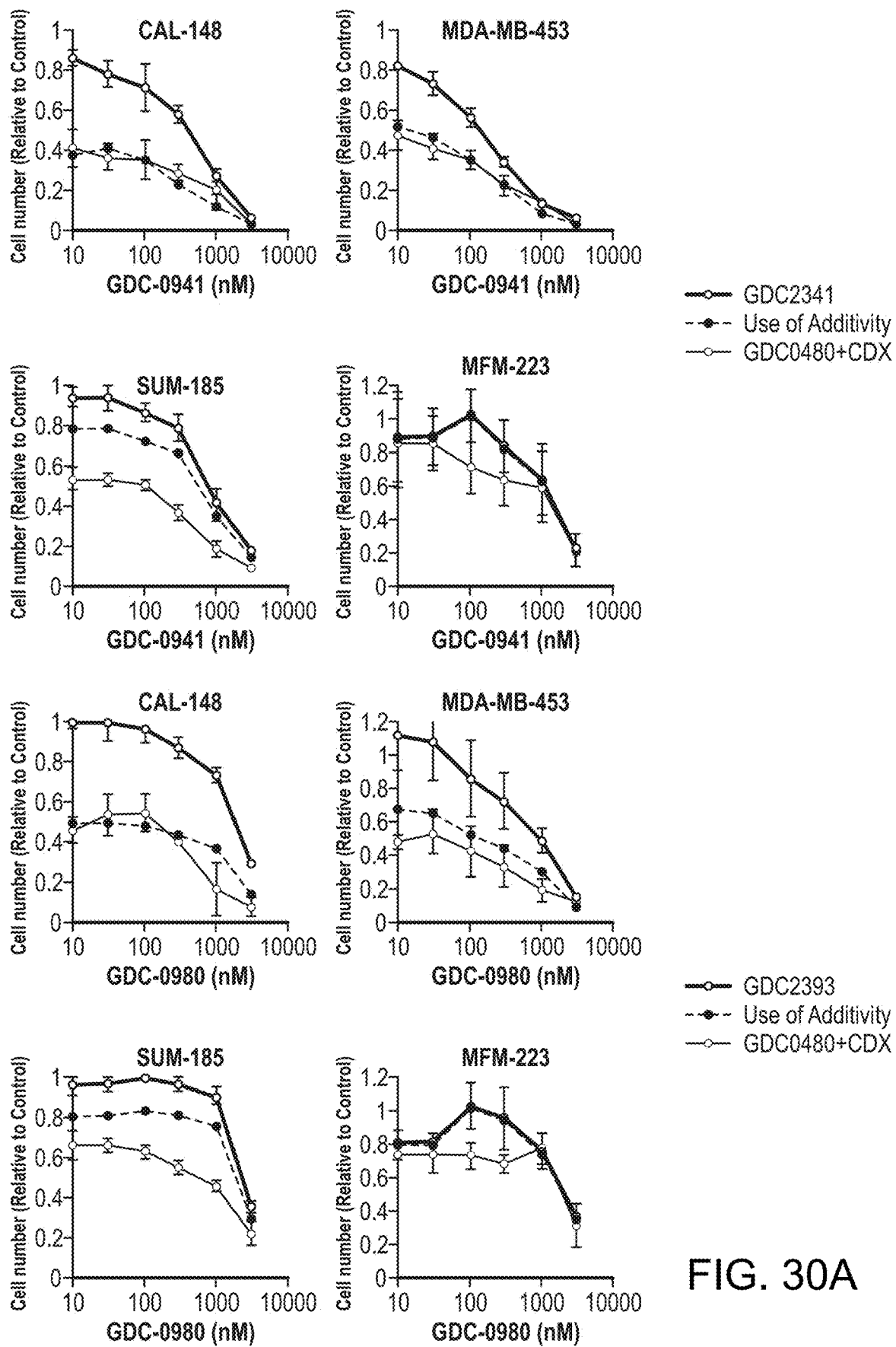
FIGS. 30A-30B: Pharmacological targeting of AR with bicalutamide increases the efficacy of GDC0941 and GDC0980 in AR-expressing TNBC. (30A) Line graphs show relative viability of AR-expressing cell lines treated with increasing doses of GDC-0941 (top) or GDC-0980 (bottom) alone or in combination with 25 μM bicalutamide (CDX). Dashed black line depicts the theoretical line of additivity of both drugs determined from the effect of bicalutamide alone and either GDC-0941 or GDC-0980 alone. (30B) Immunoblots from three AR-expressing TNBC cell lines treated with either bicalutamide (CDX), GDC-0941, GDC0980 alone or bicalutamide in combination with either GDC-0941 or GDC-0980 for 24 h or 48 h were probed for AR, PARP, p-AKT, AKT, p-S6, S6 and GAPDH.
Figure 30B:
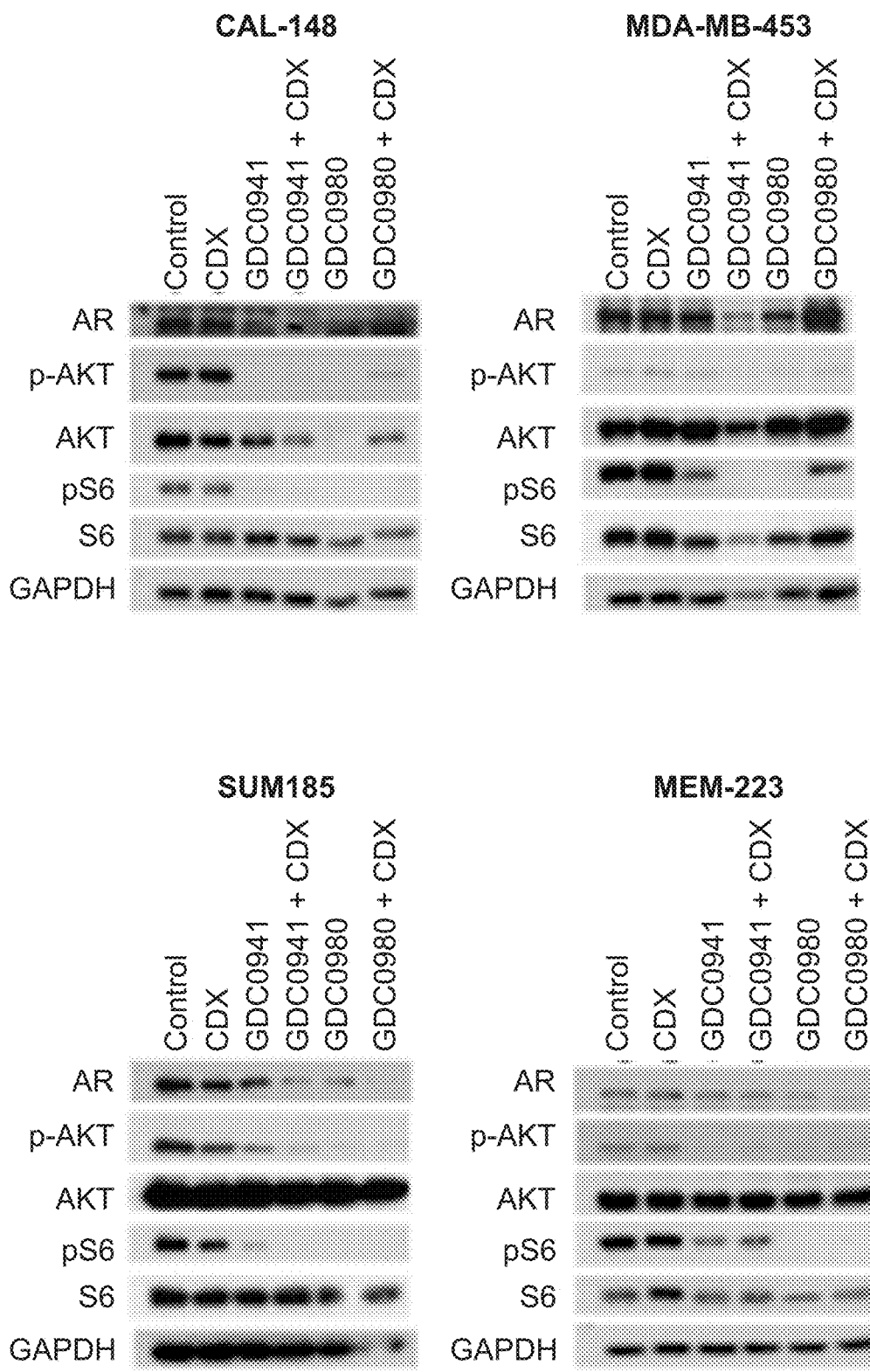

Given that knockdown of AR increased the efficacy of PI3K inhibitors, pharmacological targeting of the AR was performed using bicalutamide. Both GDC-0941 and GDC-0980 displayed efficacy in AR-expressing TNBC cell lines alone and viability could be decreased further with the addition of 25 µM bicalutamide (CDX) across multiple concentrations of PI3K inhibitors (FIG. 30A). PI3K inhibition in combination with bicalutamide decreased cell viability in an additive or synergistic manner, as demonstrated by viabilities at, or below, the line of additivity. Immunoblot analysis was performed on cell lystates from untreated cells or cells treated alone or in combination with CDX, GDC-0941 and GDC-0980 to evaluate attenuation of the PI3K/mTOR pathway. Both GDC-0941 and GDC-0980 decreased activated AKT (p-5473), however, GDC-0980 was more effective at decreasing mTOR activity as measured by the decrease in levels of phosphorylated S6 (FIG. 30B). In contrast, bicalutamide (CDX) had minimal effect on either the PI3K/mTOR pathway or AR levels. Interestingly, GDC-0980 alone decreased AR levels and this decrease could be increased further by the addition of bicalutamide, suggesting that mTOR signaling contributes to the stability of AR protein, similar to crosstalk observed in prostate cancer (FIG. 30B) (Carver et al., Cancer Cell, 19:575-586 (2011)).

Figure 31A:
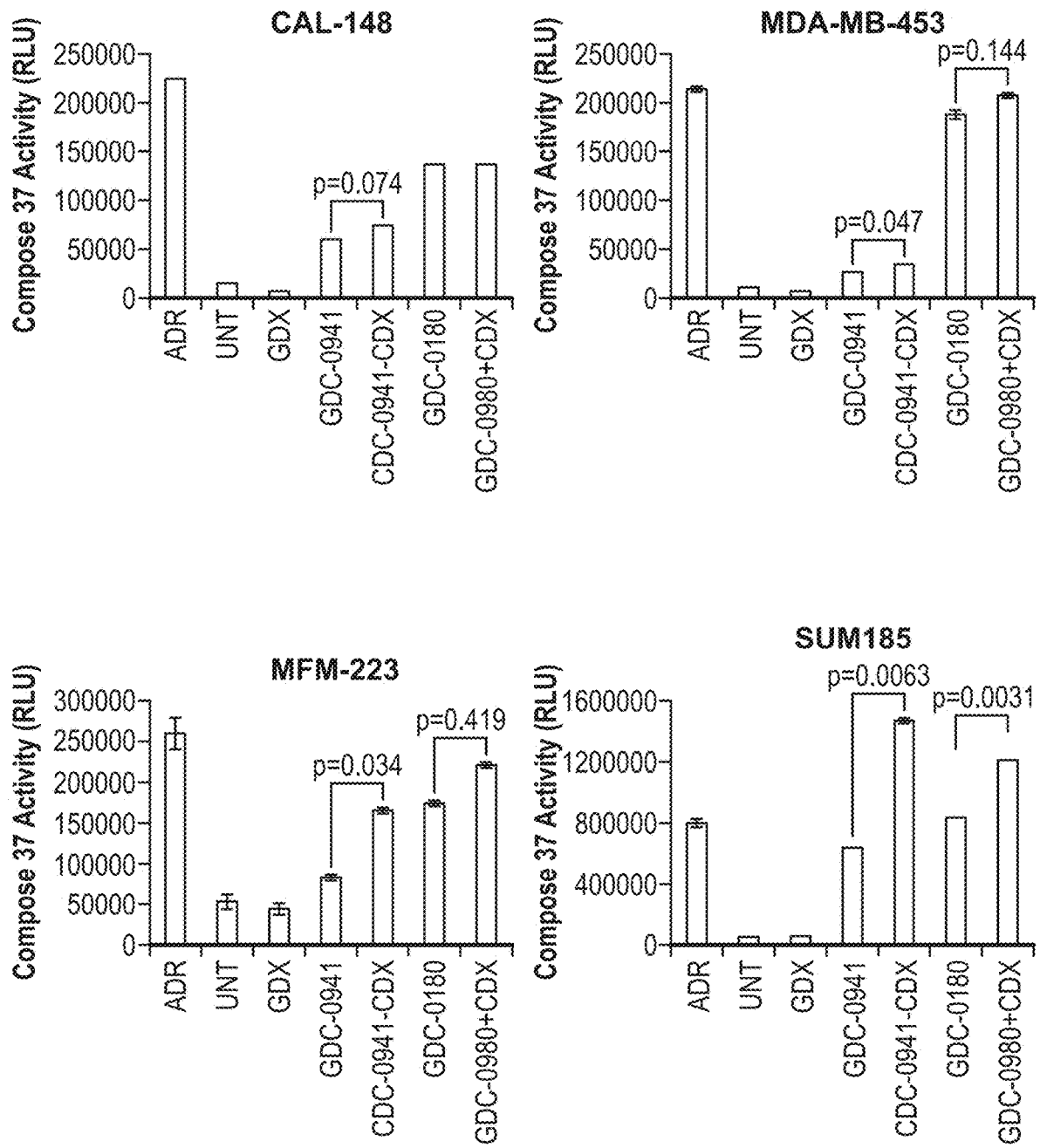
FIGS. 31A-31B: Combined inhibition of AR and PI3K increases apoptotic cell death in AR+TNBC cell lines. (31A) Bar graphs display relative caspase 3/7 activity (RLU) normalized to viable cell number 48 hrs after treatment with vehicle, positive control (3 μM adriamycin, ADR), 50 μM bicalutamide (CDX) and 3 μM GDC-0941 or 1 μM GDC-0980 alone or in combination with CDX. (31B) Histograms show representative cell cycle analysis of MDA-MB-453 cells treated with similar conditions as above. Indicated percentages represent the fraction of hypodiploid DNA (sub-G1), indicative of late stage apoptotic DNA fragmentation.
Figure 31B:
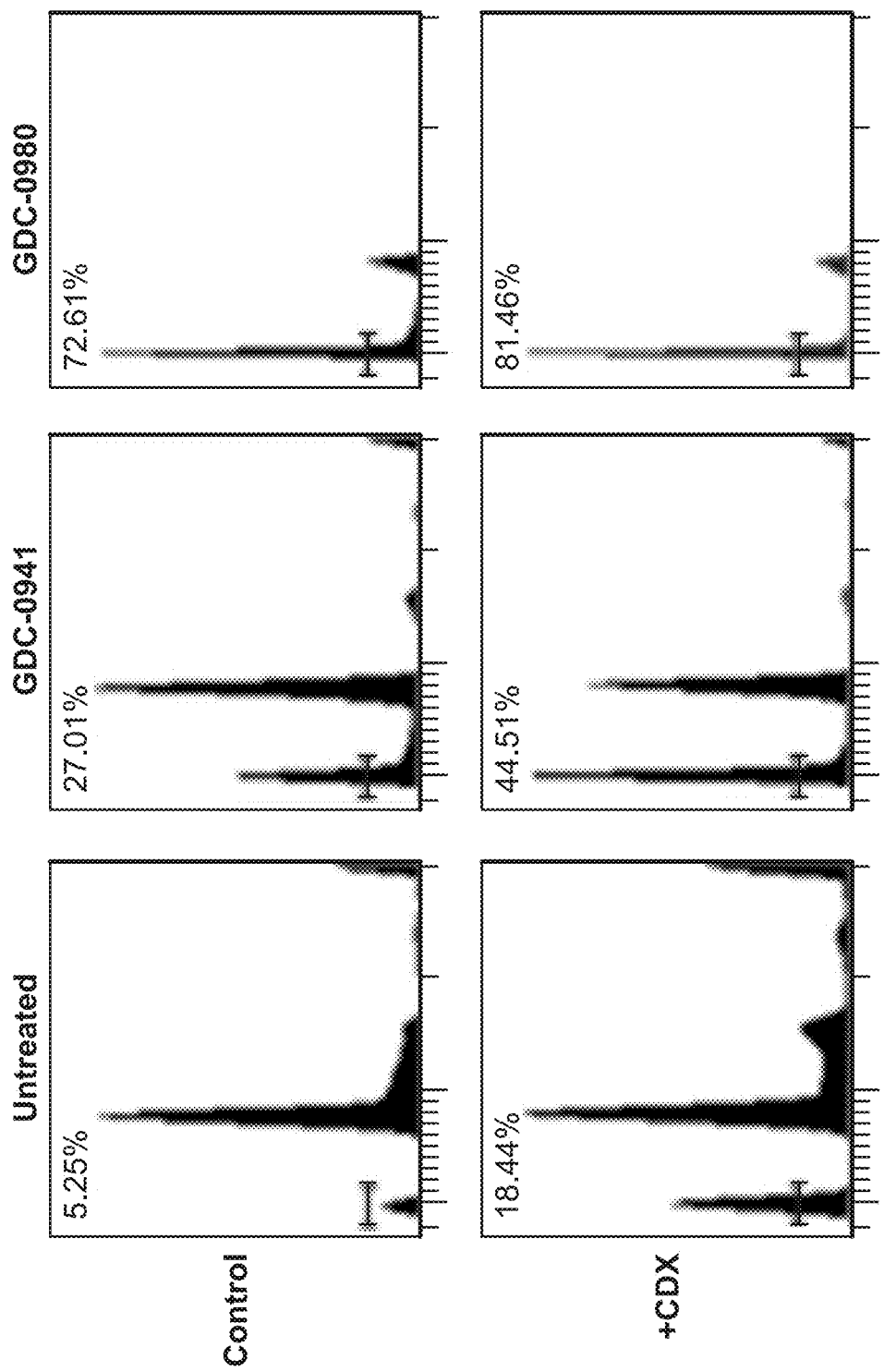

To determine if the decreased viability observed in AR-positive TNBC cell lines that were treated with the combination of pathway inhibitors described above was attributed to apoptotic cell death, activated caspase 3/7 levels after drug treatments were measured (FIGS. 31A-31B). Cells were treated with a high dose of adriamycin (ADR, 3□M) to measure the ability of cells to engage the apoptotic pathway. With exception of MFM-223 cells, each of the cell lines underwent robust caspase activation after 48 h of ADR treatment. While bicalutamide treatment did not induce caspase activation, treatment with both GDC-0941 and GDC-0980 alone caused caspase activation and the levels of apoptosis could be increased in combination with bicalutamide (FIG. 31A).

In addition to caspase activation, the percentage of sub 2N DNA (sub-G1)-containing cells (indicative of late stage apoptotic DNA fragmentation) was quantitated by FACs analysis. While bicalutamide treatment did not result in caspase activation, there was an increase in the sub-G1 fraction 48 h after treatment (5.25% to 18.44%) (FIG. 31B). Treatment with GDC-0941 or GDC-0980 resulted in higher sub-G1 fraction that increased in combination with bicalutamide, consistent with the caspase activation described above (FIG. 31B). Therefore, the decreased viability of AR-positive TNBC cell lines treated with a combination of AR and PI3K inhibitors can be, in part, attributed to apoptosis.

Simultaneous Targeting of AR and PI3K Decreases Viability of AR-Expressing Cell Lines Grown in a 3-D Forced Suspension Assay.

Figure 32A:
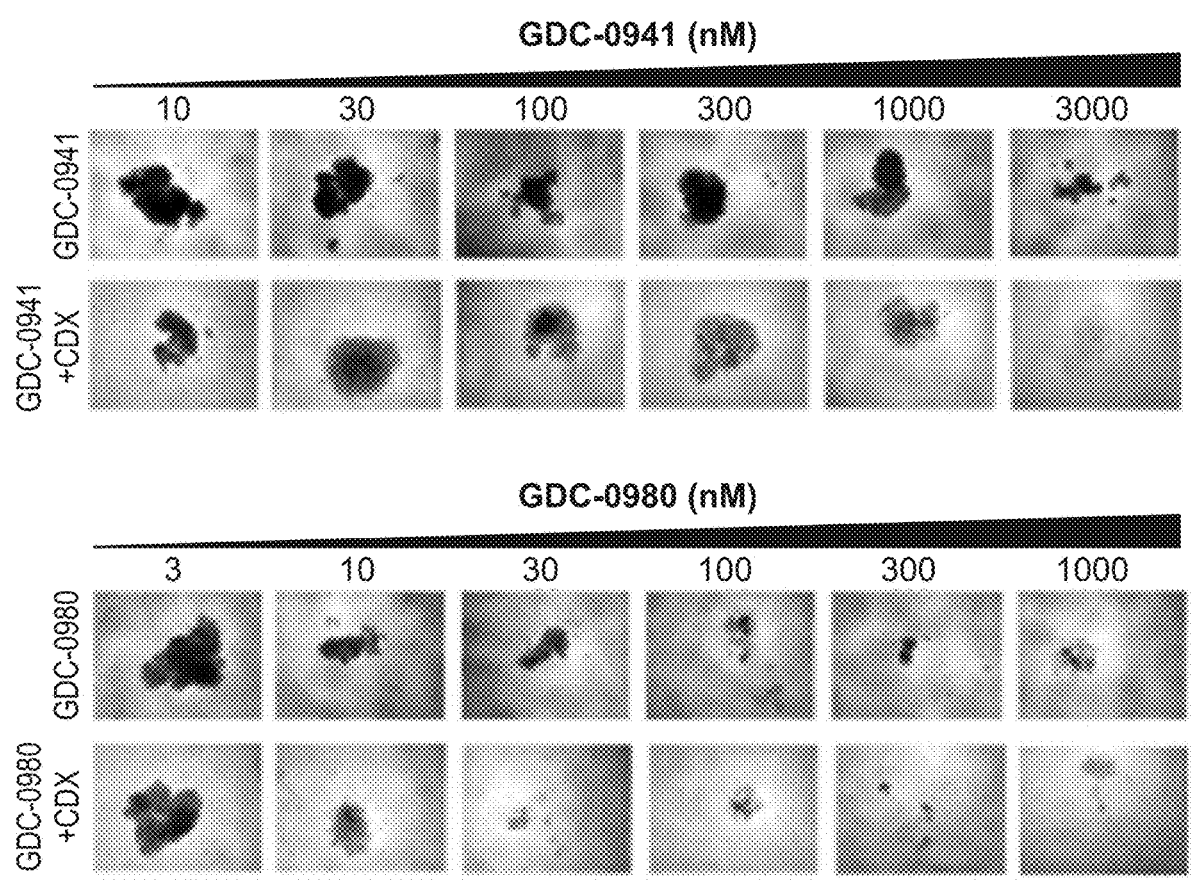
FIGS. 32A-32C: Simultaneous targeting of AR and PI3K decreases viability of AR-expressing cell lines grown in a 3-D forced suspension assay and inhibits in vivo xenograft growth. (31A) Representative images display 3-D cell aggregates of MDA-MB-453 cells treated with increasing doses of GDC-0941 or GDC-0980 in the absence or presence of 25 μM bicalutamide (CDX). (32B) Line graphs display relative viability of 3-D cell aggregates treated with GDC-0941 or GDC-0980 alone or in combination with 25 μM bicalutamide (CDX). Dashed black line depicts the theoretical line of additivity determined from the effect of bicalutamide alone and either GDC-0941 or GDC-0980 alone. (32C) Nude mice bearing established tumors from AR-positive TNBC cell lines (CAL-148 and MDA-MB-453) were treated with either bicalutamide (CDX, black hashed line), NVP-BEZ235, GDC-0980 or with the combination of bicalutamide and either NVP-BEZ235 (blue hashed line) or GDC-0980 (red hashed line). Serial tumor volumes ($mm^3$) were measured at the indicated days. Each data point represents mean tumor volume of 16 tumors; error bars represent SEM.
Figure 32B:
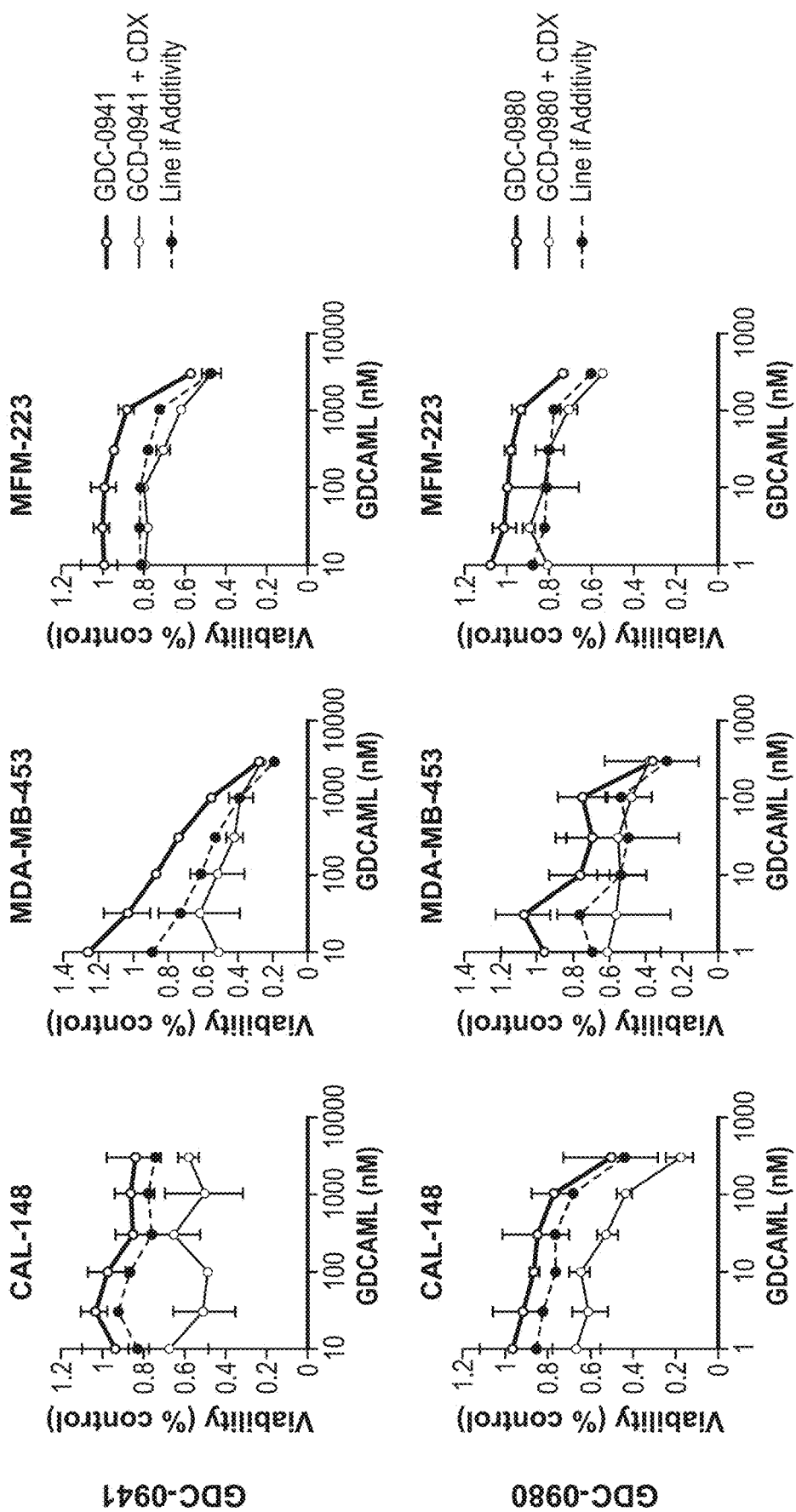
Figure 32C:
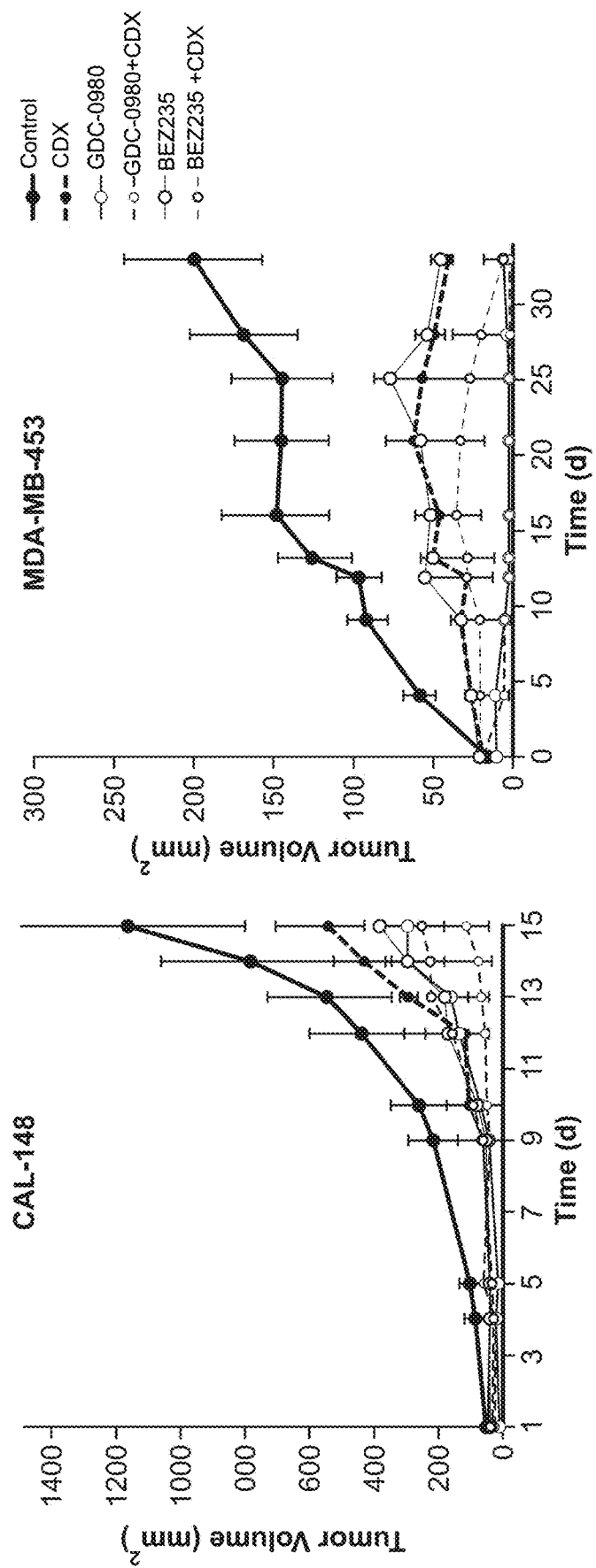
Figure 35:
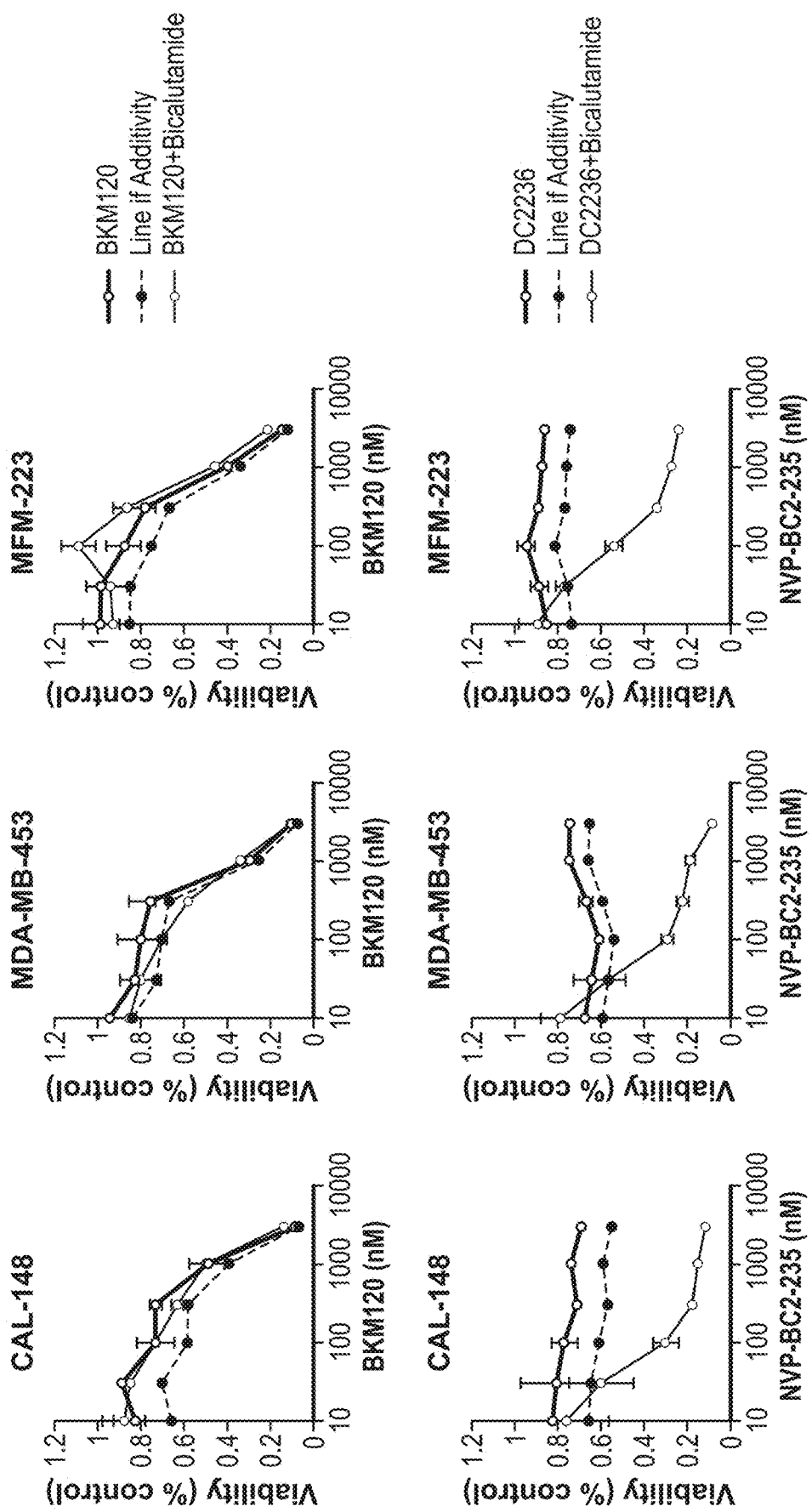
FIG. 35: Pharmacological targeting of AR with bicalutamide increases the efficacy of BKM120 and NVP-BEZ235 in AR-expressing TNBC. Line graphs show relative viability of AR-expressing cell lines treated with increasing doses of BKM120 (top) or NVP-BEZ235 (bottom) alone or in combination with 25 μM bicalutamide (CDX). Dashed black line depicts the theoretical line of additivity determined from the effect of bicalutamide alone and either BKM120 or NVP-BEZ235 alone.
Figure 36A:
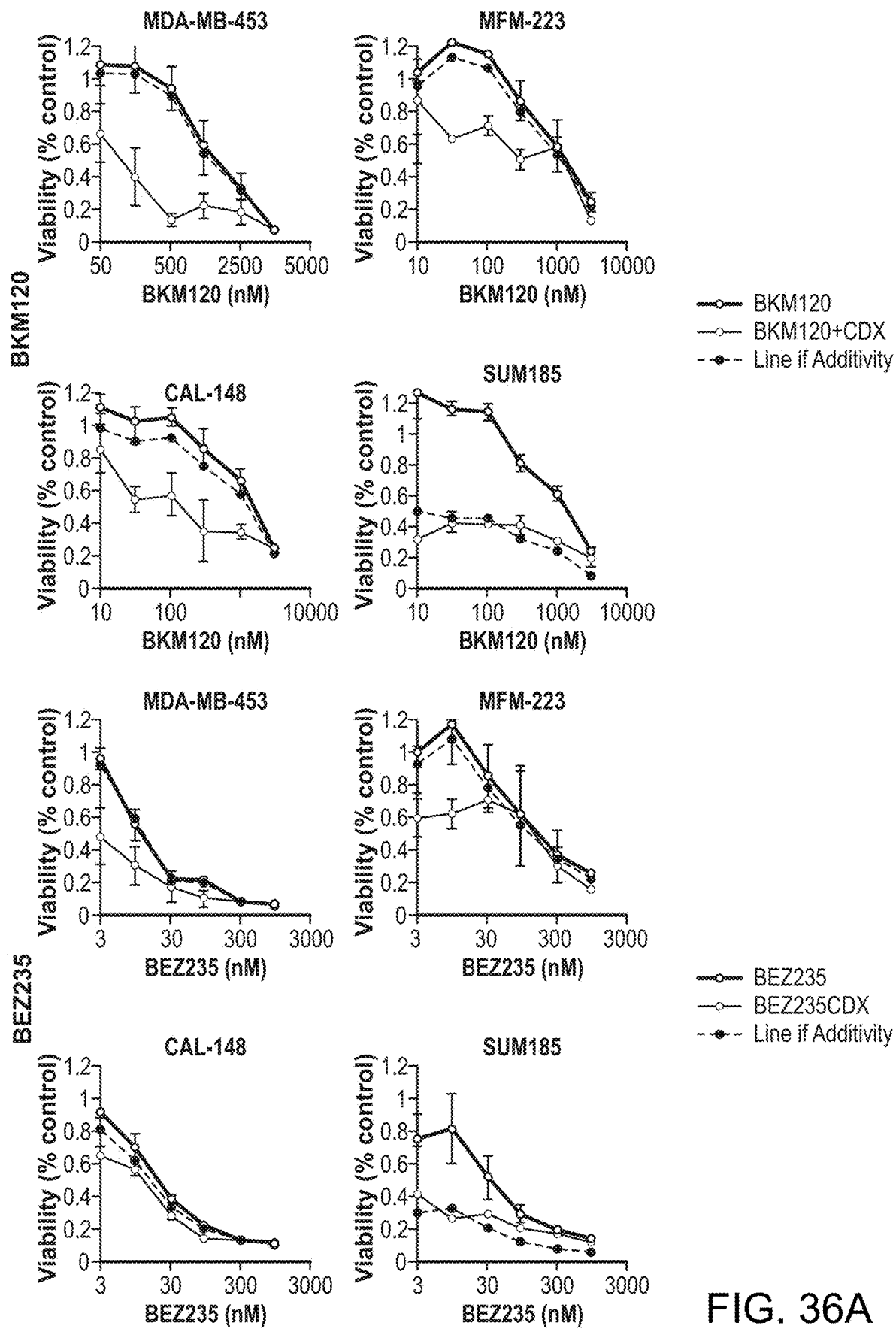
FIGS. 36A-36B: Simultaneous targeting of AR and PI3K decreases viability of AR-expressing cell lines grown in a 3-D forced suspension assay. (36A) Line graphs display relative viability of 3-D cell aggregates treated with BKM120 or NVP-BEZ235 alone or in combination with 25 uM bicalutamide (CDX). Dashed black line depicts the theoretical line of additivity determined from the effect of bicalutamide alone and either BKM120 or NVP-BEZ235 alone. (36B) Immunoblots from three AR-expressing TNBC cell lines treated with either bicalutamide (CDX), BKM-120, BEZ235 alone or in combination with bicalutamide for 24 h or 48 h. Western blots were probed for AR, PARP, p-AKT, AKT, p-S6, S6 and GAPDH.
Figure 36B:
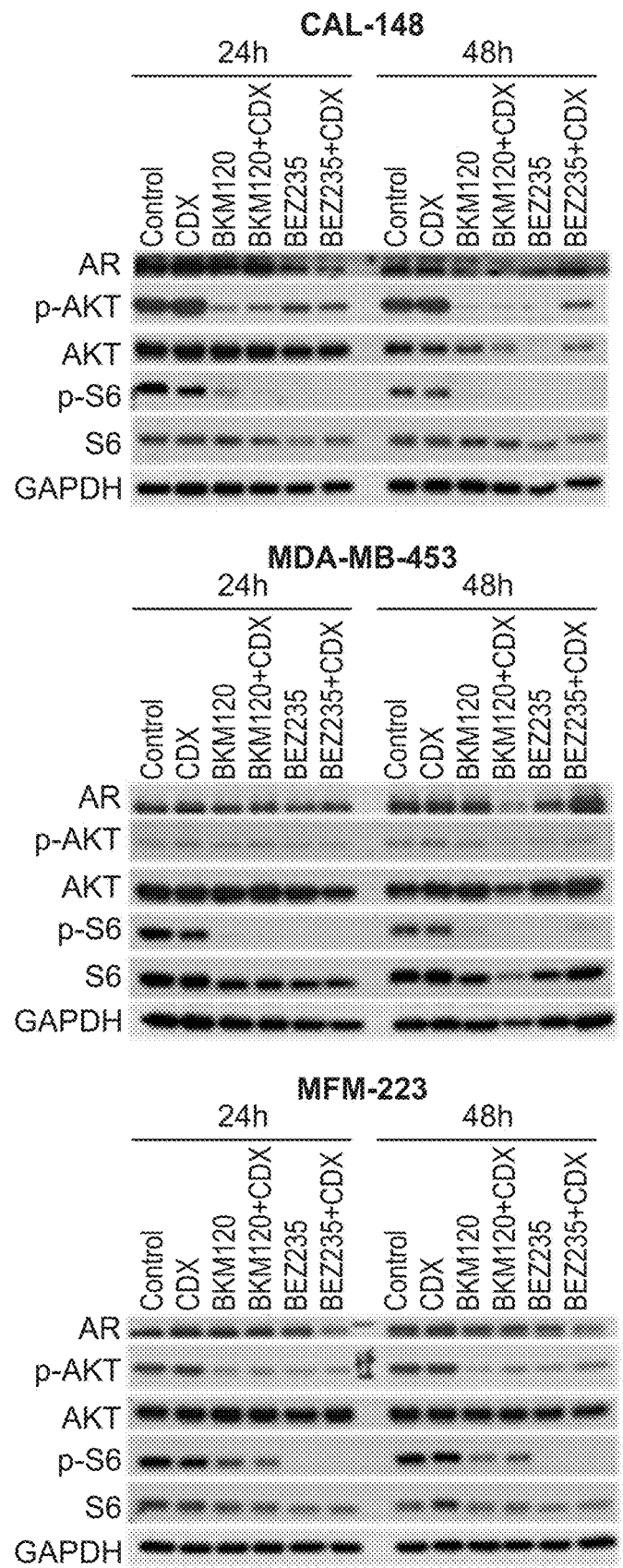

Since cell viability and drug sensitivity can be influenced by 2-D versus 3-D growth conditions, combined targeting of AR and PI3K/mTOR was evaluated in a 3-D forced suspension assay devoid of matrix. Cell lines were grown in forced suspension in agarose coated 96-well plates and treated with GDC-0941 or GDC0980 alone or in combination with bicalutamide (FIGS. 32A-32C). Increasing doses of GDC-0941 and GDC-0980 alone decreased cell aggregate size and viability in AR-expressing TNBC cell lines to a lesser degree when compared to similar treatments in 2-D (FIGS. 32A and 32B). However, the addition of bicalutamide was either additive or synergistic with PI3K/mTOR inhibition (FIG. 32B). Similar results were obtained when PI3K was inhibited with BKM120 or PI3K and mTOR were targeted with NVP-BEZ235 (FIG. 35). Together, these results indicate that simultaneous targeting of AR and PI3K/mTOR is more effective than either agent alone in AR-expressing TNBC.

PI3K is Activated after Pharmacological Inhibition of AR.

Figure 37:
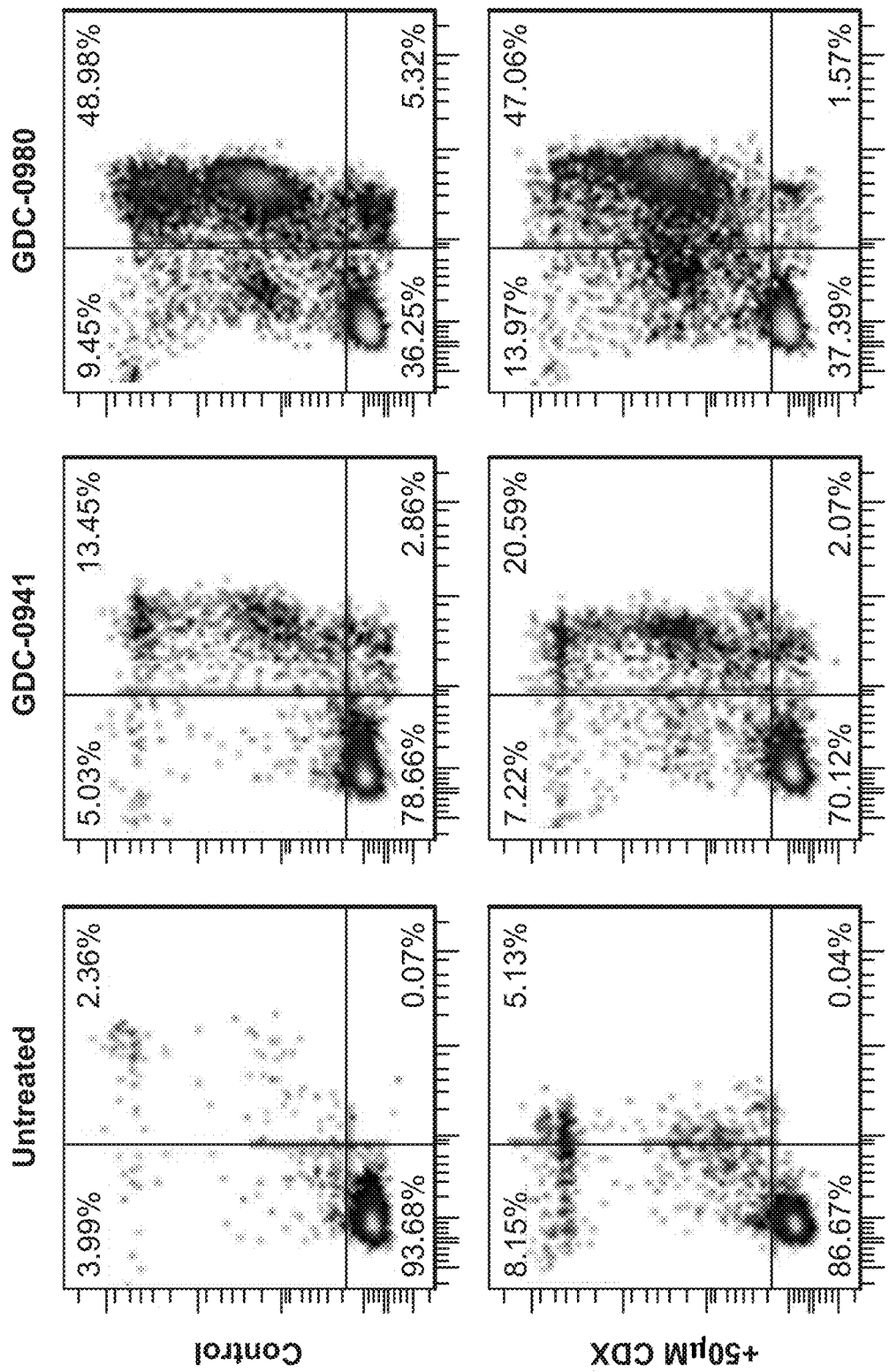
FIG. 37: Combined Targeting of PI3K and AR increase apoptosis detected by annexin V and propidium iodide (PI) staining. Scattergrams show the percentage of viable (lower left quadrant, annexin V and PI negative), early apoptotic (lower right quadrant, annexin V-positive and PI-negative), or late apoptotic/necrotic (upper right quadrant, annevin V and PI positive) cells following 48 hrs of treatment with either GDC-0941 or GDC-0980 alone or in combination with 50 μM bicalutamide (CDX).
Figure 38A:
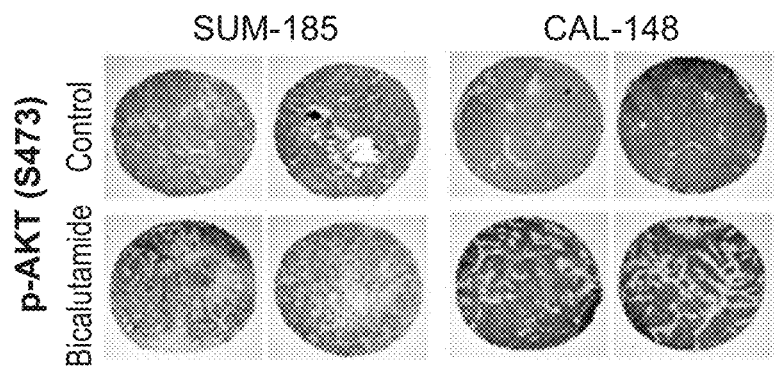
FIGS. 38A-38C: Genetic and pharmacological targeting of AR increases p-AKT.
Figure 38B:
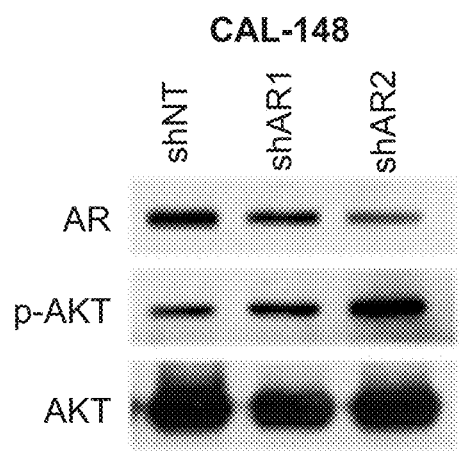
Figure 38C:
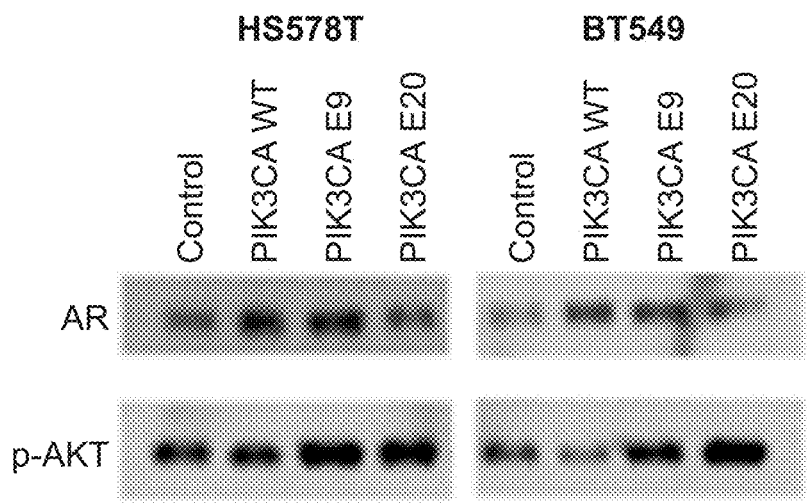
Figure 39:
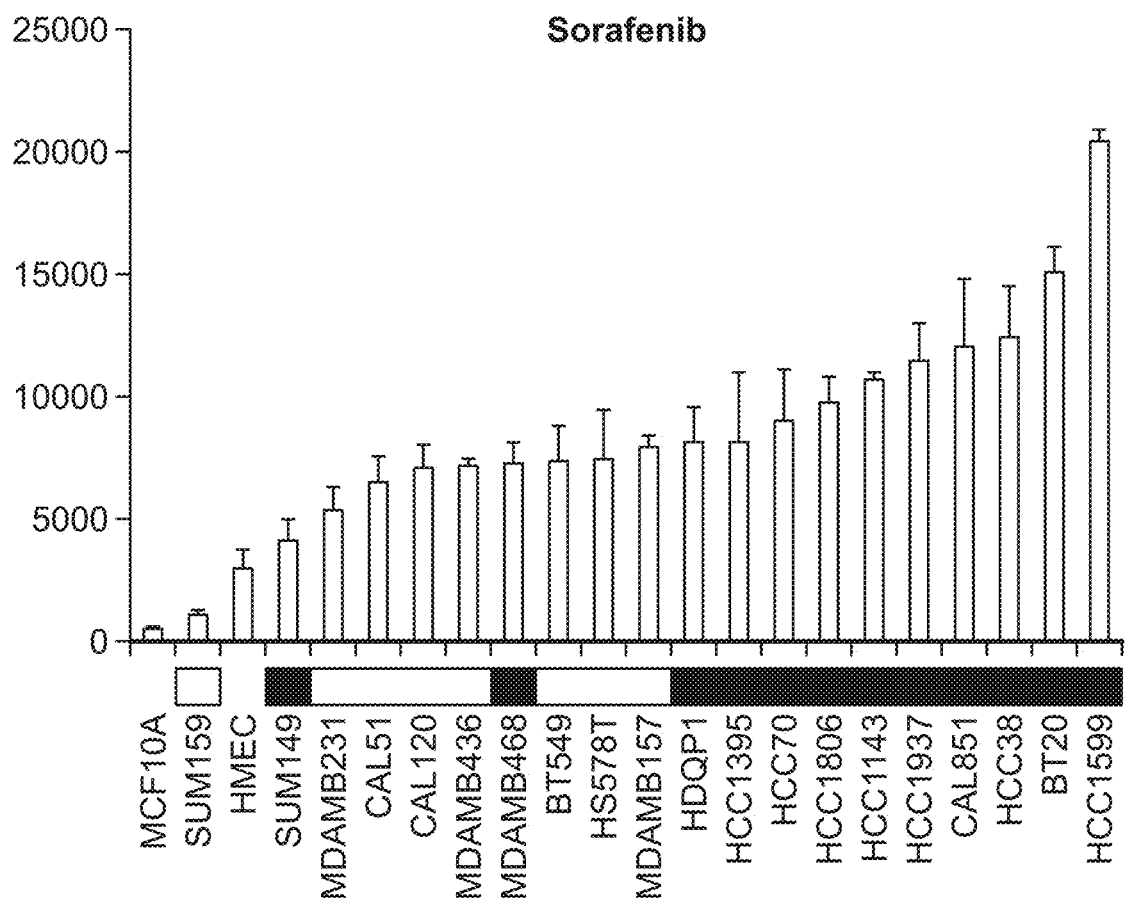
FIG. 39: PDGFR inhibition selectively inhibits viability of mesenchymal-like TNBC cell lines. Bar graph displays the half-maximal inhibitory concentration (nM) of the PDGFR inhibitor sorafenib for a panel of TNBC cell lines.

As described in Example 1, evaluation of bicalutamide in AR-expressing TNBC xenografts demonstrated significant reduction in tumor burden, however over time tumor growth occurred in the presence of drug, consistent with evolution of bicalutamide-resistant tumor cells. Since crosstalk between AR and PI3K has been demonstrated in prostate cancer, whether the level of PI3K activity changed between untreated and bicalutamide-resistant xenograft tumor cells was examined. Phospho-AKT (S473) levels were elevated in bicalutamide-resistant xenograft tumor cells (FIG. 37). Consistent with these findings were the findings herein of dose-dependent increases in p-AKT in cell lines upon genetic silencing of AR by shRNA (FIG. 38B).

Simultaneous Inhibition of AR and PI3K Signaling Decreases the Growth of LAR Cell Line-Derived Xenograft Tumors.

In order to further validate and investigate the combined targeting of AR and PI3K in AR-expressing TNBC in vivo, xenograft tumors in nude mice was established using two representative AR-positive TNBC cell lines (CAL-148 and MDA-MB-453). Following tumor establishment (25-50 mm$^3$), mice were either treated with vehicle, bicalutamide, NVP-BEZ235, GDC-0980 alone or either NVP-BEZ235 or GDC-0980 in combination with bicalutamide. While each single agent alone significantly decreased tumor growth, both PI3K/mTOR inhibitors in combination with bicalutamide inhibited tumor growth to the greatest extent (FIG. 32C). Thus, the combined inhibition of AR and PI3K appears to be a rational treatment strategy for AR-expressing TNBC and should be considered in future clinical trial design.

Discussion

Herein we show that activating mutations in PIK3CA are a frequent event in a subset of AR-expressing TNBC (LAR) that display luminal gene expression patterns. The data herein provide the preclinical rationale for targeting AR in combination with PI3K/mTOR inhibition.

Higher levels of p-AKT in cell line xenografts after prolonged treatment with bicalutamide and increased p-AKT after siRNA knockdown of AR in cell lines is demonstrated herein. The data show that combined targeting of AR and PI3K pathway inhibition can overcome the PI3K pathway activation after AR inhibition. These studies demonstrate that both pathways cross-regulate each other by reciprocal feedback and coordinately support survival when either is repressed. The feedback between the AR and PI3K pathway may, in part, explain the enrichment of PIK3CA mutations observed in AR-positive TNBC, as this co-evolution may be necessary to overcome the increased PTEN levels driven by AR signaling.

Methods

PIK3CA Mutation Evaluation.

Figure 33A:
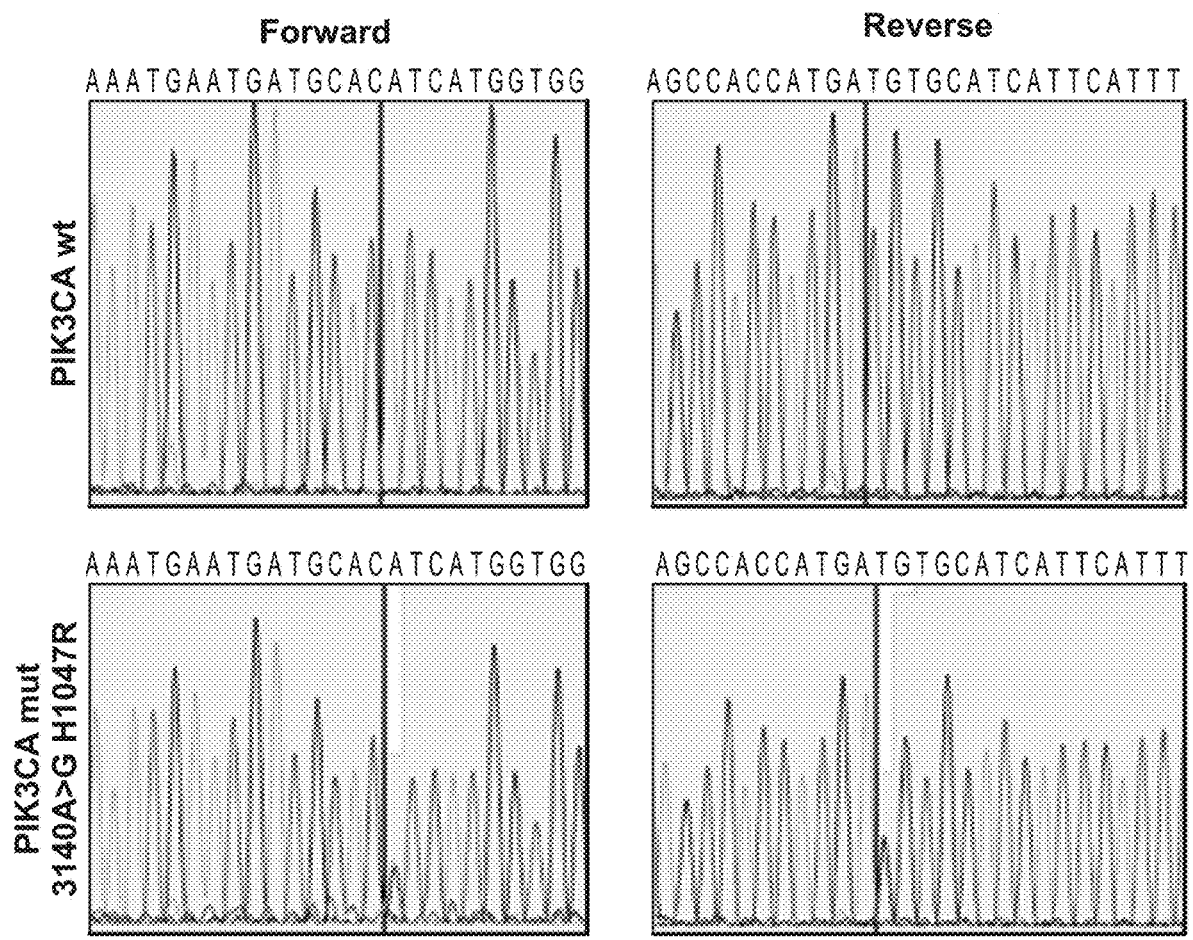
FIGS. 33A-33B: Detection of PIK3CA mutations by Sanger and digital droplet PCR. (33A) Electropherograms display representative results from sanger sequencing of the E20 amplicon in a PIK3CA wild-type (top) or a H1047R PIK3CA mutant sample. (33B) Scatterplot shows the percent of cells with mutant PIK3CA detected by digital droplet compared to Sanger sequencing.
Figure 33B:
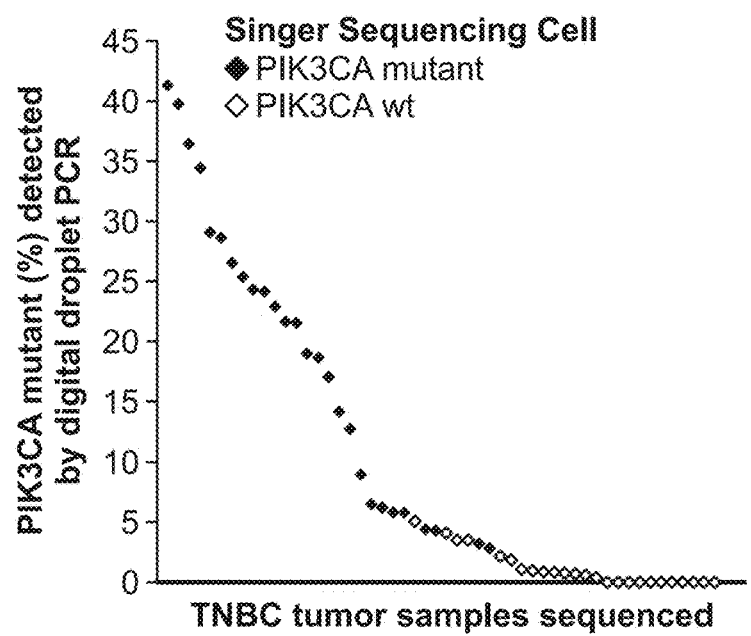

Two independent methods were used to identify PIK3CA mutations in tumor samples. Samples were identified as mutant if they had greater than 5% of the cells positive by microdroplet PCR, as there was complete concordance with Sanger sequencing calls, or called mutant by Sanger when microdroplet samples were 5% and >1% (FIGS. 33A-33B).

Sanger

To detect mutations in PIK3CA (H1047), a 588 bp fragment was PCR-amplified from exon 20 of PIK3CA using the following amplification primers; foreword: TGACATTT-GAGCAAAGACCTG (SEQ ID NO: 1), reverse: CATAA-CATGAAATTGCGCATT (SEQ ID NO: 2). Sanger sequencing was performed on the PCR amplicon using the following internal sequencing primers; Exon Forward: ACATCATTTGCTCCAAACTGA (SEQ ID NO: 3) Reverse: CCTATGCAATCGGTCTTTGC (SEQ ID NO: 4) (Samuels et al., Science, 304:554 (2004)).

Droplet Digital PCR

The TaqMan PCR reaction mixture was assembled from a 2×ddPCR Mastermix (Bio-Rad), 20× primer, and probes (final concentrations of 900 and 250 nM, respectively) and template (variable volume) in a final volume of 20 μL. Each assembled ddPCR reaction mixture was then loaded into the sample well of an eight-channel disposable droplet generator cartridge (Bio-Rad). A volume of 70 μL of droplet generation oil (Bio-Rad) was loaded into the oil well for each channel. The cartridge was placed into the droplet generator (Bio-Rad). The cartridge was removed from the droplet generator, where the droplets that collected in the droplet well were then manually transferred with a multichannel pipet to a 96-well PCR plate. The plate was heat-sealed with a foil seal and then placed on a conventional thermal cycler and amplified to the end-point (40 cycles). Thermal cycling conditions were 95° C.×10 min (1 cycle), 94° C.×30 s and 57° C.×60 s (40 cycles), and 12° C. hold. After PCR, the 96-well PCR plate was loaded on the droplet reader (Bio-Rad), which automatically reads the droplets from each well of the plate. Analysis of the ddPCR data was performed with QuantaSoft analysis software (Bio-Rad) that accompanied the droplet reader. Primer sequences: Forward: 5'GATAAAACTGAGCAAGAGGCTTTGG' (SEQ ID NO: 5), Reverse: 5'GCTGTTTAATTGTGTGGAAGATCCAA' (SEQ ID NO: 6), Wild type probe: 5'-VIC-CCACCAT-GATGTGCA-MGB-3 (SEQ ID NO: 7), 'H1047L probe:5'-FAM-CCACCATGATGAGCA-MGB-3' (SEQ ID NO: 8), H1047R probe: 5'-FAM-CCACCATGATGCGCA-MGB-3' (SEQ ID NO: 9).

Subtyping TNBC Cases and Validating PIK3CA Mutations in the TCGA.

RNA-seq (lvl 3), somatic mutations (lvl2) and reverse phase protein array (RPPA, lvl3) data for breast cancer was downloaded from The Cancer Genome Atlas (tcga-data.n-ci.nih.gov/). RNA-seq data (RPKM) was combined and molecularly subtyped using the online TNBCtype software according to published methods (Chen et al., Cancer Informatics, 11:147-1556 (2012)). After removal of potential ER positive, 137 TNBC samples were identified and assigned a molecular subtype.

Reverse Phase Protein Array on TNBC Cell Lines.

Tumor or cell lysates were two-fold-serial diluted for 5 dilutions (from undiluted to 1:16 dilution) and arrayed on nitrocellulose-coated slide in 11×11 format. Samples were probed with antibodies by CSA amplification approach and visualized by DAB colorimetric reaction. Slides were scanned on a flatbed scanner to produce 16-bit tiff image and the density was quantified by MicroVigene. Relative protein levels for each sample were determined by interpolation of each dilution curves from the standard curve (supercurve) of the slide (antibody) as previously described (Zhang et al., Bioinformatics, 25:650-654 (2009)). These values were Log 2 transformed and normalized for protein loading by transformation a to linear value. Linear normalized data was then median-centered for heatmap comparisons.

Cell Proliferation/Viability Assays and IC$_{50}$ Determinations.

All cell lines were maintained in culture as previously described (JCI ref). Breast cancer cell lines and HMECs were seeded (3,000-10,000 cells) in quadruplicate wells in 96-well plates. Media was then replaced with either fresh media (control) or media containing half-log serial dilutions of the following drugs: GDC-0941 (10-nM-3000 nM), GDC0980 (1 nM-300 nM), BKM120 (10-nM-3000 nM) and NVP-BEZ235 (1 nM-300 nM) purchased from Selleck Chemicals (Houston, TX) or in combination with bicalutamide (Sigma, St. Louis, MO). Viability was determined from measuring fluorescent intensity after metabolic reduction of Alamar Blue in the presence/absence of drug after 72 hours. Viability assays were performed in triplicate and replicates were normalized to untreated wells. Inhibitory concentration ($IC_{50}$) values were determined after double-log transformation of dose response curves as previously described (Lehmann et al., J Clin Invest, 121:2750-2767 (2011)).

Quantification of Apoptosis

Caspase 3/7 Activity

Cell lines were seeded in triplicate in 96-well plates. Media was removed and replaced with media containing vehicle (control) or indicated drugs. After 48 hrs, apoptosis was determined by measuring luciferase from activated caspase 3/7 upon addition of Caspase-Glo reagent (Promega, Madison, WI). Relative levels of caspase activity were normalized to viable cell number determined by metabolic reduction of Alamar blue.

shRNA Knockdown of AR

293FT cells were transfected with Lipofectamine 2000 (Invitrogen, Grand Island, NY) the packaging vectors PAX2 and pMD2.g (Addgene, Cambridge, MA) along with pLKO.1-puro Misson shRNA constructs (Sigma) targeting AR or a non-targeting control. Viral media was harvested 48 h post-transfection and added to target cells along with polybrene (10 µg/mL). 72 h post-infection MDA-MB-453 (8,000 cells/well), CAL-148 (5,000 cells/well) and MFM-223 (7,000 cells/well) seeded in quadruplicate in 96-well plates. Following overnight attachment media was replaced with fresh media (control) or media containing half-log dilutions of drugs. Following incubation in drug for 72 h viability was measured with alamarBlue as previously described (Lehmann et al., J Clin Invest, 121:2750-2767 (2011)).

Forced Suspension Viability Assay

CAL-148, MFM-223 and MDA-MB-453 cells were plated (10,000 cells/well) in quadruplicate into 96-well plates coated with 0.9% agarose diluted in corresponding media. Following 5 d of growth, cells were then treated with increasing half-log concentrations of GDC-0941 (10-3000 nM), GDC0980 (1 nM -300 nM), BKM120 (10 nM-3000 nM) and NVP-BEZ235 (1 nM-300 nM) alone or in combination with 25 µM bicalutamide (CDX) for an additional 72 h, upon which cells were imaged and viability determined by Alamar blue.

Immunostaining

Formalin fixed paraffin embedded (FFPE) tissue were used for immunohistochemical studies. Androgen receptor (AR) expression and p-AKT expression were evaluated in FFPE tissue using the DAKO (Carpinteria, CA) antibody: AR (clone AR411) at a 1:50 dilution and AKT p473 (Cell signaling, CA) at a 1:200 dilution for 1 h at room temperature. FFPE tissue was subject to antigen retrieval with high pH buffer (pH 8.0) followed by overnight incubation with an AR (1:30) or Ki67 (1:75) antibody dilution overnight.

Immunoblotting

Cells were trypsinized, lysed and relative protein expression was determined by Western blot as previously described (JCI reference) with the following antibodies; the AR polyclonal antibody, SC-N20 (Santa Cruz Biotechnology), pS6-Ser235/236 (Cell Signaling #4856), S6 (Cell Signaling #2317), pAKT-5473 (Cell Signaling #9271), AKT (Cell Signaling #9272), PARP (Cell Signaling #9542) and GAPDH (Millipore).

Xenograft Tumor Studies.

Five-week-old female athymic nude-Foxnlnu mice (Harlan Sprague-Dawley) were injected (s.c.) with either ~4×10$^6$ (CAL-148) or ~10×10$^6$ (MDA-MB-453) cells suspended in media (200 µL) into each flank using a 22-gauge needle. Once tumors reached a volume of 25-50 mm$^3$, mice were randomly allocated to treatment or vehicle arms. Treatments included bicalutamide p.o. (100 mg/kg/d), GDC0980 p.o. (7.5 mg/kg/d) in 5% DMSO, 0.5% carboxymethyl cellulose (MCT) or NVP-BEZ235 p.o. (50 mg/kg/d) in 0.5% MCT or the combination of bicalutamide and either GDC-0980 or NVP-BEZ235 according to the above concentrations. Tumor diameters were serially measured at the indicated times with digital calipers and tumor volumes were calculated as width$^2$×length/2.

Supplemental Results

Validation of Digital Droplet PIK3CA Mutant PCR Primers

Primers were validated using on cell lines with known PIK3CA status cells. The percentage of DNA reflected the frequency of mutant PIK3CA alleles similar to expected genotype status; HMECwt/wt=0.01%, MDA-MB-453 wt/mut=61.19% and SUM-185mut/mut=97.09% (FIG. 26A). The slightly higher mutant frequency in the heterozygous mutant cell line MDA-MB-453 is likely caused by chromosomal aneuploidy. Digital droplet PCR was far more quantitative than Sanger sequencing and both methods were 100% concordant when mutant DNA was present at levels greater than 5% (FIGS. 33A-33B).

Example 3

Cell proliferation/viability assays and $IC_{50}$ determinations. All cell lines were maintained in culture as previously described herein. Breast cancer cell lines and HMECs were seeded (3,000-10,000 cells) in quadruplicate wells in 96-well plates. Media was then replaced with either fresh media (control) or media containing half-log serial dilutions of the following drugs: Sorafenib, OSi-906, BMS-754807 and PF2341066 purchased from Selleck Chemicals (Houston, TX) Viability was determined from measuring fluorescent intensity after metabolic reduction of Alamar Blue in the presence/absence of drug after 72 hours. Viability assays were performed in triplicate and replicates were normalized to untreated wells. Inhibitory concentration ($IC_{50}$) values were determined after double-log transformation of dose response curves.

PDGFR inhibition selectively inhibits viability of mesenchymal-like TNBC cell lines. Bar graph displays the half-maximal inhibitory concentration (nM) of the PDGFR inhibitor sorafenib for a panel of TNBC cell lines. Colorbar below designates the TNBC subtype (basal-like=black, mesenchymal-like=grey) or normal cells (white).

IGF1R inhibition selectively inhibits viability of mesenchymal-like TNBC cell lines. Bar graph displays the half-maximal inhibitory concentration (nM) of the IGF1R inhibitor OSI-906 for a panel of TNBC cell lines. Colorbar below designates the TNBC subtype (basal-like=black, mesenchymal-like=grey) or normal cells (white).

IGF1R inhibition selectively inhibits viability of mesenchymal-like TNBC cell lines. Bar graph displays the half-maximal inhibitory concentration (nM) of the IGF1R inhibitor BMS-754807 for a panel of TNBC cell lines. Colorbar below designates the TNBC subtype (basal-like=black, mesenchymal-like=grey) or normal cells (white).

MET inhibition selectively inhibits viability of mesenchymal-like TNBC cell lines. Bar graph displays the half-maximal inhibitory concentration (nM) of the MET inhibitor PF2341066 for a panel of TNBC cell lines. Colorbar below designates the TNBC subtype (basal-like=black, mesenchymal-like=grey) or normal cells (white).

TABLE 1

Breast cancer GE data sets used to derive the TNBC training set

| Data Set | Country | Case Definitions | BC cases | IHC | N (% TN) | False Positive (%) ER | False Positive (%) PR | False Positive (%) HER | Refs. |
|---|---|---|---|---|---|---|---|---|---|
| GSE-494[A] | Sweden | Breast cancers from patients treated in Uppsala County, Sweden, between 1987 and 1989 | 251 | ER, PR | 25(10) | 3.6 | 2.8 | | Miller LD, et al. An expression signature for p53 status in human breast cancer predicts mutation status, transcriptional effects, and patient survival. *Proc Natl Acad Sci U.S.A.* 2005; 102(38): 13550-13555. |
| GSE-904[A] | USA | Frozen tissue samples from primary, sporadic and 4 BRCA1-mutant breast obtained through the Harvard Breast SPORE | 43 | ER, PR, HER2 | 17(40) | 0.0 | 0.0 | | Richardson AL, et al. X chromosomal abnormalities in basal-like human breast cancer. *Cancer Cell.* 2006; 9(2): 121-132. |
| GSE-2109[A,B] | USA | The international genomics consortium collection of breast cancer tissue samples processed by the expO biospecimen repository, obtained from community hospitals | 351 | Variable[O] | 60(17) | | | | |
| GSE-7390[A,D] | Europe | Lymp node-negative breast cancer patients, systemically untreated, performed at the Bordet Institute and part of the TRANSBIG consortium | 198 | ER | 29(15) | 2.5 | | | Desmedt C, et al. Strong time dependence of the 76-gene prognostic signature for node-negative breast cancer patients in the TRANSBIG multicenter independent validation series. *Clin Cancer Res.* 2007; 13(11): 3207-3214. |
| E-TABM-15g[E] | USA | Frozen tumors collected from patients that received adjuvant chemotherapy (typically Adriamycin and CTX) at UC San Francisco and the California Pacific Medical Center between 1989 and 1997 | 100 | ER, PR, HER2 | 30(23) | 0.8 | 2.3 | 2.3 | Chin K, et al. Genomic and transcriptional aberrations linked to breast cancer pathophysiologies. *Cancer Cell.* 2006; 10(6): 529-541. |
| Gse-2034[A] | Netherlands | Lymph node-negative relapse-free patients (80) and lymph node-negative patients that developed a distant metastasis (106) treated at Erasmus Medical Center | 286 | ER | 53(19) | 3.1 | | | Wang Y, et al. Gene-expression profiles to predict distant metastasis of lymph-node-negative primary breast cancer. *Lancet.* 2005; 365(9460): 671-679. |
| GSE-2990[A] | Sweden, United Kingdom | Invasive breast cancer from Uppsala, Sweden (88), of which 64 received tamoxifen only, or from John Radcliffe, Oxford, United Kingdom (101) of which all received mixed hormone and chemotherapy | 189 | ER | 11(6) | 1.1 | | | Sotiriou C, et al. Gene expression profiling in breast cancer: understanding the molecular basis of histologic grade to improve prognosis. *J Natl Cancer Inst.* 2006; 98(4): 262-272. |
| GSE-1456[A] | Sweden | Breast cancer patients receiving surgery at Kanolinska Hospital between 1994 and 1996 | 159 | NA | 22(14) | | | | Pawitan Y, et al. Gene expression profiling spares early breast cancer patients from adjuvant therapy: derived and validated in two population-based cohorts. *Breast Cancer Res.* 2005; 7(6): R953-R964. |
| GSE-22513[A], GSE-28821, GSE-28796 | USA | Invasive breast cancer pretreatment biopsies taken from patients at the Vanderbilt-Ingram Cancer Center | 112 | ER, PR, HER2 | 25(22) | 0.0 | 0.0 | 0.0 | |
| GSE-11121[A] | Germany | Lymph node-negative breast cancer patients treated at the Johannes Gutenberg University Mainz between 1988 and 1998. Patients were all treated with surgery without adjuvant therapy | 200 | NA | 19(10) | | | | Schmidt M, et al. The humoral immune system has a key prognostic impact in node-negative breast cancer. *Cancer Res.* 2008; 68(13): 5405-5413. |
| GSE-2603[A] | USA | Primary breast cancers surgically resected at the Memorial Sloan-Kettering Cancer Center | 99 | ER, PR | 32(32) | 0.0 | 0.0 | | Minn AJ, et al. Genes that mediate breast cancer metastasis to lung. *Nature.* 2005; 436(7050): 518-524. |

TABLE 1-continued

Breast cancer GE data sets used to derive the TNBC training set

| Data Set | Country | Case Definitions | BC cases | IHC | N (% TN) | False Positive (%) | | | Refs. |
|---|---|---|---|---|---|---|---|---|---|
| | | | | | | ER | PR | HER | |
| MDA133[F] | USA | Tumors from preoperative paclitaxel and 5-FU, doxorubicin, and CTX performed at the University of Texas MD Anderson Cancer Center | 133 | ER, PR, HER2 | 21(16) | 0.0 | 3.0 | 0.8 | Gibson GR, Qian D, Ku JK, Lai LL. Metaplastic breast cancer: clinical features and outcomes. *Am Surg.* 2005;71(9): 725-730. |
| GSE-5364[A] | Singapore | Tumors from the National Cancer Centre of Singapore | 183 | NA | 31(17) | | | | Yu K. et al. A precisely regulated gene expression cassette potently modulates metastasis and survival in multiple solid cancers. *PLoS Genet.* 2008;4(7): e1000129. |
| GSE-1561[A] | Belgium | Tumors from patients with invasive or inflammatory breast cancers treated with 5-FU, epirubicin, and CTX obtained by the European Organization for Research and Treatment, Brussels, Belgium | 49 | ER, PR | 16(33) | 0.0 | 0.0 | | Farmer P, et al. Identification of molecular apocrine breast tumours by microarray analysis. *Oncogene.* 2005;24(29): 4660-4671. |
| TOTAL | | | 2353 | | 386(16) | 1.7 | 1.7 | .09 | |

TABLE 2

Breast cancer GE data sets used to derive the TNBC validation set

| Data Set | Country | Case Definitions | BC cases | IHC | N (% TN) | False Positive (%) ER | PR | HER | Refs. |
|---|---|---|---|---|---|---|---|---|---|
| GSE-5327[A,B] | Netherlands | Tumors from patients with lymph node-negative breast cancer, who did not receive systemic neoadjuvant or adjuvant therapy (EMC-344) at Erasmus Medical Center, Rotterdam, Netherlands treated between 1980 and 1995 | 58 | N/A | 17(30) | | | | Minn AJ, et al. Genes that mediate breast cancer metastasis to lung. Nature. 2005; 436(7050): 518-524. |
| GSE-5874[A] | USA | Primary breast cancers between 1993 and 2003 from patients receiving neoadjuvant chemotherapy collected at Baltimore hospitals | 95 | ER, HER2 | 17(35) | 8.3 | | 0.0 | Boersma BJ, et al. A stromal gene signature associated with inflammatoiy breast cancer. Int J Cancer. 2008; 122(6): 1324-1332. |
| GSE-12276[A] | Netherlands | Lymph node-negative breast cancers from patients with metastatic disease (114) following relapse after chemotherapy (EMC-192) and patients (48) without adjuvant systemic therapy (EMC-286) at Erasmus Medical Center, Rotterdam, Netherlands | 204 | N/A | 46(24) | | | | Bos PD, et al. Genes that mediate breast cancer metastasis to the brain. Nature. 2009; 459(7249): 1005-1009. |
| GSE-16446[A,D] | Europe | Tumors from patients with ER-negative primary breast cancers treated with single-agent neoadjuvant epirubicin at European hospitals and coordinated at the Institut Jules Borde, Brussels, Belgium | 120 | HER | 46(38) | | | 2.5 | Li Y, et al. Amplification of LAPTM4B and YWHAZ contributes to chemotherapy resistance and recurrence of breast cancer. Nat Med. 2010; 16(2): 214-218. |
| GSE-18864[A,C] | USA | Tumors from patients with stage II or III TNBCs treated with cisplatin at the Dana-Farber/Harvard Cancer | 24 | ER, PR, HER2 | 24(100) | | | | Li Y, et al. Amplification of LAPTM4B and YWHAZ contributes to chemotherapy resistance and recurrence of breast cancer. Nat Med. 2010; 16(2): 214-218. |
| GSE-19615[A] | USA | Breast cancers from patients and treated with adjuvant chemotherapy obtained from the Harvard Breast SPORE, Boston, Massachusetts, diagnosed between 2000 and 2003 | 115 | ER, PR, HER2 | 30(26) | 0.0 | 0.9 | 3.5 | Li Y, et al. Amplification of LAPTM4B and YWHAZ contributes to chemotherapy resistance and recurrence of breast cancer. Nat Med. 2010; 16(2): 214-218. |
| GSE-20194[A] | USA | Pretreatment tumors obtained from stage I-III breast cancers at the University of Texas M.D. Anderson Cancer Center | 278 | ER, PR, HER2 | 27(23) | 2.6 | 4.3 | 0.0 | Juul N, et al. Assessment of an RNA interference screen-derived mitotic and ceramide pathway metagene as a predictor of response to neoadjuvant paclitaxel for primary triple-negative breast cancer: a retrospective analysis of five clinical trials. Lancet Oncol. 2010; 11 (4): 358-365. |
| TOTAL | | | 894 | N/A | 201(22) | 1.7 | 2.6 | 1.7 | |

[A]Source: GEO.
[B]GSE-5327 and GSE-16446 data sets are derived from ER-negative tumors by IHC.
[C]GSE18864 data set includes only ER, PR and HER2 negative tuomrs by IHC.

TABLE 3

Assignment of TNBC cell lines to subtypes

| TNBC Subtype | Cell Line | Subtype Correlation (P Value) | Histology | Mutations[A] | Intrinsic Subtype[B] | Basal Subtype[C] |
|---|---|---|---|---|---|---|
| Basal-like | | | | | | |
| BL1 | HCC2157 | 0.66 (0.00) | DC | BRCA1; STAT4; UTX | Basal | Basal A |
| | HCC1599 | 0.62 (0.00) | DC | BRCA2: TP53; CTNND1; TOP2B; CAMK1G | Basal | Basal A |
| | HCC1937 | 0.28 (0.00) | DC | BRCA1; TP53; MAPK13; MDC1 | HER2 | Basal A |
| | HCC1143 | 0.26 (0.00) | IDC | TP53 | Basal | Basal A |
| | HCC3153 | 0.24 (0.00) | | BRCA1 | | Basal A |
| | MDA-MB-468 | 0.19 (0.06) | DC | PTEN, RB1; SMAD4; TP53 | | Basal A |
| | HCC38 | 0.19 (0.01) | DC | CDKN2A; TP53 | Unclassified | Basal B |
| BLs | SUM149PT | 0.30 (0.00) | INF | BRCA1 | Unclassified | Basal B |
| | CAL-851 | 0.25 (0.00) | IGA | RB1; TP53 | Basal | |
| | HCC70 | 0.24 (0.04) | DC | PTEN; TP53 | Basal | Basal A |
| | HCC1806 | 0.22 (0.00) | ASCC | CDKN2A; TP53; UTX | Unclassified | Basal A |
| | HDQ-P1 | 0.18 (0.17) | IDC | TP53 | | |
| | HCC1187 | 0.22 (0.00) | DC | TP53; CTNNA1; DDX18; HUWE1; NFKBIA | Basal | Basal A |
| | DU4475 | 0.17 (0.00) | DC | APC; BRAPL MAP2K4; RB1 | Unclassified | |
| Mesenchymal-like | | | | | | |
| M | BT-549 | 0.21 (0.00) | IDC | PTEN; RB1; TP53 | Unclassified | Basal B |
| | CAL-51 | 0.17 (0.00) | AC | PIK3CA | Luminal B | |
| | CAL-120 | 0.09 (0.00) | AC | TP53 | Unclassified | Basal B |
| MSL | HS578T | 0.29 (0.00) | CS | CDKN2A; HRAS; TP53 | Unclassified | Basal B |
| | MDA-MB-157 | 0.25 (0.00) | MBC | NF1; TP53 | Unclassified | Basal B |
| | SUM159PT | 0.14 (0.00) | ANC | PIK3CA; TP53; HRAS | Unclassified | Basal B |
| | MDA-MB-436 | 0.13 (0.00) | IDC | BRCA1; TP53 | Unclassified | Basal B |
| | MDA-MB-231 | 0.12 (0.00) | IDC | BRAP; CDKN2A; KRAS; NF2; TP53; PDGFRA | Unclassified | Basal B |
| LAR | | | | | | |
| LAR | MDA-MB-453 | 0.53 (0.00) | AC | PIK3CA; CDH1; PTEN | Luminal A | Luminal |
| | SUM185PE | 0.39 (0.00) | DC | PIK3CA | Luminal A | Luminal |
| | HCC2185 | 0.34 (0.00) | | PIK3CA | Luminal A | Luminal |
| | CAL-148 | 0.32 (0.00) | AC | PIK3CA; RB1; TP53; PTEN | Luminal A | |
| | MFM-223 | 0.31 (0.00) | AC | PIK3CA; TPS 3 | Luminal A/B | |
| Unclassified | HCC1395 | | DC | ATR; BRCA2; CDKN3A PTEN: FGFR1; PDGFRB; TP53 | Basal | |
| | BT20 | | IDC | CDKN2A; PIK3CA; TP53 | HER2 | Basal A |
| | SW527 | | | | | Luminal B |

[A] Source: mutations taken from COSMIC database (www.sanger.ac.uk/genetics/CGP/cosmic/).
[B] Molecular subtype determined by correlation with UNC/intrinsic breast centroids (29).
[C] Basal subtype obtained from Neve RM et al. (32).
AC, adenocarcinoma;
ANC, anaplastic carcinoma;
ASCC, acantholytic squamous cell carcinoma;
C, carcinoma;
CS, carcinosarcoma;
DC, ductal carcinoma;
IDC, invasive ductal carcinoma;
IGA, invasive galactopharic adenocarcinoma;
INF, inflammatory ductal carcinoma;
MC, metaplastic carcinoma and MBC, medullaiy breast cancer.

TABLE 4

Top gene ontologies for TNBC subtypes in the training and validation datasets

| Subtype | Training Set (386) | Validation Set (201) |
|---|---|---|
| BL1 | DNA REPLICATION REACTOME | CELL CYCLE KEGG |
| | CELL CYCLE KEGG | DNA REPLICATION REACTOME |
| | RNA POLYMERASE | G2 PATHWAY |
| | CELL CYCLE KEGG | METHIONINE METABOLISM |
| | GLYCOSPHINGOLIPID BIOSYNTHESIS NEO LACTOSERIES | CHOLESTEROL BIOSYNTHESIS |
| | | CELL CYCLE |
| | ATR EBRCA PATHWAY | RNA POLYMERASE |
| | UBIQUITIN MEDIATED PROTEOLYSIS | ATREBRCA PATHWAY |
| | G2 PATHWAY | G1 TO S CELL CYCLE REACTOME |
| | PROTEASOME | CASPASE CASCADE |
| | G1 TO S CELL CYCLE REACTOME | GLUTAMATE METABOLISM |
| | METHIONINE METABOLISM | AMINOACYL TRNA BIOSYNTHESIS |

TABLE 4-continued

Top gene ontologies for TNBC subtypes in the training and validation datasets

| Subtype | Training Set (386) | Validation Set (201) |
|---|---|---|
| | FAS PATHWAY<br>CHOLESTEROL BIOSYNTHESIS<br>PYRIMIDINE METABOLISM<br>AMINOACYL TRNA BIOSYNTHESIS<br>DNA POLYMERASE<br>CARBON FIXATION<br>ALANINE AND ASPARTATE METABOLISM<br>PROTEASOME<br>CELLCYCLE PATHWAY<br>CDMAC PATHWAY<br>KREBS TCA CYCLE | GLYCOSPHINGOLIPID BIOSYNTHESIS NEO LACTOSERIES<br>G1 AND S PHASES<br>CYSTEINE METABOLISM<br>ATM PATHWAY<br>MRNA PROCESSING REACTOME<br>BIOSYNTHESIS OF STEROIDS<br>KREBS TCA CYCLE<br>PYRIMIDINE METABOLISM<br>PROTEASOME PATHWAY<br>SELENOAMINO ACID METABOLISM<br>CELL CYCLE PATHWAY<br>ALANINE AND ASPARTATE METABOLISM<br>GAQ PATHWAY<br>AMINOACYL TRNA BIOSYNTHESIS<br>FAS PATHWAY<br>PROTEASOME |
| BL2 | PORPHYRN AND CHLOROPHYLL METABOLISM<br>GATA3 PATHWAY<br>STEM PATHWAY<br>PARKISONS DISEASE<br>STARCH AND SUCROSE METABOLISM<br>EGF PATHWAY<br>INSULIN PATHWAY<br>RENAL CELL CARCINOMA<br>WNT SIGNALING<br>AMINOACYL TRNA BIOSYNTHESIS<br>GALACTOSE METABOLISM<br>O GLYCAN BIOSYNTHESIS<br>ATM PATHWAY<br>HUNTINGTONS DISEASE<br>IL6 PATHWAY<br>G1 TO S CELL CYCLE REACTOME<br>FOCAL ADHESION<br>IGF1R PATHWAY<br>UBIQUITIN MEDIATED PROTEOLYSIS<br>GLIOMA<br>TPO PATHWAY<br>G2 PATHWAY<br>PORPHYRN AND CHLOROPHYLL METABOLISM<br>GATA3 PATHWAY<br>STEM PATHWAY<br>PARKISONS DISEASE<br>STARCH AND SUCROSE METABOLISM<br>EGF PATHWAY<br>INSULIN PATHWAY<br>RENAL CELL CARCINOMA<br>WNT SIGNALING<br>AMINOACYL TRNA BIOSYNTHESIS<br>GALACTOSE METABOLISM<br>O GLYCAN BIOSYNTHESIS<br>ATM PATHWAY<br>HUNTINGTONS DISEASE<br>IL6 PATHWAY<br>G1 TO S CELL CYCLE REACTOME<br>FOCAL ADHESION<br>IGF1R PATHWAY<br>UBIQUITIN MEDIATED PROTEOLYSIS<br>GLIOMA<br>TPO PATHWAY<br>G2 PATHWAY | BLADDER CANCER<br>GATA3 PATHWAY<br>EPITHELIAL CELL SIGNALING IN HELICOBACTER<br>CARDIAC EGF PATHWAY<br>NICOTINATE AND NICOTINAMIDE METABOLISM<br>EDG1 PATHWAY<br>PANTOTHENATE AND COA BIOSYNTHESIS<br>TOLL PATHWAY<br>RENIN ANGIOTENSIN SYSTEM<br>ECM RECEPTOR INTERACTION<br>PHOTOSYNTHESIS<br>NTH PATHWAY<br>AMINOSUGARS METABOLISM<br>EICOSANOID SYNTHESIS<br>DORSO VENTRAL AXIS FORMATION<br>NGF PATHWAY<br>SPRY PATHWAY<br>ECM PATHWAY<br>MET PATHWAY<br>CDMAC PATHWAY<br>ARF PATHWAY<br>P38 MAPK PATHWAY<br>CHOLERA INFECTION<br>HYPERTROPHY MODEL<br>WNT BETA CATENIN PATHWAY<br>ERK PATHWAY<br>FMLP PATHWAY<br>GLYCOLYSIS<br>BLADDER CANCER<br>GATA3 PATHWAY<br>EPITHELIAL CELL SIGNALING IN HELICOBACTER<br>CARDIAC EGF PATHWAY<br>NICOTINATE AND NICOTINAMIDE METABOLISM<br>EDG1 PATHWAY<br>PANTOTHENATE AND COA BIOSYNTHESIS<br>TOLL PATHWAY<br>RENIN ANGIOTENSIN SYSTEM<br>ECM RECEPTOR INTERACTION<br>PHOTOSYNTHESIS<br>NTH PATHWAY<br>AMINOSUGARS METABOLISM<br>EICOSANOID SYNTHESIS<br>DORSO VENTRAL AXIS FORMATION<br>NGF PATHWAY<br>SPRY PATHWAY<br>ECM PATHWAY<br>MET PATHWAY<br>CDMAC PATHWAY<br>ARF PATHWAY<br>P38 MAPK PATHWAY<br>CHOLERA INFECTION<br>HYPERTROPHY MODEL<br>WNT BETA CATENIN PATHWAY<br>ERK PATHWAY<br>FMLP PATHWAY<br>GLYCOLYSIS |
| IM | CTLA4 PATHWAY<br>NO2 IL12 PATHWAY<br>TH1 TH2 PATHWAY<br>CSK PATHWAY | NO IL12 PATHWAY<br>CTLA4 PATHWAY<br>IL12 PATHWAY<br>TYPE I DIABETES MELLITUS |

TABLE 4-continued

Top gene ontologies for TNBC subtypes in the training and validation datasets

| Subtype | Training Set (386) | Validation Set (201) |
|---|---|---|
| | NKT PATHWAY | NK CELL PATHWAY |
| | COMPLIMENT PATHWAY | TH1 TH2 PATHWAY |
| | IL7 PATHWAY | TNFR2 PATHWAY |
| | PROTEASOME | CSK PATHWAY |
| | NK CELLS PATHWAY | IL7 PATHWAY |
| | TYPE I DIABETES MELLITUS | AMI PATHWAY |
| | AMP PATHWAY | ANTIGEN PROCESSING AND PRESENTATION |
| | ANTIGEN PROCESSING AND PRESENTATION | NFKB PATHWAY |
| | IL12 PATHWAY | TUMOR NECROSIS FACTOR PATHWAY |
| | LAIR PATHWAY | PROTEASOME |
| | TNFR2 PATHWAY | NKT PATHWAY |
| | CD PATHWAY | T CELL SIGNAL TRANSDUCTION |
| | TID PATHWAY | DEATH PATHWAY |
| | APOPTOSIS GENMAPP | APOPTOSIS GENMAPP |
| | NFKB PATHWAY | CD40 PATHWAY |
| | PROTEASOME PATHWAY | RELA PATHWAY |
| | T CELL SIGNAL TRANSDUCTION | TOB1 PATHWAY |
| | TUMOR NECROSIS FACTOR PATHWAY | APOPTOSIS |
| | CASPASE PATHWAY | APOPTOSIS KEGG |
| | APOPTOSIS | T CELL RECEPTOR SIGNALING PATHWAY |
| | NATURAL KILLER CELL MEDIATED CYTOTOXICITY | CYTOKINE PATHWAY |
| | TOB1 PATHWAY | CASPASE PATHWAY |
| | B CELL RECEPTOR SIGNALING PATHWAY | TID PATHWAY |
| | T CELL RECEPTOR SIGNALING PATHWAY | IL2 PATHWAY |
| | CYTOKINE PATHWAY | NATURAL KILLER CELL MEDIATED CYTOTOXICITY |
| | CELL ADHESION MOLECULES | CASPASE CASCADE |
| | DEATH PATHWAY | LAIR PATHWAY |
| | APOPTOSIS KEGG | HEMATOPOIETIC CELL LINEAGE |
| | TOLL LIKE RECEPTORS SIGNALING PATHWAY | IL3 PATHWAY |
| | PROTEASOME | COMP PATHWAY |
| | HEMATOPOIETIC CELL LINEAGE | TCR PATHWAY |
| | RELA PATHWAY | B CELL RECEPTOR SIGNALING PATHWAY |
| | IL2 PATHWAY | STEM PATHWAY |
| | MITOCHONDRIA PATHWAY | MITOCHONDRIA PATHWAY |
| | TOLL PATHWAY | TOLL PATHWAY |
| | B CELL ANTIGEN RECEPTOR | STRESS PATHWAY |
| | INFLAM PATHWAY | IL2RB PATHWAY |
| | IL2RB PATHWAY | INFLAM PATHWAY |
| | IL3 PATHWAY | CYTOKINE CYTOKINE RECEPTOR INTERACTION |
| | STEM PATHWAY | PIP3 SIGNALING IN B LYMPHOCYTES |
| | BCR SIGNALING PATHWAY | TOLL LIKE RECEPTORS SIGNALING PATHWAY |
| | HIVNEF PATHWAY | 41B PATHWAY |
| | TCR PATHWAY | B CELL RECEPTOR SIGNALING PATHWAY |
| | CASPASE CASCADE | BCR SIGNALING PATHWAY |
| | PIP3 SIGNALING IN B LYMPHOCYTES | PROTEASOME |
| | NTH PATHWAY | CERAMIDE PATHWAY |
| | 41B PATHWAY | APOPTOSIS |
| | CCR5 PATHWAY | JAX STAT SIGNALING PATHWAY |
| | CYTOKINE CYTOKINE RECEPTOR INTERACTION | EPO PATHWAY |
| | INTERLEUKIN 4 PATHWAY | NTH PATHWAY |
| | STRESS PATHWAY | CD40 PATHWAYMAP |
| | IL1R PATHWAY | CALCINEURIN NF AT SIGNALING |
| | APOPTOSIS | HIV NEP PATHWAY |
| | EICOSANOID SYNTHESIS | EICOSANOID SYNTHESIS |
| | UBIQUITIN MEDIATED PROTEOLYSIS | BCR PATHWAY |
| | CELL CYCLE PATHWAY | FC EPSILON RI SIGNALING PATHWAY |
| | CALCINEURIN NF AT SIGNALING | KERATINOCYTE PATHWAY |
| | FC EPSILON RI SIGNALING PATHWAY | AMINOACYL TRNA BIOSYNTHESIS |
| | AMINOACYL TRNA BIOSYNTHESIS | CELL CYCLE PATHWAY |
| | JAK STAT SIGNALING PATHWAY | B CELL RECEPTOR COMPLEXES |
| | FAS PATHWAY | IL8 PATHWAY |
| | PTEN PATHWAY | PROTEASOME PATHWAY CCR5 PATHWAY |
| | B CELL RECEPTOR COMPLEXES | ATR BRCA PATHWAY |
| | DNA REPLICATION REACTOME | GHP PATHWAY |
| | FFOLATEBIOSYNTHESIS | FOLATE BIOSYNTHESIS |
| | ATR BRCA PATHWAY | PEPTIDE GPCRS |
| | IL6 PATHWAY | GLEEVEC PATHWAY |
| | LEUKOCYTE TRANSENDOTHELIAL MIGRATION | FAS PATHWAY |
| | GLEEVEC PATHWAY | ABC TRANSPORTERS GENERAL |
| | TNFR PATHWAY | INTERLEUKIN 4 PATHWAY |
| | COMPLIMENT AND COAGULATION CASCADES | IL4 RECEPTOR IN B LYPHOCYTES |
| | BCR PATHWAY | ADIPOCYTOKINE SIGNALING PATHWAY |
| | EPO PATHWAY | PROSTAGLANDIN AND LEUKOTRIENE METABOLISM |
| | GH PATHWAY | CDMAC PATHWAY |
| | TPO PATHWAY | TPO PATHWAY |
| | AMINOACYL TRNA BIOSYNTHESIS | HSP PATHWAY |

TABLE 4-continued

Top gene ontologies for TNBC subtypes in the training and validation datasets

| Subtype | Training Set (386) | Validation Set (201) |
|---|---|---|
| | PEPTIDES GPCRS<br>N GLYCAN BIOSYNTHESIS<br>ALZHEIMERS DISEASE<br>ACUTE MYELOID LEUKEMIA<br>GAQ PATHWAY<br>CD40 PATHWAYMAP<br>METHIONINEMETABOLISM<br>CPCR CLASS B SECRETIN LIKE<br>IL4 RECEPTOR IN B LYPHOCYTES<br>CERAMIDE PATHWAY<br>FCER1 PATHWAY<br>G1 TO S CELL CYCLE REACTOME<br>PARKINSONS DISEASE<br>CHEMICAL PATHWAY<br>CELL CYCLE KEGG<br>NARE INTERACTIONS IN VESICULAR TRANSPORT<br>ATM PATHWAY<br>NICOTINATE AND NICOTINAMIDE METABOLISM<br>KERATINOCYTE PATHWAY<br>HYPERTROPHY MODEL<br>ADIPOCYTOKINE SIGNALING PATHWAY<br>FML PATHWAY<br>OCITYOSELLUM DISODIUM CAMP CHEMOTAXIS<br>PEPTIDES PATHWAY<br>PANCREATIC CANCER<br>RAS SIGNALING PATHWAY<br>RAC PATHWAY<br>AMINOSUGARS METABOLISM | TNFR1 PATHWAY<br>INOSITOL PHOSPHATE METABOLISM<br>ACUTE MYELOID LEUKEMIA<br>LEUKOCYTE TRANSENDOTHELIAL MIGRATION<br>IL1R PATHWAY<br>IL1R ATROPHY<br>OVARIAN INFERTILITY GENE<br>PTEN PATHWAY |
| M | CELL COMMUNICATION<br>HEPARAN SULFATE BIOSYNTHESIS<br>ECM RECEPTOR INTERACTION<br>ALK PATHWAY<br>UCAL PAIN PATHWAY<br>STRIATED MUSCLE CONTRACTION<br>BASAL CELL CARCINOMA<br>REGULATION OF THE ACTIN CYTOSKELETON BY RHO GTPASES<br>TGFB SIGNALING PATHWAY<br>JDAC PATHWAY<br>HEDGEHOG SIGNALING PATHWAY<br>INOSITOL PHOSPHATE METABOLISM<br>IGF1 PATHWAY<br>ECM PATHWAY<br>ERK5 PATHWAY<br>FOCAL ADHESION<br>EDG1 PATHWAY<br>CARM EER PATHWAY<br>INSULIN PATHWAY<br>ETHER LIPD METABOLISM<br>TEL PATHWAY<br>NOTCH SIGNALING PATHWAY | PTEN PATHWAY<br>DNA REPLICATION REACTOME<br>RIBOSOME<br>TRANSLATION FACTORS<br>RNA POLYMERASE<br>DNA POLYMERASE<br>BASAL TRANSCRIPTION FACTORS<br>IGF1 MTOPATHWAY<br>RNA REPLICATION REACTOME<br>CHOLESTEROL BIOSYNTHESIS<br>GLYCOSLPHYSPHATIDYLINOSITAL ANCHOR<br>ECM PATHWAY<br>UCAL PATHWAY<br>EIF4 PATHWAY<br>RIBOSOMAL PROTEINS<br>CELL CYCLE KEGG<br>MTOR PATHWAY<br>REGULATION OF THE ACTIN CYTOSKELETON BY RHO GTPASES<br>GPASES<br>G1 TO S CELL CYCLE REACTOME<br>MRNA PROCESSING REACTOME<br>UBIQUITIN MEDIATED PROTEOLYSIS<br>WNT PATHWAY<br>ALK PATHWAY<br>G2 PATHWAY<br>TEL PATHWAY<br>CELL CYCLE<br>ATR BRCA PATHWAY |
| MSL | PROSTAGLANDIN SYNTHESIS REGULATION<br>BAD PATHWAY<br>LAIR PATHWAY<br>IL7 PATHWAY<br>COMP PATHWAY<br>REMIN ANGIOTENSION SYSTEM<br>AMP PATHWAY<br>CSK PATHWAY<br>ERYTH PATHWAY<br>ECM RECEPTOR INTERACTION<br>TOB1 PATHWAY<br>COMPLEMENT AND COAGULATION CASCADES<br>CARDIAC EGF PATHWAY<br>HISTIDINE METABOLISM<br>GATA3 PATHWAY<br>NDKDTNAMIN PATHWAY<br>GCRS PATHWAY<br>FOCAL ADHESION<br>BETA ALANINE METABOLISM | NO2 IL12 PATHWAY<br>CSK PATHWAY<br>LAIR PATHWAY<br>TOB1 PATHWAY<br>CTLA4 PATHWAY<br>AMP PATHWAY<br>TH1 TH2 PATHWAY<br>RENIN ANGIOTENSION SYSTEM<br>PAR1 PATHWAY<br>NKT PATHWAY<br>IL7 PATHWAY<br>NK CELLS PATHWAY<br>CD PATHWAY<br>ERYTH PATHWAY<br>HEMATOPOIETIC CELL LINEAGE<br>TYPE 1 DIABETES MELLITUS<br>IL3 PATHWAY<br>GLYCOSAMINOGLYCAN DEGRADATION<br>IL12 PATHWAY |

TABLE 4-continued

Top gene ontologies for TNBC subtypes in the training and validation datasets

| Subtype | Training Set (386) | Validation Set (201) |
|---|---|---|
| | INTRINSIC PATHWAY | IL2 PATHWAY |
| | PAR1 PATHWAY | PROSTAGLANDIN SYNTHESIS REGULATION |
| | ALK PATHWAY | EICOSANOID SYNTHESIS |
| | CALCINEURIN PATHWAY | COMP PATHWAY |
| | NTH PATHWAY | CCR5 PATHWAY |
| | CTLA4 PATHWAY | GLYCAN STRUCTURES DEGRADATION |
| | GCR PATHWAY | CALCINEURIN PATHWAY |
| | HEMATOPOIETIC CELL LINEAGE | COMPLEMENT AND COAGULATION CASCADE |
| | NO1 PATHWAY | ECM RECEPTOR INTERACTION |
| | VIP PATHWAY | TCR PATHWAY |
| | UCAL PAIN PATHWAY | TNFR2 PATHWAY |
| | EDG1 PATHWAY | NO1 PATHWAY |
| | IL3 PATHWAY | INTRINSIC PATHWAY |
| | IGF1 PATHWAY | STATIN PATHWAY PHARMGK3 |
| | TCR PATHWAY | ALKALOID BIOSYNTHESIS II |
| | EICOSANOID SYNTHESIS | LEUKOCYTE TRANSENDOTHELIAL MIGRATION |
| | NK CELLS PATHWAY | CELL ADHESION MOLECULES |
| | VALINE AND ISOLEUCINE DEGRADATION | INFLAM PATHWAY |
| | PPARA PATHWAY | MEF2D PATHWAY |
| | SPRY PATHWAY | IL2RB PATHWAY |
| | HDAC PATHWAY | WNT BETA CATENIN PATHWAY |
| | STATIN PATHWAY | FOCAL ADHESION |
| | GLYCAN STRUCTURES DEGRADATION | NTH PATHWAY |
| | SMOOTH MUSCLE CONTRACTION | BCR PATHWAY |
| | TH1 TH2 PATHWAY | BCR SIGNALING PATHWAY |
| | ECM PATHWAY | GLYCEROLIPID METABOLISM |
| | PDGR PATHWAY | HISTIDINE METABOLISM |
| | INTEGRIN MEDIATED CELL ADHESION KEGG | GATA3 PATHWAY |
| | FATTY ACID METABOLISM | PEPTIDE GPCRS |
| | NKT PATHWAY | PIP3 SIGNALING IN B LYMPHOCYTES |
| | CXCR4 PATHWAY | CYTOKINE CYTOKINE RECEOTIR INTERACTION |
| | TOLL PATHWAY | INOITOL PHOSPHATE METABOLISM |
| | TNFR2 PATHWAY | BAD PATHWAY |
| | LEUKOCYTE TRANSENDOTHELIAL MIGRATION | MONOAMINE GPCRS |
| | PPAR SIGNALING PATHWAY | NFKB PATHWAY |
| | AMYOTROPHIC LATERAL SCLEROSIS | ECM PATHWAY |
| | GLYCEROLIPID METABOLISM | 1 AND 2 METHYLNAPHTHALENE DEGRADATION |
| | GLYCOSPHINGOLIPID METABOLISM | B CLL RECEPTOR SIGNALING PATHWAY |
| | MTOR PATHWAY | VIP PATHWAY |
| | NICOTINATE AND NICOTINAMIDE METABOLISM | CARDIAC EGF PATHWAY |
| | PGC1 PATHWAY | IL4 RECEPTOR IN B LYPHOCYTES |
| | MET PATHWAY | GH PATHWAY |
| | WNT BETA CATENIN PATHWAY | NATURAL KILLER CELL MEDIATED CYTOTOXICITY |
| | TPO PATHWAY | CYTOTOXICITY |
| | BUTANOATE METABOLISM | RAC1 PATHWAY |
| | TGF BETA SIGNALING PATHWAY | EDG1 PATHWAY |
| | GSK3 PATHWAY | BETA ALANINE METABOLISM |
| | GLYCOSAMINOGLYCAN DEGRADATION | UCAL PAIN PATHWAY |
| | PROPNOATE METABOLISM | GPCR PATHWAY |
| | CELL COMMUNICATION | ERK1 ERK2 MAPK PATHWAY |
| | OVARIAN INFERTILITY GENES | INTERGRIN MEDIATED CELL ADHESION KEGG |
| | VALINE LEUCINE AND ISOLEUCINE DEGRADATION | ARACHIDONIC ACID METABOLISM |
| | BILE ACID BIOSYNTHESIS | ABC TRANSPORTERS GENERAL |
| | IL5 PATHWAY | RHO PATHWAY |
| | BCR SIGNALING PATHWAY | JAK STAT SIGNALING PATHWAY |
| | CELL ADHESION MOLECULES | HDAC PATHWAY |
| | B CLL RECEPTOR SIGNALING PATHWAY | BILE ACID BIOSYNTHESIS |
| | BCR PATHWAY | TOLL PATHWAY |
| | PTEN PATHWAY | BPA PATHWAY |
| | MCAL PAIN PATHWAY | NDKDTHAMIN PATHWAY |
| | 1 AND 2 METHYLNAPHTHALENE DEGRADATION | SMOOTH MUSCLE CONTRACTION |
| | GFCDB CLASS B SECRETIN LIKE | CALCIUM SIGNALING PATHWAY |
| | IL2 PATHWAY | GLYCEROLIPID METABOLISM |
| | MELANOMA | ANTIGEN PROCESSING AND PRESENTATION |
| | INTERGRIN PATHWAY | ADIPOCYTOKINE SIGNALING PATHWAY |
| | ALKALOID BIOSYNTHESIS II | |
| | ETHER LIPID METABOLISM | |
| | NUCLEAR RECEPTORS CK1 PATHWAY | |
| | TYPE I DIABETES MELLITUS | |
| | ND2IL12 PATHWAY | |
| | RHO PATHWAY | |
| | CYTOKINE CTYOKINE RECEPTOR INTERACTION | |
| | BLOOD CLOTTING CASCADE | |
| | INFLAM PATHWAY | |
| | DICYTOSTELIUM DISODIUM CAMP | |

TABLE 4-continued

Top gene ontologies for TNBC subtypes in the training and validation datasets

| Subtype | Training Set (386) | Validation Set (201) |
|---|---|---|
| LAR | CHEMOTAXIS PATHWAY<br>DIFFERENTIATION PATHWAY IN PC12 CELLS<br>CHOLESTEROL BIOSYNTHESIS<br>PENTOSE AND GLUCURONATE<br>INTERCONVERSIONS<br>BIOSYNTHESIS OF STEROIDS<br>TYROSINE METABOLISM<br>GAMMA HEXACHLOROCYCLOHEXANE<br>DEGRADATION<br>PORPHYRIN AND CHLOROPHYLL METABOLISM<br>PHENYLALANINE METABOLISM<br>CHREB PATHWAY<br>GLUTATHIONE METABOLISM<br>1 AND 2 METHYLNAPHTHALENE DEGRADATION<br>GLYCOSPHINGOLIPID METABOLISM<br>PORPHYRIN AND CHLOROPHYLL METABOLISM<br>ANDROGEN AND ESTROGEN METABOLISM<br>PHENILALANINE METABOLISM<br>CITRATE CYCLE TCA CYCLE<br>METABOLISM OF XENOBIOTICS BY CYTOCHROME P450<br>EICOSANOID SYNTHESIS<br>VALINE LEUCINE AND ISOLEUCINE DEGRADATION<br>GLYCAN STRUCTURES DEGRADATION<br>ANCHOR BIOSYNTHESIS<br>BUTANOATE METABOLISM<br>ARGININE AND PROLINE METABOLISM<br>GLUTATHIONE METABOLISM<br>CK1 PATHWAY<br>CITRATE CYCLE<br>PANTOTHENATE AND COA BIOSYNTHESIS<br>PROPANOATE METABOLISM<br>FATTY ACID METABOLISM<br>GLUTAMATE METABOLISM<br>N GLYCAN BIOSYNTHESIS<br>HISTIDINE METABOLISM<br>BILE ACID BIOSYNTHESIS<br>GLUTAMATE METABOLISM<br>TRYPTOPHAN METABOLISM<br>ALANINE AND ASPARTATE METABOLISM<br>PPAR SIGNALING PATHWAY<br>CREB PATHWAY<br>ATP SYNTHESIS<br>FLAGELLAR ASSEMBLY<br>TYPE III SECRETION SYSTEM<br>SPRY PATHWAY<br>ERYTH PATHWAY<br>PHOTOSYNTHESIS<br>MCAL PAIN PATHWAY<br>FRUCTOSE AND MANNOSE METABOLISM<br>GLYCOSAMINOGLYCAN DEGRADATION<br>SPHINGOLIPID METABOLISM<br>GLUTAMATE METABOLISM<br>GLYCEROLIPID METABOLISM<br>SNARE INTERACTIONS IN VESICULARE TRANSPORT<br>SELENAMINO ACID METABOLISM<br>PENTOSE PHOSPHATE PATHWAY<br>NO1 PATHWAY<br>STARCH AND SUCROSE METABOLISM<br>CYSTEINE METABOLISM<br>GATA3 PATHWAY<br>ABO TRANSPORTERS GENERAL<br>UREA CYCLE AND METABOLISM OF AMINO GROUPS<br>OXIDATIVE PHOSPHORLATION<br>KREBS TCA CYCLE<br>AMINOSUGARS METABOLISM<br>ARACHONDIC ACID METABOLISM<br>NAPHTHALENE AND ANTHRACENE DEGRADATION<br>OXIDATIVE PHOSPHORYATION | GLUTATHIONE METABOLISM<br>PENTOSE AND GLUCURONATE INTERCONVERSIONS<br>CHOLESTEROL BIOSYNTHESIS<br>TYROSINE METABOLISM<br>BIOSYNTHESIS OF STEROIDS<br>PORPHYRIN AND CHLOROPHYLL METABOLISM<br>ANDROGEN AND ESTROGEN METABOLISM<br>GLYCOSPHINGOLIPID METABOLISM<br>TYPE I SECRETION SYSTEM<br>GAMMA HEXACHLOROCYCLOHEXANE DEGRADATION<br>FLAGELLAR ASSEMBLY<br>CITRATE CYCLE TCA CYCLE<br>PHENYLALANINE METABOLISM<br>ATP SYNTHESIS<br>PHOTOSYNTHESIS<br>STARCH AND SUCROSE METABOLISM<br>PORPHYRIN AND CHLOROPHYLL METABOLISM<br>ARGININE AND PROLINE METABOLISM<br>METABOLISM OF XENOBIOTICS BY CYTOCHROME P450<br>FRUCTOSE AND MANNOSE METABOLISM<br>CARBON FIXATION<br>GLYCAN STRUCTURES DEGRADATION<br>COMP PATHWAY<br>PARKINSONS DISEASE<br>PANTOTHENATE AND COA BIOSYNTHESIS<br>FATTY ACID METABOLISM<br>RENIN ANGIOTENSIN SYSTEM<br>TYROSINE METABOLISM<br>GLUTAMATE METABOLISM<br>ALANINE AND ASPARTATE METABOLISM<br>EICOSANOID SYNTHESIS<br>GLYCOSAMINOGLYCAN DEGRADATION<br>PHENILALANINE METABOLISM<br>CREB PATHWAY<br>CK1 PATHWAY<br>MONOAMINE GPCRS<br>PHINGOLIPID METABOLISM<br>P53 HYPOXIA PATHWAY<br>TRYPTOPHAN METABOLISM<br>NICOTINATE AND NICOTINAMIDE METABOLISM<br>GLUTAMATE METABOLISM<br>UCAL PAIN PATHWAY<br>KREBS TCA CYCLE<br>OXIDATIVE PHOSPHORYLATION<br>HISTIDINE METABOLISM<br>GALACTOSE METABOLISM<br>PENTOSE PHOTPHATE PATHWAY<br>N GLYCAN BIOSYNTHESIS<br>LINOLEIC ACID METABOLISM<br>BLOOD CLOTTING CASCADE<br>ARACHONDIC ACID METABOLISM<br>MCAL PAIN PATHWAY<br>ERYTH PATHWAY<br>ABO TRANSPORTERS GENERAL<br>BUTANOATE METABOLISM<br>O GLYCAN BIOSYNTHESIS<br>PPAR SIGNALING PATHWAY<br>VALINE LEUCINE ISOLEUCINE DEGRADATION<br>NO1 PATHWAY<br>COMPLEMENT AND COAGULATION CASCADES |
| UNC | DNA REPLICATION REACTOME<br>ATR BRC PATHWAY<br>DNA POLYMERASE<br>CELL CYCLE KEGG<br>CELLCYCLE PATHWAY<br>G1 TO S CELL CYCLE REACTOME | |

TABLE 4-continued

Top gene ontologies for TNBC subtypes in the training and validation datasets

| Subtype | Training Set (386) | Validation Set (201) |
|---|---|---|
| | CELL CYCLE | |
| | B1 PATHWAY | |
| | G1 AND S PHASES | |
| | BASAL TRANSCRIPTION FACTORS | |
| | RNA TRANSCRIPTING REACTOME | |
| | AMINOACYL TRNA BIOSYNTHESIS | |
| | ARNA POLYMERASE | |
| | PYRIMIDINE METABOLISM | |
| | CARM ER PATHWAY | |
| | PYRIMIDINE METABOLISM | |
| | ALANINE AND ASPARTATE METABOLISM | |
| | G2 PATHWAY | |
| | P53 PATHWAY | |
| | SELENOAMINO ACID PATHWAY | |
| | GLUTAMATE METABOLISM | |
| | PENTOSE PHOSPHATE PATHWAY | |

Bold-shared between training and validation set

TABLE 5

Cell Line Culture Conditions

| Cell Line | Site OF Origin | Tumor Type | BRCA1 Mutation | Source | Media |
|---|---|---|---|---|---|
| BT20 | PB | IDC | | ATCC | EMEM 10% FBS |
| BT549 | [B | ODC | | ATCC | RPMI 10% FBS |
| CAL120 | PE | AC | | DSMZ | DMEM 10% FBS |
| CAL148 | PE | AC | | DSMZ | DMEM 20% + 2 Mm L-glutamine + 1 µg/ml EGF |
| CAL851 | PE | IGA | | DSMZ | DMEM 10% FBS + 2 Mm L-glutamine |
| DU4475 | CN | DC | | ATCC | RPMI 10% FBS |
| HCC1143 | PB | IDC | | ATCC | RPMI 10% FBS |
| HCC1187 | PB | DC | | ATCC | RPMI 10% FBS |
| HCC1395 | PB | DC | | ATCC | RPM" 10% FBS |
| HCC1599 | PB | DC | | ATCC | RPMI 10% FBS |
| HCC1806 | PB | ASCC | | ATCC | RPMI glutamax 10% FBS |
| HCC1937 | PB | DC | X | ATCC | RPM (glutamax 10% FBS |
| HCC38 | PB | DC | | ATCC | RPMI 10% FBS |
| HCC70 | PB | DC | | ATCC | RPMI 10% FBS |
| HDQP1 | PB | IDC | | DSMZ | DMEM 10% FBS |
| HS578T | PB | CS | | ATCC | DMEM 10% FBS |
| MDAMB157 | PB | MC | | ATCC | DMEM 10% FBS |
| MDAMB231 | PE | IDC | | ATCC | DMEM 10% FBS |
| MDAM436 | PE | IDC | X | ATCC | DMEM 10% FBS |
| MDAM453 | PE | AC | | ATCC | DMEM 10% FBS |
| MDAM468 | PE | DC | | ATCC | DMEM 10% FBS |
| MFM223 | PE | AC | | DSMZ | MEM (with Earle's sals) + 15% FBS + 2 Mm L-glutamine + 1x insulin-transferrin-sodium s |
| MT3 | PE | C | | DSMZ | RPMI 10% FBS |
| SUM149PT | PB | INF | X | Asterand | Hams F12 5% FBS + 1 µg/ml hydrocortisone + 5 µg/ml insulin |
| SUM159PT | PB | ANC | | Asterand | Hams F12 5% FBS + 1 µg/ml hydrocortisone + 5 µg/ml insulin |
| SUM185 | PE | DC | | Asterand | Hams F12 5% FBS + 1 µg/ml hydrocortisone + 5 µg/ml insulin |
| SW527 | PE | | | ATCC | DMEM 10% FBS |

Tumour Type (AC, adenocarcinoma; ANC, anaplastic carcinoma; ASCC, acantholytic squamous cell carcinoma; CS, Carcinosarcoma; DC ductal carcinoma; C, carcinoma; CS, arcinosarcoma; IDC, invasive d; Isolation (PB, primary breast; PE, pleural effusion; CN cutaneous nodule)

TABLE 6A

| | | Gene Categories | | | |
|---|---|---|---|---|---|
| BLI | BL2 | IM | M | MSL | LAR |
| ACTG2 | ALXO5 | ADAMDEC1 | ACTA2 | ABCA8 [L] | ABCA12 |
| ADAMDEC1 | CLCA2 | AIM2 | ACTG2 | ABCB1 | AKAP12 |
| ANP32E | COL5A1 | ALOX5 | BCL11A | ACTA2 | AKR1B10 |
| APOCBEC3A | CTSC | ANP32E | BGN [E] | ACTG2 | AKR1D1 |
| ATR3 | CXCL12 | APOBEC3A | CAV1 [E] | AKAP12 | ALCAM [G] |
| AURKA [A] | DHCR24 | APOBEC3G | CAV2 [E] | ALDHA1 [L] | ALDH3B2 [G] |
| AURKB [A] | EGFR [D] | BCL2AA | CCND2 [E] | ALOX5 | ALOX15B |
| AZGP1 | EPHA2 [D] | BIRC3 | COL3A1 [E] | AOC3 | APOD [G] |
| BCL11A | GALNT10 | BTK3A3 | COL5A1 [E] | APOBEC3G | AR |
| BIRC5 | GBP2 | BYK [I] | COL5A2 [E] | APOD | AZGP1 |
| BUB1 [A] | GPR87 | C1QA | COL6A3 [E] | AZGP1 | BLVRB |
| CCL5 | HTRA1 | C1QB | CTNNB1 [E] | BCL2 | C4B |
| CCNA2 [A] | MET [D] | C4B | DKK2 [E] | BGN [E] | CADPS2 |
| CENPA [A] | MME | CASP1 | DKK3 [E] | BMP2 [E] | CLCA2 |
| CENPF [A] | PYCARD | CCL19 [H] | EN1 | C4B | CLDN8 |
| CHEK1 [C] | RSAD2 | CCL3 [H] | EPHB3 | CAV1 [E] | COL5A1 |
| CKAP2 | S100A7 | CCL4 [H] | FBN1 [E] | CAV2 [E] | COL6A3 |
| COBL | S100A8 | CCL5 [H] | FOXC1 | CCND2 [E] | CRAT |
| CTSS | S100A9 | CCL8 [H] | FZD4 [E] | CCR2 [H] | CUX2 |
| CXCL10 | TNFSF10 | CCR1 [H] | GNG11 | CD2 | DHCR24 [G] |
| CXCL11 | TP63 | CCR2 [H] | GPR161 | CD37 | DHRS2 |
| CXCL13 | | CCR5 [H] | HTRA1 | CD3D | EAR2 |
| CXCL9 | | CCR7 [H] | IGF1 [E] | CD48 | FAH |
| EN1 | | CD2 [K] | IGF2 [E] | CD52 | FASN [G] |
| EPHB3 | | CD37 [K] | IGFBP4 | CD69 | FBN1 |
| EXO1 [C] | | CD38 [K] | IGFBP5 | CD74 | FKBP5 [G] |
| FANCA [C] | | CD3D [K] | KCNK5 | CKAP2 | FMO5 |
| FANCG [C] | | CD48 [K] | LAMB1 | COL3A1 [E] | FOXA1 [G] |
| GBP1 | | CD52 [K] | MFGE8 | COL3A1 [E] | G6PD |
| IFI44L | | CD69 [K] | MIA | COL5A2 [E] | GALNT10 |
| IFIH1 | | CD74 [K] | MICALL1 | COL6A3 [E] | GALNT7 |
| IGKC | | CD8A [K] | MMP2 [E] | CORO1A | GGT1 |
| IGKV1D-13 | | CKAP2 | NOTCH1 [E] | CSF2RB | GGTLC3 |
| IGKV4-1 | | CORO1A | PDGFRA | CTNNB1 [E] | HGD |
| ITPKB | | CSF2RB | PDGFRB | CXCL12 [H] | HMGCS2 |
| IVD | | CTSC | PMP22 | CXCL13 [H] | HSD17B11 |
| LOC100130100 | | CTSS | ROPN1 | CYTIP | HTRA1 |
| LOC339562 | | CXCL10 [H] | S100A1 | DKK2 [E] | INPP4B |
| LOC652493 | | CXCL11 [H] | SCRG1 | DKK3 [E] | IQGAP2 |
| MCM10 [A] | | CXCL13 [H] | SFPR4 | DPYD | KCNMA1 |
| MDC1 [C] | | CXCL14 [H] | SMAD6 [E] | ENG | KMO |
| MFGE8 | | CXCL9 [H] | SMAD7 [E] | EPAS1 | KRT18 [G] |
| MIA | | CXCR4 [H] | SNAI2 | EVI2A | KYNU |
| MICALL1 | | CXCR6 [H] | SOX10 | EVI2B | LRRC17 |
| MSH2 [C] | | CYBB | SPARC [E] | FBN1 [E] | MLPH |
| MUC5B | | CYTIP | SPOCK1 | FCFL2 | MSX2 |
| MYBL1 | | DDX60 | SRPX | FGL2 | PIP [G] |
| MYC [B] | | DPYD | SYNM | FYB | POU2AF1 |
| NBN [C] | | EN1 | TAGLN [E] | FZD4 [E] | RARRES3 |
| NRAS [C] | | EVI2A | TCF4 [E] | GALNT10 | S100A7 |
| NTN3 | | EVI2B | TCF7L2 [E] | GALNT7 | S100A8 |
| PADI2 | | FGL2 | TGFB1 [E] | GIMAP6 | S100A9 |
| PLK1 [A] | | FYB | TGFB2 [E] | GNG11 | SERHL2 |
| PMP22 | | GBP1 | TGFB3 [E] | GZMA | SIDT1 |
| POU2AF1 | | GBP2 | TGFBIL1 [E] | HCLS1 | SPARCL1 |
| PRC1 [A] | | GIMAP6 | TGFBR1 [E] | HLA-DMZ | SPDEF [G] |
| PSBM9 | | GNLY | TGFBR2 [E] | HLA-DPB1 | SPOCK1 |
| RAD21 [A] | | GZMA | TGFBR3 [E] | HLA-DRA | TARP |
| RAD51 [C] | | GZMB | TRPS1 | HLA-DRB1 | TFAP2B |
| RAD54BP [C] | | HCLS1 | TWIST1 [E] | HOXA10MEIS1 | TNFSF10 |
| ROPN1 | | HCP5 | WWP2 | HOXA5 | TP53G1 |
| RRSAD2 | | HERC5 | ZEB1 [E] | HSD17B11 | TRGC2 |
| RTP4 | | HLA-DMA | ZEB2 [E] | HTRA1 | TRGV9 |
| S100A1 | | HLA-DPB1 | | IGF1 [E] | TRIM36 |
| SCRG1 | | HLA-DRA | | IGF2 [E] | UGT2B38 |
| SOX10 | | HLA-DRB1 | | IGFBP4 | XBP1 [G] |
| SYNM | | IDO1 | | IGFBP5 | ZBTB16 |
| TAP1 | | IF135 | | IGKC | |
| TCF7L1 | | IF144L | | IGKV1D-13 | |
| TP53BP2 [C] | | IFIH1 | | IGKV4-1 | |
| TRPS1 | | IGKC | | IL23A | |

TABLE 6A-continued

| Gene Categories | | | | | |
|---|---|---|---|---|---|
| BLI | BL2 | IM | M | MSL | LAR |
| TTK [B] | | IFNG [J] | | IL2RG | |
| UBD [B] | | IGKV1D-13 | | IQGAP2 | |
| | | IGKV4-1 | | IRF8 | |
| | | IL10RA [J] | | ITPKB | |
| | | IL15RA [J] | | IVD | |
| | | IL16 [J] | | KDR | |
| | | IL18 [J] | | LAMB1 | |
| | | IL18R1 [J] | | LCK | |
| | | IL2RN [J] | | LHFP | |
| | | IL23A [J] | | LOC100130100 | |
| | | IL2RA [J] | | LOC652493 | |
| | | IL2RB [J] | | LRRC17 | |
| | | IL2RG [J] | | LTB | |
| | | IL4 [J] | | MEIS2 [L] | |
| | | IL6 [J] | | MEOX1 [L] | |
| | | IL7 [J] | | MEOX2 [L] | |
| | | IRF1 [J] | | MMP2 | |
| | | IRF7 [J] | | MSX1ITGAV | |
| | | IRF8 [J] | | NGFR | |
| | | ITK | | NOTCH1 | |
| | | IVD | | NT5E | |
| | | JAK1 [J] | | NTN3 | |
| | | KYNU | | | |
| | | LAMP3 | | | |
| | | LCK | | PDGFRA | |
| | | LOC100130100 | | PDGFRB | |
| | | LOC339562 | | PER1 | |
| | | LOC652493 | | PLAC8 | |
| | | LTB | | PMP22 | |
| | | LYN [I] | | POU2AF1 | |
| | | NPKB1 [I] | | PROCR [L] | |
| | | NKG7 | | PTPRC | |
| | | NTN3 | | RAC2 [E] | |
| | | OAS1 | | ROPN1 | |
| | | OAS2 | | SAMSN1 | |
| | | OASL | | SELL | |
| | | PLAC8 | | SFPR4 | |
| | | POU2AF1 | | SMAD6 [E] | |
| | | PSMB9 | | SMAD7 [E] | |
| | | PTPRC | | SNAI2 [E] | |
| | | PYCARD | | SPARC [E] | |
| | | RAC2 [I] | | SPARCL1 [E] | |
| | | RARRES3 | | SPOCK1 | |
| | | RELB | | SRGN | |
| | | RSAD2 | | SRPX | |
| | | RTP4 | | SYNM | |
| | | S100A8 | | TAGLN [E] | |
| | | SAMSN1 | | TCF4 [E] | |
| | | SELL | | TCF7L2 [E] | |
| | | SLAMF7 | | TEK | |
| | | SNX10 | | TERF2IP | |
| | | SRGN | | TGFB1 [E] | |
| | | STAT1 [I] | | TGFB1L1 [E] | |
| | | STAT4 [I] | | TGFB2 [E] | |
| | | STAT5A [I] | | TGFB3 [E] | |
| | | TAP1 | | TGFBR1 [E] | |
| | | TARP | | TGFBR2 [E] | |
| | | TFEC | | TGFBR3 [E] | |
| | | TNFAIP2 | | THBS4 | |
| | | TNFSF17 | | THY1 [L] | |
| | | TNFSF10 | | TIE1 | |
| | | TRAC | | TNFRSF17 | |
| | | TRGC2 | | TRAC | |
| | | TRGV9 | | TRIM22 | |
| | | TRIM22 | | TWIST1 [E] | |
| | | UBD | | VCAM1 | |
| | | UB2EL6 | | VIM [E] | |

TABLE 6A-continued

Gene Categories

| BL1 | BL2 | IM | M | MSL | LAR |
|---|---|---|---|---|---|
| | | WARS | | XBP1 | |
| | | | | ZBTB16 | |
| | | | | ZEB1 [E] | |
| | | | | ZEB2 [E] | |

[A] Cell division
[B] Cell proliferation
[C] DNA damage
[D] Growth factor
[E] ECM/TGFB
[F] WNT
[G] AR responsive
[H] Chemokine
[I] Immune signal transduction
[J] Cytokine signaling
[K] Surface antigen
[L] mesenchymal stem genes

TABLE 6B

TNBC Subtype Mutations

| BL1 | BL2 | IM | M | MSL | LAR |
|---|---|---|---|---|---|
| TOP2B | BRCA1 | TP53 | APC | APC | MAP3K1 |
| ATM | BRCA2 | STAT4 | BRAF | BRAF | PIK3CA |
| ATR | CDKN2A | STAT1 | CTNNB1 | BCRA | RB1 |
| BRCA1 | PTCH1 | RET | FGFR1 | CDKN2A | TP53 |
| BRCA2 | PTCH2 | NFKBIA | GLI1 | CTNNB1 | |
| CAMK1G | PTEN | MAP2K4 | HRAS | FGFR1 | |
| CDKN2A | RB1 | HUWE1 | KRAS | HRAS | |
| CLSPN | RET | BRAF | NOTCH1 | KRAS | |
| CTNND1 | TP53 | | NOTCH4 | NF1 | |
| HDAC4 | UTX | | PIK3CA | NF2 | |
| MAPK13 | | | PTEN | PDGFRA | |
| MDC1 | | | RB1 | PDGFRB | |
| NOTCH1 | | | | TP53 | PIK3CA |
| PTEN | | | | | TP53 |
| RB1 | | | | | |
| SMAD4 | | | | | |
| SMARCAL1 | | | | | |
| STAT4 | | | | | |
| TIMELESS | | | | | |
| TP53 | | | | | |
| UTX | | | | | |

TABLE 6C

Cell Line Source

| Cell Line | Subtype | Source | Website | Product No. |
|---|---|---|---|---|
| HCC1143 | BL1 | ATCC | http://www.atcc.org/ATCCAdvancedCatalogSearch/ProductDetails/tabid/452/Default.aspx?ATTCNum=CRL-2321&Template=cellBiology | CRL-2321 |
| HCC1599 | BL1 | ATCC | http://www.atcc.org/ATCCAdvancedCatalogSearch/ProductDetails/tabid/452/Default.aspx?ATTCNum=CRL-2331&Template=cellBiology | CRL-2331 |
| HCC38 | BL1 | ATCC | http://www.atcc.org/ATCCAdvancedCatalogSearch/ProductDetails/tabid/452/Default.aspx?ATTCNum=CRL-2314&Template=cellBiology | CRL-2314 |
| HCC2157 | BL1 | ATCC | http://www.atcc.org/ATCCAdvancedCatalogSearch/ProductDetails/tabid/452/Default.aspx?ATTCNum=CRL-2340&Template=cellBiology | CRL-2340 |
| HCC1937 | BL1 | ATCC | http://www.atcc.org/ATCCAdvancedCatalogSearch/ProductDetails/tabid/452/Default.aspx?ATTCNum=CRL-2321&Template=cellBiology | CRL-2336 |
| HCC3153 | BL1 | NA | NA | NA |
| MDA-MB-468 | BL1 | ATCC | http://www.atcc.org/ATCCAdvancedCatalogSearch/ProductDetails/tabid/452/Default.aspx?ATTCNum=HTB-132&Template=cellBiology | HTB-132 |
| CAL-851 | BL2 | DSMZ | http://www.dsmz.de/catalogus/details/culture/ACC-440.html?tx_dsmzresources_pi5[returnPid]=192 | ACC-440 |
| HCC70 | BL2 | ATCC | http://www.atcc.org/ATCCAdvancedCatalogSearch/ProductDetails/tabid/452/Default.aspx?ATTCNum=CRL-2315&Template=cellBiology | CRL-2315 |
| HDQP1 | BL2 | DSMZ | http://www.dsmz.de/catalogus/details/culture/ACC-494.html?tx_dsmzresources_pi5[returnPid]=192 | ACC-494 |
| SUM149PT | BL2 | Asterand | http://www.asterand.com/Asterand/human-tissues/149PT.htm | SUM-149PT |
| HCC1806 | BL2 | ATCC | http://www.atcc.org/ATCCAdvancedCatalogSearch/ProductDetails/tabid/452/Default.aspx?ATTCNum=CRL-2335&Template=cellBiology | CRL-2335 |
| DU4475 | IM | ATCC | http://www.atcc.org/ATCCAdvancedCatalogSearch/ProductDetails/tabid/452/Default.aspx?ATTCNum=HTB-123 | HTB-123 |
| HCC1187 | IM | ATCC | http://www.atcc.org/ATCCAdvancedCatalogSearch/ProductDetails/tabid/452/Default.aspx?ATTCNum=CRL-2322&Template=cellBiology | CRL-2322 |
| CAL-148 | LAR | DSMZ | http://www.dsmz.de/catalogus/details/culture/ACC-460.html?tx_dsmzresources_pi5[returnPid]=192 | ACC-460 |
| MFM223 | LAR | DSMZ | http://www.dsmz.de/catalogus/details/culture/ACC-422.html?tx_dsmzresources_pi5[returnPid]=192 | ACC-422 |

TABLE 6C-continued

Cell Line Source

| Cell Line | Subtype | Source | Website | Product No. |
|---|---|---|---|---|
| SUM185PE | LAR | Asterand | http://www.asterand.com/Asterand/human-tissues/185PE.htm | SUM-185PE |
| MDA-MB-453 | LAR | ATCC | http://www.atcc.org/ATCCAdvancedCatalogSearch/ProductDetails/tabid/452/Default.aspx?ATTCNum=HTB-131&Template=cellBiology | HTB-131 |
| HCC2185 | LAR | NA | NA | NA |
| BT549 | M | ATCC | http://www.atcc.org/ATCCAdvancedCatalogSearch/ProductDetails/tabid/452/Default.aspx?ATTCNum=HTB-122&Template=cellBiology | HTB-122 |
| CAL-120 | M | DSMZ | http://www.dsmz.de/catalogus/details/culture/ACC-459.html?tx_dsmzresources_pi5[returnPid]=192 | ACC-459 |
| CAL-51 | M | DSMZ | http://www.dsmz.de/catalogus/details/culture/ACC-302.html?tx_dsmzresources_pi5[returnPid]=192 | ACC-302 |
| HS578T | MSL | ATCC | http://www.atcc.org/ATCCAdvancedCatalogSearch/ProductDetails/tabid/452/Default.aspx?ATTCNum=HTB-126&Template=cellBiology | HTB-126 |
| MDA-MB-157 | MSL | ATCC | http://www.atcc.org/ATCCAdvancedCatalogSearch/ProductDetails/tabid/452/Default.aspx?ATTCNum=HTB-24&Template=cellBiology | HTB-24 |
| MDA-MN-436 | MSL | ATCC | http://www.atcc.org/ATCCAdvancedCatalogSearch/ProductDetails/tabid/452/Default.aspx?ATTCNum=HTB-130&Template=cellBiology | HTB-130 |
| SUM159PT | MSL | Asterand | http://www.asterand.com/Asterand/human-tissues/159PT.htm | SUM-159PT |
| MDA-MB-231 | MSL | ATCC | http://www.atcc.org/ATCCAdvancedCatalogSearch/ProductDetails/tabid/452/Default.aspx?ATTCNum=HTB-26&Template=cellBiology | HTB-26 |
| BT20 | | ATCC | http://www.atcc.org/ATCCAdvancedCatalogSearch/ProductDetails/tabid/452/Default.aspx?ATTCNum=HTB-19&Template=cellBiology | HTB-19 |
| HCC1395 | | ATCC | http://www.atcc.org/ATCCAdvancedCatalogSearch/ProductDetails/tabid/452/Default.aspx?ATTCNum=CRL-2324&Template=cellBiology | CRL-2324 |
| SW527 | | ATCC | http://www.atcc.org/ATCCAdvancedCatalogSearch/ProductDetails/tabid/452/Default.aspx?ATTCNum=CRL-7940&Template=cellBiology | CRL-7940 |
| MCF10A | | ATCC | http://www.atcc.org/ATCCAdvancedCatalogSearch/ProductDetails/tabid/452/Default.aspx?ATTCNum=CRL-10317&Template=cellBiology | CRL-10317 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining and treating a triple negative breast cancer (TNBC) subtype in a human individual in need thereof comprising:
   a) determining expression of at least ABCA12, ADAMDEC1, AKR1B10, ALCAM, ALDH3B2, ALOX15B, ALOX5, ANP32E, APOBEC3G, APOD, AR, AZGP1, BCL11A, BCL2A1, BIRC3, C1QA, CADPS2, CCL5, CCR2, CD2, CD38, CLCA2, COBL, COL5A1, COL5A2, COL6A3, CRAT, CTSC, CTSS, CXCL10, CXCL11, CXCL13, DDX60, DHCR24, DHRS2, EAF2, EN1, EPHB3, FASN, FGL2, FOXA1, FOXC1, FZD4, G6PD, GALNT10, GBP1, GBP2, GGT1, GGTLC3, GNLY, GPR161, GPR87, GZMA, GZMB, HGD, HMGCS2, HTRA1, IDO1, IGKC, IL15, INPP4B, IRF1, ITPKB, KCNK5, KCNMA1, KMO, KRT18, KYNU, LAMP3, LOC652493, LTB, MCM10, MFGE8, MIA, MICALL1, MLPH, MME, MMP2, MSX2, MUC5B, MYBL1, NKG7, NTN3, OAS1, PADI2, PIP, PLACE, PSMB9, PTPRC, RARRES3, ROPN1, S100A1, S100A7, S100A8, S100A9, SCRG1, SELL, SEMA4D, SERHL2, SIDT1, SOX10, SPDEF, STAT1, SYNM, TAP1, TCF7L1, TFAP2B, TGFBI, THY1, TNFSF10, TP53BP2, TP53TG1, TP63, TRIM36, TRPS1, UBD, UBE2L6, UGT2B28, WARS, and XBP1 genes in one or more TNBC cells of the individual;
   b) comparing the expression of the genes in the TNBC cells with the expression of the genes in a control;
   c) determining an increased expression of at least one of the genes in the TNBC cells as compared to the expression of the genes in the control;
   d) determining if the TNBC subtype is TNBC IM or TNBC LAR from the increased expression of at least one of the genes; and
   e) administering a treatment protocol for the individual based on the TNBC subtype;
   wherein determining that the TNBC is the TNBC IM subtype includes determining increased expression of one or more genes selected from the group consisting of BCL2A1, BIRC3, C1QA, CD38, DDX60, GNLY, GZMB, IDO1, IL15, IRF1, LAMP3, NKG7, SEMA4D, STAT1, TAP1, UBE2L6, and WARS in the TNBC cells compared to the control;
   wherein determining that the TNBC is the TNBC LAR subtype includes determining increased expression of one or more genes selected from the group consisting of ABCA12, AKR1B10, ALCAM, ALDH3B2, ALOX15B, AR, CADPS2, CRAT, DHRS2, EAF2, FASN, FOXA1, G6PD, GGTLC3, HGD, HMGCS2, INPP4B, KCNMA1, KMO, KRT18, MLPH, MSX2, PIP, SERHL2, SIDT1, SPDEF, TFAP2B, TP53TG1, TRIM36, and UGT2B28 in the TNBC cells compared to the control;
   wherein the treatment protocol for the TNBC IM subtype includes treating the individual with an immune checkpoint inhibitor and the treatment protocol for the TNBC LAR subtype includes treating the individual with an AR antagonist alone or in combination with PI3K inhibitors; and
   wherein the control is selected from the group consisting of corresponding cells from one or more individuals that do not have TNBC, non-TNBC cells from the individual, a standard control established by assaying individuals that do not have TNBC, and combinations thereof.

2. The method of claim 1 wherein the TNBC cells are selected from the group consisting of epithelial cells, mesenchymal cells, immune cells, and combinations thereof.

3. The method of claim 1 wherein the control is the non-TNBC cells from the individual.

4. The method of claim 1 wherein the non-cancer cell is the corresponding cells from one or more individuals that do not have TNBC.

5. The method of claim 1 wherein determining that the TNBC is the TNBC IM subtype includes selectively determining an increased expression of a gene combination comprising CCL19, CCL3, CCL4, CCL5, CCL8, CCR1, CCR2, CCR5, CCR7, CD2, CD37, CD38, CD3D, CD48, CD52, CD69, CD74, and CD8A in the TNBC cells compared to the control.

6. The method of claim 1 wherein determining that the TNBC is the TNBC IM subtype further comprises detecting one or more mutated genes.

7. The method of claim 6 wherein the one or more mutated genes are selected from the group consisting of TP53, CTNNA1, DDX18, HUWE1, NFKBIA, APC, BRAF, MAP2K4, RB1, STAT4, STAT1, RET, and combinations thereof.

8. The method of claim 1 wherein the TNBC IM subtype is detected in the individual and the individual is treated with one or more immune checkpoint inhibitors.

9. The method of claim 1 wherein determining that the TNBC is the TNBC LAR subtype includes selectively detecting increased expression of a gene combination comprising AR, DHCR24, ALCAM, GATA2, GATA3, IDIH1, IDIH2, CDH11, ERBB3, CUX2, FGFR4, HOPX, FASN, FKBP5, APOD, PIP, SPDEF, CLDN8, FOXA1, KRT18, and XBP1 in the TNBC cells compared to the control.

10. The method of claim 1 wherein determining that the TNBC is the TNBC LAR subtype further comprises detecting one or more mutated genes.

11. The method of claim 10 wherein the one or more mutated genes are selected from the group consisting of PIK3CA, CDH1, PTEN, RB1, TP53, MAP3K1, and combinations thereof.

12. The method of claim 1 wherein the TNBC LAR subtype is detected in the individual and the individual is treated with one or more drugs that inhibit androgen receptor (AR).

13. The method of claim 12 wherein the one or more drugs that inhibit AR are selected from the group consisting of bicalutamide, MVD3100, abiraterone, and combinations thereof.

14. The method of claim 12 further comprising treating the individual with a PI3K inhibitor a PI3K/mTOR inhibitor or a combination thereof.

15. The method of claim 14 wherein the PI3K inhibitor is BKM-120, GDC0941 or a combination thereof, and the PI3K/mTOR inhibitor is NVP-BEZ235, GDC0980 or a combination thereof.

16. The method of claim 12 further comprising treating the individual with an inhibitor of HSP90.

17. The method of claim 16 wherein the inhibitor of HSP90 is DMAG.

* * * * *